(12) United States Patent
Miller et al.

(10) Patent No.: US 12,365,910 B2
(45) Date of Patent: Jul. 22, 2025

(54) METHODS AND COMPOSITIONS FOR MODIFYING ROOT ARCHITECTURE IN PLANTS

(71) Applicant: PAIRWISE PLANTS SERVICES, INC., Durham, NC (US)

(72) Inventors: Marisa Miller, Durham, NC (US); Julius Mojica, Durham, NC (US); HaeJin Kim, Durham, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 63 days.

(21) Appl. No.: 17/679,509

(22) Filed: Feb. 24, 2022

(65) Prior Publication Data

US 2022/0380792 A1    Dec. 1, 2022

Related U.S. Application Data

(60) Provisional application No. 63/153,473, filed on Feb. 25, 2021.

(51) Int. Cl.
| | |
|---|---|
| C12N 15/82 | (2006.01) |
| A01H 1/06 | (2006.01) |
| A01H 6/46 | (2018.01) |
| C12N 15/11 | (2006.01) |
| C12N 15/113 | (2010.01) |

(52) U.S. Cl.
CPC ........ *C12N 15/8261* (2013.01); *A01H 6/4684* (2018.05); *C12N 15/8273* (2013.01); *A01H 1/06* (2013.01); *C12N 15/113* (2013.01)

(58) Field of Classification Search
CPC .......................... A01H 6/4684; C12N 15/8261
See application file for complete search history.

(56) References Cited

U.S. PATENT DOCUMENTS

| | | |
|---|---|---|
| 10,513,708 B2 | 12/2019 | Dardick et al. |
| 2012/0317678 A1 | 12/2012 | Uga |
| 2013/0212743 A1 | 8/2013 | Kuroha et al. |
| 2018/0094272 A1 | 4/2018 | Dardick et al. |
| 2020/0199604 A1* | 6/2020 | Lippman ............ C12N 15/1082 |

FOREIGN PATENT DOCUMENTS

| | | |
|---|---|---|
| EP | 2518148 A1 | 10/2012 |
| WO | 2022182834 | 9/2022 |

OTHER PUBLICATIONS

Sharma et al., 2021, Genomic prediction and QTL mapping of root system architecture and above-ground agronomic traits in rice (*Oryza sativa* L.) with a multitrait index and Bayesian networks. G3, 11(10), jkab178. (Year: 2021).*
Guo et al., 2004, Protein tolerance to random amino acid change. Proceedings of the National Academy of Sciences, 101(25), 9205-9210. (Year: 2004).*
Ashraf et al., 2019, Evolution of Deeper Rooting 1-like homoeologs in wheat entails the C-terminus mutations as well as gain and loss of auxin response elements. PLoS One, 14(4), e0214145. (Year: 2019).*
Schnable et al., 2009, The B73 maize genome: complexity, diversity, and dynamics. science, 326(5956), 1112-1115. (Year: 2009).*
Omori et al., 2007, QTL mapping of root angle in F2 populations from maize 'B73'x teosinte '*Zea luxurians*'. Plant Root, 1, 57-65. ( Year: 2007).*
Waite et al., 2021, The roles of the IGT gene family in plant architecture: past, present, and future. Current Opinion in Plant Biology, 59, 101983. (Year: 2021).*
Guo et al., 2022, Root system architecture differences of maize cultivars affect yield and nitrogen accumulation in Southwest China. Agriculture, 12(2), 209. (Year: 2022).*
NCBI Global Alignment of SEQ ID No. 72 with SEQ ID No. 75. Accessed in https://blast.ncbi.nlm.nih.gov, in Jun. 14, 2024. (Year: 2024).*
Uga et al., 2013, Control of root system architecture by Deeper Rooting 1 increases rice yield under drought conditions, Nature Genetics. 45(9): 1097-1102 (reference included in IDS submitted in Jun. 21, 2022). (Year: 2013).*
Hagen et al., 2002, Auxin-responsive gene expression: genes, promoters and regulatory factors. Plant molecular biology, 49, 373-385. (Year: 2002).*
Alignment of SEQ ID No. 72 and 73 to NCBI nucleotide database, https://blast.ncbi.nlm.nih.gov/Blast.cgi, accessed Jan. 27, 2025. (Year: 2025).*
Description of Locus LOC103640271 aligned to SEQ ID No. 74,https://blast.ncbi.nlm.nih.gov/Blast.cgi, accessed Jan. 27, 2025. (Year: 2020).*
International Search Report and the Written Opinion of the International Searching Authority corresponding to International Patent Application No. PCT/US2022/017645 (17 pages) (mailed May 30, 2022).
Ashraf, Almas, et al., "Evolution of Deeper Rooting 1-like homoeologs in wheat entails the C-terminus mutations as well as gain and loss of auxin response elements", PLoS ONE. 14(4):e0214145 (2019).
Guseman, Jessica M., et al., "DRO1 influences root system architecture in *Arabidopsis* and Prunus species", The Plant Journal. 89:1093-1105 (2017).
Kitomi, Yuka, et al., "Root angle modifications by the DRO1 homolog improve rice yields in saline paddy fields", PNAS. 117(35):21242-21250 (2020).
Uga, Yusaku, et al., "Control of root system architecture by Deeper Rooting 1 increases rice yield under drought conditions", Nature Genetics. 45(9): 1097-1102 (2013).
Zhao, Yiting, et al., "INDITT02 transposon conveys auxin-mediated DRO1 transcription for rice drought avoidance", Plant Cell and Environment. 44(6):1846-1857 (2021).

(Continued)

*Primary Examiner* — Amjad Abraham
*Assistant Examiner* — Santosh Sharma
(74) *Attorney, Agent, or Firm* — Myers Bigel, P.A.

(57) ABSTRACT

This invention relates to compositions and methods for modifying root architecture in a plant through modification of endogenous DEEPER ROOTING 1 (DRO1) nucleic acids. The invention further relates to plants produced using the methods and compositions of the invention.

9 Claims, No Drawings

Specification includes a Sequence Listing.

(56) References Cited

OTHER PUBLICATIONS

International Search Report and Written Opinion corresponding to International Application No. PCT/US2023/066579, mailed Oct. 5, 2023 (21 pages).

International Search Report and Written Opinion corresponding to International Application No. PCT/US2024/038266, dated Oct. 29, 2024 (18 pages).

Boer, D. Roeland, et al., "Structural Basis for DNA Binding Specificity by the Auxin-Dependent ARF Transcription Factors", Cell. 156: 577-589, 2014.

Chen, Lei, et al., "The Lonely Guy gene family: from mosses to wheat, the key to the formation of active cytokinins in plants", Plant Biotechnology Journal 20: 625-645, 2022,.

Doll, Nicolas M., et al., "Signaling in Early Maize Kernel Development", Molecular Plant. 10: 375-388, 2017.

Kuroha, Takeshi, et al., "Functional Analyses of Lonely Guy Cytokinin-Activating Enzymes Reveal the Importance of the Direct Activation Pathway in *Arabisopsis*", The Plant Cell 21: 3152-3169, 2009.

Leyser, Ottoline, "Auxin Signaling", Plant Physiology 176: 465-479, 2018.

Mandal, Sayanti, et al., "Cytokinins: A Genetic Target for Increasing Yield Potential in the CRISPR Era", Frontiers in Genetics 13:883930, 2022.

Rodriguez-Leal, Daniel, et al., "Engineering Quantitative Trait Variation for Crop Improvement by Genome Editing", Cell 171(2): 470-480, 2017.

Rodriguez-Leal, Daniel, et al., "Evolution of buffering in a genetic circuit controlling plant stem cell proliferation". Nature Genetics. 51: 786-792, 2019.

Swathik Clarancia, P., et al., "Isolation, characterization and expression analysis of novel water deficit stress-responsive Deeper Rooting 1 (DRO1) gene from drought-tolerant Erianthus arundinaceus", Journal of Sugarcane Research 10: 1-11, 2020.

Tokunaga, Hiroki, et al., "*Arabidopsis* lonely guy (LOG) multiple mutants reveal a central role of the LOG-dependent pathway in cytokinin activation", The Plant Journal 69: 355-365, 2012.

"History of A0A804R698", UniProtKB, 2018. Retrieved from https://www.uniprot.org/uniprotkb/A0A804R698/history on Sep. 23, 2024.

Galli, et al., "The DNA binding landscape of the maize Auxin Response Factor family", Nature Communications. 9:4526, 2018.

Lanctot, et al., "Specificity in Auxin Responses Is Not Explained by the Promoter Preferences of Activator ARFs", bioRxiv preprint doi: https://doi.org/10.1101/843391, posted Nov. 15, 2019.

Walcher, et al., "Bipartite Promoter Element Required for Auxin Response", Plant Physiology 158: 273-282, 2012.

\* cited by examiner

METHODS AND COMPOSITIONS FOR MODIFYING ROOT ARCHITECTURE IN PLANTS

STATEMENT OF PRIORITY

This application claims the benefit, under 35 U.S.C. § 119(e), of U.S. Provisional Application No. 63/153,473 filed on Feb. 25, 2021, the entire contents of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 1499.58 ST25.txt, 427,653 bytes in size, generated on Feb. 24, 2022 and filed via EFS-Web, is provided in lieu of a paper copy. This Sequence Listing is hereby incorporated herein by reference into the specification for its disclosures.

FIELD OF THE INVENTION

This invention relates to compositions and methods for modifying root architecture in a plant through modification of endogenous DEEPER ROOTING 1 (DRO1) nucleic acids. The invention further relates to plants produced using the methods and compositions of the invention.

BACKGROUND OF THE INVENTION

The development of roots and its vascular system was important in the evolution of plants during the early Devonian period (Boyce, C. K. *The evolutionary history of roots and leaves*. In: Holbrook N M, Zwieniecki M A (eds.), *Vascular transport in plants*: 479-499. Elsevier, Amsterdam). As sessile organisms, plants have adapted their root system for optimized nutrient and water acquisition.

Yield in crop and horticultural plants is limited by many factors including their capacity to absorb water and nutrients. Thus, one strategy for yield improvement is to breed plants with improved root system architecture, and artificial selection has capitalized on the variation created by natural selection for improved root architecture.

The present invention overcomes the shortcomings in the art by providing improved methods and compositions for modifying root architecture and improving yield traits.

SUMMARY OF THE INVENTION

One aspect of the invention provides a plant or plant part thereof comprising at least one (e.g., one or more) non-natural mutation in an endogenous gene encoding a DEEPER ROOTING 1 (DRO1) polypeptide, wherein the mutation is in a cis-regulatory element of the endogenous gene.

Another aspect of the invention provides a plant cell comprising an editing system, the editing system comprising (a) a CRISPR-Cas associated effector protein; and (b) a guide nucleic acid (gRNA, gDNA, crRNA, crDNA, sgRNA, sgDNA) comprising a spacer sequence with complementarity to an endogenous target gene encoding a DRO1 in the plant cell.

An additional aspect of the invention provides a plant cell comprising a base editing system comprising: (a) a CRISPR-Cas associated effector protein; (b) a cytidine deaminase or adenosine deaminase; and (c) a guide nucleic acid (gRNA) having a spacer sequence with complementarity to an endogenous target gene encoding DRO1.

A further aspect of the invention provides a plant cell comprising at least one non-natural mutation (e.g., one or more) in a cis-regulatory element of a DEEPER ROOTING 1 (DRO1) gene, wherein the at least one non-natural mutation is a base substitution, base insertion or a base deletion that is introduced using an editing system that comprises a nucleic acid binding domain that binds to a target site in the DRO1 gene, the DRO1 gene (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77.

Also provided is a method of providing a plurality of plants having enhanced root architecture, the method comprising planting two or more plants of the invention in a growing area, thereby providing a plurality of plants having enhanced root architecture as compared to a plurality of control plants not comprising the at least one non-natural mutation, optionally wherein the plurality of plants having enhanced root architecture exhibit increased root biomass, steeper root angle and/or longer roots and/or improved yield traits.

The invention further provides a method of producing/breeding a transgene-free genome-edited plant, comprising: (a) crossing a plant of the invention with a transgene free plant, thereby introducing the mutation into the plant that is transgene-free; and (b) selecting a progeny plant that comprises the mutation but is transgene-free, thereby producing a transgene free genome-edited plant.

Another aspect of the invention provides a method for editing a specific site in the genome of a plant cell, the method comprising: cleaving, in a site-specific manner, a target site within an endogenous DEEPER ROOTING 1 (DRO1) gene in the plant cell, the endogenous DRO1 gene: (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77, thereby generating an edit in the endogenous DRO1 gene of the plant cell.

An additional aspect of the invention provides a method for making a plant, comprising: (a) contacting a population of plant cells that comprise an endogenous gene encoding a DEEPER ROOTING 1 (DRO1) polypeptide with a nuclease targeted to the endogenous gene, wherein the nuclease is linked to a nucleic acid binding domain that binds to a target site in the endogenous gene, the endogenous gene (i) comprising a nucleotide sequence having at least 80% sequence identity to the nucleotide sequence of any one of SEQ ID NOs:72 or 75; (ii) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (iii) comprising a coding sequence having at least 80% sequence identity to the nucleotide sequence of SEQ ID NO:73 or SEQ ID NO:76; and/or (iv) encoding a polypeptide sequence having at least 80% identity to the amino acid sequence of any one of SEQ ID NO:74 or SEQ ID NO:77; (b) selecting a plant cell from the population comprising a mutation in the endogenous gene encoding a DRO1 polypeptide, wherein the mutation is a substitution and/or a deletion of at least one amino acid residue in a polypeptide of (ii) or in a polypeptide encoded by any one of the nucleotide sequences of (i); and (c) growing the selected plant cell into a plant comprising the mutation in the endogenous gene encoding a DRO1 polypeptide.

In an additional aspect, a method for modifying/enhancing/improving the root architecture of a plant, comprising (a) contacting a plant cell comprising a endogenous gene encoding a DEEPER ROOTING 1 (DRO1) polypeptide with a nuclease targeted to the endogenous gene, wherein the nuclease is linked to a nucleic acid binding domain that binds to a target site in the endogenous gene, the endogenous gene: (i) comprising a nucleotide sequence having at least 80% sequence identity to the nucleotide sequence of any one of SEQ ID NOs:72 or 75; (ii) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (iii) comprising a coding sequence having at least 80% sequence identity to the nucleotide sequence of SEQ ID NO:73 or SEQ ID NO:76; and/or (iv) encoding a polypeptide sequence having at least 80% identity to the amino acid sequence of any one of SEQ ID NO:74 or SEQ ID NO:77, thereby producing a plant cell comprising a mutation in the endogenous gene encoding a DRO1 polypeptide; and (b) growing the plant cell into a plant, thereby modifying/enhancing/improving the root architecture of the plant.

In another aspect, a method is provided for producing a plant or part thereof comprising at least one cell (e.g., one or more) having a mutation in an endogenous DEEPER ROOTING 1 (DRO1) gene, the method comprising contacting a target site in the endogenous DRO1 gene in the plant or plant part with a nuclease comprising a cleavage domain and a nucleic acid binding domain, wherein the nucleic acid binding domain of the nuclease binds to a target site in the endogenous DRO1 gene, wherein the endogenous DRO1 gene: (a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77, thereby producing a plant or part thereof comprising at least one cell having a mutation in the endogenous DRO1 gene.

In a further aspect, a method of producing a plant or part thereof comprising a mutation in an endogenous DEEPER ROOTING 1 (DRO1) gene having enhanced/improved root architecture, the method comprising contacting a target site in an endogenous DRO1 gene in the plant or plant part with a nuclease comprising a cleavage domain and a nucleic acid binding domain, wherein the nucleic acid binding domain of the nuclease binds to a target site in the endogenous DRO1 gene, wherein the endogenous DRO1 gene: (a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77, thereby producing a plant or part thereof having a mutated endogenous DRO1 gene and having enhanced/improved root architecture, and optionally exhibiting increased root biomass, steeper root angle and/or longer roots and/or improved yield traits.

An additional aspect of the invention provides a guide nucleic acid that that binds to a target site in an endogenous gene encoding DEEPER ROOTING 1 (DRO1), the endogenous gene: (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77.

A further aspect of the invention provides a system comprising a guide nucleic acid of the invention and a CRISPR-Cas effector protein that associates with the guide nucleic acid.

Another aspect of the invention provides gene editing system comprising a CRISPR-Cas effector protein in association with a guide nucleic acid, wherein the guide nucleic acid comprises a spacer sequence that is complementary to and binds to a DEEPER ROOTING 1 (DRO1) gene.

An additional aspect of the invention provides a complex comprising a CRISPR-Cas effector protein comprising a cleavage domain and a guide nucleic acid, wherein the guide nucleic acid binds to a target site in a DEEPER ROOTING 1 (DRO1) gene, the DRO1 gene (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77, wherein the cleavage domain cleaves a target strand in the DRO1 gene.

A further aspect provides an expression cassette comprising: (a) polynucleotide encoding CRISPR-Cas effector protein comprising a cleavage domain and (b) a guide nucleic acid that binds to a target site in a DEEPER ROOTING 1 (DRO1) gene, wherein the guide nucleic acid comprises a spacer sequence that is complementary to and binds to the target site in the DRO1 gene, the DRO1 gene: (i) comprising a nucleotide sequence having at least 80% sequence identity to the nucleotide sequence of any one of SEQ ID NOs:72 or 75; (ii) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (iii) comprising a coding sequence having at least 80% sequence identity to the nucleotide sequence of SEQ ID NO:73 or SEQ ID NO:76; and/or (iv) encoding a polypeptide sequence having at least 80% identity to the amino acid sequence of any one of SEQ ID NO:74 or SEQ ID NO:77.

Another aspect of the invention provides a nucleic acid comprising a mutated DEEPER ROOTING 1 (DRO1) gene, wherein the mutated DRO1 gene comprises a mutation in a cis-regulatory region.

A further aspect provides a mutated nucleic acid encoding a DEEPER ROOTING 1 (DRO1) polypeptide, the mutated nucleic acid comprising a cis-regulatory element having a mutation, optionally the mutation is in an Auxin Responsive Element (ARE), wherein the mutation disrupts the binding of Auxin Responsive Factor (ARF) to the ARE of the nucleic acid.

Further provided are plants comprising in their genome one or more DEEPER ROOTING 1 (DRO1) genes having a non-natural mutation produced by the methods of the invention as well as polypeptides, polynucleotides, nucleic acid constructs, expression cassettes and vectors for making a plant of this invention.

These and other aspects of the invention are set forth in more detail in the description of the invention below.

BRIEF DESCRIPTION OF THE SEQUENCES

SEQ ID NOs:1-17 are exemplary Cas12a amino acid sequences useful with this invention.

SEQ ID NOs:18-20 are exemplary Cas12a nucleotide sequences useful with this invention.

SEQ ID NO:21-22 are exemplary regulatory sequences encoding a promoter and intron.

SEQ ID NOs:23-29 are exemplary cytosine deaminase sequences useful with this invention.

SEQ ID NOs:30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs:42-44 provides an example of a protospacer adjacent motif position for a Type V CRISPR-Cas12a nuclease.

SEQ ID NOs:45-47 provide example peptide tags and affinity polypeptides useful with this invention.

SEQ ID NOs:48-58 provide example RNA recruiting motifs and corresponding affinity polypeptides useful with this invention.

SEQ ID NOs:59-60 are example Cas9 polypeptide sequences useful with this invention.

SEQ ID NOs:61-71 are example Cas9 polynucleotide sequences useful with this invention.

SEQ ID NO:72 or SEQ ID NO:75 are example DRO1 genomic sequences.

SEQ ID NO:73 or SEQ ID NO:76 are example DRO1 coding (cds) sequences.

SEQ ID NO:74 or SEQ ID NO:77 are example DRO1 polypeptide sequences.

SEQ ID NO:78 or SEQ ID NO:79 are example target regions of example DRO1 genomic sequences.

SEQ ID NOs:80-83 are example spacer sequences for targeting a DRO1 gene.

SEQ ID NO:84 and SEQ ID NO:85 example edited DRO1 genomic sequences.

SEQ ID NO:86 and SEQ ID NO:87 are example portions deleted from a DRO1 genomic sequence (e.g., SEQ ID NO:72).

SEQ ID NO:88 and SEQ ID NO:89 example edited DRO1 genomic sequences.

SEQ ID NO:90 is an example portion deleted from a DRO1 genomic sequence (e.g., SEQ ID NO:75).

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

Unless otherwise defined, the term "at least one" has the same meaning as "one or more" (e.g., 1, 2, 3, 4, 5 and the like).

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 15%, 20%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In some embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the reference organism.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is nonfunctional.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypomorphic mutation" is a mutation that results in increased expression of the gene product and/or increased activity of the gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-water stress conditions in a plant relative to a control plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety, or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

A plant in which at least one (e.g., one or more) DRO1 gene is modified as described herein (e.g., comprises a modification as described herein) may have improved yield traits as compared to a plant that does not comprise the modification in the at least one DRO1 gene. As used herein, "improved yield traits" refers to any plant trait associated with growth, for example, biomass, yield, nitrogen use efficiency (NUE), inflorescence size/weight, fruit yield, fruit quality, fruit size, seed size, seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, size and/or weight of root mass, or any combination thereof. Thus, in some aspects, "improved yield traits" may include, but is not limited to, increased inflorescence production, increased fruit production (e.g., increased number, weight and/or size of fruit; e.g., increase number, weight, and/or size of ears for, e.g., maize), increased fruit quality, increased number, size and/or weight of roots, increased meristem size, increased seed size, increased biomass, increased leaf size, increased nitrogen use efficiency, increased height, increased internode number and/or increased internode length as compared to a control plant or part thereof (e.g., a plant that does not comprise a mutated endogenous DRO1 nucleic acid (e.g., a mutated DRO1 gene)). Improved yield traits can also result from increased planting density of plants of the invention. Thus, in some aspects, a plant of the invention is capable of being planted at an increased density (as a consequence of altered plant architecture resulting from the endogenous mutation), which results in improved yield traits as compared to a control plant that is planted at the same density. In some aspects, improved yield traits can be expressed as quantity of grain produced per area of land (e.g., bushels per acre of land).

As used herein a "control plant" means a plant that does not contain an edited DRO1 gene or genes as described herein that imparts an enhanced/improved trait (e.g., yield trait) or altered phenotype. A control plant is used to identify and select a plant edited as described herein and that has an enhanced trait or altered phenotype. A suitable control plant can be a plant of the parental line used to generate a plant comprising a mutated DRO1 gene(s), for example, a wild type plant devoid of an edit in an endogenous DRO1 gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of a mutated DRO1 gene as described herein, known as a negative segregant, or a negative isogenic line.

An enhanced trait may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and increased water use efficiency as compared to a control plant. An altered phenotype may be, for example, plant height, biomass, canopy area, anthocyanin content, chlorophyll content, water applied, water content, and water use efficiency.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a plant resulting from mutations in a DRO1 gene(s) as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a mutation in an endogenous DRO1 gene as described herein relative to a plant not comprising the mutation, such as a wild-type plant, or a negative segregant. In some cases, the trait modification can be evaluated quantitatively. For example, the trait modification can entail an increase or decrease in an observed trait characteristics or phenotype as compared to a control plant. It is known that there can be natural variations in a modified trait. Therefore, the trait modification observed entails a change of the normal distribution and magnitude of the trait characteristics or phenotype in the plants as compared to a control plant.

The present disclosure relates to a plant with improved economically important characteristics, more specifically increased yield. More specifically the present disclosure relates to a plant comprising a mutation(s) in a DRO1 gene(s) as described herein, wherein the plant has increased yield as compared to a control plant devoid of said mutation(s). In some embodiments, plants produced as described herein exhibit increased yield or improved yield trait components as compared to a control plant. In some embodiments, a plant of the present disclosure exhibits an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter), which can also influence the composition of seeds; and/or increased seed volume, which can also influence the composition of seeds. In one embodiment, increased yield can be increased seed yield, for example, increased seed weight; increased number of filled seeds; and increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs.

The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

The terms "enhanced root architecture," "modified root architecture," or "improved root architecture" may be used interchangeably and refer to root architecture that provides an improvement in the ability of a plant to uptake water and nutrients, in particular, when the plant is growing under environmental conditions that may limit water and nutrient uptake (e.g., drought conditions) in a plant not comprising the enhanced root architecture. Enhanced root architecture may be characterized by a phenotype that includes, but is not limited to, increased root biomass, steeper root angle and/or longer roots and/or improved yield traits.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, 900, 950 or 1000 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. As an example, a "fragment" or "portion" (or region) of a nucleic acid encoding a DRO1 polypeptide may be about 10, 15, 20, 25 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 420, 440, 460, 480, 500, 520, 540, 560, 580, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 or more consecutive nucleotides of a DRO1 nucleic acid, or any range or value therein, optionally wherein the fragment, portion or region may be targeted for editing to provide a plant having enhanced root architecture and/or may result in improved yield traits in the plant. Such a nucleic acid fragment may be, where appropriate, included in a larger polynucleotide of which it is a constituent. As a further example, a repeat sequence of guide nucleic acid of this invention may comprise a portion of a wild type CRISPR-Cas repeat sequence (e.g., a wild Type CRISR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment or portion (or region) may comprise, consist essentially of or consist of about 10, 15, 20, 25, 30, 35, 40, 45, 50, 60, 70, 80, 90, 100, 150, 200, 250, 300, 350, 400, 450, 500, 550, 600, 660, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2300, 2400, 2500, or more or more consecutive nucleotides in the 5' region of a DRO1 nucleic acid, which fragment or portion may comprise a target for editing of the DRO1 gene as described herein in order to provide improved or enhanced root architecture and/or improved yield traits in a plant. In some embodiments, a portion or region of a DRO1 gene that may be targeted for editing may be from about nucleotide 1 to about nucleotide 2235, from about nucleotide 1200 to about nucleotide 2235, from about nucleotide 1200 to about nucleotide 1850 or from about nucleotide 1474 to about nucleotide 1835 with reference to nucleotide numbering of SEQ ID NO:72, or from about nucleotide 1 to about nucleotide 2478, from about nucleotide 1200 to about nucleotide 2478, from about nucleotide 1200 to about nucleotide 2412 or from about nucleotide 2095 to about nucleotide 2412 with reference to nucleotide numbering of SEQ ID NO:75.

In some embodiments, a nucleic acid fragment or portion (or region) may be edited as described herein, wherein the edit results in a deletion. In some embodiments, the edit may be in a DRO1 nucleic acid in which 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 36, 37, 38, 39, 40 or 45 to about 50, 55, 60, 65, 70, 75, 80, 85, 90, 95 or 100 or more consecutive nucleotides may be deleted from the DRO1 nucleic acid, e.g., from about nucleotide 1 to about nucleotide 2235, from about nucleotide 1200 to about nucleotide 2235, from about nucleotide 1200 to about nucleotide 1850, or from about nucleotide 1474 to about nucleotide 1835 (optionally, wherein the deletion may be from about nucleotide 1470 to about nucleotide 1492 (see, e.g., SEQ ID NO:86), or from about nucleotide 1792 to about nucleotide 1812 (see, e.g., SEQ ID NO:87)) with reference to nucleotide numbering of SEQ ID NO:72, or from about nucleotide 1 to about nucleotide 2478, from about nucleotide 1200 to about nucleotide 2478, from about nucleotide 1200 to about nucleotide 2412, or from about nucleotide 2095 to about nucleotide 2412 (optionally, wherein the deletion may be from about nucleotide 2110 to about nucleotide 2117 (e.g., TCCGATCC), from about nucleotide 2405 to about nucleotide 2405 (e.g., CTTC), or from about nucleotide 2111 to about nucleotide 2121 (see, e.g., SEQ ID NO:90)) with reference to nucleotide numbering of SEQ ID NO:75. In some embodiments, a deletion of nucleotides from a DRO1 gene as described herein may result in a dominant negative mutation, a semi-dominant mutation, a weak loss-of-function mutation, a hypomorphic mutation or a recessive mutation, which when comprised in a plant can result in the plant exhibiting enhanced root architecture and/or improved yield traits as compared to a plant not comprising the deletion.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, 290, 300, 350, 400 or more consecutive amino acids of a reference polypeptide.

A "region" of a polynucleotide or a polypeptide refers to a portion of consecutive nucleotides or consecutive amino acid residues of that polynucleotide or a polypeptide, respectively. For example, a "region" of a DRO1 polynucleotide sequence may include, but is not limited to, consecutive nucleotides from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) with reference to nucleotide numbering of SEQ ID NO:72, or from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79) with reference to nucleotide numbering of SEQ ID NO:75.

In some embodiments, a "sequence-specific nucleic acid binding domain" (e.g., a sequence-specific DNA binding domain; e.g., a sequence-specific DNA binding polypeptide/protein) may bind to a DRO1 gene (e.g., SEQ ID NO:72, SEQ ID NO:75,) and/or to one or more fragments, portions, or regions of a DRO1 nucleic acid (e.g., portions or regions 5' of the first exon of the DRO1 gene as described herein).

As used herein with respect to nucleic acids, the term "functional fragment" refers to nucleic acid that encodes a functional fragment of a polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in in-frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. In some embodiments, a deletion or an insertion is an in-frame or out-of-frame deletion or an in-frame or out-of-frame insertion, e.g., an in-frame or out-of-frame deletion or an in-frame or out-of-frame insertion in an endogenous DRO1 nucleic acid. In some embodiments, a deletion or an insertion is an in-frame or out-of-frame deletion or an in-frame or out-of-frame insertion, e.g., an in-frame or out-of-frame deletion or an in-frame or out-of-frame insertion in a cis-regulatory element/region of an endogenous DRO1 gene (e.g., the region 5' of the first exon of the DRO1 gene as described herein). In some embodiments, a cis regulatory element of an endogenous DRO1 gene is promoter, an enhancer, a silencer, or an insulator. In some embodiments, a cis regulatory element of an endogenous DRO1 gene is an Auxin Responsive Element (ARE) and the mutation is in the ARE, optionally wherein the mutation disrupts the binding of an Auxin Responsive Factor (ARF) to the endogenous DRO1 gene in the plant or part thereof, optionally resulting in the plant comprising the mutation in its endogenous DRO1 gene having enhanced root architecture and/or improved yield traits. In some embodiments, a mutation in an endogenous DRO1 gene of a plant that is mutated as described herein may be in a cis-regulatory element of the DRO1 gene that is not associated with ARE, optionally where the mutation results in enhanced root architecture and/or improved yield traits.

A "cis-regulatory element" of an endogenous DRO1 gene as use herein refers to regulatory elements located in the region of a DRO1 gene that is 5' of the start codon of the first exon in the DRO1 gene. For example, a cis-regulatory element may be located in a DRO1 gene from about nucleotide 1 to about nucleotide 2235, from about nucleotide 1200 to about nucleotide 2235, from about nucleotide 1200 to about nucleotide 1850 or from about nucleotide 1474 to about nucleotide 1835 with reference to nucleotide numbering of SEQ ID NO:72, or from about nucleotide 1 to about nucleotide 2478, from about nucleotide 1200 to about nucleotide 2478, from about nucleotide 1200 to about nucleotide 2412 or from about nucleotide 2095 to about nucleotide 2412 with reference to nucleotide numbering of SEQ ID NO:75. In some embodiments, a deletion in a cis-regulatory element of an endogenous DRO1 gene may be from about nucleotide 1470 to about nucleotide 1492 (see, e.g., SEQ ID NO:86), or from about nucleotide 1792 to about nucleotide 1812 (see, e.g., SEQ ID NO:87)) with reference to nucleotide numbering of SEQ ID NO:72, or from about nucleotide 2110 to about nucleotide 2117 (e.g., TCCGATCC), from about nucleotide 2405 to about nucleotide 2405 (e.g., CTTC), or from about nucleotide 2111 to about nucleotide 2121 (see, e.g., SEQ ID NO:90)) with reference to nucleotide numbering of SEQ ID NO:75.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity, e.g., substantial complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide.

As used herein, the phrase "substantially identical," or "substantial identity" in the context of two nucleic acid molecules, nucleotide sequences or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more nucleotides in length, and any range therein, up to the full length of the sequence. In some embodiments, nucleotide sequences can be substantially identical over at least about 20 consecutive nucleotides (e.g., about 20, 21, 22, 23, 24, 25, 26, 27, 28, 29, 30, 31, 32, 33, 34, 35, 36, 37, 38, 39, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2500, 3000, 3500, 4000 or more nucleotides). In some embodiments, two or more DRO1 genes may be substantially identical to one another over at least about 10, 20, 30, 40, 50, 100, 200, 300, 400, 500, 600, 700, 800, 900, 1000, 1100, 1200, 1300, 1400, or 1500 to about 2000, 2050, 2100, 2150, 2200, 2250, 2300, 2350, 2400, 2450, 2500, 2510, 2520, 2530, 2540, 2550, 2600, 2650, 2700, 2750, 2800, 2850, 2900, 2950, 3000, 3050, 3100, 3150, 3200, 3250, 3300, 3350, 3400, 3450, 3490, 3500, 3600, 3700, 3800, 3900, 4000, 4100, 4200, 4300, 4400, 4500, 4600, 4700, 4800, 4900, 5000, 5100, 5200, or 5300 or more consecutive nucleotides of a DRO1 gene, e.g., SEQ ID NO:72 or SEQ ID NO:75, optionally over about 10, 20, 30, 40, 50, 60, 70, 80, 90, 100, 110, 120, 130, 140, 150, 200, 210, 220, 230, 240, 250, 260, 270, 280, 290, 300, 310, 320, 330, 340, 350, 360, 370, 380, 390, 400, 420, 440, 460, or 480 consecutive nucleotides to about 500, 520, 540, 560, 580, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 or more consecutive nucleotides of a DRO1 gene, e.g., SEQ ID NO:72 or SEQ ID NO:75.

In some embodiments of the invention, the substantial identity exists over a region of consecutive amino acid residues of a polypeptide of the invention that is about 3 amino acid residues to about 10, 11, 12, 13, 14, 15, 16, 17, 18, 19, or 20 amino acid residues, about 5 amino acid residues to about 25, 30, 35, 40, 45, 50 or 60 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8, 9, 10, 11, 12, 13, 14, or more consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 275, 300, 325, 350, 400, 450, 500, or more amino acids in length or more consecutive amino acid residues). In some embodiments, two or more DRO1 polypeptides may be substantially identical to one another over at least about 10 to about 280 consecutive amino acid residues of the amino acid sequence of, for example, SEQ ID NO:74 or SEQ ID NO:77; e.g., over at least about 10, 11, 12, 13, 14, 15, 16, 17, 18, 19, 20, 25, 30, 35, 40, 45, 50, 60, 70, 71, 72, 73, 74, 75, 76, 77, 78, 79, 80, 85, 90, 95, 100, 105, 110, 120, 125, 130, 135, 140, 145, 150, 155, 160, 165, 170, 175, 200, 205, 210, 215, 220, 225, 230, 235, 240, 245, 250, 255, 260, 265, 270, 275, or 280, or more consecutive amino acid residues of the amino acid sequence of, for example, SEQ ID NO:74 or SEQ ID NO:77. In some embodiments, a substantially identical nucleotide or protein sequence may perform substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific DNA binding domain/protein (e.g., a sequence-specific DNA binding domain/protein from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

A polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron may be referred to as a "promoter region" (e.g., Ubi1 promoter and intron) (see, e.g., SEQ ID NO:21 and SEQ ID NO:22).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain (e.g., DNA binding domain/polypeptide) and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid, or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g. extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) Annu. Rev. Biochem. 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as (3-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604, 121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2 USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA2-6 promoter from *arabidopsis* (U.S. Pat. No. 7,141, 424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) Proc. Natl. Acad. Sci. USA 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) Mol. Gen. Genet. 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) Mol. Gen. Genet. 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/ expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain (e.g., sequence-specific DNA binding domain), a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited to, a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g., higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CRISPR-Cas endonuclease CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid protein, the reverse transcriptase and the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions. In addition, RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

The term "regulating" as used in the context of a polypeptide "regulating" a phenotype, for example, a balance between inactive and active cytokinins in a plant, means the ability of the polypeptide to affect the expression of a gene or genes such that a phenotype such as the cytokinin balance is modified.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

The capacity of plants to absorb water and nutrients can limit yield. Therefore, one strategy for yield improvement is to breed plants to have an enhanced root system architecture. A steep, rapidly developing root system can allow a plant to optimize uptake of water and nutrients below the shallower soil strata, where water and nutrients are transiently available. Furthermore, early development of long roots may facilitate drought tolerance and reduce water-deficit related yield costs. Finally, a steeper root system may facilitate high-density planting as by limiting inter-plant competition.

Current approaches to enhance root architecture involves mutagenesis and transgenic over-expression methods with some success in improving root system architecture. The present invention is directed to generation of plants comprising one or more nucleotide modifications within cis-regulatory elements of the DRO1 gene (e.g., Auxin responsive elements (Auxin-RE)) in order to alleviate, for example, Auxin-dependent repression that may then lead to improved root system architecture characterized by one or more of the following: increased root biomass, steeper root angle, and longer roots. The present invention will provide the further advantage of producing plants with an improved root system but without a transgene. In some embodiments, the present invention is directed to disruption of auxin-responsive element of DRO1 to alleviate auxin-dependent repression leading to improved root system architecture, and optionally, improved yield traits.

Accordingly, in some embodiments, the present invention is directed to generating mutations in endogenous DRO1 genes, optionally wherein the mutation is in a cis-regulatory element of the DRO1 gene, optionally a promoter, an enhancer, a silencer, or an insulator. In some embodiments, a cis-regulatory element of the DRO1 gene may be an Auxin Responsive Element (ARE) and the mutation is in the ARE and optionally, disrupts the binding of an Auxin Responsive Factor (ARF) to the endogenous gene in the plant or part thereof.

In some embodiments, the present invention provides a plant or plant part thereof comprising at least one (e.g., one or more) non-natural mutation in at least one endogenous gene encoding a DEEPER ROOTING 1 (DRO1) polypeptide, wherein the mutation is in a cis-regulatory element of the endogenous gene. A cis-regulatory element can include, but is not limited to, a promoter, an enhancer, a silencer, or an insulator, optionally wherein the cis-regulatory element is an Auxin Responsive Element (ARE)). In some embodiments, the at least one non-natural mutation in an endogenous gene encoding DRO1 is located in a cis-regulatory element of the endogenous gene, optionally in an Auxin Responsive Element (ARE), wherein the ARE is an Auxin Responsive Factor (ARF) binding site. In some embodiments, the cis regulatory element is an Auxin Responsive Element (ARE) and the mutation is in the ARE and disrupts the binding of an Auxin Responsive Factor (ARF) to the endogenous gene in the plant or part thereof. In some embodiments, a cis-regulatory element of an endogenous DRO1 gene is located in a region of the gene from about nucleotide 1 to about nucleotide 2235, from about nucleotide 1200 to about nucleotide 2235, from about nucleotide 1200 to about nucleotide 1850 or from about nucleotide 1474 to about nucleotide 1835 with reference to nucleotide numbering of SEQ ID NO:72, or from about nucleotide 1 to about nucleotide 2478, from about nucleotide 1200 to about nucleotide 2478, from about nucleotide 1200 to about nucleotide 2412 or from about nucleotide 2095 to about nucleotide 2412 with reference to nucleotide numbering of SEQ ID NO:75, optionally located from about nucleotide 1200 to about nucleotide 1850 or from about nucleotide 1474 to about nucleotide 1835 with reference to nucleotide numbering of SEQ ID NO:72 or from about nucleotide 1200 to about nucleotide 2412 or from about nucleotide 2095 to about nucleotide 2412 with reference to nucleotide numbering of SEQ ID NO:75. In some embodiments, a mutation in a cis-regulatory element of an endogenous DRO1 gene in a plant results in the plant having enhanced root architecture, wherein the enhanced root architecture is as compared to a plant or plant part (e.g., an isogenic plant) not comprising the same mutation. Enhanced root architecture may be characterized by one or more of the following phenotypes of increased root biomass, steeper root angle and/or longer roots and may further result in the plant exhibiting improved yield traits.

In some embodiments, a plant comprising at least one non-natural mutation in at least one endogenous DRO1 gene encoding a DRO1 protein has improved yield traits compared to an isogenic plant (e.g., wild type unedited plant or a null segregant) that does not comprise the mutation. In some embodiments, a plant comprising at least one non-natural mutation as described herein produces a mutated DRO1 gene having at least 90% identity to any one of the nucleotide sequences of SEQ ID NOs:84, 85, 88, or 89.

In some embodiments, an endogenous gene encoding DRO1(a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77.

A non-natural mutation in an endogenous DEEPER ROOTING 1 (DRO1) gene in a plant may be any type of mutation including, but not limited to, a point mutation, a base substitution, a base deletion and/or a base insertion, optionally wherein the at least one non-natural mutation results in a frame shift mutation (in-frame or out-of-frame). A mutation useful with this invention can include, but is not limited to, a substitution, a deletion and/or an insertion of one or more bases in a cis-regulatory element of an endogenous DRO1 gene. In some embodiments, at least one non-natural mutation may comprise a base substitution to an A, a T, a G, or a C, which optionally, results in frameshift mutation in the DRO1 gene. In some embodiments, a plant comprising an endogenous DRO1 gene that has at least one non-natural mutation in a DRO1 gene as described herein exhibits enhanced root architecture, optionally improved yield traits, as compared to a plant that does not comprise the at least one non-natural mutation in a DRO1 gene.

In some embodiments, the at least one non-natural mutation in an endogenous DRO1 gene may be a deletion (e.g., a deletion of one or more consecutive base pairs, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, or 100, or more (e.g., 110, 120, 130, 140, 150, and the like) consecutive base pairs of SEQ ID NO:72 or SEQ ID NO:75 (e.g., a deletion in the region of a DRO1 gene that is 5' of the first exon). In some embodiments, a deletion may be in a cis-regulatory element of the endogenous DRO1 gene, wherein the deletion may be located from about nucleotide 1470 to about nucleotide 1492 (see, e.g., SEQ ID NO:86), or from about nucleotide 1792 to about nucleotide 1812 (see, e.g., SEQ ID NO:87)) with reference to nucleotide numbering of SEQ ID NO:72, or from about nucleotide 2110 to about nucleotide 2117 (e.g., TCCGATCC), from about nucleotide 2405 to about nucleotide 2405 (e.g., CTTC), or from about nucleotide 2111 to about nucleotide 2121 (see, e.g., SEQ ID NO:90)) with reference to nucleotide numbering of SEQ ID NO:75, optionally wherein the nucleic acid sequence of the mutated endogenous DRO1 gene comprising the deletion is at least 90% identical to any one of the nucleotide sequences of SEQ ID NOs:84, 85, 88, or 89.

In some embodiments, at least one non-natural mutation may produce a dominant negative mutation, a semi-dominant mutation, a weak loss-of-function mutation, or a hypomorphic mutation. In some embodiments, the at least one non-natural mutation is a dominant negative mutation. In some embodiments, the at least one non-natural mutation is a semi-dominant mutation. In some embodiments, the at least one non-natural mutation is a recessive mutation. In some embodiments, a plant comprising the mutation in the DRO1 gene exhibits improved yield traits (e.g., increased pod production, increased seed production, increased seed size, increased seed weight, increased nodule number, increase nodule activity, and/or increased nitrogen fixation) as compared to a control plant (e.g., an isogenic plant not comprising the mutation).

In some embodiments, a plant cell comprising an editing system is provided, the editing system comprising: (a) a CRISPR-Cas associated effector protein; and (b) a guide nucleic acid (gRNA, gDNA, crRNA, crDNA, sgRNA, sgDNA) comprising a spacer sequence with complementarity to a region in an endogenous target gene encoding a DRO1 protein in the plant cell, optionally wherein the editing system further comprises a cytidine deaminase or adenosine deaminase. In some embodiments, the editing system generates a mutation in the endogenous target gene encoding a DRO1 protein. The endogenous target gene encoding a DRO1 protein may be any DRO1 gene in which, when a cis-regulating element of the endogenous DRO1 gene in the plant is modified, the plant exhibits a modified root architecture and, optionally, improved yield traits. In some embodiments, an endogenous DRO1 gene to which the spacer sequence of the guide nucleic acid is complementary (a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from nucleotide 2095 to about nucleotide 2412 (e.g., SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77. In some embodiments, a spacer sequence useful with this invention can include, but is not limited to, a nucleotide sequence of any one of SEQ ID NOs:80-83.

In some embodiments, a plant cell is provided comprising at least one non-natural mutation in cis-regulatory element of a DEEPER ROOTING 1 (DRO1) gene, wherein the at least one non-natural mutation is a base substitution, base insertion or a base deletion that is introduced using an editing system that comprises a nucleic acid binding domain (e.g., a DNA binding domain) that binds to a target site in the DRO1 gene, the DRO1 gene (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77. In some embodiments, a plant cell is provided comprising at least one non-natural mutation in an Auxin Responsive Factor (ARF) binding site of a DEEPER ROOTING 1 (DRO1) gene that prevents or reduces binding of an ARF polypeptide to the DRO1 gene, wherein the at least one non-natural mutation is a base substitution, base insertion or a base deletion that is introduced using an editing system that comprises a nucleic acid binding domain that binds to a target site in the DRO1 gene, the DRO1 gene (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77, optionally wherein the at least one non-natural mutation is a base deletion resulting in a nucleic acid sequence having at least 90% identity to any one of the nucleotide sequences of SEQ ID NOs:84, 85, 88, or 89. In some embodiments, the nuclease is a zinc finger nuclease, a transcription activator-like effector nuclease (TALEN), an endonuclease (e.g. Fok1) or a CRISPR-Cas effector protein. In some embodiments, the nucleic acid binding domain of the editing system is from a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein.

In some embodiments, the editing system comprises a nucleic acid binding domain (e.g., a DNA binding domain) that binds to a target site in the endogenous DRO1 gene, the target site having at least 80% sequence identity to at least 20 consecutive nucleotides (e.g., 20, 21, 22, 23, 24, 25 or more consecutive nucleotides) of a nucleic acid that encodes the amino acid sequence of SEQ ID NO:74 or SEQ ID NO:77, optionally having at least 80% sequence identity to at least 20 consecutive nucleotides (e.g., 20, 21, 22, 23, 24, 25 or more consecutive nucleotides) of a region that is 5' of the first exon of the DRO1 gene, e.g., a region of the endogenous DRO1 gene that is located from about nucleotide 1 to about nucleotide 2235, from about nucleotide 1200 to about nucleotide 2235, from about nucleotide 1200 to about nucleotide 1850, or from about nucleotide 1474 to about nucleotide 1835 with reference to nucleotide numbering of SEQ ID NO:72, or from about nucleotide 1 to about nucleotide 2478, from about nucleotide 1200 to about nucleotide 2478, from about nucleotide 1200 to about nucleotide 2412 or from about nucleotide 2095 to about nucleotide 2412 with reference to nucleotide numbering of SEQ ID NO:75, wherein the edit is made in a cis regulatory element of the DRO1 gene. In some embodiments, a target site in a DRO1 gene is within a region of the DRO1 gene, the region comprising a sequence having at least 80% sequence identity to a sequence comprising located from about nucleotide 1200 to about nucleotide 1850 or from about nucleotide 1474 to about nucleotide 1835 with reference to nucleotide numbering of SEQ ID NO:72 or from about nucleotide 1200 to about nucleotide 2412 or from about nucleotide 2095 to about nucleotide 2412 with reference to nucleotide numbering of SEQ ID NO:75. In some embodiments, a deletion in a cis-regulatory element of an endogenous DRO1 gene may be located from about nucleotide 1470 to about nucleotide 1492 (see, e.g., SEQ ID NO:86), or from about nucleotide 1792 to about nucleotide 1812 (see, e.g., SEQ ID NO:87)) with reference to nucleotide numbering of SEQ ID NO:72, or from about nucleotide 2110 to about nucleotide 2117 (e.g., TCCGATCC), from about nucleotide 2405 to about nucleotide 2405 (e.g., CTTC), or from about nucleotide 2111 to about nucleotide 2121 (see, e.g., SEQ ID NO:90)) with reference to nucleotide numbering of SEQ ID NO:75, optionally wherein the resulting mutated DRO1 nucleic acid comprises at least 90% sequence identity to any one of the nucleotide sequences of SEQ ID NOs:84, 85, 88, or 89.

In some embodiments, the editing system further comprises a nuclease, and the nucleic acid binding domain (e.g., a DNA binding domain) binds to a target site in the DRO1 gene, wherein the DRO1 gene comprises (a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77, the target site having at least 80% sequence identity to at least 20 consecutive nucleotides (e.g., 20, 21, 22, 23, 24, 25 or more consecutive nucleotides) of a nucleic acid having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835, or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412, and the at least one non-natural mutation is made following cleavage by the nuclease.

In some embodiments, the at least one non-natural mutation is a point mutation. In some embodiments, a non-natural mutation can be a base substitution to an A, a T, a G, or a C, optionally wherein the base substitution results in an amino acid substitution. In some embodiments, the at least one non-natural mutation may be a base deletion or a base insertion of at least one or at least two or more (e.g., about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more) consecutive bases. In some embodiments, the at least one non-natural mutation results in a deletion of all or a portion of a cis-regulatory element of the DRO1 gene that results in a plant having modified/enhanced root architecture, optionally wherein the deletion may be located from about nucleotide 1470 to about nucleotide 1492 (see, e.g., SEQ ID NO:86), or from about nucleotide 1792 to about nucleotide 1812 (see, e.g., SEQ ID NO:87)) with reference to nucleotide numbering of SEQ ID NO:72, or from about nucleotide 2110 to about nucleotide 2117 (e.g., TCCGATCC), from about nucleotide 2405 to about nucleotide 2405 (e.g., CTTC), or from about nucleotide 2111 to about nucleotide 2121 (see, e.g., SEQ ID NO:90)) with reference to nucleotide numbering of SEQ ID NO:75. In some embodiments, the at least one non-natural mutation is a semi-dominant mutation, a dominant negative mutation or a recessive mutation.

Non-limiting examples of a plant or part thereof useful with this invention include any monocot or dicot plant including, but not limited to, corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, blackberry, raspberry, black raspberry, or a *Brassica* spp. In some embodiments, the plant or part thereof may be a corn plant or part of a corn plant. In some embodiments, a plant may be regenerated from a plant part of this invention including, for example, a cell. In some embodiments, a plant of this invention comprising at least one non-natural mutation in a DRO1 gene comprises improved root architecture and/or yield traits.

In some embodiments, a plant or part thereof comprising a mutation as described herein can be a corn plant or part thereof, wherein the corn plant or part thereof comprises at least one non-natural mutation in an endogenous DEEPER ROOTING 1 (DRO1) gene having the gene identification number (gene ID) of Zm00001d022133, Zm00001d047263, or Zm00001d020620. In some embodiments, a plant or part thereof comprising a mutation as described herein can be wheat, optionally wherein the least one non-natural mutation in an endogenous gene encoding DRO1 is in the A genome, the B genome, the D genome or in any combination thereof.

Also provided herein is a method of providing a plurality of plants having improved/enhanced root architecture, optionally having improved yield traits, the method comprising planting two or more plants of the invention in a growing area, thereby providing a plurality of plants having improved yield traits as compared to a plurality of control plants not comprising the at least one non-natural mutation (e.g., as compared to an isogenic wild type plant not comprising the mutation). A growing area can be any area in which a plurality of plants can be planted together, including, but not limited to, a field (e.g., a cultivated field, an agricultural field), a growth chamber, a greenhouse, a recreational area, a lawn, and/or a roadside, and the like.

In some embodiments, a method of producing/breeding a transgene-free edited plant is provided, the method comprising: crossing a plant of the present invention (e.g., a plant comprising a mutation in a DRO1 gene and having enhanced root architecture with a transgene free plant, thereby introducing the at least one non-natural mutation into the plant that is transgene-free (e.g., into progeny plants); and selecting a progeny plant that comprises the at least one non-natural mutation and is transgene-free, thereby producing a transgene free edited (e.g. base edited) plant.

In some embodiments, a method for editing a specific site in the genome of a plant cell, the method comprising: cleaving, in a site-specific manner, a target site within an endogenous DEEPER ROOTING 1 (DRO1) gene in the plant cell, the endogenous DRO1 gene: (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77, thereby generating an edit in the endogenous DRO1 gene of the plant cell. In some embodiments, a plant may be regenerated from the plant cell comprising the edit in the endogenous DRO1 gene to produce a plant comprising the edit in its genome (i.e., in its endogenous DRO1 gene). A plant comprising the edit in an endogenous DRO1 gene can exhibit improved/enhanced root architecture when compared to a control plant that does not comprise the edit in the endogenous DRO1 gene. In some embodiments, enhanced root architecture is characterized by one or more of the following phenotypes of increased root biomass, steeper root angle and/or longer roots, optionally wherein the plant having enhanced root architecture further exhibits improved yield traits.

In some embodiments, the edit results in a non-natural mutation, optionally wherein the non-natural mutation is a point mutation. In some embodiments, the edit produces at least one non-natural mutation that is a base insertion and/or a base deletion, wherein the base deletion or insertion is in a cis-regulatory element of the endogenous DRO1 gene, optionally wherein the cis-regulatory element is a promoter, an enhancer, a silencer, an insulator, optionally an Auxin Responsive Element (ARE). In some embodiments, the mutation is in the ARE and disrupts the binding of an Auxin Responsive Factor (ARF) to the endogenous DRO1 gene in the plant or part thereof. In some embodiments, the edit in the endogenous DRO1 gene of the plant cell produces a mutated DRO1 gene having at least 90% sequence identity to any one of the nucleotide sequences of SEQ ID NOs:84, 85, 88, or 89. In some embodiments, the method of editing produces a non-natural mutation that is a semi-dominant mutation, a dominant negative mutation, or a recessive mutation.

In some embodiments, a method for making a plant is provided, the method comprising: (a) contacting a population of plant cells that comprise an endogenous gene encoding a DEEPER ROOTING 1 (DRO1) polypeptide with a nuclease targeted to the endogenous gene, wherein the nuclease is linked to a DNA binding domain that binds to a target site in the endogenous gene, the endogenous gene: (i) comprising a nucleotide sequence having at least 80% sequence identity to the nucleotide sequence of any one of SEQ ID NOs:72 or 75; (ii) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (iii) comprising a coding sequence having at least 80% sequence identity to the nucleotide sequence of SEQ ID NO:73 or SEQ ID NO:76; and/or (iv) encoding a polypeptide sequence having at least 80% identity to the amino acid sequence of any one of SEQ ID NO:74 or SEQ ID NO:77; (b) selecting a plant cell from the population comprising a mutation in the endogenous gene encoding a DRO1 polypeptide, wherein the mutation is a substitution and/or a deletion (e.g., a substitution and/or a deletion in a polynucleotide of (ii)); and (c) growing the selected plant cell into a plant comprising the mutation in the endogenous gene encoding a DRO1 polypeptide. In some embodiments, the deletion results in a dominant allele, a semidominant allele or a recessive allele of the wild type endogenous DRO1 gene; and growing the selected plant cell provides a plant comprising the dominant allele, semidominant allele or recessive allele of the endogenous DRO1 gene. In some embodiments, the deletion in the endogenous DRO1 gene of the plant cell results in a mutated DRO1 gene having at least 90% sequence identity to any one of the nucleotide sequences of SEQ ID NOs:84, 85, 88, or 89.

In some embodiments, a method for enhancing the root architecture of a plant is provided, the method comprising (a) contacting a plant cell comprising an endogenous gene encoding a DEEPER ROOTING 1 (DRO1) polypeptide with a nuclease targeted to the endogenous gene, wherein the nuclease is linked to a DNA binding domain that binds to a target site in the endogenous gene, the endogenous gene: (i) comprising a nucleotide sequence having at least 80% sequence identity to the nucleotide sequence of any one of SEQ ID NOs:72 or 75; (ii) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (iii) comprising a coding sequence having at least 80% sequence identity to the nucleotide sequence of SEQ ID NO:73 or SEQ ID NO:76; and/or (iv) encoding a polypeptide sequence having at least 80% identity to the amino acid sequence of any one of SEQ ID NO:74 or SEQ ID NO:77, thereby producing a plant cell comprising a mutation in the endogenous gene encoding a DRO1 polypeptide; and (b) growing the plant cell into a plant, thereby enhancing the root architecture of the plant. In some embodiments, the mutation may be a base deletion that results in a mutated DRO1 gene having at least 90% identity to any one of one of SEQ ID NOs:84, 85, 88, or 89.

In some embodiments, producing a plant or part thereof comprising at least one cell having a mutation in an endogenous DEEPER ROOTING 1 (DRO1) gene, the method comprising contacting a target site in the endogenous DRO1 gene in the plant or plant part with a nuclease comprising a cleavage domain and a DNA-binding domain, wherein the DNA binding domain of the nuclease binds to a target site in the endogenous DRO1 gene, wherein the endogenous DRO1 gene: (a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77, thereby producing a plant or part thereof comprising at least one cell having a mutation in the endogenous DRO1 gene. In some embodiments, the mutation in the endogenous DRO1 gene is in a cis-regulatory element, optionally wherein the mutation in the cis-regulatory element is a dominant negative mutation, a recessive mutation or a semi-dominant mutation. In some embodiments, the mutation in the endogenous DRO1 gene results in the endogenous DRO1 gene having reduced binding of an Auxin Responsive Factor (ARF), optionally wherein the mutation is a dominant negative mutation, a recessive mutation or a semi-dominant mutation. In some embodiments, the mutation introduced into the endogenous DRO1 gene may be a base deletion that results in a mutated DRO1 gene having at least 90% identity to any one of one of SEQ ID NOs:84, 85, 88, or 89.

In some embodiments, a method of producing a plant or part thereof comprising a mutation in an endogenous DEEPER ROOTING 1 (DRO1) gene having enhanced/improved root architecture, the method comprising contacting a target site in an endogenous DRO1 gene in the plant or plant part with a nuclease comprising a cleavage domain and a nucleic acid binding domain, wherein the nucleic acid binding domain of the nuclease binds to a target site in the endogenous DRO1 gene, wherein the endogenous DRO1 gene: ((a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77, thereby producing a plant or part thereof having a mutated endogenous DRO1 gene and having enhanced/improved root architecture. In some embodiments, the mutated endogenous DRO1 gene may comprise at least 90% identity to any one of one of SEQ ID NOs:84, 85, 88, or 89. In some embodiments, the mutated DRO1 gene in the plant or plant part having a mutated endogenous DRO1 gene and having enhanced/improved root architecture may have reduced binding to an Auxin Responsive Factor (ARF). In some embodiments, the plant that is produced exhibits enhanced root architecture as compared to a control plant, optionally wherein the plant having enhanced root architecture comprises at least one of the following phenotypes of increased root biomass, steeper root angle and longer roots, and/or optionally improved yield traits, as compared to a plant that does not comprise the mutation and enhanced root architecture.

In some embodiments, the target site is in a region of the DRO1 gene located from about nucleotide 1200 to about nucleotide 1850 or from about nucleotide 1474 to about nucleotide 1835 with reference to nucleotide numbering of SEQ ID NO:72, or from about nucleotide 1200 to about nucleotide 2412 or from about nucleotide 2095 to about nucleotide 2412 with reference to nucleotide numbering of SEQ ID NO:75.

In some embodiments, a nuclease contacting a plant cell, a population of plant cells and/or a target site cleaves an endogenous DRO1 gene, thereby introducing a mutation into the endogenous DRO1 gene, optionally wherein the mutation is introduced into a region of the endogenous DRO1 gene that is 5' of the first exon, e.g., in a cis-regulatory element of the DRO1 gene. In some embodiments, the cis-regulatory element may be a promoter, an enhancer, a silencer, or an insulator, optionally an Auxin Responsive Factor (ARF) binding site. In some embodiments, the ARF binding site is a cis-regulatory element, e.g., Auxin Responsive Element (ARE). In some embodiments, the mutation may be a base substitution, a base insertion and/or a base deletion. In some embodiments, the mutation is a non-natural mutation, optionally wherein the non-natural mutation is a dominant negative mutation, a semi-dominant mutation, or a recessive mutation. In some embodiments, the non-natural mutation results in a mutated DRO1 gene having at least 90% identity to any one of one of SEQ ID NOs:84, 85, 88, or 89

A nuclease useful with the invention may be any nuclease that can be utilized to edit/modify a target nucleic acid. Such nucleases include, but are not limited to, a zinc finger nuclease, transcription activator-like effector nucleases (TALEN), endonuclease (e.g., Fok1) and/or a CRISPR-Cas effector protein. Likewise, any nucleic acid binding domain useful with the nuclease of the invention may be any DNA binding domain that can be utilized to edit/modify a target nucleic acid. Such DNA binding domains include, but are not limited to, a zinc finger, transcription activator-like DNA binding domain (TAL), an argonaute and/or a CRISPR-Cas effector DNA binding domain.

In some embodiments, a method of editing an endogenous DRO1 gene in a plant or plant part is provided, the method comprising contacting a target site in DRO1 gene in the plant or plant part with a cytosine base editing system comprising a cytosine deaminase and a nucleic acid binding domain that binds to a target site in the endogenous DRO1 gene, wherein the endogenous DRO1 gene: (a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77, thereby producing the plant or part thereof comprising an endogenous DRO1 gene having a mutation resulting from the contact with the cytosine base editing system, and optionally wherein the plant exhibits improved root architecture, optionally improved yield traits.

In some embodiments, a method of editing an endogenous DRO1 gene in a plant or plant part is provided, the method comprising contacting a target site in DRO1 gene in the plant or plant part with an adenosine base editing system comprising an adenosine deaminase and a nucleic acid binding domain that binds to a target site in the DRO1 gene, wherein the endogenous DRO1 gene: (a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (e.g., SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (e.g., SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77, thereby producing the plant or part thereof comprising an endogenous DRO1 gene having a mutation resulting from the contact with the adenosine base editing system, and optionally wherein plant exhibits improved root architecture, optionally improved yield traits.

In some embodiments, a method of detecting a mutant DRO1 gene (a mutation in an endogenous DRO1 gene) is provided, the method comprising detecting in the genome of a plant a mutation as described herein in an endogenous DRO1 nucleic acid. In some embodiments, the present invention provides a method of detecting a mutation in an endogenous DRO1 gene, comprising detecting in the genome of a plant a mutated DRO1 gene produced as described herein (see, e.g., SEQ ID NO:84, SEQ ID NO:85, SEQ ID NO:88, and/or SEQ ID NO:89).

In some embodiments, a method of detecting a mutant DRO1 gene (a mutation in an endogenous DRO1 gene) is provided, the method comprising detecting in the genome of a plant a mutation in a region of a DRO1 gene that is 5' of the first exon, optionally in a cis-regulatory element located, for example, from about nucleotide 1 to about nucleotide 2235, from about nucleotide 1200 to about nucleotide 2235, from about nucleotide 1200 to about nucleotide 1850, or from about nucleotide 1474 to about nucleotide 1835 with reference to nucleotide numbering of SEQ ID NO:72, or from about nucleotide 1 to about nucleotide 2478, from about nucleotide 1200 to about nucleotide 2478, from about nucleotide 1200 to about nucleotide 2412 or from about nucleotide 2095 to about nucleotide 2412 with reference to nucleotide numbering of SEQ ID NO:75. In some embodiments, the mutation is an insertion, a deletion or substitution of at least one nucleotide (e.g., a deletion of at least 1, 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 55, 60, 65, 70, 75, 80, 85, 90, 95, 100, or more consecutive bases; e.g., an insertion and/or substitution of at least one nucleotide (e.g., an insertion and/or substitution of at least 1, 2, 3, 4, 5, 6, 7, 8, 9 10, 11, 12, 13, 14, 15, 16, 17, 18, 19, or 20 or more bases, optionally consecutive bases)).

In some embodiments, the present invention provides a method of producing a plant comprising a mutation in an endogenous DRO1 gene and at least one polynucleotide of interest, the method comprising crossing a plant of the invention comprising at least one mutation in an endogenous DRO1 gene (a first plant) with a second plant that comprises the at least one polynucleotide of interest to produce progeny plants; and selecting progeny plants comprising at least one mutation in the DRO1 gene and the at least one polynucleotide of interest, thereby producing the plant comprising a mutation in an endogenous DRO1 gene and at least one polynucleotide of interest.

Further provided is a method of producing a plant comprising a mutation in an endogenous DRO1 gene and at least one polynucleotide of interest, the method comprising introducing at least one polynucleotide of interest into a plant of the present invention comprising at least one mutation in a DRO1 gene, thereby producing a plant comprising at least one mutation in a DRO1 gene and at least one polynucleotide of interest.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, disease resistance, improved yield traits, increased nutrient use efficiency and/or abiotic stress resistance.

A DRO1 gene useful with this invention includes any DRO1 gene in which, when a cis-regulating element of the endogenous DRO1 gene in the plant is modified, the plant exhibits a modified root architecture and, optionally, improved yield traits In some embodiments, the mutation in an endogenous DRO1 gene may be a non-natural mutation. In some embodiments, a plant comprising at least one non-natural mutation in at least one endogenous DRO1 gene encoding a DRO1 protein exhibits improved/enhanced root architecture, and optionally, improved yield traits, compared to an isogenic plant that does not comprise the mutation.

In some embodiments, the non-natural mutation may be any mutation in an endogenous DRO1 gene that results in improved/enhanced root architecture, and optionally, improved yield traits, when comprised in a plant. In some embodiments, the at least one non-natural mutation in an endogenous DRO1 gene is a point mutation, optionally a base substitution, a base insertion and/or a base deletion. In some embodiments, the at least one non-natural mutation in an endogenous DRO1 gene is a semi-dominant mutation, a dominant negative mutation and/or a recessive mutation. In some embodiments, the at least one non-natural mutation in an endogenous DRO1 gene in a plant may be a substitution, a deletion and/or an insertion that results in a plant exhibiting improved/enhanced root architecture, and optionally, improved yield traits. In some embodiments, enhanced root architecture is characterized by one or more of the following phenotypes of increased root biomass, steeper root angle and/or longer roots, optionally improved yield traits. In some embodiments, the at least one non-natural mutation in an endogenous DRO1 gene in a plant may be a substitution, a deletion and/or an insertion that results in a semi-dominant, dominant negative mutation or a recessive mutation and a plant having improved/enhanced root architecture, and optionally, improved yield traits. In some embodiments, the at least one non-natural mutation may be a base substitution to an A, a T, a G, or a C.

In some embodiments, the present invention provides a guide nucleic acid (e.g., gRNA, gDNA, crRNA, crDNA) that binds to a target site in a an endogenous gene encoding DEEPER ROOTING 1 (DRO1), the DRO1 gene: (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77. In some embodiments, the target site is in a region of the DRO1 gene located from about nucleotide 1200 to about nucleotide 1850 or from about nucleotide 1474 to about nucleotide 1835 with reference to nucleotide numbering of SEQ ID NO:72, or from about nucleotide 1200 to about nucleotide 2412 or from about nucleotide 2095 to about nucleotide 2412 with reference to nucleotide numbering of SEQ ID NO:75.

Example spacer sequences useful with a guide of this invention may comprise complementarity to a fragment or portion (or region) of a nucleotide sequence (a) having at least 80% sequence identity to the nucleotide sequence of any one of SEQ ID NOs:72 or 75; (b) having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (SEQ ID NO:79); (c) having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77.

In some embodiments, a target nucleic acid is any endogenous DRO1 gene in a plant or part thereof in which a cis-regulating element of the endogenous DRO1 gene in the plant may be modified as described herein, resulting in the plant exhibiting a modified root architecture and, optionally, improved yield traits. In some embodiments, a target site in a target nucleic acid may comprise a sequence having at least 80% sequence identity to a region, portion or fragment of SEQ ID NOs:72 or 75, (e.g., a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412).

In some embodiments, a guide nucleic acid comprises a spacer having the nucleotide sequence of any one of SEQ ID NOs:80-83.

In some embodiments, a system is provided that comprises a guide nucleic acid of the present invention and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

In some embodiments, the present invention provides a non-natural mutated endogenous DRO1 gene in a plant cell that comprises a nucleic acid sequence having at least 90% identity to any one of SEQ ID NOs:84, 85, 88, or 89. In some embodiments, the present invention provides a non-natural mutated endogenous DRO1 gene that comprises a nucleic acid sequence having at least 90% identity to any one of SEQ ID NOs:84, 85, 88, or 89.

As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

In some embodiments, a gene editing system is provided, the gene editing system comprising a CRISPR-Cas effector protein in association with a guide nucleic acid, wherein the guide nucleic acid comprises a spacer sequence that binds to a DEEPER ROOTING 1 (DRO1) gene. In some embodiments, a DRO1 gene targeted by the gene editing system (a) comprises a nucleotide sequence having at least 80% sequence identity to the nucleotide sequence of any one of SEQ ID NOs:72 or 75; (b) comprises a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (SEQ ID NO:79); (c) comprises a coding sequence having at least 80% sequence identity to the nucleotide sequence of SEQ ID NO:73 or SEQ ID NO:76; and/or (d) encodes a polypeptide sequence having at least 80% identity to the amino acid sequence of any one of SEQ ID NO:74 or SEQ ID NO:77. In some embodiments, the spacer sequence binds to a cis-regulatory element of the DRO1 gene. In some embodiments, the cis-regulatory element is a promoter, an enhancer, a silencer, or an insulator, optionally, an Auxin Responsive Element (ARE) of the endogenous gene encoding DRO1.

In some embodiments, the guide nucleic acid of a gene editing system can comprise a spacer sequence that has complementarity to a region, portion or fragment of: (a) a nucleotide sequence having at least 80% sequence identity to any one of the nucleotide sequences of SEQ ID NOs:72 or 75; (b) a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (SEQ ID NO:79); (c) a nucleotide sequence having at least 80% sequence identity to the nucleotide sequence of SEQ ID NO:73 or SEQ ID NO:76; and/or (d) a nucleotide sequence encoding a polypeptide sequence having at least 80% identity to the amino acid sequence of any one of SEQ ID NO:74 or SEQ ID NO:77. In some embodiments, a spacer sequence used for targeting a DRO1 gene binds to a cis-regulatory element of the DRO1 gene, optionally wherein the cis-regulatory element is an Auxin Responsive Element (ARE) of the endogenous gene encoding DRO1. In some embodiments, a gene editing system may further comprise a tracr nucleic acid that associates with the guide nucleic acid and a CRISPR-Cas effector protein, optionally wherein the tracr nucleic acid and the guide nucleic acid are covalently linked. In some embodiments, a spacer sequence of a guide nucleic acid useful for targeting an endogenous DRO1 gene as described herein can include, but is not limited to, comprises a nucleotide sequence of any one of SEQ ID NOs:80-83.

In some embodiments, a guide nucleic acid is provided that binds to a target site in an endogenous DRO1 gene having the gene identification number (gene ID) of Zm00001d022133, Zm00001d047263, or Zm00001d020620. In some embodiments, the guide nucleic acid comprises a spacer sequence having complementarity to a target site in a cis-regulatory element of the endogenous DRO1 gene, the DRO1 gene having the gene identification number (gene ID) of Zm00001d0047263, Zm00001d020620 or Zm00001d022133.

The present invention further provides a complex comprising CRISPR-Cas effector protein comprising a cleavage domain and a guide nucleic acid, wherein the guide nucleic acid binds to a target site in an endogenous DEEPER ROOTING 1 (DRO1) gene, the endogenous DRO1 (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77, wherein the cleavage domain cleaves a target strand in the DRO1 gene.

Also provided herein are expression cassettes comprising (a) polynucleotide encoding CRISPR-Cas effector protein comprising a cleavage domain and (b) a guide nucleic acid that binds to a target site in an endogenous DEEPER ROOTING 1 (DRO1) gene, wherein the guide nucleic acid comprises a spacer sequence that is complementary to and binds to the target site in the endogenous DRO1 gene, the endogenous DRO1 gene: (a) comprising a nucleotide sequence having at least 80% sequence identity to the nucleotide sequence of any one of SEQ ID NOs:72 or 75; (b) comprising a nucleotide sequence having at least 80% sequence identity to a region of SEQ ID NO:72 from about nucleotide 1 to about nucleotide 2235, from about nucleotide 1200 to about nucleotide 2235, from about nucleotide 1200 to about nucleotide 1850 or from about nucleotide 1474 to about nucleotide 1835 (SEQ ID NO:78) or a region of SEQ ID NO:75 from about nucleotide 1 to about nucleotide 2478, from about nucleotide 1200 to about nucleotide 2478, from about nucleotide 1200 to about nucleotide 2412 or from about nucleotide 2095 to about nucleotide 2412 (SEQ ID NO:79); (c) comprising a coding sequence having at least 80% sequence identity to the nucleotide sequence of SEQ ID NO:73 or SEQ ID NO:76; and/or (d) encoding a polypeptide sequence having at least 80% identity to the amino acid sequence of any one of SEQ ID NO:74 or SEQ ID NO:77. In some embodiments, the target site in an endogenous DRO1 gene is in a region of the DRO1 gene located from about nucleotide 1200 to about nucleotide 1850 or from about nucleotide 1474 to about nucleotide 1835 with reference to nucleotide numbering of SEQ ID NO:72, or from about nucleotide 1200 to about nucleotide 2412 or from about nucleotide 2095 to about nucleotide 2412 with reference to nucleotide numbering of SEQ ID NO:75.

An editing system useful with this invention can be any site-specific (sequence-specific) genome editing system now known or later developed, which system can introduce mutations in target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide, and/or a guide nucleic acid (comprising a spacer having substantial complementarity or full complementarity to a target site).

In some embodiments, an editing system can comprise one or more sequence-specific nucleic acid binding domains (e.g., sequence-specific DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing a DRO1 polypeptide may comprise contacting a target nucleic acid (e.g., a nucleic acid encoding a DRO1 polypeptide, e.g., the cis-regulating element of the nucleic acid encoding a DRO1 polypeptide) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a DRO1 gene may comprise contacting a target nucleic acid (e.g., a nucleic acid encoding a DRO1 polypeptide, e.g., the cis-regulating element of the nucleic acid encoding a DRO1 polypeptide) with a sequence-specific nucleic acid binding fusion protein (e.g., a sequence-specific nucleic acid binding protein (e.g., a CRISPR-Cas effector protein or domain) fused to a peptide tag, a deaminase fusion protein comprising a deaminase domain (e.g., an adenine deaminase and/or a cytosine deaminase)) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fuse to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous DRO1 gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantageous of the various methods of recruiting proteins for use in the editing to the target site, such methods including both non-covalent and covalent interactions between the proteins and nucleic acids used in the selected process of genome editing.

In some embodiments, the present invention provides a method of producing a plant comprising a mutation in an endogenous DRO1 gene and at least one polynucleotide of interest, the method comprising crossing a first plant, which is a plant of the present invention, with a second plant that comprises the at least one polynucleotide of interest to produce progeny plants; and selecting progeny plants comprising the mutation in the DRO1 gene and the at least one polynucleotide of interest, thereby producing the plant comprising a mutation in an endogenous DRO1 gene and at least one polynucleotide of interest.

In some embodiments, a method of producing a plant comprising a mutation in an endogenous DRO1 gene and at least one polynucleotide of interest is provided, the method comprising introducing at least one polynucleotide of interest into a plant of the present invention, thereby producing a plant comprising a mutation in a DRO1 gene and at least one polynucleotide of interest.

In some embodiments, a method of producing a plant comprising a mutation in an endogenous DRO1 gene and exhibiting a phenotype of improved root architecture (optionally, exhibiting improved yield traits, increased root biomass, steeper root angle and/or longer roots) is provided, comprising crossing a first plant, which is the plant of the present invention, with a second plant that exhibits a phenotype of improved root architecture; and selecting progeny plants comprising the mutation in the DRO1 gene and a phenotype of improved root architecture, thereby producing the plant comprising a mutation in an endogenous DRO1 gene and exhibiting a phenotype of improved root architecture as compared to a control plant.

Further provided is a method of controlling weeds in a container (e.g., pot, or seed tray and the like), a growth chamber, a greenhouse, a field, a recreational area, a lawn, or on a roadside, comprising applying an herbicide to one or more (a plurality) plants of the present invention growing in a container, a growth chamber, a greenhouse, a field, a recreational area, a lawn, or on a roadside, thereby controlling the weeds in the container, the growth chamber, the greenhouse, the field, the recreational area, the lawn, or on the roadside in which the one or more plants are growing.

In some embodiments, a method of reducing insect predation on a plant is provided, comprising applying an insecticide to one or more plants of the present invention, thereby reducing insect predation on the one or more plants, optionally wherein the one or more plants are growing in a container, a growth chamber, a greenhouse, a field, a recreational area, a lawn, or on a roadside. In some embodiments, a method of reducing fungal disease on a plant is provided, comprising applying a fungicide to one or more canola plants of the present invention, thereby reducing fungal disease on the one or more plants, optionally wherein the one or more plants are growing in a container, a growth chamber, a greenhouse, a field, a recreational area, a lawn, or on a roadside.

A polynucleotide of interest can be any polynucleotide of interest, such as those described herein and can include, but is not limited to, a polynucleotide that confers herbicide tolerance, insect resistance, disease resistance, increased yield, increased nutrient use efficiency or abiotic stress resistance.

In some embodiments, the mutation or modification of an endogenous DRO1 gene may be an insertion, a deletion and/or a point mutation that results in a plant having, for example, improved/enhanced root architecture and/or improved yield traits compared to a control plant that does not comprise the at least one non-natural mutation in the endogenous DRO1 gene.

In some embodiments, a plant part may be a cell. In some embodiments, the plant or plant part thereof may be any plant or part thereof as described herein. In some embodiments, a plant useful with this invention may be corn, soybean, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp. In some embodiments, the plant may be a corn plant and the plant part, including a cell, may be from a corn plant. In some embodiments, the plant may be a wheat plant and the plant part, including a cell, may be from a wheat plant.

In some embodiments, a mutated DEEPER ROOTING 1 (DRO1) nucleic acid is provided, the mutated DRO1 nucleic acid comprising at least one mutation, wherein at least one mutation is in a cis-regulatory element, optionally, wherein at least one mutation is in a an Auxin Responsive Element (ARE), which mutation that disrupts the binding of Auxin Responsive Factor (ARF) to the ARE of the nucleic acid, optionally wherein the mutated nucleic acid comprises a sequence having at least 90% sequence identity (e.g., 90, 91, 92, 93, 94, 95, 96, 97, 98, 99, or 100%) to any one of SEQ ID NOs:84, 85, 88, or 89. In some embodiments, the mutated nucleic acid comprises the sequence of any one of SEQ ID NOs:84, 85, 88, or 89. In some embodiments, a plant comprising the mutated DRO1 nucleic acid is provided. In some embodiments, the plant may be a corn plant or a wheat plant. In some embodiments, a corn plant or part thereof comprising the mutated DRO1 nucleic acid is provided, optionally wherein the mutation is in a DRO1 gene having the gene identification number (gene ID) of Zm00001d0047263, Zm00001d022133 or Zm00001d020620, and the corn plant exhibits enhanced root architecture, optionally exhibiting one or of the following phenotypes of increased root biomass, steeper root angle and/or longer roots and/or improved yield traits, as compared to a plant that does not comprise the mutation. In some embodiments, the invention provides a corn plant or plant part thereof comprising at least one non-natural mutation in an endogenous DRO1 gene having the gene identification number (gene ID) of Zm00001d0047263, Zm00001d022133 or Zm00001d020620. In some embodiments, the at least one non-natural mutation is in a cis-regulatory element of the endogenous DRO1 gene having the gene identification number (gene ID) of Zm00001d0047263, Zm00001d022133 or Zm00001d020620, optionally wherein the at least one non-natural mutation is a dominant negative mutation, semidominant mutation or recessive mutation. In some embodiments, a wheat plant or part thereof comprising the mutated DRO1 nucleic acid is provided, optionally wherein the nucleic acid is comprised in the A genome, the B genome, the D genome or in any combination thereof, in the wheat plant, and the wheat plant exhibits enhanced root architecture.

In some embodiments, a mutation that is introduced into an endogenous DRO1 gene polypeptide is a non-natural mutation. In some embodiments, a mutation that is introduced into an endogenous DRO1 gene may be a substitution, an insertion and/or a deletion of one or more nucleotides as described herein. In some embodiments, a mutation that is introduced into an endogenous DRO1 gene may be a deletion, optionally a deletion of all or a portion of a cis-regulatory element of the DRO1 gene. In some embodiments, the mutation in an endogenous DRO1 gene may result in a modified root architecture as compared to a wild type DRO1 gene.

In some embodiments, a sequence-specific nucleic acid binding domain (DNA binding domains) of an editing system useful with this invention can be from, for example, a polynucleotide-ceded endonuclease, a CRISPR-Cas endonuclease CRISPR-Cas effector protein), a zinc finger nuclease, a transcription activator-like effector nuclease (TALEN) and/or an Argonaute protein.

In some embodiments, a sequence-specific nucleic acid binding domain/protein may be a CRISPR-Cas effector protein, optionally wherein the CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. Example Cas9 sequences include, but are not limited to, the amino acid sequences of SEQ ID NOs:59-60 or the polynucleotide sequences of SEQ ID NOs:61-71.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339(6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from Leptotrichia shahii, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease (see, e.g., SEQ ID NOs:1-20). Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, a cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode an uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs:31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific nucleic acid binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to generate a mutated DRO1 gene.

The nucleic acid constructs of the invention encoding a base editor comprising a sequence-specific nucleic acid binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas4, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids* Res. 35(Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g., protospacer) (e.g., a portion of consecutive nucleotides of a DRO1 gene, wherein the DRO1 gene (a) comprises a nucleotide sequence having at least 80% sequence identity to the nucleotide sequence of any one of SEQ ID NOs:72, 75, 78, or 79; (b) comprises a coding sequence having at least 80% sequence identity to the nucleotide sequence of SEQ ID NO:73 or SEQ ID NO:76; and/or (c) encodes a polypeptide sequence having at least 80% identity to the amino acid sequence of any one of SEQ ID NO:74 or SEQ ID NO:77, e.g., SEQ ID NOs:80-83). A spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. In some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (such as for a Type V CRISPR-Cas system), or the 3' region of a spacer sequence of a guide nucleic acid may be identical to a target DNA, while the 5' region of the spacer may be substantially complementary to the target DNA (such as for a Type II CRISPR-Cas system), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

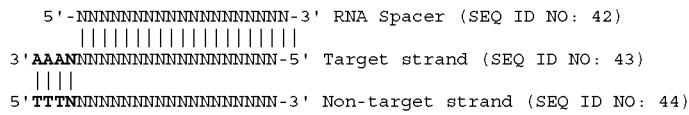

```
5'-NNNNNNNNNNNNNNNNNNNN-3'  RNA Spacer (SEQ ID NO: 42)
   ||||||||||||||||||||
3'-AAANNNNNNNNNNNNNNNNNNNN-5'  Target strand (SEQ ID NO: 43)
   ||||
5'-TTTNNNNNNNNNNNNNNNNNNNN-3'  Non-target strand (SEQ ID NO: 44)
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains/proteins, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. In some embodiments, a peptide tag may also include phosphorylated tyrosines in specific sequence contexts recognized by SH2 domains, characteristic consensus sequences containing phosphoserines recognized by 14-3-3 proteins, proline rich peptide motifs recognized by SH3 domains, PDZ protein interaction domains or the PDZ signal sequences, and an AGO hook motif from plants. Peptide tags are disclosed in WO2018/136783 and U.S. Patent Application Publication No. 2017/0219596, which are incorporated by reference for their disclosures of peptide tags. Any epitope that may be linked to a polypeptide and for which there is a corresponding affinity polypeptide that may be linked to another polypeptide may be used with this invention as a peptide tag. A peptide tag may comprise or be present in one copy or in 2 or more copies of the peptide tag (e.g., multimerized peptide tag or multimerized epitope) (e.g., about 2, 3, 4, 5, 6, 7, 8, 9, 10, 11, 12, 13, 14, 15, 16, 17, 18, 9, 20, 21, 22, 23, 24, or 25 or more peptide tags). When multimerized, the peptide tags may be fused directly to one another or they may be linked to one another via one or more amino acids (e.g., 1, 2, 3, 4, 5, 6, 7, 8, 9, 10, 11, 12, 13, 14, 15, 16, 17, 18, 19, 20 or more amino acids, optionally about 3 to about 10, about 4 to about 10, about 5 to about 10, about 5 to about 15, or about 5 to about 20 amino acids, and the like, and any value or range therein. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5):910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs:45-47.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs:48-58.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs, e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag;

DmrA-DmrC heterodimer induced by a compound; bifunctional ligand (e.g., fusion of two protein-binding chemicals together, e.g. dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific nucleic acid binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any plant comprising an endogenous DRO1 gene comprising a cis-regulatory element may be modified as described herein to enhance root architecture, and optionally increase yield, in the plant. Non-limiting examples of plants that may be modified as described herein may include, but are not limited to, turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), Cannabis (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, or sunflower.

In some embodiments, a plant that may be modified as described herein may include, but is not limited to, corn, soybean, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp (e.g., *B. napus, B. oleraceae, B. rapa, B. juncea*, and/or *B. nigra*). In some embodiments, a plant that may be modified as described herein is a dicot. In some embodiments, a plant that may be modified as described herein is a monocot. In some embodiments, a plant that may be modified as described herein is corn (i.e., *Zea mays*). In some embodiments, a plant that may be modified as described herein is wheat (i.e., *Triticum* spp.).

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the Cry1A, Cry1Ab, Cry1Ac, Cry1IA, Cry1IIA, Cry1IIB2, Cry9c Cry2Ab, Cry3Bb and Cry1F proteins or toxic fragments thereof and also hybrids or combinations thereof, especially the Cry1F protein or hybrids derived from a Cry1F protein (e.g. hybrid Cry1A-Cry1F proteins or toxic fragments thereof), the Cry1A-type proteins or toxic fragments thereof, preferably the Cry1Ac protein or hybrids derived from the Cry1Ac protein (e.g. hybrid Cry1Ab-Cry1Ac proteins) or the Cry1Ab or Bt2 protein or toxic fragments thereof, the Cry2Ae, Cry2Af or Cry2Ag proteins or toxic fragments thereof, the Cry1A.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci US A. 28; 93(11):5389-94, the Cry proteins as described in WO2001/47952, the insecticidal proteins from Xenorhabdus (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g. WO2007/024782), a mutated *Arabidopsis* ALS/AHAS gene (e.g. U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-

230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN' (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS1 1 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/ SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession N° PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDTO9Y (corn, ATCC Accession No PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEN™, INTACTA RR2 PRO®, VISTIVE GOLD®, and/or XTENDFLEX™ trade names.

The invention will now be described with reference to the following examples. It should be appreciated that these examples are not intended to limit the scope of the claims to the invention but rather are intended to be exemplary of certain embodiments. Any variations in the exemplified methods that occur to the skilled artisan are intended to fall within the scope of the invention.

EXAMPLES

Example 1. Design of the Genomic Editing Construct for DRO1

The genomic sequences of Zm00001d022133 and Zm00001d047263 (DRO1) (*Zea mays*) were identified from a proprietary maize line. Using these reference sequences, spacer sequences SEQ ID NO: 80-83 were designed for use in gene editing constructs. Each editing construct contained a CRISPR-Cas effector and a pair of spacer sequences designed to target the 5' cis-regulatory region of each DRO1 gene to generate edits that will effect expression and/or repression of DRO1.

Example 2. Transformation and Selection of Edited E0 Plants

Dried excised maize embryos were transformed using *Agrobacterium* to deliver the editing constructs. Healthy non-chimeric plants (E0) were selected and transferred from media to growth media and ultimately transferred to a greenhouse to complete the plants' life cycle. Tissue was collected from regenerating plants (E0 generation) for DNA extraction and subsequent molecular screening was employed to assess transgene copy and editing efficacy. Plants identified to be (1) healthy, non-chimeric and fertile, with (2) no transgenes or low transgene copy number and (3) 5' cis-regulatory region of DRO1 were selfed to produce the E1 generation.

Example 3: Analysis of CE43182

The E0 plant, CE43182, was determined to be edited in the upstream region of the Zm00001d047263 (SEQ ID NO:72) (DRO1) gene. The DRO1 gene was determined to be compound heterozygous for one deletion, and homozygous for a second deletion. In one of the copies of the DRO1 gene, 23 bp were deleted corresponding to positions 1470-1492 (inclusive) with reference to the nucleotide sequence numbering of SEQ ID NO:72 (deleted sequence is ATTTTATGGACTATAGACACACT (SEQ ID NO:86)) and 23 bp were deleted corresponding to positions 1790-1812 with reference to the nucleotide sequence numbering of SEQ ID NO:72 (deleted sequence is GTAGTTGGCAGCATGTGCTTTCT (SEQ ID NO:87)). This edited DRO1 genomic sequence is shown in SEQ ID NO:84.

In the second copy of the DRO1 gene, 23 bp were deleted which corresponding to positions 1790-1812 with reference to the nucleotide sequence numbering of SEQ ID NO:72 (deleted sequence is GTAGTTGGCAGCATGTGCTTTCT (SEQ ID NO:87)). This edited DRO1 genomic sequence is shown in SEQ ID NO:85.

Both of the deletions (that corresponding to positions 1470-1492 and that corresponding to positions 1790-1812) remove AuxRE binding sites from the promoter of the DRO1 gene.

Example 4: Analysis of CE42454

The E0 plant, CE42454, was determined to be edited in the upstream region of the Zm00001d022133 (SEQ ID NO:75) (DRO1) gene. The DRO1 gene in this plant was determined to be complex and contained various edits which segregated in the E2 generation. Two E2 plants were selected for further analysis, CE108013 and CE108012. The edited DRO1 gene in CE108013 was determined to be homozygous for an 8 bp deletion corresponding to positions 2110-2117 with reference to the nucleotide sequence numbering of SEQ ID NO:75 (deleted sequence is TCCGATCC) and to be homozygous for a 4 bp deletion corresponding to positions 2405-2408 with reference to the nucleotide sequence numbering of SEQ ID NO:75 (deleted sequence is CTTC). This edited DRO1 genomic sequence is shown in SEQ ID NO:88.

The edited DRO1 gene in CE108012 was determined to be homozygous for an 11 bp deletion corresponding to positions 2111-2121 with reference to the nucleotide sequence numbering of SEQ ID NO:75 (deleted sequence is CCGATCCACCA (SEQ ID NO:90)). This edited DRO1 genomic sequence is shown in SEQ ID NO:89.

All of the deletions in CE108012 and CE108013 are expected to remove/alter AuxRE binding sites from the promoter of the DRO1 gene.

Example 5: Root Phenotype Analysis of DRO1 Edited Lines

The E2 generation of CE43182 was generated by allowing the E0 plant to self-pollinate to generate the seed of the E1 generation. The E1 seed was planted and a single plant was self-pollinated to give rise to the seed of the E2 generation. The E2 seed was grown in an aeroponics system until the plants reached the V3 stage of growth. Additionally, the edited lines CE108013 and CE108012, as further described in Example 4, were grown in an aeroponics system for evaluation.

Aeroponic grown plants were photographed and the images analyzed computationally to determine the angle of root growth. The angle of root growth was measured at the junction of the root to the mainstem and the architecture of the root system was compared to wildtype, non-edited, plants. The data in Table 1 outlines the results observed.

TABLE 1

Data for the root phenotype analysis of DRO1 edited lines.

| Genotype | Edited gene | Root angle (°) (mean and standard deviation) | Statistical significance compared to WT (p value) | Notes |
|---|---|---|---|---|
| CE43182 (compound deletions) (50 plants) | Zm00001d047263 (SEQ ID NO: 72) | 137.0 +/− 7.5 | 0.04 | Significant increase in root angle |
| CE108013 (homozygous for 8 bp and 4 bp deletion) (44 plants) | Zm00001d022133 (SEQ ID NO: 75) | 136.8 +/− 8.4 | 0.075 | Suggests root angle was affected by edit and follow up needed |
| CE108012 (homozygous 11 bp deletion) (34 plants) | Zm00001d022133 (SEQ ID NO: 75) | 139.2 +/− 8.2 | 0.002 | Significant increase in root angle |
| Wild type (54 plants) | N/A | 133.1 +/− 6.5 | n/a | |

| Genotype | Edited gene | Root length (mm) (mean and standard deviation) | Statistical significance compared to WT (p value) | Notes |
|---|---|---|---|---|
| CE43182 (compound deletions) (38 plants) | Zm00001d047263 (SEQ ID NO: 72) | 431.8 +/− 6.1 | 0.470 | |
| CE108013 (homozygous for 8 bp and 4 bp deletion) (40 plants) | Zm00001d022133 (SEQ ID NO: 75) | 435.2 +/− 5.8 | 0.747 | |
| CE108012 (homozygous 11 bp deletion) (30 plants) | Zm00001d022133 (SEQ ID NO: 75) | 436.1 +/− 5.3 | 0.433 | |
| Wild type (44 plants) | N/A | 433.9 +/− 6.1 | N/A | |

| Genotype | Edited gene | Root width (mm) (mean and standard deviation) | Statistical significance compared to WT (p value) | Notes |
|---|---|---|---|---|
| CE43182 (compound deletions) (40 plants) | Zm00001d047263 (SEQ ID NO: 72) | 93.9 +/− 16.8 | 0.012 | Significant decrease in root width |
| CE108013 (homozygous for 8 bp and 4 bp deletion) (36 plants) | Zm00001d022133 (SEQ ID NO: 75) | 103.6 +/− 17.9 | 0.746 | |
| CE108012 (homozygous 11 bp deletion) (30 plants) | Zm00001d022133 (SEQ ID NO: 75) | 103.4 +/− 17.6 | 0.758 | |
| Wild type (50 plants) | N/A | 107.9 +/− 15.7 | N/A | |

TABLE 1-continued

Data for the root phenotype analysis of DRO1 edited lines.

| Genotype | Edited gene | Root area (mm²) (mean and standard deviation) | Statistical significance compared to WT (p value) | Notes |
|---|---|---|---|---|
| CE43182 (compound deletions) (50 plants) | Zm00001d047263 (SEQ ID NO: 72) | 4190 +/− 890 | 0.99 | |
| CE108013 (homozygous for 8 bp and 4 bp deletion) (44 plants) | Zm00001d022133 (SEQ ID NO: 75) | 4187 +/− 699 | 0.99 | |
| CE108012 (homozygous 11 bp deletion) (34 plants) | Zm00001d022133 (SEQ ID NO: 75) | 3914 +/− 984 | 0.69 | |
| Wild type (54 plants) | N/A | 4156 +/− 817 | N/A | |

The foregoing is illustrative of the present invention and is not to be construed as limiting thereof. The invention is defined by the following claims, with equivalents of the claims to be included therein.

That which is claimed is:

1. A corn plant or plant part thereof comprising a mutated gene, wherein the mutated gene is an endogenous DEEPER ROOTING 1 (DRO1) gene that comprises at least one mutation, wherein the at least one mutation is in a cis-regulatory element of the endogenous DRO1 gene, wherein the endogenous DRO1 gene is devoid of the at least one mutation and
- encodes a polypeptide sequence having at least 95% identity to the amino acid sequence of SEQ ID NO:74 or SEQ ID NO:77,
- wherein the at least one mutation is a deletion of consecutive nucleotides located in a region of the cis regulatory element from nucleotide 1474 to nucleotide 1835 with reference to nucleotide numbering of SEQ ID NO:72 or from nucleotide 2095 to nucleotide 2412 with reference to nucleotide numbering of SEQ ID NO:75,
- wherein the deletion removes an AuxRE binding site and results in a corn plant that exhibits steeper root angle as compared to an isogenic corn plant or plant part not comprising the same deletion.

2. The corn plant or part thereof of claim 1, wherein the deletion is a deletion of 2 consecutive base pairs to 100 consecutive base pairs.

3. The corn plant or plant part thereof of claim 1, wherein the at least one mutation produces a mutated DRO1 gene having at least 95% identity to any one of the nucleotide sequences of SEQ ID NOs:84, 85, 88, or 89.

4. A corn plant regenerated from the plant part of claim 1.

5. The corn plant of claim 4 comprising a mutated DRO1 gene having at least 95% identity to any one of the nucleotide sequences of SEQ ID NOs:84, 85, 88, or 89.

6. A method of producing a corn plant or part thereof comprising a mutation in an endogenous DEEPER ROOTING 1 (DRO1) gene having enhanced/improved root architecture, the method comprising contacting a target site in an endogenous DRO1 gene in the corn plant or plant part with a nuclease comprising a cleavage domain and a nucleic acid binding domain, wherein the nucleic acid binding domain of the nuclease binds to a target site in the endogenous DRO1 gene, wherein the endogenous DRO1 gene encodes a polypeptide sequence having at least 95% identity to the amino acid sequence of SEQ ID NO:74 or SEQ ID NO:77, thereby producing a corn plant or part thereof having a mutated endogenous DRO1 gene and having enhanced/improved root architecture, wherein the mutation is a deletion of consecutive nucleotides located in a region of a cis regulatory element of the endogenous DRO1 gene, the region of the cis-regulatory element located from about nucleotide 1474 to about nucleotide 1835 with reference to nucleotide numbering of SEQ ID NO:72 or from about nucleotide 2095 to about nucleotide 2412 with reference to nucleotide numbering of SEQ ID NO:75 and the deletion removes an AuxRE binding site,
- wherein the corn plant having enhanced root architecture comprises a phenotype of steeper root angle, as compared to a corn plant that does not comprise the mutation and enhanced root architecture.

7. The method of claim 6, wherein the target site is in a region of the DRO1 gene located from about nucleotide 1474 to about nucleotide 1835 with reference to nucleotide numbering of SEQ ID NO:72, or from about nucleotide 2095 to about nucleotide 2412 with reference to nucleotide numbering of SEQ ID NO:75.

8. The method of claim 6, wherein the nuclease cleaves the endogenous DRO1 gene and the mutation is introduced into a region of the endogenous DRO1 gene comprising a nucleotide sequence having at least 95% sequence identity to SEQ ID NO:78 or SEQ ID NO:79.

9. The method of claim 6, wherein the mutation is a base deletion resulting in a mutated DRO1 gene having at least 95% identity to any one of one of SEQ ID NOs:84, 85, 88, or 89.

* * * * *

UNITED STATES PATENT AND TRADEMARK OFFICE
CERTIFICATE OF CORRECTION

| | | |
|---|---|---|
| PATENT NO. | : 12,365,910 B2 | Page 1 of 1 |
| APPLICATION NO. | : 17/679509 | |
| DATED | : July 22, 2025 | |
| INVENTOR(S) | : Miller et al. | |

It is certified that error appears in the above-identified patent and that said Letters Patent is hereby corrected as shown below:

In the Specification

Column 28, Line 22: Please correct "(3-conglycinin" to read --β-conglycinin--

Column 28, Line 47: Please correct "ZmSTK2 USP" to read --ZmSTK2_USP--

Column 28, Line 51: Please correct "PLA2-6" to read --$PLA_2$-δ--

Column 28, Line 52: Please correct "ZrnC5" to read --ZmC5--

Column 54, Lines 13-14: Please correct "endonuclease CRISPR-Cas" to read --endonuclease (e.g., CRISPR-Cas--

Column 60, Line 57: Please correct "Cas4, Cas4," to read --Cas4, Cas5,--

Column 64, Line 44: Please correct "5'-NGG-3-3'" to read --5'-NGG-3'--

Column 72, Line 6: Please correct "JOPLIN'" to read --JOPLIN1--

Column 74, Line 2: Please correct "MZDTO9Y" to read --MZDT09Y--

Signed and Sealed this
Eighteenth Day of November, 2025

John A. Squires
*Director of the United States Patent and Trademark Office*

SEQUENCE LISTING

```
<160> NUMBER OF SEQ ID NOS: 90

<210> SEQ ID NO 1
<211> LENGTH: 1228
<212> TYPE: PRT
<213> ORGANISM: Unknown
<220> FEATURE:
<223> OTHER INFORMATION: Lachnospiraceae sp.

<400> SEQUENCE: 1

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Asp Phe Phe Glu Gly Glu Phe
    210                 215                 220

Phe Asn Phe Val Leu Thr Gln Glu Gly Ile Asp Val Tyr Asn Ala Ile
225                 230                 235                 240
```

```
Ile Gly Gly Phe Val Thr Glu Ser Gly Glu Lys Ile Lys Gly Leu Asn
                245                 250                 255
Glu Tyr Ile Asn Leu Tyr Asn Gln Lys Thr Lys Gln Lys Leu Pro Lys
            260                 265                 270
Phe Lys Pro Leu Tyr Lys Gln Val Leu Ser Asp Arg Glu Ser Leu Ser
        275                 280                 285
Phe Tyr Gly Glu Gly Tyr Thr Ser Asp Glu Val Leu Glu Val Phe
    290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
                325                 330                 335
Phe Val Lys Asn Gly Pro Ala Ile Ser Thr Ile Ser Lys Asp Ile Phe
            340                 345                 350
Gly Glu Trp Asn Val Ile Arg Asp Lys Trp Asn Ala Glu Tyr Asp Asp
        355                 360                 365
Ile His Leu Lys Lys Lys Ala Val Val Thr Glu Lys Tyr Glu Asp Asp
    370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
            420                 425                 430
Glu Lys Leu Phe Asp Ala Asp Phe Val Leu Glu Lys Ser Leu Lys Lys
        435                 440                 445
Asn Asp Ala Val Val Ala Ile Met Lys Asp Leu Leu Asp Ser Val Lys
    450                 455                 460
Ser Phe Glu Asn Tyr Ile Lys Ala Phe Phe Gly Glu Gly Lys Glu Thr
465                 470                 475                 480
Asn Arg Asp Glu Ser Phe Tyr Gly Asp Phe Val Leu Ala Tyr Asp Ile
                485                 490                 495
Leu Leu Lys Val Asp His Ile Tyr Asp Ala Ile Arg Asn Tyr Val Thr
            500                 505                 510
Gln Lys Pro Tyr Ser Lys Asp Lys Phe Lys Leu Tyr Phe Gln Asn Pro
        515                 520                 525
Gln Phe Met Gly Gly Trp Asp Lys Asp Lys Glu Thr Asp Tyr Arg Ala
    530                 535                 540
Thr Ile Leu Arg Tyr Gly Ser Lys Tyr Tyr Leu Ala Ile Met Asp Lys
545                 550                 555                 560
Lys Tyr Ala Lys Cys Leu Gln Lys Ile Asp Lys Asp Asp Val Asn Gly
                565                 570                 575
Asn Tyr Glu Lys Ile Asn Tyr Lys Leu Leu Pro Gly Pro Asn Lys Met
            580                 585                 590
Leu Pro Lys Val Phe Phe Ser Lys Lys Trp Met Ala Tyr Tyr Asn Pro
        595                 600                 605
Ser Glu Asp Ile Gln Lys Ile Tyr Lys Asn Gly Thr Phe Lys Lys Gly
    610                 615                 620
Asp Met Phe Asn Leu Asn Asp Cys His Lys Leu Ile Asp Phe Phe Lys
625                 630                 635                 640
Asp Ser Ile Ser Arg Tyr Pro Lys Trp Ser Asn Ala Tyr Asp Phe Asn
                645                 650                 655
Phe Ser Glu Thr Glu Lys Tyr Lys Asp Ile Ala Gly Phe Tyr Arg Glu
```

```
                    660             665             670
        Val Glu Glu Gln Gly Tyr Lys Val Ser Phe Glu Ser Ala Ser Lys Lys
                    675             680             685
        Glu Val Asp Lys Leu Val Glu Glu Gly Lys Leu Tyr Met Phe Gln Ile
                    690             695             700
        Tyr Asn Lys Asp Phe Ser Asp Lys Ser His Gly Thr Pro Asn Leu His
        705             710             715             720
        Thr Met Tyr Phe Lys Leu Leu Phe Asp Glu Asn Asn His Gly Gln Ile
                        725             730             735
        Arg Leu Ser Gly Gly Ala Glu Leu Phe Met Arg Arg Ala Ser Leu Lys
                        740             745             750
        Lys Glu Glu Leu Val Val His Pro Ala Asn Ser Pro Ile Ala Asn Lys
                    755             760             765
        Asn Pro Asp Asn Pro Lys Lys Thr Thr Thr Leu Ser Tyr Asp Val Tyr
        770             775             780
        Lys Asp Lys Arg Phe Ser Glu Asp Gln Tyr Glu Leu His Ile Pro Ile
        785             790             795             800
        Ala Ile Asn Lys Cys Pro Lys Asn Ile Phe Lys Ile Asn Thr Glu Val
                        805             810             815
        Arg Val Leu Leu Lys His Asp Asp Asn Pro Tyr Val Ile Gly Ile Asp
                        820             825             830
        Arg Gly Glu Arg Asn Leu Leu Tyr Ile Val Val Asp Gly Lys Gly
                    835             840             845
        Asn Ile Val Glu Gln Tyr Ser Leu Asn Glu Ile Ile Asn Asn Phe Asn
        850             855             860
        Gly Ile Arg Ile Lys Thr Asp Tyr His Ser Leu Leu Asp Lys Lys Glu
        865             870             875             880
        Lys Glu Arg Phe Glu Ala Arg Gln Asn Trp Thr Ser Ile Glu Asn Ile
                        885             890             895
        Lys Glu Leu Lys Ala Gly Tyr Ile Ser Gln Val Val His Lys Ile Cys
                        900             905             910
        Glu Leu Val Glu Lys Tyr Asp Ala Val Ile Ala Leu Glu Asp Leu Asn
                    915             920             925
        Ser Gly Phe Lys Asn Ser Arg Val Lys Val Glu Lys Gln Val Tyr Gln
                    930             935             940
        Lys Phe Glu Lys Met Leu Ile Asp Lys Leu Asn Tyr Met Val Asp Lys
        945             950             955             960
        Lys Ser Asn Pro Cys Ala Thr Gly Gly Ala Leu Lys Gly Tyr Gln Ile
                        965             970             975
        Thr Asn Lys Phe Glu Ser Phe Lys Ser Met Ser Thr Gln Asn Gly Phe
                        980             985             990
        Ile Phe Tyr Ile Pro Ala Trp Leu Thr Ser Lys Ile Asp Pro Ser Thr
                        995             1000            1005
        Gly Phe Val Asn Leu Leu Lys Thr Lys Tyr Thr Ser Ile Ala Asp
                    1010            1015            1020
        Ser Lys Lys Phe Ile Ser Ser Phe Asp Arg Ile Met Tyr Val Pro
                    1025            1030            1035
        Glu Glu Asp Leu Phe Glu Phe Ala Leu Asp Tyr Lys Asn Phe Ser
                    1040            1045            1050
        Arg Thr Asp Ala Asp Tyr Ile Lys Lys Trp Lys Leu Tyr Ser Tyr
                    1055            1060            1065
        Gly Asn Arg Ile Arg Ile Phe Arg Asn Pro Lys Lys Asn Asn Val
                    1070            1075            1080
```

```
Phe Asp Trp Glu Glu Val Cys Leu Thr Ser Ala Tyr Lys Glu Leu
    1085            1090                1095

Phe Asn Lys Tyr Gly Ile Asn Tyr Gln Gln Gly Asp Ile Arg Ala
    1100            1105                1110

Leu Leu Cys Glu Gln Ser Asp Lys Ala Phe Tyr Ser Ser Phe Met
    1115            1120                1125

Ala Leu Met Ser Leu Met Leu Gln Met Arg Asn Ser Ile Thr Gly
    1130            1135                1140

Arg Thr Asp Val Asp Phe Leu Ile Ser Pro Val Lys Asn Ser Asp
    1145            1150                1155

Gly Ile Phe Tyr Asp Ser Arg Asn Tyr Glu Ala Gln Glu Asn Ala
    1160            1165                1170

Ile Leu Pro Lys Asn Ala Asp Ala Asn Gly Ala Tyr Asn Ile Ala
    1175            1180                1185

Arg Lys Val Leu Trp Ala Ile Gly Gln Phe Lys Lys Ala Glu Asp
    1190            1195                1200

Glu Lys Leu Asp Lys Val Lys Ile Ala Ile Ser Asn Lys Glu Trp
    1205            1210                1215

Leu Glu Tyr Ala Gln Thr Ser Val Lys His
    1220            1225

<210> SEQ ID NO 2
<211> LENGTH: 1307
<212> TYPE: PRT
<213> ORGANISM: Acidaminococcus sp.

<400> SEQUENCE: 2

Met Thr Gln Phe Glu Gly Phe Thr Asn Leu Tyr Gln Val Ser Lys
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
                35                  40                  45

Glu Leu Lys Pro Ile Ile Asp Arg Ile Tyr Lys Thr Tyr Ala Asp Gln
            50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
                100                 105                 110

Arg Thr Asp Asn Leu Thr Asp Ala Ile Asn Lys Arg His Ala Glu Ile
            115                 120                 125

Tyr Lys Gly Leu Phe Lys Ala Glu Leu Phe Asn Gly Lys Val Leu Lys
            130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
```

```
              210                 215                 220
Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
                450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
                610                 615                 620

Pro Ile Leu Leu Ser Asn Asn Phe Ile Glu Pro Leu Glu Ile Thr Lys
625                 630                 635                 640
```

```
Glu Ile Tyr Asp Leu Asn Asn Pro Glu Lys Glu Pro Lys Lys Phe Gln
            645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
            690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
        1010                1015                1020

Asn Cys Leu Val Leu Lys Asp Tyr Pro Ala Glu Lys Val Gly Gly
        1025                1030                1035

Val Leu Asn Pro Tyr Gln Leu Thr Asp Gln Phe Thr Ser Phe Ala
        1040                1045                1050
```

-continued

```
Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 3
<211> LENGTH: 1241
<212> TYPE: PRT
<213> ORGANISM: Butyrivibrio proteoclasticus

<400> SEQUENCE: 3

Met Leu Leu Tyr Glu Asn Tyr Thr Lys Arg Asn Gln Ile Thr Lys Ser
1               5                   10                  15

Leu Arg Leu Glu Leu Arg Pro Gln Gly Lys Thr Leu Arg Asn Ile Lys
                20                  25                  30

Glu Leu Asn Leu Leu Glu Gln Asp Lys Ala Ile Tyr Ala Leu Leu Glu
            35                  40                  45

Arg Leu Lys Pro Val Ile Asp Glu Gly Ile Lys Asp Ile Ala Arg Asp
        50                  55                  60

Thr Leu Lys Asn Cys Glu Leu Ser Phe Glu Lys Leu Tyr Glu His Phe
65                  70                  75                  80

Leu Ser Gly Asp Lys Lys Ala Tyr Ala Lys Glu Ser Glu Arg Leu Lys
                85                  90                  95

Lys Glu Ile Val Lys Thr Leu Ile Lys Asn Leu Pro Glu Gly Ile Gly
            100                 105                 110
```

-continued

```
Lys Ile Ser Glu Ile Asn Ser Ala Lys Tyr Leu Asn Gly Val Leu Tyr
            115                 120                 125

Asp Phe Ile Asp Lys Thr His Lys Asp Ser Glu Glu Lys Gln Asn Ile
        130                 135                 140

Leu Ser Asp Ile Leu Glu Thr Lys Gly Tyr Leu Ala Leu Phe Ser Lys
145                 150                 155                 160

Phe Leu Thr Ser Arg Ile Thr Thr Leu Glu Gln Ser Met Pro Lys Arg
                165                 170                 175

Val Ile Glu Asn Phe Glu Ile Tyr Ala Ala Asn Ile Pro Lys Met Gln
            180                 185                 190

Asp Ala Leu Glu Arg Gly Ala Val Ser Phe Ala Ile Glu Tyr Glu Ser
        195                 200                 205

Ile Cys Ser Val Asp Tyr Tyr Asn Gln Ile Leu Ser Gln Glu Asp Ile
    210                 215                 220

Asp Ser Tyr Asn Arg Leu Ile Ser Gly Ile Met Asp Glu Asp Gly Ala
225                 230                 235                 240

Lys Glu Lys Gly Ile Asn Gln Thr Ile Ser Glu Lys Asn Ile Lys Ile
                245                 250                 255

Lys Ser Glu His Leu Glu Glu Lys Pro Phe Arg Ile Leu Lys Gln Leu
            260                 265                 270

His Lys Gln Ile Leu Glu Glu Arg Glu Lys Ala Phe Thr Ile Asp His
        275                 280                 285

Ile Asp Ser Asp Glu Glu Val Val Gln Val Thr Lys Glu Ala Phe Glu
    290                 295                 300

Gln Thr Lys Glu Gln Trp Glu Asn Ile Lys Ile Asn Gly Phe Tyr
305                 310                 315                 320

Ala Lys Asp Pro Gly Asp Ile Thr Leu Phe Ile Val Val Gly Pro Asn
                325                 330                 335

Gln Thr His Val Leu Ser Gln Leu Ile Tyr Gly Glu His Asp Arg Ile
            340                 345                 350

Arg Leu Leu Leu Glu Glu Tyr Glu Lys Asn Thr Leu Glu Val Leu Pro
        355                 360                 365

Arg Arg Thr Lys Ser Glu Asp Ala Arg Tyr Asp Lys Phe Val Asn Ala
    370                 375                 380

Val Pro Lys Lys Val Ala Lys Glu Ser His Thr Phe Asp Gly Leu Gln
385                 390                 395                 400

Lys Met Thr Gly Asp Asp Arg Leu Phe Ile Leu Tyr Arg Asp Glu Leu
                405                 410                 415

Ala Arg Asn Tyr Met Arg Ile Lys Glu Ala Tyr Gly Thr Phe Glu Arg
            420                 425                 430

Asp Ile Leu Lys Ser Arg Arg Gly Ile Lys Gly Asn Arg Asp Val Gln
        435                 440                 445

Glu Ser Leu Val Ser Phe Tyr Asp Glu Leu Thr Lys Phe Arg Ser Ala
    450                 455                 460

Leu Arg Ile Ile Asn Ser Gly Asn Asp Glu Lys Ala Asp Pro Ile Phe
465                 470                 475                 480

Tyr Asn Thr Phe Asp Gly Ile Phe Glu Lys Ala Asn Arg Thr Tyr Lys
                485                 490                 495

Ala Glu Asn Leu Cys Arg Asn Tyr Val Thr Lys Ser Pro Ala Asp Asp
            500                 505                 510

Ala Arg Ile Met Ala Ser Cys Leu Gly Thr Pro Ala Arg Leu Arg Thr
        515                 520                 525
```

-continued

```
His Trp Trp Asn Gly Glu Glu Asn Phe Ala Ile Asn Asp Val Ala Met
    530                 535                 540
Ile Arg Arg Gly Asp Glu Tyr Tyr Phe Val Leu Thr Pro Asp Val
545                 550                 555                 560
Lys Pro Val Asp Leu Lys Thr Lys Asp Glu Thr Asp Ala Gln Ile Phe
                565                 570                 575
Val Gln Arg Lys Gly Ala Lys Ser Phe Leu Gly Leu Pro Lys Ala Leu
                580                 585                 590
Phe Lys Cys Ile Leu Glu Pro Tyr Phe Glu Ser Pro Glu His Lys Asn
                595                 600                 605
Asp Lys Asn Cys Val Ile Glu Glu Tyr Val Ser Lys Pro Leu Thr Ile
                610                 615                 620
Asp Arg Arg Ala Tyr Asp Ile Phe Lys Asn Gly Thr Phe Lys Lys Thr
625                 630                 635                 640
Asn Ile Gly Ile Asp Gly Leu Thr Glu Glu Lys Phe Lys Asp Asp Cys
                        645                 650                 655
Arg Tyr Leu Ile Asp Val Tyr Lys Glu Phe Ile Ala Val Tyr Thr Arg
                660                 665                 670
Tyr Ser Cys Phe Asn Met Ser Gly Leu Lys Arg Ala Asp Glu Tyr Asn
        675                 680                 685
Asp Ile Gly Glu Phe Phe Ser Asp Val Asp Thr Arg Leu Cys Thr Met
690                 695                 700
Glu Trp Ile Pro Val Ser Phe Glu Arg Ile Asn Asp Met Val Asp Lys
705                 710                 715                 720
Lys Glu Gly Leu Leu Phe Leu Val Arg Ser Met Phe Leu Tyr Asn Arg
                    725                 730                 735
Pro Arg Lys Pro Tyr Glu Arg Thr Phe Ile Gln Leu Phe Ser Asp Ser
                740                 745                 750
Asn Met Glu His Thr Ser Met Leu Leu Asn Ser Arg Ala Met Ile Gln
                755                 760                 765
Tyr Arg Ala Ala Ser Leu Pro Arg Arg Val Thr His Lys Lys Gly Ser
    770                 775                 780
Ile Leu Val Ala Leu Arg Asp Ser Asn Gly Glu His Ile Pro Met His
785                 790                 795                 800
Ile Arg Glu Ala Ile Tyr Lys Met Lys Asn Asn Phe Asp Ile Ser Ser
                805                 810                 815
Glu Asp Phe Ile Met Ala Lys Ala Tyr Leu Ala Glu His Asp Val Ala
                820                 825                 830
Ile Lys Lys Ala Asn Glu Asp Ile Ile Arg Asn Arg Arg Tyr Thr Glu
            835                 840                 845
Asp Lys Phe Phe Leu Ser Leu Ser Tyr Thr Lys Asn Ala Asp Ile Ser
    850                 855                 860
Ala Arg Thr Leu Asp Tyr Ile Asn Asp Lys Val Glu Glu Asp Thr Gln
865                 870                 875                 880
Asp Ser Arg Met Ala Val Ile Val Thr Arg Asn Leu Lys Asp Leu Thr
                885                 890                 895
Tyr Val Ala Val Val Asp Glu Lys Asn Asn Val Leu Glu Glu Lys Ser
                900                 905                 910
Leu Asn Glu Ile Asp Gly Val Asn Tyr Arg Glu Leu Leu Lys Glu Arg
            915                 920                 925
Thr Lys Ile Lys Tyr His Asp Lys Thr Arg Leu Trp Gln Tyr Asp Val
    930                 935                 940
Ser Ser Lys Gly Leu Lys Glu Ala Tyr Val Glu Leu Ala Val Thr Gln
```

```
                945                 950                 955                 960
        Ile Ser Lys Leu Ala Thr Lys Tyr Asn Ala Val Val Val Glu Ser
                        965                 970                 975

Met Ser Ser Thr Phe Lys Asp Lys Phe Ser Phe Leu Asp Glu Gln Ile
                        980                 985                 990

Phe Lys Ala Phe Glu Ala Arg Leu  Cys Ala Arg Met Ser  Asp Leu Ser
                        995                1000                1005

Phe Asn Thr Ile Lys Glu Gly  Glu Ala Gly Ser Ile  Ser Asn Pro
                    1010                1015                1020

Ile Gln Val Ser Asn Asn Asn  Gly Asn Ser Tyr Gln  Asp Gly Val
                    1025                1030                1035

Ile Tyr Phe Leu Asn Asn Ala  Tyr Thr Arg Thr Leu  Cys Pro Asp
                    1040                1045                1050

Thr Gly Phe Val Asp Val Phe  Asp Lys Thr Arg Leu  Ile Thr Met
                    1055                1060                1065

Gln Ser Lys Arg Gln Phe Phe  Ala Lys Met Lys Asp  Ile Arg Ile
                    1070                1075                1080

Asp Asp Gly Glu Met Leu Phe  Thr Phe Asn Leu Glu  Glu Tyr Pro
                    1085                1090                1095

Thr Lys Arg Leu Leu Asp Arg  Lys Glu Trp Thr Val  Lys Ile Ala
                    1100                1105                1110

Gly Asp Gly Ser Tyr Phe Asp  Lys Asp Lys Gly Glu  Tyr Val Tyr
                    1115                1120                1125

Val Asn Asp Ile Val Arg Glu  Gln Ile Ile Pro Ala  Leu Leu Glu
                    1130                1135                1140

Asp Lys Ala Val Phe Asp Gly  Asn Met Ala Glu Lys  Phe Leu Asp
                    1145                1150                1155

Lys Thr Ala Ile Ser Gly Lys  Ser Val Glu Leu Ile  Tyr Lys Trp
                    1160                1165                1170

Phe Ala Asn Ala Leu Tyr Gly  Ile Ile Thr Lys Lys  Asp Gly Glu
                    1175                1180                1185

Lys Ile Tyr Arg Ser Pro Ile  Thr Gly Thr Glu Ile  Asp Val Ser
                    1190                1195                1200

Lys Asn Thr Thr Tyr Asn Phe  Gly Lys Lys Phe Met  Phe Lys Gln
                    1205                1210                1215

Glu Tyr Arg Gly Asp Gly Asp  Phe Leu Asp Ala Phe  Leu Asn Tyr
                    1220                1225                1230

Met Gln Ala Gln Asp Ile Ala  Val
                    1235                1240

<210> SEQ ID NO 4
<211> LENGTH: 1238
<212> TYPE: PRT
<213> ORGANISM: Candidatus Methanoplasma termitum

<400> SEQUENCE: 4

Met Asn Asn Tyr Asp Glu Phe Thr Lys Leu Tyr Pro Ile Gln Lys Thr
1               5                  10                  15

Ile Arg Phe Glu Leu Lys Pro Gln Gly Arg Thr Met Glu His Leu Glu
                20                  25                  30

Thr Phe Asn Phe Phe Glu Glu Asp Arg Asp Arg Ala Glu Lys Tyr Lys
            35                  40                  45

Ile Leu Lys Glu Ala Ile Asp Glu Tyr His Lys Lys Phe Ile Asp Glu
        50                  55                  60
```

-continued

His Leu Thr Asn Met Ser Leu Asp Trp Asn Ser Lys Gln Ile Ser
65                  70                  75                  80

Glu Lys Tyr Tyr Lys Ser Arg Glu Glu Lys Asp Lys Lys Val Phe Leu
            85                  90                  95

Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
            115                 120                 125

Leu Lys Glu Glu Ile Tyr Lys Lys Gly Asn His Gln Glu Ile Asp Ala
130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
            195                 200                 205

Glu Ser Ala Leu Val Ala His Asn Ile Lys Met Asp Ile Val Phe Ser
210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Gly Lys Ser Ser
                260                 265                 270

Lys Gly Arg Ile His Met Thr Pro Leu Phe Lys Gln Ile Leu Ser Glu
            275                 280                 285

Lys Glu Ser Phe Ser Tyr Ile Pro Asp Val Phe Thr Glu Asp Ser Gln
            290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
            340                 345                 350

Val Ser Asn Val Ile Phe Gly Glu Trp Gly Thr Leu Gly Gly Leu Met
            355                 360                 365

Arg Glu Tyr Lys Ala Asp Ser Ile Asn Asp Ile Asn Leu Glu Arg Thr
370                 375                 380

Cys Lys Lys Val Asp Lys Trp Leu Asp Ser Lys Glu Phe Ala Leu Ser
385                 390                 395                 400

Asp Val Leu Glu Ala Ile Asp Arg Thr Gly Asn Asn Asp Ala Phe Asn
            405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
            435                 440                 445

Ser Ile His Ile Ile Lys Thr Leu Leu Asp Ser Val Gln Gln Phe Leu
            450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile

```
            485                 490                 495
Val Pro Leu Tyr Asn Lys Val Arg Asn Tyr Leu Thr Lys Asn Asn Leu
            500                 505                 510

Asn Thr Lys Lys Ile Lys Leu Asn Phe Lys Asn Pro Thr Leu Ala Asn
            515                 520                 525

Gly Trp Asp Gln Asn Lys Val Tyr Asp Tyr Ala Ser Leu Ile Phe Leu
            530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
                565                 570                 575

Met Val Tyr Lys Gln Ile Pro Gly Pro Asn Lys Asn Leu Arg Pro Val
                580                 585                 590

Phe Leu Thr Ser Thr Lys Gly Lys Lys Glu Tyr Lys Pro Ser Lys Glu
                595                 600                 605

Ile Ile Glu Gly Tyr Glu Ala Asp Lys His Ile Arg Gly Asp Lys Phe
                610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
                645                 650                 655

Glu Ser Tyr Gly Asp Ile Ser Glu Phe Tyr Leu Asp Val Glu Lys Gln
                660                 665                 670

Gly Tyr Arg Met His Phe Glu Asn Ile Ser Ala Glu Thr Ile Asp Glu
                675                 680                 685

Tyr Val Glu Lys Gly Asp Leu Phe Leu Phe Gln Ile Tyr Asn Lys Asp
690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Lys Leu
                725                 730                 735

Asn Gly Glu Ala Glu Leu Phe Tyr Arg Asp Lys Ser Asp Ile Lys Glu
                740                 745                 750

Ile Val His Arg Glu Gly Glu Ile Leu Val Asn Arg Thr Tyr Asn Gly
                755                 760                 765

Arg Thr Pro Val Pro Asp Lys Ile His Lys Leu Thr Asp Tyr His
770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
                820                 825                 830

Ala Asn Gly Lys Lys Asn Leu Asn Lys Met Val Ile Glu Lys Phe Leu
                835                 840                 845

Ser Asp Glu Lys Ala His Ile Ile Gly Ile Asp Arg Gly Glu Arg Asn
                850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
                900                 905                 910
```

```
Gly Lys Ile Lys Asp Leu Lys Glu Gly Tyr Leu Ser Lys Ala Val His
        915                 920                 925

Glu Ile Thr Lys Met Ala Ile Gln Tyr Asn Ala Ile Val Val Met Glu
930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Gly Val Leu Asn Ala
            980                 985                 990

Tyr Gln Leu Thr Asn Pro Leu Glu Ser Phe Ala Lys Leu Gly Lys Gln
        995                 1000                1005

Thr Gly Ile Leu Phe Tyr Val Pro Ala Ala Tyr Thr Ser Lys Ile
    1010                1015                1020

Asp Pro Thr Thr Gly Phe Val Asn Leu Phe Asn Thr Ser Ser Lys
    1025                1030                1035

Thr Asn Ala Gln Glu Arg Lys Glu Phe Leu Gln Lys Phe Glu Ser
    1040                1045                1050

Ile Ser Tyr Ser Ala Lys Asp Gly Gly Ile Phe Ala Phe Ala Phe
    1055                1060                1065

Asp Tyr Arg Lys Phe Gly Thr Ser Lys Thr Asp His Lys Asn Val
    1070                1075                1080

Trp Thr Ala Tyr Thr Asn Gly Glu Arg Met Arg Tyr Ile Lys Glu
    1085                1090                1095

Lys Lys Arg Asn Glu Leu Phe Asp Pro Ser Lys Glu Ile Lys Glu
    1100                1105                1110

Ala Leu Thr Ser Ser Gly Ile Lys Tyr Asp Gly Gly Gln Asn Ile
    1115                1120                1125

Leu Pro Asp Ile Leu Arg Ser Asn Asn Asn Gly Leu Ile Tyr Thr
    1130                1135                1140

Met Tyr Ser Ser Phe Ile Ala Ala Ile Gln Met Arg Val Tyr Asp
    1145                1150                1155

Gly Lys Glu Asp Tyr Ile Ile Ser Pro Ile Lys Asn Ser Lys Gly
    1160                1165                1170

Glu Phe Phe Arg Thr Asp Pro Lys Arg Arg Glu Leu Pro Ile Asp
    1175                1180                1185

Ala Asp Ala Asn Gly Ala Tyr Asn Ile Ala Leu Arg Gly Glu Leu
    1190                1195                1200

Thr Met Arg Ala Ile Ala Glu Lys Phe Asp Pro Asp Ser Glu Lys
    1205                1210                1215

Met Ala Lys Leu Glu Leu Lys His Lys Asp Trp Phe Glu Phe Met
    1220                1225                1230

Gln Thr Arg Gly Asp
    1235

<210> SEQ ID NO 5
<211> LENGTH: 1281
<212> TYPE: PRT
<213> ORGANISM: Eubacterium eligens

<400> SEQUENCE: 5

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
```

-continued

```
                20                  25                  30
    Gln Glu His Ile Ile Gln Asn Gly Leu Ile Gln Glu Asp Glu Leu Arg
                    35                  40                  45
    Gln Glu Lys Ser Thr Glu Leu Lys Asn Ile Met Asp Asp Tyr Tyr Arg
        50                  55                  60
    Glu Tyr Ile Asp Lys Ser Leu Ser Gly Val Thr Asp Leu Asp Phe Thr
    65                  70                  75                  80
    Leu Leu Phe Glu Leu Met Asn Leu Val Gln Ser Ser Pro Ser Lys Asp
                    85                  90                  95
    Asn Lys Lys Ala Leu Glu Lys Glu Gln Ser Lys Met Arg Glu Gln Ile
                100                 105                 110
    Cys Thr His Leu Gln Ser Asp Ser Asn Tyr Lys Asn Ile Phe Asn Ala
                115                 120                 125
    Lys Leu Leu Lys Glu Ile Leu Pro Asp Phe Ile Lys Asn Tyr Asn Gln
                130                 135                 140
    Tyr Asp Val Lys Asp Lys Ala Gly Lys Leu Glu Thr Leu Ala Leu Phe
    145                 150                 155                 160
    Asn Gly Phe Ser Thr Tyr Phe Thr Asp Phe Phe Glu Lys Arg Lys Asn
                    165                 170                 175
    Val Phe Thr Lys Glu Ala Val Ser Thr Ser Ile Ala Tyr Arg Ile Val
                    180                 185                 190
    His Glu Asn Ser Leu Ile Phe Leu Ala Asn Met Thr Ser Tyr Lys Lys
                    195                 200                 205
    Ile Ser Glu Lys Ala Leu Asp Glu Ile Glu Val Ile Glu Lys Asn Asn
                210                 215                 220
    Gln Asp Lys Met Gly Asp Trp Glu Leu Asn Gln Ile Phe Asn Pro Asp
    225                 230                 235                 240
    Phe Tyr Asn Met Val Leu Ile Gln Ser Gly Ile Asp Phe Tyr Asn Glu
                    245                 250                 255
    Ile Cys Gly Val Val Asn Ala His Met Asn Leu Tyr Cys Gln Gln Thr
                260                 265                 270
    Lys Asn Asn Tyr Asn Leu Phe Lys Met Arg Lys Leu His Lys Gln Ile
                275                 280                 285
    Leu Ala Tyr Thr Ser Thr Ser Phe Glu Val Pro Lys Met Phe Glu Asp
                290                 295                 300
    Asp Met Ser Val Tyr Asn Ala Val Asn Ala Phe Ile Asp Glu Thr Glu
    305                 310                 315                 320
    Lys Gly Asn Ile Ile Gly Lys Leu Lys Asp Ile Val Asn Lys Tyr Asp
                    325                 330                 335
    Glu Leu Asp Glu Lys Arg Ile Tyr Ile Ser Lys Asp Phe Tyr Glu Thr
                    340                 345                 350
    Leu Ser Cys Phe Met Ser Gly Asn Trp Asn Leu Ile Thr Gly Cys Val
                    355                 360                 365
    Glu Asn Phe Tyr Asp Glu Asn Ile His Ala Lys Gly Lys Ser Lys Glu
                370                 375                 380
    Glu Lys Val Lys Lys Ala Val Lys Glu Asp Lys Tyr Lys Ser Ile Asn
    385                 390                 395                 400
    Asp Val Asn Asp Leu Val Glu Lys Tyr Ile Asp Glu Lys Glu Arg Asn
                    405                 410                 415
    Glu Phe Lys Asn Ser Asn Ala Lys Gln Tyr Ile Arg Glu Ile Ser Asn
                    420                 425                 430
    Ile Ile Thr Asp Thr Glu Thr Ala His Leu Glu Tyr Asp Asp His Ile
                435                 440                 445
```

-continued

```
Ser Leu Ile Glu Ser Glu Lys Ala Asp Glu Met Lys Lys Arg Leu
    450             455                 460

Asp Met Tyr Met Asn Met Tyr His Trp Ala Lys Ala Phe Ile Val Asp
465             470                 475                 480

Glu Val Leu Asp Arg Asp Glu Met Phe Tyr Ser Asp Ile Asp Asp Ile
                485                 490                 495

Tyr Asn Ile Leu Glu Asn Ile Val Pro Leu Tyr Asn Arg Val Arg Asn
            500                 505                 510

Tyr Val Thr Gln Lys Pro Tyr Asn Ser Lys Lys Ile Lys Leu Asn Phe
        515                 520                 525

Gln Ser Pro Thr Leu Ala Asn Gly Trp Ser Gln Ser Lys Glu Phe Asp
    530                 535                 540

Asn Asn Ala Ile Ile Leu Ile Arg Asp Asn Lys Tyr Tyr Leu Ala Ile
545                 550                 555                 560

Phe Asn Ala Lys Asn Lys Pro Asp Lys Lys Ile Ile Gln Gly Asn Ser
                565                 570                 575

Asp Lys Lys Asn Asp Asn Asp Tyr Lys Lys Met Val Tyr Asn Leu Leu
            580                 585                 590

Pro Gly Ala Asn Lys Met Leu Pro Lys Val Phe Leu Ser Lys Lys Gly
        595                 600                 605

Ile Glu Thr Phe Lys Pro Ser Asp Tyr Ile Ile Ser Gly Tyr Asn Ala
    610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
                645                 650                 655

Arg Lys Tyr Glu Phe Lys Phe Ser Ala Thr Asp Ser Tyr Ser Asp Ile
            660                 665                 670

Ser Glu Phe Tyr Arg Glu Val Glu Met Gln Gly Tyr Arg Ile Asp Trp
        675                 680                 685

Thr Tyr Ile Ser Glu Ala Asp Ile Asn Lys Leu Asp Glu Glu Gly Lys
    690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
                725                 730                 735

Glu Asn Leu Asp Lys Ile Ile Lys Leu Asn Gly Gln Ala Glu Leu Phe
            740                 745                 750

Tyr Arg Arg Ala Ser Val Lys Asn Pro Val Lys His Lys Lys Asp Ser
        755                 760                 765

Val Leu Val Asn Lys Thr Tyr Lys Asn Gln Leu Asp Asn Gly Asp Val
    770                 775                 780

Val Arg Ile Pro Ile Pro Asp Asp Ile Tyr Asn Glu Ile Tyr Lys Met
785                 790                 795                 800

Tyr Asn Gly Tyr Ile Lys Glu Ser Asp Leu Ser Glu Ala Ala Lys Glu
                805                 810                 815

Tyr Leu Asp Lys Val Glu Val Arg Thr Ala Gln Lys Asp Ile Val Lys
            820                 825                 830

Asp Tyr Arg Tyr Thr Val Asp Lys Tyr Phe Ile His Thr Pro Ile Thr
        835                 840                 845

Ile Asn Tyr Lys Val Thr Ala Arg Asn Asn Val Asn Asp Met Val Val
    850                 855                 860
```

```
Lys Tyr Ile Ala Gln Asn Asp Asp Ile His Val Gly Ile Asp Arg
865                 870                 875                 880

Gly Glu Arg Asn Leu Ile Tyr Ile Ser Val Ile Asp Ser His Gly Asn
                885                 890                 895

Ile Val Lys Gln Lys Ser Tyr Asn Ile Leu Asn Asn Tyr Asp Tyr Lys
            900                 905                 910

Lys Lys Leu Val Glu Lys Glu Lys Thr Arg Glu Tyr Ala Arg Lys Asn
        915                 920                 925

Trp Lys Ser Ile Gly Asn Ile Lys Glu Leu Lys Glu Gly Tyr Ile Ser
    930                 935                 940

Gly Val Val His Glu Ile Ala Met Leu Ile Val Glu Tyr Asn Ala Ile
945                 950                 955                 960

Ile Ala Met Glu Asp Leu Asn Tyr Gly Phe Lys Arg Gly Arg Phe Lys
                965                 970                 975

Val Glu Arg Gln Val Tyr Gln Lys Phe Glu Ser Met Leu Ile Asn Lys
            980                 985                 990

Leu Asn Tyr Phe Ala Ser Lys Glu Lys Ser Val Asp Glu Pro Gly Gly
        995                 1000                1005

Leu Leu Lys Gly Tyr Gln Leu Thr Tyr Val Pro Asp Asn Ile Lys
    1010                1015                1020

Asn Leu Gly Lys Gln Cys Gly Val Ile Phe Tyr Val Pro Ala Ala
    1025                1030                1035

Phe Thr Ser Lys Ile Asp Pro Ser Thr Gly Phe Ile Ser Ala Phe
    1040                1045                1050

Asn Phe Lys Ser Ile Ser Thr Asn Ala Ser Arg Lys Gln Phe Phe
    1055                1060                1065

Met Gln Phe Asp Glu Ile Arg Tyr Cys Ala Glu Lys Asp Met Phe
    1070                1075                1080

Ser Phe Gly Phe Asp Tyr Asn Asn Phe Asp Thr Tyr Asn Ile Thr
    1085                1090                1095

Met Gly Lys Thr Gln Trp Thr Val Tyr Thr Asn Gly Glu Arg Leu
    1100                1105                1110

Gln Ser Glu Phe Asn Asn Ala Arg Arg Thr Gly Lys Thr Lys Ser
    1115                1120                1125

Ile Asn Leu Thr Glu Thr Ile Lys Leu Leu Leu Glu Asp Asn Glu
    1130                1135                1140

Ile Asn Tyr Ala Asp Gly His Asp Ile Arg Ile Asp Met Glu Lys
    1145                1150                1155

Met Asp Glu Asp Lys Lys Ser Glu Phe Phe Ala Gln Leu Leu Ser
    1160                1165                1170

Leu Tyr Lys Leu Thr Val Gln Met Arg Asn Ser Tyr Thr Glu Ala
    1175                1180                1185

Glu Glu Gln Glu Asn Gly Ile Ser Tyr Asp Lys Ile Ile Ser Pro
    1190                1195                1200

Val Ile Asn Asp Glu Gly Glu Phe Phe Asp Ser Asp Asn Tyr Lys
    1205                1210                1215

Glu Ser Asp Asp Lys Glu Cys Lys Met Pro Lys Asp Ala Asp Ala
    1220                1225                1230

Asn Gly Ala Tyr Cys Ile Ala Leu Lys Gly Leu Tyr Glu Val Leu
    1235                1240                1245

Lys Ile Lys Ser Glu Trp Thr Glu Asp Gly Phe Asp Arg Asn Cys
    1250                1255                1260

Leu Lys Leu Pro His Ala Glu Trp Leu Asp Phe Ile Gln Asn Lys
```

```
                    1265                1270                1275
Arg Tyr Glu
        1280

<210> SEQ ID NO 6
<211> LENGTH: 1300
<212> TYPE: PRT
<213> ORGANISM: Francisella novicida

<400> SEQUENCE: 6

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Val Asn Tyr Ser Ser
            180                 185                 190

Asn Asp Ile Pro Thr Ser Ile Ile Tyr Arg Ile Val Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350
```

```
Gln Ser Phe Tyr Glu Gln Ile Ala Ala Phe Lys Thr Val Glu Glu Lys
            355                 360                 365
Ser Ile Lys Glu Thr Leu Ser Leu Leu Phe Asp Asp Leu Lys Ala Gln
370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
                405                 410                 415
Val Leu Glu Tyr Ile Thr Gln Gln Ile Ala Pro Lys Asn Leu Asp Asn
            420                 425                 430
Pro Ser Lys Lys Glu Gln Glu Leu Ile Ala Lys Thr Glu Lys Ala
            435                 440                 445
Lys Tyr Leu Ser Leu Glu Thr Ile Lys Leu Ala Leu Glu Glu Phe Asn
            450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
Asp Asn Leu Ala Gln Ile Ser Ile Lys Tyr Gln Asn Gln Gly Lys Lys
            500                 505                 510
Asp Leu Leu Gln Ala Ser Ala Glu Asp Asp Val Lys Ala Ile Lys Asp
            515                 520                 525
Leu Leu Asp Gln Thr Asn Asn Leu Leu His Lys Leu Lys Ile Phe His
            530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
            580                 585                 590
Asp Glu Lys Phe Lys Leu Asn Phe Glu Asn Ser Thr Leu Ala Asn Gly
            595                 600                 605
Trp Asp Lys Asn Lys Glu Pro Asp Asn Thr Ala Ile Leu Phe Ile Lys
            610                 615                 620
Asp Asp Lys Tyr Tyr Leu Gly Val Met Asn Lys Lys Asn Asn Lys Ile
625                 630                 635                 640
Phe Asp Asp Lys Ala Ile Lys Glu Asn Lys Gly Glu Gly Tyr Lys Lys
                645                 650                 655
Ile Val Tyr Lys Leu Leu Pro Gly Ala Asn Lys Met Leu Pro Lys Val
            660                 665                 670
Phe Phe Ser Ala Lys Ser Ile Lys Phe Tyr Asn Pro Ser Glu Asp Ile
            675                 680                 685
Leu Arg Ile Arg Asn His Ser Thr His Thr Lys Asn Gly Ser Pro Gln
            690                 695                 700
Lys Gly Tyr Glu Lys Phe Glu Phe Asn Ile Glu Asp Cys Arg Lys Phe
705                 710                 715                 720
Ile Asp Phe Tyr Lys Gln Ser Ile Ser Lys His Pro Glu Trp Lys Asp
                725                 730                 735
Phe Gly Phe Arg Phe Ser Asp Thr Gln Arg Tyr Asn Ser Ile Asp Glu
            740                 745                 750
Phe Tyr Arg Glu Val Glu Asn Gln Gly Tyr Lys Leu Thr Phe Glu Asn
            755                 760                 765
Ile Ser Glu Ser Tyr Ile Asp Ser Val Val Asn Gln Gly Lys Leu Tyr
```

-continued

```
                770             775             780
Leu Phe Gln Ile Tyr Asn Lys Asp Phe Ser Ala Tyr Ser Lys Gly Arg
785                 790             795                 800

Pro Asn Leu His Thr Leu Tyr Trp Lys Ala Leu Phe Asp Glu Arg Asn
                805             810             815

Leu Gln Asp Val Val Tyr Lys Leu Asn Gly Glu Ala Glu Leu Phe Tyr
            820             825             830

Arg Lys Gln Ser Ile Pro Lys Lys Ile Thr His Pro Ala Lys Glu Ala
        835             840             845

Ile Ala Asn Lys Asn Lys Asp Asn Pro Lys Lys Glu Ser Val Phe Glu
    850             855             860

Tyr Asp Leu Ile Lys Asp Lys Arg Phe Thr Glu Asp Lys Phe Phe Phe
865             870             875             880

His Cys Pro Ile Thr Ile Asn Phe Lys Ser Ser Gly Ala Asn Lys Phe
                885             890             895

Asn Asp Glu Ile Asn Leu Leu Leu Lys Glu Lys Ala Asn Asp Val His
            900             905             910

Ile Leu Ser Ile Asp Arg Gly Glu Arg His Leu Ala Tyr Tyr Thr Leu
        915             920             925

Val Asp Gly Lys Gly Asn Ile Ile Lys Gln Asp Thr Phe Asn Ile Ile
    930             935             940

Gly Asn Asp Arg Met Lys Thr Asn Tyr His Asp Lys Leu Ala Ala Ile
945             950             955             960

Glu Lys Asp Arg Asp Ser Ala Arg Lys Asp Trp Lys Lys Ile Asn Asn
                965             970             975

Ile Lys Glu Met Lys Glu Gly Tyr Leu Ser Gln Val Val His Glu Ile
            980             985             990

Ala Lys Leu Val Ile Glu Tyr Asn Ala Ile Val Val Phe Glu Asp Leu
        995             1000            1005

Asn Phe Gly Phe Lys Arg Gly Arg Phe Lys Val Glu Lys Gln Val
    1010            1015            1020

Tyr Gln Lys Leu Glu Lys Met Leu Ile Glu Lys Leu Asn Tyr Leu
    1025            1030            1035

Val Phe Lys Asp Asn Glu Phe Asp Lys Thr Gly Gly Val Leu Arg
    1040            1045            1050

Ala Tyr Gln Leu Thr Ala Pro Phe Glu Thr Phe Lys Lys Met Gly
    1055            1060            1065

Lys Gln Thr Gly Ile Ile Tyr Tyr Val Pro Ala Gly Phe Thr Ser
    1070            1075            1080

Lys Ile Cys Pro Val Thr Gly Phe Val Asn Gln Leu Tyr Pro Lys
    1085            1090            1095

Tyr Glu Ser Val Ser Lys Ser Gln Glu Phe Phe Ser Lys Phe Asp
    1100            1105            1110

Lys Ile Cys Tyr Asn Leu Asp Lys Gly Tyr Phe Glu Phe Ser Phe
    1115            1120            1125

Asp Tyr Lys Asn Phe Gly Asp Lys Ala Ala Lys Gly Lys Trp Thr
    1130            1135            1140

Ile Ala Ser Phe Gly Ser Arg Leu Ile Asn Phe Arg Asn Ser Asp
    1145            1150            1155

Lys Asn His Asn Trp Asp Thr Arg Glu Val Tyr Pro Thr Lys Glu
    1160            1165            1170

Leu Glu Lys Leu Leu Lys Asp Tyr Ser Ile Glu Tyr Gly His Gly
    1175            1180            1185
```

```
Glu Cys Ile Lys Ala Ala Ile Cys Gly Glu Ser Asp Lys Lys Phe
            1190                1195                1200

Phe Ala Lys Leu Thr Ser Val Leu Asn Thr Ile Leu Gln Met Arg
        1205                1210                1215

Asn Ser Lys Thr Gly Thr Glu Leu Asp Tyr Leu Ile Ser Pro Val
        1220                1225                1230

Ala Asp Val Asn Gly Asn Phe Phe Asp Ser Arg Gln Ala Pro Lys
        1235                1240                1245

Asn Met Pro Gln Asp Ala Asp Ala Asn Gly Ala Tyr His Ile Gly
        1250                1255                1260

Leu Lys Gly Leu Met Leu Leu Gly Arg Ile Lys Asn Asn Gln Glu
        1265                1270                1275

Gly Lys Lys Leu Asn Leu Val Ile Lys Asn Glu Glu Tyr Phe Glu
        1280                1285                1290

Phe Val Gln Asn Arg Asn Asn
        1295                1300

<210> SEQ ID NO 7
<211> LENGTH: 1206
<212> TYPE: PRT
<213> ORGANISM: Unknown
<220> FEATURE:
<223> OTHER INFORMATION: Lachnospiraceae sp.

<400> SEQUENCE: 7

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Gln Asp
        195                 200                 205

Ser Leu Phe Ile Val Glu Thr Phe Asn Lys Thr Leu Thr Gln Asp Gly
    210                 215                 220

Ile Asp Thr Tyr Asn Ser Gln Val Gly Lys Ile Asn Ser Ser Ile Asn
225                 230                 235                 240
```

-continued

Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Ser
            260                 265                 270

Phe Ile Asp Glu Phe Gln Ser Asp Glu Val Leu Ile Asp Asn Val Glu
            275                 280                 285

Ser Tyr Gly Ser Val Leu Ile Glu Ser Leu Lys Ser Ser Lys Val Ser
            290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Val Ile Val Phe Glu Asn
                325                 330                 335

Trp Arg Thr Phe Asp Asp Leu Leu Asn Gln Glu Tyr Asp Leu Ala Asn
            340                 345                 350

Glu Asn Lys Lys Lys Asp Asp Lys Tyr Phe Glu Lys Arg Gln Lys Glu
            355                 360                 365

Leu Lys Lys Asn Lys Ser Tyr Ser Leu Glu His Leu Cys Asn Leu Ser
            370                 375                 380

Glu Asp Ser Cys Asn Leu Ile Glu Asn Tyr Ile His Gln Ile Ser Asp
385                 390                 395                 400

Asp Ile Glu Asn Ile Ile Asn Asn Glu Thr Phe Leu Arg Ile Val
            405                 410                 415

Ile Asn Glu His Asp Arg Ser Arg Lys Leu Ala Lys Asn Arg Lys Ala
                420                 425                 430

Val Lys Ala Ile Lys Asp Phe Leu Asp Ser Ile Lys Val Leu Glu Arg
            435                 440                 445

Glu Leu Lys Leu Ile Asn Ser Ser Gly Gln Glu Leu Glu Lys Asp Leu
            450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
                485                 490                 495

Ser Thr Glu Lys Val Lys Leu Asn Phe Asn Arg Ser Thr Leu Leu Asn
            500                 505                 510

Gly Trp Asp Arg Asn Lys Glu Thr Asp Asn Leu Gly Val Leu Leu Leu
            515                 520                 525

Lys Asp Gly Lys Tyr Tyr Leu Gly Ile Met Asn Thr Ser Ala Asn Lys
            530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
            565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
            595                 600                 605

Leu Glu Asp Cys His Asn Leu Ile Asp Phe Phe Lys Glu Ser Ile Ser
            610                 615                 620

Lys His Glu Asp Trp Ser Lys Phe Gly Phe Lys Phe Asp Thr Gln Ala
625                 630                 635                 640

Ser Tyr Asn Asp Ile Ser Glu Phe Tyr Arg Glu Val Glu Lys Gln Gly
                645                 650                 655

```
Tyr Lys Leu Thr Tyr Thr Asp Ile Asp Glu Thr Tyr Ile Asn Asp Leu
            660                 665                 670

Ile Glu Arg Asn Glu Leu Tyr Leu Phe Gln Ile Tyr Asn Lys Asp Phe
        675                 680                 685

Ser Met Tyr Ser Lys Gly Lys Leu Asn Leu His Thr Leu Tyr Phe Met
    690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Ile Lys Asn Lys Asn Pro Asn
        740                 745                 750

Arg Ala Arg Thr Lys Glu Thr Ser Thr Phe Ser Tyr Asp Ile Val Lys
        755                 760                 765

Asp Lys Arg Tyr Ser Lys Asp Lys Phe Thr Leu His Ile Pro Ile Thr
        770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
                805                 810                 815

Gly Glu Arg Asn Leu Leu Tyr Val Val Val Ile Asp Ser Lys Gly Asn
                820                 825                 830

Ile Leu Glu Gln Ile Ser Leu Asn Ser Ile Ile Asn Lys Glu Tyr Asp
        835                 840                 845

Ile Glu Thr Asp Tyr His Ala Leu Leu Asp Glu Arg Glu Gly Gly Arg
850                 855                 860

Asp Lys Ala Arg Lys Asp Trp Asn Thr Val Glu Asn Ile Arg Asp Leu
865                 870                 875                 880

Lys Ala Gly Leu Tyr Leu Gln Val Val Asn Val Val Ala Lys Leu Val
                885                 890                 895

Leu Lys Tyr Asn Ala Ile Ile Cys Leu Glu Asp Leu Asn Phe Gly Phe
        900                 905                 910

Lys Arg Gly Arg Gln Lys Val Glu Lys Gln Val Tyr Gln Lys Phe Glu
        915                 920                 925

Lys Met Leu Ile Asp Lys Leu Asn Tyr Leu Val Ile Asp Lys Ser Arg
930                 935                 940

Glu Gln Thr Ser Pro Lys Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr Met Lys Cys Glu Asn Val Glu Lys
    995                 1000                1005

Ser Lys Arg Phe Phe Asp Gly Phe Asp Phe Ile Arg Phe Asn Ala
    1010                1015                1020

Leu Glu Asn Val Phe Glu Phe Gly Phe Asp Tyr Arg Ser Phe Thr
    1025                1030                1035

Gln Arg Ala Cys Gly Ile Asn Ser Lys Trp Thr Val Cys Thr Asn
    1040                1045                1050

Gly Glu Arg Ile Ile Lys Tyr Arg Asn Pro Asp Lys Asn Asn Met
    1055                1060                1065

Phe Asp Glu Lys Val Val Val Val Thr Asp Glu Met Lys Asn Leu
```

-continued

```
              1070                1075                1080

Phe Glu Gln Tyr Lys Ile Pro Tyr Glu Asp Gly Arg Asn Val Lys
    1085                1090                1095

Asp Met Ile Ile Ser Asn Glu Glu Ala Glu Phe Tyr Arg Arg Leu
    1100                1105                1110

Tyr Arg Leu Leu Gln Gln Thr Leu Gln Met Arg Asn Ser Thr Ser
    1115                1120                1125

Asp Gly Thr Arg Asp Tyr Ile Ile Ser Pro Val Lys Asn Lys Arg
    1130                1135                1140

Glu Ala Tyr Phe Asn Ser Glu Leu Ser Asp Gly Ser Val Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Ser Glu Gly Glu Lys Ile
    1175                1180                1185

Asn Leu Ala Met Thr Asn Ala Glu Trp Leu Glu Tyr Ala Gln Thr
    1190                1195                1200

His Leu Leu
    1205

<210> SEQ ID NO 8
<211> LENGTH: 1233
<212> TYPE: PRT
<213> ORGANISM: Unknown
<220> FEATURE:
<223> OTHER INFORMATION: Lachnospiraceae sp.

<400> SEQUENCE: 8

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
                20                  25                  30

Arg Glu Gln Lys Leu Leu Glu Gln Asp Ala Ala Phe Arg Lys Leu Val
            35                  40                  45

Glu Thr Val Thr Pro Ile Val Asp Asp Cys Ile Arg Lys Ile Ala Asp
    50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
```

```
            210                 215                 220
Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                    245                 250                 255

Arg Gly Asp Lys Asp Glu Ser Pro Leu Pro Lys Leu Lys Lys Leu His
                260                 265                 270

Lys Gln Ile Leu Met Pro Val Glu Lys Ala Phe Phe Val Arg Val Leu
            275                 280                 285

Ser Asn Asp Ser Asp Ala Arg Ser Ile Leu Glu Lys Ile Leu Lys Asp
        290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
                340                 345                 350

Glu Ser Lys Arg Ile Ser Glu Leu Met Glu Thr Leu Ser Pro Lys Glu
            355                 360                 365

Arg Lys Glu Ser Lys Lys Arg Leu Glu Gly Leu Glu Glu His Ile Arg
        370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
                405                 410                 415

Met Arg Lys Glu Lys Asp Leu Arg Thr Leu Leu Ser Lys Glu Asp Val
                420                 425                 430

Lys Ile Arg Gly Asn Arg His Asn Thr Leu Ile Val Lys Asn Tyr Phe
            435                 440                 445

Asn Ala Trp Thr Val Phe Arg Asn Leu Ile Arg Ile Leu Arg Arg Lys
        450                 455                 460

Ser Glu Ala Glu Ile Asp Ser Asp Phe Tyr Asp Val Leu Asp Asp Ser
465                 470                 475                 480

Val Glu Val Leu Ser Leu Thr Tyr Lys Gly Glu Asn Leu Cys Arg Ser
                485                 490                 495

Tyr Ile Thr Lys Lys Ile Gly Ser Asp Leu Lys Pro Glu Ile Ala Thr
                500                 505                 510

Tyr Gly Ser Ala Leu Arg Pro Asn Ser Arg Trp Trp Ser Pro Gly Glu
            515                 520                 525

Lys Phe Asn Val Lys Phe His Thr Ile Val Arg Arg Asp Gly Arg Leu
        530                 535                 540

Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
                565                 570                 575

Thr Ile Phe Leu Pro Lys Leu Val Phe Lys Asp Pro Glu Ala Phe Phe
                580                 585                 590

Arg Asp Asn Pro Glu Ala Asp Glu Phe Val Phe Leu Ser Gly Met Lys
            595                 600                 605

Ala Pro Val Thr Ile Thr Arg Glu Thr Tyr Glu Ala Tyr Arg Tyr Lys
        610                 615                 620

Leu Tyr Thr Val Gly Lys Leu Arg Asp Gly Glu Val Ser Glu Glu Glu
625                 630                 635                 640
```

-continued

Tyr Lys Arg Ala Leu Leu Gln Val Leu Thr Ala Tyr Lys Glu Phe Leu
                645                 650                 655

Glu Asn Arg Met Ile Tyr Ala Asp Leu Asn Phe Gly Phe Lys Asp Leu
                660                 665                 670

Glu Glu Tyr Lys Asp Ser Ser Glu Phe Ile Lys Gln Val Glu Thr His
                675                 680                 685

Asn Thr Phe Met Cys Trp Ala Lys Val Ser Ser Gln Leu Asp Asp
690                 695                 700

Leu Val Lys Ser Gly Asn Gly Leu Leu Phe Glu Ile Trp Ser Glu Arg
705                 710                 715                 720

Leu Glu Ser Tyr Tyr Lys Tyr Gly Asn Glu Lys Val Leu Arg Gly Tyr
                725                 730                 735

Glu Gly Val Leu Leu Ser Ile Leu Lys Asp Glu Asn Leu Val Ser Met
                740                 745                 750

Arg Thr Leu Leu Asn Ser Arg Pro Met Leu Val Tyr Arg Pro Lys Glu
                755                 760                 765

Ser Ser Lys Pro Met Val Val His Arg Asp Gly Ser Arg Val Val Asp
770                 775                 780

Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
                805                 810                 815

Lys Ala Arg Lys Ile Leu Asp Asn Lys Lys Val Lys Val Lys Val Leu
                820                 825                 830

Glu Ser Glu Arg Val Lys Trp Ser Lys Phe Tyr Asp Glu Gln Phe Ala
                835                 840                 845

Val Thr Phe Ser Val Lys Lys Asn Ala Asp Cys Leu Asp Thr Thr Lys
                850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
                900                 905                 910

Gly Ala Arg Asp Val Asp Trp Lys Glu Arg Phe Arg Gln Val Thr Lys
                915                 920                 925

Asp Arg Asn Glu Gly Tyr Asn Glu Trp Asp Tyr Ser Arg Thr Ser Asn
930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Glu Lys Met Ser Asn
                965                 970                 975

Ala Phe Lys Asp Lys Tyr Ser Phe Leu Asp Asp Val Thr Phe Lys Gly
                980                 985                 990

Phe Glu Thr Lys Lys Leu Ala Lys Leu Ser Asp Leu His Phe Arg Gly
                995                 1000                1005

Ile Lys Asp Gly Glu Pro Cys Ser Phe Thr Asn Pro Leu Gln Leu
                1010                1015                1020

Cys Gln Asn Asp Ser Asn Lys Ile Leu Gln Asp Gly Val Ile Phe
                1025                1030                1035

Met Val Pro Asn Ser Met Thr Arg Ser Leu Asp Pro Asp Thr Gly
                1040                1045                1050

Phe Ile Phe Ala Ile Asn Asp His Asn Ile Arg Thr Lys Lys Ala
1055                1060                1065

Lys Leu Asn Phe Leu Ser Lys Phe Asp Gln Leu Lys Val Ser Ser
1070                1075                1080

Glu Gly Cys Leu Ile Met Lys Tyr Ser Gly Asp Ser Leu Pro Thr
1085                1090                1095

His Asn Thr Asp Asn Arg Val Trp Asn Cys Cys Cys Asn His Pro
1100                1105                1110

Ile Thr Asn Tyr Asp Arg Glu Thr Lys Lys Val Glu Phe Ile Glu
1115                1120                1125

Glu Pro Val Glu Glu Leu Ser Arg Val Leu Glu Glu Asn Gly Ile
1130                1135                1140

Glu Thr Asp Thr Glu Leu Asn Lys Leu Asn Glu Arg Glu Asn Val
1145                1150                1155

Pro Gly Lys Val Val Asp Ala Ile Tyr Ser Leu Val Leu Asn Tyr
1160                1165                1170

Leu Arg Gly Thr Val Ser Gly Val Ala Gly Gln Arg Ala Val Tyr
1175                1180                1185

Tyr Ser Pro Val Thr Gly Lys Lys Tyr Asp Ile Ser Phe Ile Gln
1190                1195                1200

Ala Met Asn Leu Asn Arg Lys Cys Asp Tyr Tyr Arg Ile Gly Ser
1205                1210                1215

Lys Glu Arg Gly Glu Trp Thr Asp Phe Val Ala Gln Leu Ile Asn
1220                1225                1230

<210> SEQ ID NO 9
<211> LENGTH: 1227
<212> TYPE: PRT
<213> ORGANISM: Unknown
<220> FEATURE:
<223> OTHER INFORMATION: Lachnospiraceae sp.

<400> SEQUENCE: 9

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
        210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
        260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
        290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
                340                 345                 350

Gly Glu Trp Asn Val Ile Arg Asp Lys Trp Asn Ala Glu Tyr Asp Asp
                355                 360                 365

Ile His Leu Lys Lys Lys Ala Val Val Thr Glu Lys Tyr Glu Asp Asp
370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
                435                 440                 445

Asn Asp Ala Val Val Ala Ile Met Lys Asp Leu Leu Asp Ser Val Lys
        450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
        530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro

-continued

```
                 595                 600                 605
Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Asn Ile Asn Lys Cys Pro Lys Asn Ile Phe Lys Ile Asn Thr Glu
                805                 810                 815

Val Arg Val Leu Leu Lys His Asp Asn Pro Tyr Val Ile Gly Ile
            820                 825                 830

Asp Arg Gly Glu Arg Asn Leu Leu Tyr Ile Val Val Asp Gly Lys
        835                 840                 845

Gly Asn Ile Val Glu Gln Tyr Ser Leu Asn Glu Ile Ile Asn Asn Phe
    850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
        915                 920                 925

Asn Ser Gly Phe Lys Asn Ser Arg Val Lys Val Glu Lys Gln Val Tyr
    930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975

Ile Thr Asn Lys Phe Glu Ser Phe Lys Ser Met Ser Thr Gln Asn Gly
            980                 985                 990

Phe Ile Phe Tyr Ile Pro Ala Trp Leu Thr Ser Lys Ile Asp Pro Ser
        995                 1000                1005

Thr Gly Phe Val Asn Leu Leu Lys Thr Lys Tyr Thr Ser Ile Ala
    1010                1015                1020
```

```
Asp Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ser Asn Lys Glu Trp Leu
    1205                1210                1215

Glu Tyr Ala Gln Thr Ser Val Lys His
    1220                1225

<210> SEQ ID NO 10
<211> LENGTH: 1264
<212> TYPE: PRT
<213> ORGANISM: Leptospira inadai

<400> SEQUENCE: 10

Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Lys Asp Lys Ile Arg Ala Glu Asp Tyr Lys
        35                  40                  45

Ala Val Lys Lys Ile Ile Asp Lys Tyr His Arg Ala Tyr Ile Glu Glu
    50                  55                  60

Val Phe Asp Ser Val Leu His Gln Lys Lys Lys Lys Asp Lys Thr Arg
65                  70                  75                  80

Phe Ser Thr Gln Phe Ile Lys Glu Ile Lys Glu Phe Ser Glu Leu Tyr
                85                  90                  95

Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
        115                 120                 125

Ser Glu Glu Val Ala Glu Lys Tyr Asn Lys Asn Leu Phe Ser Lys Glu
    130                 135                 140

Leu Ile Arg Asn Glu Ile Glu Lys Phe Cys Glu Thr Asp Glu Glu Arg
```

```
            145                 150                 155                 160
Lys Gln Val Ser Asn Phe Lys Ser Phe Thr Thr Tyr Phe Thr Gly Phe
                    165                 170                 175

His Ser Asn Arg Gln Asn Ile Tyr Ser Asp Glu Lys Lys Ser Thr Ala
                    180                 185                 190

Ile Gly Tyr Arg Ile Ile His Gln Asn Leu Pro Lys Phe Leu Asp Asn
                195                 200                 205

Leu Lys Ile Ile Glu Ser Ile Gln Arg Arg Phe Lys Asp Phe Pro Trp
    210                 215                 220

Ser Asp Leu Lys Lys Asn Leu Lys Lys Ile Asp Lys Asn Ile Lys Leu
225                 230                 235                 240

Thr Glu Tyr Phe Ser Ile Asp Gly Phe Val Asn Val Leu Asn Gln Lys
                245                 250                 255

Gly Ile Asp Ala Tyr Asn Thr Ile Leu Gly Gly Lys Ser Glu Glu Ser
                260                 265                 270

Gly Glu Lys Ile Gln Gly Leu Asn Glu Tyr Ile Asn Leu Tyr Arg Gln
            275                 280                 285

Lys Asn Asn Ile Asp Arg Lys Asn Pro Leu Asn Val Lys Ile Leu Phe
    290                 295                 300

Lys Gln Ile Leu Gly Asp Arg Glu Thr Lys Ser Phe Ile Pro Glu Ala
305                 310                 315                 320

Phe Pro Asp Asp Gln Ser Val Leu Asn Ser Ile Thr Glu Phe Ala Lys
                325                 330                 335

Tyr Leu Lys Leu Asp Lys Lys Lys Ser Ile Ala Glu Leu Lys
                340                 345                 350

Lys Phe Leu Ser Ser Phe Asn Arg Tyr Glu Leu Asp Gly Ile Tyr Leu
            355                 360                 365

Ala Asn Asp Asn Ser Leu Ala Ser Ile Ser Thr Phe Leu Phe Asp Asp
    370                 375                 380

Trp Ser Phe Ile Lys Lys Ser Val Ser Phe Lys Tyr Asp Glu Ser Val
385                 390                 395                 400

Gly Asp Pro Lys Lys Ile Lys Ser Pro Leu Lys Tyr Glu Lys Glu
                405                 410                 415

Lys Glu Lys Trp Leu Lys Gln Lys Tyr Tyr Thr Ile Ser Phe Leu Asn
                420                 425                 430

Asp Ala Ile Glu Ser Tyr Ser Lys Ser Gln Asp Glu Lys Arg Val Lys
            435                 440                 445

Ile Arg Leu Glu Ala Tyr Phe Ala Glu Phe Lys Ser Lys Asp Asp Ala
    450                 455                 460

Lys Lys Gln Phe Asp Leu Leu Glu Arg Ile Glu Glu Ala Tyr Ala Ile
465                 470                 475                 480

Val Glu Pro Leu Leu Gly Ala Glu Tyr Pro Arg Asp Arg Asn Leu Lys
                485                 490                 495

Ala Asp Lys Lys Glu Val Gly Lys Ile Lys Asp Phe Leu Asp Ser Ile
            500                 505                 510

Lys Ser Leu Gln Phe Phe Leu Lys Pro Leu Leu Ser Ala Glu Ile Phe
    515                 520                 525

Asp Glu Lys Asp Leu Gly Phe Tyr Asn Gln Leu Glu Gly Tyr Tyr Glu
530                 535                 540

Glu Ile Asp Ile Ser Gly His Leu Tyr Asn Lys Val Arg Asn Tyr Leu
545                 550                 555                 560

Thr Gly Lys Ile Tyr Ser Lys Glu Lys Phe Lys Leu Asn Phe Glu Asn
                565                 570                 575
```

-continued

Ser Thr Leu Leu Lys Gly Trp Asp Glu Asn Arg Val Ala Asn Leu
         580             585             590

Cys Val Ile Phe Arg Glu Asp Gln Lys Tyr Tyr Leu Gly Val Met Asp
         595             600             605

Lys Glu Asn Asn Thr Ile Leu Ser Asp Ile Pro Lys Val Lys Pro Asn
610                 615             620

Glu Leu Phe Tyr Glu Lys Met Val Tyr Lys Leu Ile Pro Thr Pro His
625             630             635             640

Met Gln Leu Pro Arg Ile Ile Phe Ser Ser Asp Asn Leu Ser Ile Tyr
            645             650             655

Asn Pro Ser Lys Ser Ile Leu Lys Ile Arg Glu Ala Lys Ser Phe Lys
         660             665             670

Glu Gly Lys Asn Phe Lys Leu Lys Asp Cys His Lys Phe Ile Asp Phe
         675             680             685

Tyr Lys Glu Ser Ile Ser Lys Asn Glu Asp Trp Ser Arg Phe Asp Phe
         690             695             700

Lys Phe Ser Lys Thr Ser Ser Tyr Glu Asn Ile Ser Glu Phe Tyr Arg
705             710             715             720

Glu Val Glu Arg Gln Gly Tyr Asn Leu Asp Phe Lys Lys Val Ser Lys
            725             730             735

Phe Tyr Ile Asp Ser Leu Val Glu Asp Gly Lys Leu Tyr Leu Phe Gln
         740             745             750

Ile Tyr Asn Lys Asp Phe Ser Ile Phe Ser Lys Gly Lys Pro Asn Leu
         755             760             765

His Thr Ile Tyr Phe Arg Ser Leu Phe Ser Lys Glu Asn Leu Lys Asp
         770             775             780

Val Cys Leu Lys Leu Asn Gly Glu Ala Glu Met Phe Phe Arg Lys Lys
785             790             795             800

Ser Ile Asn Tyr Asp Glu Lys Lys Arg Glu Gly His His Pro Glu
            805             810             815

Leu Phe Glu Lys Leu Lys Tyr Pro Ile Leu Lys Asp Lys Arg Tyr Ser
            820             825             830

Glu Asp Lys Phe Gln Phe His Leu Pro Ile Ser Leu Asn Phe Lys Ser
            835             840             845

Lys Glu Arg Leu Asn Phe Asn Leu Lys Val Asn Glu Phe Leu Lys Arg
850             855             860

Asn Lys Asp Ile Asn Ile Ile Gly Ile Asp Arg Gly Glu Arg Asn Leu
865             870             875             880

Leu Tyr Leu Val Met Ile Asn Gln Lys Gly Glu Ile Leu Lys Gln Thr
            885             890             895

Leu Leu Asp Ser Met Gln Ser Gly Lys Gly Arg Pro Glu Ile Asn Tyr
            900             905             910

Lys Glu Lys Leu Gln Glu Lys Glu Ile Glu Arg Asp Lys Ala Arg Lys
         915             920             925

Ser Trp Gly Thr Val Glu Asn Ile Lys Glu Leu Lys Glu Gly Tyr Leu
         930             935             940

Ser Ile Val Ile His Gln Ile Ser Lys Leu Met Val Glu Asn Asn Ala
945             950             955             960

Ile Val Val Leu Glu Asp Leu Asn Ile Gly Phe Lys Arg Gly Arg Gln
            965             970             975

Lys Val Glu Arg Gln Val Tyr Gln Lys Phe Glu Lys Met Leu Ile Asp
         980             985             990

```
Lys Leu Asn Phe Leu Val Phe Lys Glu Asn Lys Pro Thr Glu Pro Gly
            995                 1000                1005

Gly Val Leu Lys Ala Tyr Gln Leu Thr Asp Glu Phe Gln Ser Phe
    1010                1015                1020

Glu Lys Leu Ser Lys Gln Thr Gly Phe Leu Phe Tyr Val Pro Ser
    1025                1030                1035

Trp Asn Thr Ser Lys Ile Asp Pro Arg Thr Gly Phe Ile Asp Phe
    1040                1045                1050

Leu His Pro Ala Tyr Glu Asn Ile Glu Lys Ala Lys Gln Trp Ile
    1055                1060                1065

Asn Lys Phe Asp Ser Ile Arg Phe Asn Ser Lys Met Asp Trp Phe
    1070                1075                1080

Glu Phe Thr Ala Asp Thr Arg Lys Phe Ser Glu Asn Leu Met Leu
    1085                1090                1095

Gly Lys Asn Arg Val Trp Val Ile Cys Thr Thr Asn Val Glu Arg
    1100                1105                1110

Tyr Phe Thr Ser Lys Thr Ala Asn Ser Ser Ile Gln Tyr Asn Ser
    1115                1120                1125

Ile Gln Ile Thr Glu Lys Leu Lys Glu Leu Phe Val Asp Ile Pro
    1130                1135                1140

Phe Ser Asn Gly Gln Asp Leu Lys Pro Glu Ile Leu Arg Lys Asn
    1145                1150                1155

Asp Ala Val Phe Phe Lys Ser Leu Leu Phe Tyr Ile Lys Thr Thr
    1160                1165                1170

Leu Ser Leu Arg Gln Asn Asn Gly Lys Lys Gly Glu Glu Glu Lys
    1175                1180                1185

Asp Phe Ile Leu Ser Pro Val Val Asp Ser Lys Gly Arg Phe Phe
    1190                1195                1200

Asn Ser Leu Glu Ala Ser Asp Asp Glu Pro Lys Asp Ala Asp Ala
    1205                1210                1215

Asn Gly Ala Tyr His Ile Ala Leu Lys Gly Leu Met Asn Leu Leu
    1220                1225                1230

Val Leu Asn Glu Thr Lys Glu Glu Asn Leu Ser Arg Pro Lys Trp
    1235                1240                1245

Lys Ile Lys Asn Lys Asp Trp Leu Glu Phe Val Trp Glu Arg Asn
    1250                1255                1260

Arg

<210> SEQ ID NO 11
<211> LENGTH: 1373
<212> TYPE: PRT
<213> ORGANISM: Moraxella bovoculi

<400> SEQUENCE: 11

Met Leu Phe Gln Asp Phe Thr His Leu Tyr Pro Leu Ser Lys Thr Val
1               5                   10                  15

Arg Phe Glu Leu Phe Ile Asp Arg Thr Leu Glu His Ile His Ala Lys
                20                  25                  30

Asn Phe Leu Ser Gln Asp Glu Thr Met Ala Asp Met His Gln Lys Val
        35                  40                  45

Lys Val Ile Leu Asp Asp Tyr His Arg Asp Phe Ile Ala Asp Met Met
    50                  55                  60

Gly Glu Val Lys Leu Thr Lys Leu Ala Glu Phe Tyr Asp Val Tyr Leu
65                  70                  75                  80
```

-continued

```
Lys Phe Arg Lys Asn Pro Lys Asp Asp Glu Leu Gln Lys Ala Gln Leu
                85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
            115                 120                 125

Leu Phe Lys Asp Gly Lys Glu Leu Gly Asp Leu Ala Lys Phe Val Ile
        130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
        435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
```

```
                500             505             510
    Phe Ala Lys Leu Leu Thr Thr Lys Thr Thr Leu Asp Asn Gln Asp Gly
                515             520             525
    Asn Phe Tyr Gly Glu Phe Gly Val Leu Tyr Asp Glu Leu Ala Lys Ile
                530             535             540
    Pro Thr Leu Tyr Asn Lys Val Arg Asp Tyr Leu Ser Gln Lys Pro Phe
    545             550             555             560
    Ser Thr Glu Lys Tyr Lys Leu Asn Phe Gly Asn Pro Thr Leu Leu Asn
                    565             570             575
    Gly Trp Asp Leu Asn Lys Glu Lys Asp Asn Phe Gly Val Ile Leu Gln
                    580             585             590
    Lys Asp Gly Cys Tyr Tyr Leu Ala Leu Leu Asp Lys Ala His Lys Lys
                    595             600             605
    Val Phe Asp Asn Ala Pro Asn Thr Gly Lys Ser Ile Tyr Gln Lys Met
                    610             615             620
    Ile Tyr Lys Tyr Leu Glu Val Arg Lys Gln Phe Pro Lys Val Phe Phe
    625             630             635             640
    Ser Lys Glu Ala Ile Ala Ile Asn Tyr His Pro Ser Lys Glu Leu Val
                    645             650             655
    Glu Ile Lys Asp Lys Gly Arg Gln Arg Ser Asp Asp Glu Arg Leu Lys
                    660             665             670
    Leu Tyr Arg Phe Ile Leu Glu Cys Leu Lys Ile His Pro Lys Tyr Asp
                    675             680             685
    Lys Lys Phe Glu Gly Ala Ile Gly Asp Ile Gln Leu Phe Lys Lys Asp
                    690             695             700
    Lys Lys Gly Arg Glu Val Pro Ile Ser Glu Lys Asp Leu Phe Lys Asp
    705             710             715             720
    Ile Asn Gly Ile Phe Ser Ser Lys Pro Lys Leu Glu Met Glu Asp Phe
                    725             730             735
    Phe Ile Gly Glu Phe Lys Arg Tyr Asn Pro Ser Gln Asp Leu Val Asp
                    740             745             750
    Gln Tyr Asn Ile Tyr Lys Lys Ile Asp Ser Asn Asp Asn Arg Lys Lys
                    755             760             765
    Glu Asn Phe Tyr Asn Asn His Pro Lys Phe Lys Lys Asp Leu Val Arg
                    770             775             780
    Tyr Tyr Tyr Glu Ser Met Cys Lys His Glu Glu Trp Glu Glu Ser Phe
    785             790             795             800
    Glu Phe Ser Lys Lys Leu Gln Asp Ile Gly Cys Tyr Val Asp Val Asn
                    805             810             815
    Glu Leu Phe Thr Glu Ile Glu Thr Arg Arg Leu Asn Tyr Lys Ile Ser
                    820             825             830
    Phe Cys Asn Ile Asn Ala Asp Tyr Ile Asp Glu Leu Val Glu Gln Gly
                    835             840             845
    Gln Leu Tyr Leu Phe Gln Ile Tyr Asn Lys Asp Phe Ser Pro Lys Ala
                    850             855             860
    His Gly Lys Pro Asn Leu His Thr Leu Tyr Phe Lys Ala Leu Phe Ser
    865             870             875             880
    Glu Asp Asn Leu Ala Asp Pro Ile Tyr Lys Leu Asn Gly Glu Ala Gln
                    885             890             895
    Ile Phe Tyr Arg Lys Ala Ser Leu Asp Met Asn Glu Thr Thr Ile His
                    900             905             910
    Arg Ala Gly Glu Val Leu Glu Asn Lys Asn Pro Asp Asn Pro Lys Lys
                    915             920             925
```

```
Arg Gln Phe Val Tyr Asp Ile Ile Lys Asp Lys Arg Tyr Thr Gln Lys
    930                 935                 940

Asp Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
            965                 970                 975

Tyr Asp Glu Val Asn Val Ile Gly Ile Asp Arg Gly Glu Arg His Leu
                980                 985                 990

Leu Tyr Leu Thr Val Ile Asn Ser Lys Gly Glu Ile Leu Glu Gln Cys
        995                 1000                1005

Ser Leu Asn Asp Ile Thr Thr Ala Ser Ala Asn Gly Thr Gln Met
    1010                1015                1020

Thr Thr Pro Tyr His Lys Ile Leu Asp Lys Arg Glu Ile Glu Arg
    1025                1030                1035

Leu Asn Ala Arg Val Gly Trp Gly Glu Ile Glu Thr Ile Lys Glu
    1040                1045                1050

Leu Lys Ser Gly Tyr Leu Ser His Val Val His Gln Ile Ser Gln
    1055                1060                1065

Leu Met Leu Lys Tyr Asn Ala Ile Val Val Leu Glu Asp Leu Asn
    1070                1075                1080

Phe Gly Phe Lys Arg Gly Arg Phe Lys Val Glu Lys Gln Ile Tyr
    1085                1090                1095

Gln Asn Phe Glu Asn Ala Leu Ile Lys Lys Leu Asn His Leu Val
    1100                1105                1110

Leu Lys Asp Lys Ala Asp Asp Glu Ile Gly Ser Tyr Lys Asn Ala
    1115                1120                1125

Leu Gln Leu Thr Asn Asn Phe Thr Asp Leu Lys Ser Ile Gly Lys
    1130                1135                1140

Gln Thr Gly Phe Leu Phe Tyr Val Pro Ala Trp Asn Thr Ser Lys
    1145                1150                1155

Ile Asp Pro Glu Thr Gly Phe Val Asp Leu Leu Lys Pro Arg Tyr
    1160                1165                1170

Glu Asn Ile Gln Ala Ser Gln Ala Phe Phe Gly Lys Phe Asp Lys
    1175                1180                1185

Ile Cys Tyr Asn Ala Asp Lys Asp Tyr Phe Glu Phe His Ile Asp
    1190                1195                1200

Tyr Ala Lys Phe Thr Asp Lys Ala Lys Asn Ser Arg Gln Ile Trp
    1205                1210                1215

Thr Ile Cys Ser His Gly Asp Lys Arg Tyr Val Tyr Asp Lys Thr
    1220                1225                1230

Ala Asn Gln Asn Lys Gly Ala Ala Lys Gly Ile Asn Val Asn Asp
    1235                1240                1245

Ile Leu Lys Ser Leu Phe Ala Arg His His Ile Asn Glu Lys Gln
    1250                1255                1260

Pro Asn Leu Val Met Asp Ile Cys Gln Asn Asn Asp Lys Glu Phe
    1265                1270                1275

His Lys Ser Leu Met Tyr Leu Leu Lys Thr Leu Leu Ala Leu Arg
    1280                1285                1290

Tyr Ser Asn Ala Ser Ser Asp Glu Asp Phe Ile Leu Ser Pro Val
    1295                1300                1305

Ala Asn Asp Glu Gly Val Phe Phe Asn Ser Ala Leu Ala Asp Asp
    1310                1315                1320
```

```
Thr Gln Pro Gln Asn Ala Asp Ala Asn Gly Ala Tyr His Ile Ala
    1325                1330                1335

Leu Lys Gly Leu Trp Leu Leu Asn Glu Leu Lys Asn Ser Asp Asp
    1340                1345                1350

Leu Asn Lys Val Lys Leu Ala Ile Asp Asn Gln Thr Trp Leu Asn
    1355                1360                1365

Phe Ala Gln Asn Arg
    1370

<210> SEQ ID NO 12
<211> LENGTH: 1352
<212> TYPE: PRT
<213> ORGANISM: Unknown
<220> FEATURE:
<223> OTHER INFORMATION: Parcubacteria bacterium

<400> SEQUENCE: 12

Met Glu Asn Ile Phe Asp Gln Phe Ile Gly Lys Tyr Ser Leu Ser Lys
 1               5                  10                  15

Thr Leu Arg Phe Glu Leu Lys Pro Val Gly Lys Thr Glu Asp Phe Leu
                20                  25                  30

Lys Ile Asn Lys Val Phe Glu Lys Asp Gln Thr Ile Asp Asp Ser Tyr
            35                  40                  45

Asn Gln Ala Lys Phe Tyr Phe Asp Ser Leu His Gln Lys Phe Ile Asp
        50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
                100                 105                 110

Arg Leu Gln Lys Glu Ile Asn Asp Ala Glu Asp Ile Ile Gln Lys Glu
            115                 120                 125

Lys Glu Lys Ile Tyr Lys Asp Val Arg Thr Leu Phe Asp Asn Glu Ala
        130                 135                 140

Glu Ser Trp Lys Thr Tyr Tyr Gln Glu Arg Glu Val Asp Gly Lys Lys
145                 150                 155                 160

Ile Thr Glu Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
                180                 185                 190

Lys Glu Lys Glu Phe Gln Ala Lys Asn Gln Pro Ser Leu Phe Val Glu
            195                 200                 205

Glu Lys Glu Asn Pro Gly Gln Lys Arg Tyr Ile Phe Asp Ser Phe Asp
        210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
                260                 265                 270

Lys Asn Asn His Thr Asp Leu Gly Phe Asp Glu Glu Asn Ile Phe Glu
            275                 280                 285

Ile Glu Arg Tyr Lys Asn Cys Leu Leu Gln Arg Glu Ile Glu His Ile
        290                 295                 300
```

-continued

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
    530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670

Gln Lys Met Ile Tyr Lys Gln Ile Ala Asp Ala Ser Lys Asp Val Pro
        675                 680                 685

Arg Leu Leu Leu Thr Ser Lys Lys Ala Met Glu Lys Phe Lys Pro Ser
    690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg

-continued

```
                725                 730                 735
Asn Cys Ile Pro Gln Tyr Ser Asn Trp Ser Phe Tyr Asp Phe Gln Phe
                    740                 745                 750

Gln Asp Thr Gly Lys Tyr Gln Asn Ile Lys Glu Phe Thr Asp Asp Val
            755                 760                 765

Gln Lys Tyr Gly Tyr Lys Ile Ser Phe Arg Asp Ile Asp Asp Glu Tyr
770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815

Leu Tyr Phe Glu His Ile Leu Ser Ala Glu Asn Leu Asn Asp Pro Val
            820                 825                 830

Phe Lys Leu Ser Gly Met Ala Glu Ile Phe Gln Arg Gln Pro Ser Val
        835                 840                 845

Asn Glu Arg Glu Lys Ile Thr Thr Gln Lys Asn Gln Cys Ile Leu Asp
850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
                885                 890                 895

Gln Val Gln Phe Asn Lys Ile Ile Asn Gln Arg Ile Ser Ser Ser Asp
            900                 905                 910

Asn Glu Met Arg Val Asn Val Ile Gly Ile Asp Arg Gly Glu Lys Asn
        915                 920                 925

Leu Leu Tyr Tyr Ser Val Val Lys Gln Asn Gly Glu Ile Ile Glu Gln
930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
                965                 970                 975

Val Lys Ile Lys Asp Leu Lys Lys Gly Tyr Ile Ser His Val Ile His
            980                 985                 990

Lys Ile Cys Gln Leu Ile Glu Lys  Tyr Ser Ala Ile Val  Val Leu Glu
        995                 1000                1005

Asp Leu Asn Met Arg Phe Lys  Gln Ile Arg Gly Gly  Ile Glu Arg
1010                1015                1020

Ser Val  Tyr Gln Gln Phe Glu  Lys Ala Leu Ile Asp  Lys Leu Gly
1025                1030                1035

Tyr Leu  Val Phe Lys Asp Asn  Arg Asp Leu Arg Ala  Pro Gly Gly
1040                1045                1050

Val Leu Asn Gly Tyr Gln Leu  Ser Ala Pro Phe Val  Ser Phe Glu
1055                1060                1065

Lys Met Arg Lys Gln Thr Gly  Ile Leu Phe Tyr Thr  Gln Ala Glu
1070                1075                1080

Tyr Thr  Ser Lys Thr Asp Pro  Ile Thr Gly Phe Arg  Lys Asn Val
1085                1090                1095

Tyr Ile  Ser Asn Ser Ala Ser  Leu Asp Lys Ile Lys  Glu Ala Val
1100                1105                1110

Lys Lys Phe Asp Ala Ile Gly  Trp Asp Gly Lys Glu  Gln Ser Tyr
1115                1120                1125

Phe Phe  Lys Tyr Asn Pro Tyr  Asn Leu Ala Asp Glu  Lys Tyr Lys
1130                1135                1140
```

```
Asn Ser Thr Val Ser Lys Glu Trp Ala Ile Phe Ala Ser Ala Pro
    1145                 1150                1155

Arg Ile Arg Arg Gln Lys Gly Glu Asp Gly Tyr Trp Lys Tyr Asp
    1160                1165                1170

Arg Val Lys Val Asn Glu Glu Phe Glu Lys Leu Leu Lys Val Trp
    1175                1180                1185

Asn Phe Val Asn Pro Lys Ala Thr Asp Ile Lys Gln Glu Ile Ile
    1190                1195                1200

Lys Lys Ile Lys Ala Gly Asp Leu Gln Gly Glu Lys Glu Leu Asp
    1205                1210                1215

Gly Arg Leu Arg Asn Phe Trp His Ser Phe Ile Tyr Leu Phe Asn
    1220                1225                1230

Leu Val Leu Glu Leu Arg Asn Ser Phe Ser Leu Gln Ile Lys Ile
    1235                1240                1245

Lys Ala Gly Glu Val Ile Ala Val Asp Glu Gly Val Asp Phe Ile
    1250                1255                1260

Ala Ser Pro Val Lys Pro Phe Phe Thr Thr Pro Asn Pro Tyr Ile
    1265                1270                1275

Pro Ser Asn Leu Cys Trp Leu Ala Val Glu Asn Ala Asp Ala Asn
    1280                1285                1290

Gly Ala Tyr Asn Ile Ala Arg Lys Gly Val Met Ile Leu Lys Lys
    1295                1300                1305

Ile Arg Glu His Ala Lys Lys Asp Pro Glu Phe Lys Lys Leu Pro
    1310                1315                1320

Asn Leu Phe Ile Ser Asn Ala Glu Trp Asp Glu Ala Ala Arg Asp
    1325                1330                1335

Trp Gly Lys Tyr Ala Gly Thr Thr Ala Leu Asn Leu Asp His
    1340                1345                1350

<210> SEQ ID NO 13
<211> LENGTH: 1260
<212> TYPE: PRT
<213> ORGANISM: Porphyromonas crevioricanis

<400> SEQUENCE: 13

Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
                20                  25                  30

Lys Ala Gly Ile Leu Lys Glu Asp Glu His Arg Ala Glu Ser Tyr Arg
            35                  40                  45

Arg Val Lys Lys Ile Ile Asp Thr Tyr His Lys Val Phe Ile Asp Ser
        50                  55                  60

Ser Leu Glu Asn Met Ala Lys Met Gly Ile Glu Asn Glu Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
```

```
                145                 150                 155                 160
Ser Val Glu Glu Ala Thr Arg Ser Leu Lys Glu Phe Asp Ser Phe Thr
                    165                 170                 175

Ser Tyr Phe Ala Gly Phe Tyr Glu Asn Arg Lys Asn Ile Tyr Ser Thr
                180                 185                 190

Lys Pro Gln Ser Thr Ala Ile Ala Tyr Arg Leu Ile His Glu Asn Leu
            195                 200                 205

Pro Lys Phe Ile Asp Asn Ile Leu Val Phe Gln Lys Ile Lys Glu Pro
        210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
                260                 265                 270

Ile Gly Lys Ile Val Thr Glu Gly Asp Gly Glu Met Lys Gly Leu Asn
            275                 280                 285

Glu His Ile Asn Leu Tyr Asn Gln Gln Arg Gly Arg Glu Asp Arg Leu
        290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
                340                 345                 350

Thr Gln Gln Leu Met Thr Ser Ile Ser Glu Tyr Asp Leu Ser Arg Ile
            355                 360                 365

Tyr Val Arg Asn Asp Ser Gln Leu Thr Asp Ile Ser Lys Lys Met Leu
        370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
                420                 425                 430

Cys Ile Ala Phe Leu Asp Asn Val Arg Asp Cys Arg Val Asp Thr Tyr
            435                 440                 445

Leu Ser Thr Leu Gly Gln Lys Glu Gly Pro His Gly Leu Ser Asn Leu
        450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
                500                 505                 510

Leu Lys Pro Leu Trp Gly Met Gly Asp Glu Pro Asp Lys Asp Glu Arg
            515                 520                 525

Phe Tyr Gly Glu Tyr Asn Tyr Ile Arg Gly Ala Leu Asp Gln Val Ile
        530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575
```

```
Trp Asp Arg Asn Lys Glu Lys Asp Asn Ser Cys Val Ile Leu Arg Lys
            580                 585                 590

Gly Gln Asn Phe Tyr Leu Ala Ile Met Asn Asn Arg His Lys Arg Ser
            595                 600                 605

Phe Glu Asn Lys Met Leu Pro Glu Tyr Lys Gly Glu Pro Tyr Phe
610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
            660                 665                 670

Phe Ser Met Asp Asp Leu His Glu Leu Ile Asp Phe Phe Lys His Ser
            675                 680                 685

Ile Glu Ala His Glu Asp Trp Lys Gln Phe Gly Phe Lys Phe Ser Asp
            690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
            755                 760                 765

Trp Arg Met Leu Phe Asp Glu Arg Asn Leu Ala Asp Val Ile Tyr Lys
            770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Lys Ser Arg
                805                 810                 815

Gln Lys Lys Gly Glu Glu Ser Leu Phe Glu Tyr Asp Leu Val Lys Asp
            820                 825                 830

Arg Arg Tyr Thr Met Asp Lys Phe Gln Phe His Val Pro Ile Thr Met
            835                 840                 845

Asn Phe Lys Cys Ser Ala Gly Ser Lys Val Asn Asp Met Val Asn Ala
850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu His Arg Asn Trp
            915                 920                 925

Gln Thr Ile Glu Gly Ile Lys Glu Leu Lys Gln Gly Tyr Leu Ser Gln
            930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
            980                 985                 990
```

Asn Tyr Leu Val Asp Lys Lys Lys Arg Pro Glu Asp Ile Gly Gly Leu
            995                 1000                1005

Leu Arg Ala Tyr Gln Phe Thr Ala Pro Phe Lys Ser Phe Lys Glu
    1010                1015                1020

Met Gly Lys Gln Asn Gly Phe Leu Phe Tyr Ile Pro Ala Trp Asn
    1025                1030                1035

Thr Ser Asn Ile Asp Pro Thr Gly Phe Val Asn Leu Phe His
    1040                1045                1050

Val Gln Tyr Glu Asn Val Asp Lys Ala Lys Ser Phe Phe Gln Lys
    1055                1060                1065

Phe Asp Ser Ile Ser Tyr Asn Pro Lys Lys Asp Trp Phe Glu Phe
    1070                1075                1080

Ala Phe Asp Tyr Lys Asn Phe Thr Lys Lys Ala Glu Gly Ser Arg
    1085                1090                1095

Ser Met Trp Ile Leu Cys Thr His Gly Ser Arg Ile Lys Asn Phe
    1100                1105                1110

Arg Asn Ser Gln Lys Asn Gly Gln Trp Asp Ser Glu Glu Phe Ala
    1115                1120                1125

Leu Thr Glu Ala Phe Lys Ser Leu Phe Val Arg Tyr Glu Ile Asp
    1130                1135                1140

Tyr Thr Ala Asp Leu Lys Thr Ala Ile Val Asp Glu Lys Gln Lys
    1145                1150                1155

Asp Phe Phe Val Asp Leu Leu Lys Leu Phe Lys Leu Thr Val Gln
    1160                1165                1170

Met Arg Asn Ser Trp Lys Glu Lys Asp Leu Asp Tyr Leu Ile Ser
    1175                1180                1185

Pro Val Ala Gly Ala Asp Gly Arg Phe Phe Asp Thr Arg Glu Gly
    1190                1195                1200

Asn Lys Ser Leu Pro Lys Asp Ala Asp Ala Asn Gly Ala Tyr Asn
    1205                1210                1215

Ile Ala Leu Lys Gly Leu Trp Ala Leu Arg Gln Ile Arg Gln Thr
    1220                1225                1230

Ser Glu Gly Gly Lys Leu Lys Leu Ala Ile Ser Asn Lys Glu Trp
    1235                1240                1245

Leu Gln Phe Val Gln Glu Arg Ser Tyr Glu Lys Asp
    1250                1255                1260

<210> SEQ ID NO 14
<211> LENGTH: 1324
<212> TYPE: PRT
<213> ORGANISM: Prevotella disiens

<400> SEQUENCE: 14

Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

```
Lys Asp Cys Lys Ser Asp Glu Glu Val Lys Lys Thr Ala Leu Arg
            100                 105                 110

Asn Lys Cys Thr Ser Ile Gln Arg Ala Met Arg Glu Ala Ile Ser Gln
            115                 120                 125

Ala Phe Leu Lys Ser Pro Gln Lys Lys Leu Leu Ala Ile Lys Asn Leu
        130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Asp Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
        355                 360                 365

Tyr Arg Asn Phe Ser Ile Asp Glu Ala Ile Asp Ala Gln Asn Ala Glu
    370                 375                 380

Leu Gln Thr Phe Asn Asn Tyr Glu Leu Ile Ala Asn Ala Leu Arg Ala
385                 390                 395                 400

Lys Ile Lys Lys Glu Thr Lys Gln Gly Arg Lys Ser Phe Glu Lys Tyr
                405                 410                 415

Glu Glu Tyr Ile Asp Lys Lys Val Lys Ala Ile Asp Ser Leu Ser Ile
            420                 425                 430

Gln Glu Ile Asn Glu Leu Val Glu Asn Tyr Val Ser Glu Phe Asn Ser
        435                 440                 445

Asn Ser Gly Asn Met Pro Arg Lys Val Glu Asp Tyr Phe Ser Leu Met
    450                 455                 460

Arg Lys Gly Asp Phe Gly Ser Asn Asp Leu Ile Glu Asn Ile Lys Thr
465                 470                 475                 480

Lys Leu Ser Ala Ala Glu Lys Leu Leu Gly Thr Lys Tyr Gln Glu Thr
                485                 490                 495

Ala Lys Asp Ile Phe Lys Lys Asp Glu Asn Ser Lys Leu Ile Lys Glu
            500                 505                 510
```

-continued

Leu Leu Asp Ala Thr Lys Gln Phe Gln His Phe Ile Lys Pro Leu Leu
        515                 520                 525

Gly Thr Gly Glu Glu Ala Asp Arg Asp Leu Val Phe Tyr Gly Asp Phe
530                 535                 540

Leu Pro Leu Tyr Glu Lys Phe Glu Leu Thr Leu Leu Tyr Asn Lys
545                 550                 555                 560

Val Arg Asn Arg Leu Thr Gln Lys Pro Tyr Ser Lys Asp Lys Ile Arg
                565                 570                 575

Leu Cys Phe Asn Lys Pro Lys Leu Met Thr Gly Trp Val Asp Ser Lys
                580                 585                 590

Thr Glu Lys Ser Asp Asn Gly Thr Gln Tyr Gly Gly Tyr Leu Phe Arg
        595                 600                 605

Lys Lys Asn Glu Ile Gly Glu Tyr Asp Tyr Phe Leu Gly Ile Ser Ser
        610                 615                 620

Lys Ala Gln Leu Phe Arg Lys Asn Glu Ala Val Ile Gly Asp Tyr Glu
625                 630                 635                 640

Arg Leu Asp Tyr Tyr Gln Pro Lys Ala Asn Thr Ile Tyr Gly Ser Ala
                645                 650                 655

Tyr Glu Gly Glu Asn Ser Tyr Lys Glu Asp Lys Lys Arg Leu Asn Lys
        660                 665                 670

Val Ile Ile Ala Tyr Ile Glu Gln Ile Lys Gln Thr Asn Ile Lys Lys
        675                 680                 685

Ser Ile Ile Glu Ser Ile Ser Lys Tyr Pro Asn Ile Ser Asp Asp Asp
        690                 695                 700

Lys Val Thr Pro Ser Ser Leu Leu Glu Lys Ile Lys Lys Val Ser Ile
705                 710                 715                 720

Asp Ser Tyr Asn Gly Ile Leu Ser Phe Lys Ser Phe Gln Ser Val Asn
                725                 730                 735

Lys Glu Val Ile Asp Asn Leu Leu Lys Thr Ile Ser Pro Leu Lys Asn
        740                 745                 750

Lys Ala Glu Phe Leu Asp Leu Ile Asn Lys Asp Tyr Gln Ile Phe Thr
        755                 760                 765

Glu Val Gln Ala Val Ile Asp Glu Ile Cys Lys Gln Lys Thr Phe Ile
770                 775                 780

Tyr Phe Pro Ile Ser Asn Val Glu Leu Glu Lys Glu Met Gly Asp Lys
785                 790                 795                 800

Asp Lys Pro Leu Cys Leu Phe Gln Ile Ser Asn Lys Asp Leu Ser Phe
                805                 810                 815

Ala Lys Thr Phe Ser Ala Asn Leu Arg Lys Arg Gly Ala Glu Asn
        820                 825                 830

Leu His Thr Met Leu Phe Lys Ala Leu Met Glu Gly Asn Gln Asp Asn
        835                 840                 845

Leu Asp Leu Gly Ser Gly Ala Ile Phe Tyr Arg Ala Lys Ser Leu Asp
850                 855                 860

Gly Asn Lys Pro Thr His Pro Ala Asn Glu Ala Ile Lys Cys Arg Asn
865                 870                 875                 880

Val Ala Asn Lys Asp Lys Val Ser Leu Phe Thr Tyr Asp Ile Tyr Lys
                885                 890                 895

Asn Arg Arg Tyr Met Glu Asn Lys Phe Leu Phe His Leu Ser Ile Val
                900                 905                 910

Gln Asn Tyr Lys Ala Ala Asn Asp Ser Ala Gln Leu Asn Ser Ser Ala
        915                 920                 925

Thr Glu Tyr Ile Arg Lys Ala Asp Asp Leu His Ile Ile Gly Ile Asp

```
              930            935            940
Arg Gly Glu Arg Asn Leu Leu Tyr Tyr Ser Val Ile Asp Met Lys Gly
945                 950            955                 960

Asn Ile Val Glu Gln Asp Ser Leu Asn Ile Ile Arg Asn Asn Asp Leu
            965                 970                 975

Glu Thr Asp Tyr His Asp Leu Leu Asp Lys Arg Glu Lys Glu Arg Lys
        980                 985                 990

Ala Asn Arg Gln Asn Trp Glu Ala  Val Glu Gly Ile Lys  Asp Leu Lys
        995                 1000                1005

Lys Gly  Tyr Leu Ser Gln Ala  Val His Gln Ile Ala  Gln Leu Met
    1010                1015                1020

Leu Lys  Tyr Asn Ala Ile Ile  Ala Leu Glu Asp Leu  Gly Gln Met
    1025                1030                1035

Phe Val  Thr Arg Gly Gln Lys  Ile Glu Lys Ala Val  Tyr Gln Gln
    1040                1045                1050

Phe Glu  Lys Ser Leu Val Asp  Lys Leu Ser Tyr Leu  Val Asp Lys
    1055                1060                1065

Lys Arg  Pro Tyr Asn Glu Leu  Gly Gly Ile Leu Lys  Ala Tyr Gln
    1070                1075                1080

Leu Ala  Ser Ser Ile Thr Lys  Asn Asn Ser Asp Lys  Gln Asn Gly
    1085                1090                1095

Phe Leu  Phe Tyr Val Pro Ala  Trp Asn Thr Ser Lys  Ile Asp Pro
    1100                1105                1110

Val Thr  Gly Phe Thr Asp Leu  Leu Arg Pro Lys Ala  Met Thr Ile
    1115                1120                1125

Lys Glu  Ala Gln Asp Phe Phe  Gly Ala Phe Asp Asn  Ile Ser Tyr
    1130                1135                1140

Asn Asp  Lys Gly Tyr Phe Glu  Phe Glu Thr Asn Tyr  Asp Lys Phe
    1145                1150                1155

Lys Ile  Arg Met Lys Ser Ala  Gln Thr Arg Trp Thr  Ile Cys Thr
    1160                1165                1170

Phe Gly  Asn Arg Ile Lys Arg  Lys Lys Asp Lys Asn  Tyr Trp Asn
    1175                1180                1185

Tyr Glu  Glu Val Glu Leu Thr  Glu Glu Phe Lys Lys  Leu Phe Lys
    1190                1195                1200

Asp Ser  Asn Ile Asp Tyr Glu  Asn Cys Asn Leu Lys  Glu Glu Ile
    1205                1210                1215

Gln Asn  Lys Asp Asn Arg Lys  Phe Phe Asp Asp Leu  Ile Lys Leu
    1220                1225                1230

Leu Gln  Leu Thr Leu Gln Met  Arg Asn Ser Asp Lys  Gly Asn
    1235                1240                1245

Asp Tyr  Ile Ile Ser Pro Val  Ala Asn Ala Glu Gly  Gln Phe Phe
    1250                1255                1260

Asp Ser  Arg Asn Gly Asp Lys  Lys Leu Pro Leu Asp  Ala Asp Ala
    1265                1270                1275

Asn Gly  Ala Tyr Asn Ile Ala  Arg Lys Gly Leu Trp  Asn Ile Arg
    1280                1285                1290

Gln Ile  Lys Gln Thr Lys Asn  Lys Asp Asp Leu Asn  Leu Ser Ile
    1295                1300                1305

Ser Ser  Thr Glu Trp Leu Asp  Phe Val Arg Glu Lys  Pro Tyr Leu
    1310                1315                1320

Lys
```

<210> SEQ ID NO 15
<211> LENGTH: 1484
<212> TYPE: PRT
<213> ORGANISM: Unknown
<220> FEATURE:
<223> OTHER INFORMATION: Peregrinibacteria bacterium
<220> FEATURE:
<221> NAME/KEY: misc_feature
<222> LOCATION: (1073)..(1073)
<223> OTHER INFORMATION: Xaa can be any naturally occurring amino acid

<400> SEQUENCE: 15

```
Met Ser Asn Phe Phe Lys Asn Phe Thr Asn Leu Tyr Glu Leu Ser Lys
 1               5                  10                  15

Thr Leu Arg Phe Glu Leu Lys Pro Val Gly Asp Thr Leu Thr Asn Met
            20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
    50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Lys Arg Lys Lys
    210                 215                 220

Asp Gly Thr Val Glu Lys Thr Glu Arg Lys Thr Glu Tyr Leu Asn Ala
225                 230                 235                 240

Tyr Gln Tyr Leu Lys Asn Asn Asn Lys Ile Thr Gln Ile Lys Asp Ala
                245                 250                 255

Glu Thr Glu Lys Met Ile Glu Ser Thr Pro Ile Ala Glu Lys Ile Phe
            260                 265                 270

Asp Val Tyr Tyr Phe Ser Ser Cys Leu Ser Gln Lys Gln Ile Glu Glu
        275                 280                 285

Tyr Asn Arg Ile Ile Gly His Tyr Asn Leu Leu Ile Asn Leu Tyr Asn
    290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
            340                 345                 350
```

-continued

```
Glu Ala Asn Lys Ser Arg Asn Glu Gly Lys Glu Ser His Ser Val Glu
            355                 360                 365

Glu Ile Ile Asn Lys Ala Gln Glu Ala Ile Asn Lys Tyr Phe Lys Ser
    370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                405                 410                 415

Met Asn Thr Ile Ser Asp Lys Tyr Phe Ala Asn Tyr His Asp Leu Gln
            420                 425                 430

Asp Arg Leu Lys Glu Ala Lys Val Phe Gln Lys Ala Asp Lys Lys Ser
        435                 440                 445

Glu Asp Asp Ile Lys Ile Pro Glu Ala Ile Glu Leu Ser Gly Leu Phe
    450                 455                 460

Gly Val Leu Asp Ser Leu Ala Asp Trp Gln Thr Thr Leu Phe Lys Ser
465                 470                 475                 480

Ser Ile Leu Ser Asn Glu Lys Leu Lys Ile Ile Thr Asp Ser Gln Thr
                485                 490                 495

Pro Ser Glu Ala Leu Leu Lys Met Ile Phe Asn Asp Ile Glu Lys Asn
            500                 505                 510

Met Glu Ser Phe Leu Lys Glu Thr Asn Asp Ile Ile Thr Leu Lys Lys
        515                 520                 525

Tyr Lys Gly Asn Lys Glu Gly Thr Glu Lys Ile Lys Gln Trp Phe Asp
    530                 535                 540

Tyr Thr Leu Ala Ile Asn Arg Met Leu Lys Tyr Phe Leu Val Lys Glu
545                 550                 555                 560

Asn Lys Ile Lys Gly Asn Ser Leu Asp Thr Asn Ile Ser Glu Ala Leu
                565                 570                 575

Lys Thr Leu Ile Tyr Ser Asp Asp Ala Glu Trp Phe Lys Trp Tyr Asp
            580                 585                 590

Ala Leu Arg Asn Tyr Leu Thr Gln Lys Pro Gln Asp Glu Ala Lys Glu
        595                 600                 605

Asn Lys Leu Lys Leu Asn Phe Asp Asn Pro Ser Leu Ala Gly Gly Trp
    610                 615                 620

Asp Val Asn Lys Glu Cys Ser Asn Phe Cys Val Ile Leu Lys Asp Lys
625                 630                 635                 640

Asn Glu Lys Lys Tyr Leu Ala Met Ile Lys Lys Gly Glu Asn Thr Leu
                645                 650                 655

Phe Gln Lys Glu Trp Thr Glu Gly Arg Gly Lys Asn Leu Thr Lys Lys
            660                 665                 670

Ser Asn Pro Leu Phe Glu Ile Asn Asn Cys Glu Ile Leu Ser Lys Met
        675                 680                 685

Glu Tyr Asp Phe Trp Ala Asp Val Ser Lys Met Ile Pro Lys Cys Ser
    690                 695                 700

Thr Gln Leu Lys Ala Val Val Asn His Phe Lys Gln Ser Asp Asn Glu
705                 710                 715                 720

Phe Ile Phe Pro Ile Gly Tyr Lys Val Thr Ser Gly Glu Lys Phe Arg
                725                 730                 735

Glu Glu Cys Lys Ile Ser Lys Gln Asp Phe Glu Leu Asn Asn Lys Val
            740                 745                 750

Phe Asn Lys Asn Glu Leu Ser Val Thr Ala Met Arg Tyr Asp Leu Ser
        755                 760                 765
```

-continued

```
Ser Thr Gln Glu Lys Gln Tyr Ile Lys Ala Phe Gln Lys Glu Tyr Trp
770             775                 780
Glu Leu Leu Phe Lys Gln Glu Lys Arg Asp Thr Lys Leu Thr Asn Asn
785             790                 795                 800
Glu Ile Phe Asn Glu Trp Ile Asn Phe Cys Asn Lys Lys Tyr Ser Glu
                805                 810                 815
Leu Leu Ser Trp Glu Arg Lys Tyr Lys Asp Ala Leu Thr Asn Trp Ile
                820                 825                 830
Asn Phe Cys Lys Tyr Phe Leu Ser Lys Tyr Pro Lys Thr Thr Leu Phe
                835                 840                 845
Asn Tyr Ser Phe Lys Glu Ser Glu Asn Tyr Asn Ser Leu Asp Glu Phe
850                 855                 860
Tyr Arg Asp Val Asp Ile Cys Ser Tyr Lys Leu Asn Ile Asn Thr Thr
865                 870                 875                 880
Ile Asn Lys Ser Ile Leu Asp Arg Leu Val Glu Gly Lys Leu Tyr
                    885                 890                 895
Leu Phe Glu Ile Lys Asn Gln Asp Ser Asn Asp Gly Lys Ser Ile Gly
                900                 905                 910
His Lys Asn Asn Leu His Thr Ile Tyr Trp Asn Ala Ile Phe Glu Asn
                915                 920                 925
Phe Asp Asn Arg Pro Lys Leu Asn Gly Glu Ala Glu Ile Phe Tyr Arg
930                 935                 940
Lys Ala Ile Ser Lys Asp Lys Leu Gly Ile Val Lys Gly Lys Lys Thr
945                 950                 955                 960
Lys Asn Gly Thr Trp Ile Ile Lys Asn Tyr Arg Phe Ser Lys Glu Lys
                965                 970                 975
Phe Ile Leu His Val Pro Ile Thr Leu Asn Phe Cys Ser Asn Asn Glu
                980                 985                 990
Tyr Val Asn Asp Ile Val Asn Thr Lys Phe Tyr Asn Phe Ser Asn Leu
                995                 1000                1005
His Phe Leu Gly Ile Asp Arg Gly Glu Lys His Leu Ala Tyr Tyr
        1010                1015                1020
Ser Leu Val Asn Lys Asn Gly Glu Ile Val Asp Gln Gly Thr Leu
        1025                1030                1035
Asn Leu Pro Phe Thr Asp Lys Asp Gly Asn Gln Arg Ser Ile Lys
        1040                1045                1050
Lys Glu Lys Tyr Phe Tyr Asn Lys Gln Glu Asp Lys Trp Glu Ala
        1055                1060                1065
Lys Glu Val Asp Xaa Trp Asn Tyr Asn Asp Leu Leu Asp Ala Met
        1070                1075                1080
Ala Ser Asn Arg Asp Met Ala Arg Lys Asn Trp Gln Arg Ile Gly
        1085                1090                1095
Thr Ile Lys Glu Ala Lys Asn Gly Tyr Val Ser Leu Val Ile Arg
        1100                1105                1110
Lys Ile Ala Asp Leu Ala Val Asn Asn Glu Arg Pro Ala Phe Ile
        1115                1120                1125
Val Leu Glu Asp Leu Asn Thr Gly Phe Lys Arg Ser Arg Gln Lys
        1130                1135                1140
Ile Asp Lys Ser Val Tyr Gln Lys Phe Glu Leu Ala Leu Ala Lys
        1145                1150                1155
Lys Leu Asn Phe Leu Val Asp Lys Asn Ala Lys Arg Asp Glu Ile
        1160                1165                1170
Gly Ser Pro Thr Lys Ala Leu Gln Leu Thr Pro Pro Val Asn Asn
```

-continued

```
            1175                1180                1185
Tyr Gly Asp Ile Glu Asn Lys Lys Gln Ala Gly Ile Met Leu Tyr
        1190                1195                1200

Thr Arg Ala Asn Tyr Thr Ser Gln Thr Asp Pro Ala Thr Gly Trp
    1205                1210                1215

Arg Lys Thr Ile Tyr Leu Lys Ala Gly Pro Glu Glu Thr Thr Tyr
1220                1225                1230

Lys Lys Asp Gly Lys Ile Lys Asn Lys Ser Val Lys Asp Gln Ile
        1235                1240                1245

Ile Glu Thr Phe Thr Asp Ile Gly Phe Asp Gly Lys Asp Tyr Tyr
    1250                1255                1260

Phe Glu Tyr Asp Lys Gly Glu Phe Val Asp Lys Thr Gly Glu
1265                1270                1275

Ile Lys Pro Lys Lys Trp Arg Leu Tyr Ser Gly Glu Asn Gly Lys
        1280                1285                1290

Ser Leu Asp Arg Phe Arg Gly Glu Arg Glu Lys Asp Lys Tyr Glu
    1295                1300                1305

Trp Lys Ile Asp Lys Ile Asp Ile Val Lys Ile Leu Asp Asp Leu
1310                1315                1320

Phe Val Asn Phe Asp Lys Asn Ile Ser Leu Leu Lys Gln Leu Lys
        1325                1330                1335

Glu Gly Val Glu Leu Thr Arg Asn Asn Glu His Gly Thr Gly Glu
    1340                1345                1350

Ser Leu Arg Phe Ala Ile Asn Leu Ile Gln Gln Ile Arg Asn Thr
1355                1360                1365

Gly Asn Asn Glu Arg Asp Asn Asp Phe Ile Leu Ser Pro Val Arg
        1370                1375                1380

Asp Glu Asn Gly Lys His Phe Asp Ser Arg Glu Tyr Trp Asp Lys
    1385                1390                1395

Glu Thr Lys Gly Glu Lys Ile Ser Met Pro Ser Ser Gly Asp Ala
1400                1405                1410

Asn Gly Ala Phe Asn Ile Ala Arg Lys Gly Ile Ile Met Asn Ala
        1415                1420                1425

His Ile Leu Ala Asn Ser Asp Ser Lys Asp Leu Ser Leu Phe Val
    1430                1435                1440

Ser Asp Glu Glu Trp Asp Leu His Leu Asn Asn Lys Thr Glu Trp
1445                1450                1455

Lys Lys Gln Leu Asn Ile Phe Ser Ser Arg Lys Ala Met Ala Lys
        1460                1465                1470

Arg Lys Lys Lys Arg Pro Ala Ala Thr Lys Lys
    1475                1480

<210> SEQ ID NO 16
<211> LENGTH: 1245
<212> TYPE: PRT
<213> ORGANISM: Porphyromonas macacae

<400> SEQUENCE: 16

Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
                20                  25                  30

Asn Ile Lys Lys Asn Gly Leu Ile Arg Arg Asp Glu Gln Arg Leu Asp
            35                  40                  45
```

```
Asp Tyr Glu Lys Leu Lys Lys Val Ile Asp Glu Tyr His Glu Asp Phe
    50                      55                      60

Ile Ala Asn Ile Leu Ser Ser Phe Ser Phe Ser Glu Glu Ile Leu Gln
65                  70                  75                   80

Ser Tyr Ile Gln Asn Leu Ser Ile Ser Glu Ala Arg Ala Lys Ile Glu
                85                  90                  95

Lys Thr Met Arg Asp Thr Leu Ala Lys Ala Phe Ser Glu Asp Glu Arg
            100                 105                 110

Tyr Lys Ser Ile Phe Lys Lys Glu Leu Val Lys Lys Asp Ile Pro Val
            115                 120                 125

Trp Cys Pro Ala Tyr Lys Ser Leu Cys Lys Lys Phe Asp Asn Phe Thr
130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
            195                 200                 205

Trp Pro Ser Phe Val Lys Thr Pro Asp Asp Leu Cys Asn Leu Lys Thr
210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
            275                 280                 285

Ser Phe Ile Ser Asp Thr Leu Glu Asn Asp Asp Gln Val Phe Cys Val
290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
            355                 360                 365

Lys Thr Glu Val Leu Met Pro Arg Lys Lys Glu Ser Val Glu Arg Tyr
370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430

Tyr Leu Val Ser Asp Gly Glu Val Ile Leu Tyr Glu Glu Gly Ser Asn
            435                 440                 445

Ile Trp Asp Glu Val Leu Ile Ala Phe Arg Asp Leu Gln Val Ile Leu
450                 455                 460

Asp Lys Asp Phe Thr Glu Lys Lys Leu Gly Lys Asp Glu Glu Ala Val
```

-continued

```
465                 470                 475                 480
Ser Val Ile Lys Lys Ala Leu Asp Ser Ala Leu Arg Leu Arg Lys Phe
                485                 490                 495
Phe Asp Leu Leu Ser Gly Thr Gly Ala Glu Ile Arg Arg Asp Ser Ser
                500                 505                 510
Phe Tyr Ala Leu Tyr Thr Asp Arg Met Asp Lys Leu Lys Gly Leu Leu
                515                 520                 525
Lys Met Tyr Asp Lys Val Arg Asn Tyr Leu Thr Lys Lys Pro Tyr Ser
            530                 535                 540
Ile Glu Lys Phe Lys Leu His Phe Asp Asn Pro Ser Leu Leu Ser Gly
545                 550                 555                 560
Trp Asp Lys Asn Lys Glu Leu Asn Asn Leu Ser Val Ile Phe Arg Gln
                565                 570                 575
Asn Gly Tyr Tyr Tyr Leu Gly Ile Met Thr Pro Lys Gly Lys Asn Leu
            580                 585                 590
Phe Lys Thr Leu Pro Lys Leu Gly Ala Glu Glu Met Phe Tyr Glu Lys
        595                 600                 605
Met Glu Tyr Lys Gln Ile Ala Glu Pro Met Leu Met Leu Pro Lys Val
        610                 615                 620
Phe Phe Pro Lys Lys Thr Lys Pro Ala Phe Ala Pro Asp Gln Ser Val
625                 630                 635                 640
Val Asp Ile Tyr Asn Lys Lys Thr Phe Lys Thr Gly Gln Lys Gly Phe
                645                 650                 655
Asn Lys Lys Asp Leu Tyr Arg Leu Ile Asp Phe Tyr Lys Glu Ala Leu
            660                 665                 670
Thr Val His Glu Trp Lys Leu Phe Asn Phe Ser Phe Ser Pro Thr Glu
        675                 680                 685
Gln Tyr Arg Asn Ile Gly Glu Phe Phe Asp Glu Val Arg Glu Gln Ala
        690                 695                 700
Tyr Lys Val Ser Met Val Asn Val Pro Ala Ser Tyr Ile Asp Glu Ala
705                 710                 715                 720
Val Glu Asn Gly Lys Leu Tyr Leu Phe Gln Ile Tyr Asn Lys Asp Phe
                725                 730                 735
Ser Pro Tyr Ser Lys Gly Ile Pro Asn Leu His Thr Leu Tyr Trp Lys
            740                 745                 750
Ala Leu Phe Ser Glu Gln Asn Gln Ser Arg Val Tyr Lys Leu Cys Gly
        755                 760                 765
Gly Gly Glu Leu Phe Tyr Arg Lys Ala Ser Leu His Met Gln Asp Thr
    770                 775                 780
Thr Val His Pro Lys Gly Ile Ser Ile His Lys Lys Asn Leu Asn Lys
785                 790                 795                 800
Lys Gly Glu Thr Ser Leu Phe Asn Tyr Asp Leu Val Lys Asp Lys Arg
                805                 810                 815
Phe Thr Glu Asp Lys Phe Phe Phe His Val Pro Ile Ser Ile Asn Tyr
            820                 825                 830
Lys Asn Lys Lys Ile Thr Asn Val Asn Gln Met Val Arg Asp Tyr Ile
        835                 840                 845
Ala Gln Asn Asp Asp Leu Gln His Gly Ile Asp Arg Gly Glu Arg Asn
        850                 855                 860
Leu Leu Tyr Ile Ser Arg Ile Asp Thr Arg Gly Asn Leu Leu Glu Gln
865                 870                 875                 880
Phe Ser Leu Asn Val Ile Glu Ser Asp Lys Gly Asp Leu Arg Thr Asp
                885                 890                 895
```

Tyr Gln Lys Ile Leu Gly Asp Arg Glu Gln Glu Arg Leu Arg Arg Arg
              900                 905                 910

Gln Glu Trp Lys Ser Ile Glu Ser Ile Lys Asp Leu Lys Asp Gly Tyr
              915                 920                 925

Met Ser Gln Val Val His Lys Ile Cys Asn Met Val Val Glu His Lys
              930                 935                 940

Ala Ile Val Val Leu Glu Asn Leu Asn Leu Ser Phe Met Lys Gly Arg
945                 950                 955                 960

Lys Lys Val Glu Lys Ser Val Tyr Gly Lys Phe Glu Arg Met Leu Val
              965                 970                 975

Asp Lys Leu Asn Tyr Leu Val Val Asp Lys Lys Asn Leu Ser Asn Glu
              980                 985                 990

Pro Gly Gly Leu Tyr Ala Ala Tyr Gln Leu Thr Asn Pro Leu Phe Ser
              995                1000                1005

Phe Glu Glu Leu His Arg Tyr Pro Gln Ser Gly Ile Leu Phe Phe
     1010                1015                1020

Val Asp Pro Trp Asn Thr Ser Leu Thr Asp Pro Ser Thr Gly Phe
     1025                1030                1035

Val Asn Leu Leu Gly Arg Ile Asn Tyr Thr Asn Val Gly Asp Ala
     1040                1045                1050

Arg Lys Phe Phe Asp Arg Phe Asn Ala Ile Arg Tyr Asp Gly Lys
     1055                1060                1065

Gly Asn Ile Leu Phe Asp Leu Asp Leu Ser Arg Phe Asp Val Arg
     1070                1075                1080

Val Glu Thr Gln Arg Lys Leu Trp Thr Leu Thr Thr Phe Gly Ser
     1085                1090                1095

Arg Ile Ala Lys Ser Lys Lys Ser Gly Lys Trp Met Val Glu Arg
     1100                1105                1110

Ile Glu Asn Leu Ser Leu Cys Phe Leu Glu Leu Phe Glu Gln Phe
     1115                1120                1125

Asn Ile Gly Tyr Arg Val Glu Lys Asp Leu Lys Lys Ala Ile Leu
     1130                1135                1140

Ser Gln Asp Arg Lys Glu Phe Tyr Val Arg Leu Ile Tyr Leu Phe
     1145                1150                1155

Asn Leu Met Met Gln Ile Arg Asn Ser Asp Gly Glu Glu Asp Tyr
     1160                1165                1170

Ile Leu Ser Pro Ala Leu Asn Glu Lys Asn Leu Gln Phe Asp Ser
     1175                1180                1185

Arg Leu Ile Glu Ala Lys Asp Leu Pro Val Asp Ala Asp Ala Asn
     1190                1195                1200

Gly Ala Tyr Asn Val Ala Arg Lys Gly Leu Met Val Val Gln Arg
     1205                1210                1215

Ile Lys Arg Gly Asp His Glu Ser Ile His Arg Ile Gly Arg Ala
     1220                1225                1230

Gln Trp Leu Arg Tyr Val Gln Glu Gly Ile Val Glu
     1235                1240                1245

<210> SEQ ID NO 17
<211> LENGTH: 1250
<212> TYPE: PRT
<213> ORGANISM: Smithella sp.

<400> SEQUENCE: 17

Met Gln Thr Leu Phe Glu Asn Phe Thr Asn Gln Tyr Pro Val Ser Lys

-continued

```
1               5                   10                  15
Thr Leu Arg Phe Glu Leu Ile Pro Gln Gly Lys Thr Lys Asp Phe Ile
                20                  25                  30
Glu Gln Lys Gly Leu Leu Lys Lys Asp Glu Asp Arg Ala Glu Lys Tyr
                35                  40                  45
Lys Lys Val Lys Asn Ile Ile Asp Glu Tyr His Lys Asp Phe Ile Glu
50                  55                  60
Lys Ser Leu Asn Gly Leu Lys Leu Asp Gly Leu Glu Lys Tyr Lys Thr
65                  70                  75                  80
Leu Tyr Leu Lys Gln Glu Lys Asp Asp Lys Asp Lys Lys Ala Phe Asp
                85                  90                  95
Lys Glu Lys Glu Asn Leu Arg Lys Gln Ile Ala Asn Ala Phe Arg Asn
                100                 105                 110
Asn Glu Lys Phe Lys Thr Leu Phe Ala Lys Glu Leu Ile Lys Asn Asp
                115                 120                 125
Leu Met Ser Phe Ala Cys Glu Glu Asp Lys Lys Asn Val Lys Glu Phe
130                 135                 140
Glu Ala Phe Thr Thr Tyr Phe Thr Gly Phe His Gln Asn Arg Ala Asn
145                 150                 155                 160
Met Tyr Val Ala Asp Glu Lys Arg Thr Ala Ile Ala Ser Arg Leu Ile
                165                 170                 175
His Glu Asn Leu Pro Lys Phe Ile Asp Asn Ile Lys Ile Phe Glu Lys
                180                 185                 190
Met Lys Lys Glu Ala Pro Glu Leu Leu Ser Pro Phe Asn Gln Thr Leu
                195                 200                 205
Lys Asp Met Lys Asp Val Ile Lys Gly Thr Thr Leu Glu Glu Ile Phe
                210                 215                 220
Ser Leu Asp Tyr Phe Asn Lys Thr Leu Thr Gln Ser Gly Ile Asp Ile
225                 230                 235                 240
Tyr Asn Ser Val Ile Gly Gly Arg Thr Pro Glu Glu Gly Lys Thr Lys
                245                 250                 255
Ile Lys Gly Leu Asn Glu Tyr Ile Asn Thr Asp Phe Asn Gln Lys Gln
                260                 265                 270
Thr Asp Lys Lys Lys Arg Gln Pro Lys Phe Lys Gln Leu Tyr Lys Gln
                275                 280                 285
Ile Leu Ser Asp Arg Gln Ser Leu Ser Phe Ile Ala Glu Ala Phe Lys
                290                 295                 300
Asn Asp Thr Glu Ile Leu Glu Ala Ile Glu Lys Phe Tyr Val Asn Glu
305                 310                 315                 320
Leu Leu His Phe Ser Asn Glu Gly Lys Ser Thr Asn Val Leu Asp Ala
                325                 330                 335
Ile Lys Asn Ala Val Ser Asn Leu Glu Ser Phe Asn Leu Thr Lys Met
                340                 345                 350
Tyr Phe Arg Ser Gly Ala Ser Leu Thr Asp Val Ser Arg Lys Val Phe
                355                 360                 365
Gly Glu Trp Ser Ile Ile Asn Arg Ala Leu Asp Asn Tyr Tyr Ala Thr
                370                 375                 380
Thr Tyr Pro Ile Lys Pro Arg Glu Lys Ser Glu Lys Tyr Glu Glu Arg
385                 390                 395                 400
Lys Glu Lys Trp Leu Lys Gln Asp Phe Asn Val Ser Leu Ile Gln Thr
                405                 410                 415
Ala Ile Asp Glu Tyr Asp Asn Glu Thr Val Lys Gly Lys Asn Ser Gly
                420                 425                 430
```

```
Lys Val Ile Ala Asp Tyr Phe Ala Lys Phe Cys Asp Asp Lys Glu Thr
    435                 440                 445

Asp Leu Ile Gln Lys Val Asn Glu Gly Tyr Ile Ala Val Lys Asp Leu
    450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
                    485                 490                 495

His Phe Val Arg Pro Leu Ser Leu Lys Asp Thr Asp Lys Glu Lys Asp
                500                 505                 510

Glu Thr Phe Tyr Ser Leu Phe Thr Pro Leu Tyr Asp His Leu Thr Gln
                515                 520                 525

Thr Ile Ala Leu Tyr Asn Lys Val Arg Asn Tyr Leu Thr Gln Lys Pro
    530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                    565                 570                 575

Arg Lys Asp Asn Leu Tyr Tyr Leu Gly Ile Met Asp Lys Arg His Asn
                580                 585                 590

Arg Ile Phe Arg Asn Val Pro Lys Ala Asp Lys Lys Asp Phe Cys Tyr
                595                 600                 605

Glu Lys Met Val Tyr Lys Leu Leu Pro Gly Ala Asn Lys Met Leu Pro
                610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                    645                 650                 655

Phe Asn Leu Asn His Cys His Lys Leu Ile Asp Phe Phe Lys Asp Ser
                660                 665                 670

Ile Asn Lys His Glu Asp Trp Lys Asn Phe Asp Phe Arg Phe Ser Ala
                675                 680                 685

Thr Ser Thr Tyr Ala Asp Leu Ser Gly Phe Tyr His Glu Val Glu His
                690                 695                 700

Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
                    725                 730                 735

Asp Phe Ser Pro Phe Ser Lys Gly Lys Pro Asn Leu His Thr Leu Tyr
                740                 745                 750

Trp Lys Met Leu Phe Asp Glu Asn Asn Leu Lys Asp Val Val Tyr Lys
                755                 760                 765

Leu Asn Gly Glu Ala Glu Val Phe Tyr Arg Lys Lys Ser Ile Ala Glu
    770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
                805                 810                 815

Asp Lys Arg Tyr Thr Ile Asp Lys Phe Gln Phe His Ile Pro Ile Thr
                820                 825                 830

Met Asn Phe Lys Ala Glu Gly Ile Phe Asn Met Asn Gln Arg Val Asn
                835                 840                 845
```

```
Gln Phe Leu Lys Ala Asn Pro Asp Ile Asn Ile Ile Gly Ile Asp Arg
    850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
                885                 890                 895

Val Asp Tyr His Asn Leu Leu Asp Lys Lys Glu Gly Asp Arg Ala Thr
            900                 905                 910

Ala Arg Gln Glu Trp Gly Val Ile Glu Thr Ile Lys Glu Leu Lys Glu
        915                 920                 925

Gly Tyr Leu Ser Gln Val Ile His Lys Leu Thr Asp Leu Met Ile Glu
930                 935                 940

Asn Asn Ala Ile Ile Val Met Glu Asp Leu Asn Phe Gly Phe Lys Arg
945                 950                 955                 960

Gly Arg Gln Lys Val Glu Lys Gln Val Tyr Gln Lys Phe Glu Lys Met
                965                 970                 975

Leu Ile Asp Lys Leu Asn Tyr Leu Val Asp Lys Asn Lys Lys Ala Asn
            980                 985                 990

Glu Leu Gly Gly Leu Leu Asn Ala Phe Gln Leu Ala Asn Lys Phe Glu
        995                 1000                1005

Ser Phe Gln Lys Met Gly Lys Gln Asn Gly Phe Ile Phe Tyr Val
    1010                1015                1020

Pro Ala Trp Asn Thr Ser Lys Thr Asp Pro Ala Thr Gly Phe Ile
    1025                1030                1035

Asp Phe Leu Lys Pro Arg Tyr Glu Asn Leu Asn Gln Ala Lys Asp
    1040                1045                1050

Phe Phe Glu Lys Phe Asp Ser Ile Arg Leu Asn Ser Lys Ala Asp
    1055                1060                1065

Tyr Phe Glu Phe Ala Phe Asp Phe Lys Asn Phe Thr Glu Lys Ala
    1070                1075                1080

Asp Gly Gly Arg Thr Lys Trp Thr Val Cys Thr Thr Asn Glu Asp
    1085                1090                1095

Arg Tyr Gln Trp Asn Arg Ala Leu Asn Asn Asn Arg Gly Ser Gln
    1100                1105                1110

Glu Lys Tyr Asp Ile Thr Ala Glu Leu Lys Ser Leu Phe Asp Gly
    1115                1120                1125

Lys Val Asp Tyr Lys Ser Gly Lys Asp Leu Lys Gln Gln Ile Ala
    1130                1135                1140

Ser Gln Glu Ser Ala Asp Phe Lys Ala Leu Met Lys Asn Leu
    1145                1150                1155

Ser Ile Thr Leu Ser Leu Arg His Asn Asn Gly Glu Lys Gly Asp
    1160                1165                1170

Asn Glu Gln Asp Tyr Ile Leu Ser Pro Val Ala Asp Ser Lys Gly
    1175                1180                1185

Arg Phe Phe Asp Ser Arg Lys Ala Asp Asp Met Pro Lys Asn
    1190                1195                1200

Ala Asp Ala Asn Gly Ala Tyr His Ile Ala Leu Lys Gly Leu Trp
    1205                1210                1215

Cys Leu Glu Gln Ile Ser Lys Thr Asp Asp Leu Lys Lys Val Lys
    1220                1225                1230

Leu Ala Ile Ser Asn Lys Glu Trp Leu Glu Phe Val Gln Thr Leu
    1235                1240                1245

Lys Gly
```

<210> SEQ ID NO 18
<211> LENGTH: 3987
<212> TYPE: DNA
<213> ORGANISM: Artificial sequence
<220> FEATURE:
<223> OTHER INFORMATION: Synthetic polynucleotide

<400> SEQUENCE: 18

```
atggccggga gcaagaagcg ccggataaag caggacacgc agttcgaggg cttcaccaac    60
ctgtaccaag tctccaagac gctccggttc gagcttatcc cgcaagggaa gaccctgaaa   120
cacatccagg aacaaggttt catcgaggag gacaaggccc gcaacgacca ctacaaggag   180
ctcaagccca taatcgatcg gatctacaag acgtacgccg accagtgcct ccaactggtg   240
cagctcgact gggagaacct gagcgccgcc attgacagct accgcaagga aaagacggag   300
gagacgcgca acgcccttat tgaggagcaa gccacctacc gcaacgccat ccacgactac   360
ttcatcgggc gcaccgacaa cctgacggac gcgatcaaca agcgccacgc ggaaatctac   420
aagggccttt tcaaggccga gctcttcaac gggaaggtcc taaaacagct cgggactgtc   480
acgacaaccg agcatgagaa cgccctcctt cgcagcttcg acaagttcac cacatacttc   540
tcgggcttct accggaaccg caagaacgtt ttcagcgccg aggacatctc caccgccatc   600
ccgcacagga tcgtccagga caacttcccc aagttcaagg agaactgcca catcttcacg   660
cgcctgatta cagccgtacc ttcacttcgt gagcacttcg agaacgtcaa aaaggccatc   720
gggatcttcg tctccacgtc catcgaggag gtattctctt tcccgttcta taaccagctc   780
ctgacccaga cgcagatcga cctctacaac cagctactgg gcggcatcag ccggggaggcc   840
gggaccgaga aaataaaggg cctcaacgaa gttctcaacc tggccatcca agaagaacgac    900
gagaccgcgc atatcatcgc atccctgccg catcgcttca ttcctttgtt caagcagata   960
ttgagcgacc ggaacaccct ctcgttcatc ctcgaagaat tcaagagcga cgaggaggtc  1020
attcagtctt tctgcaagta caagacgctc ctacggaatg agaatgtgct ggagaccgcg  1080
gaggcactct tcaatgagct gaactccatt gacctgaccc acatcttcat tagccacaag  1140
aaactggaga cgatctccag cgccctgtgc gaccactggg acactctccg caacgccctc  1200
tacgaacgcc ggatctccga acttaccggc aagataacta agtcggctaa ggagaaggtg  1260
caacggagcc tcaagcacga ggacatcaac cttcaggaaa tcatctcagc cgcgggcaag  1320
gagctgagcg aggcgtttaa gcagaaaaca tcggagatac tgagccacgc gcacgcggcc  1380
ctggatcaac cgctgccgac gactctcaag aagcaagagg agaaggaaat ccttaagtcc  1440
cagctcgact cgctgctcgg cctctatcac ttgctcgact ggttcgcggt tgatgagtcc  1500
aacgaggtgg acccggagtt ctccgcgcgc ctcacgggta ttaagctgga gatggagcca  1560
agcttaagct tctacaacaa ggcccgcaac tacgcgacca aaaaaccgta ctcagtcgag  1620
aaattcaagc tgaatttcca gatgcctaca ttggcgaggg ggtgggacgt gaaccgcgag  1680
aagaacaatg gagccatcct gttcgtcaaa aatgggttgt actacctggg catcatgccc  1740
aagcagaagg gccgttacaa ggccctgtca ttcgagccta cgagaagac ctcggagggc  1800
ttcgacaaga tgtactacga ctatttcccg gacgccgcca agatgatccc gaagtgctcc  1860
acgcagctca agccgtcac ggcccacttc cagacgcata ccacgccgat acttctgagc  1920
aacaacttca ttgagccgct agagatcacg aaggagatat acgacctaaa caaccccgaa  1980
aaggagccca agaagttcca gacagcctac gctaagaaga caggtgatca gaagggatat  2040
```

| | |
|---|---|
| agggaggcac tctgcaagtg gatcgacttc acgcgcgact tcctgtcgaa atatacaaag | 2100 |
| acgaccagca ttgacctaag ttctctccgc ccatcctccc agtacaagga tctgggcgag | 2160 |
| tattatgcgg agctgaaccc attgctgtac cacatcagct tccagaggat cgccgagaag | 2220 |
| gagattatgg acgcggtgga gacggggaaa ctatacctgt tccaaatata taacaaggac | 2280 |
| ttcgctaaag ggcaccacgg gaagcccaac ctgcacacac tctactggac gggcttgttt | 2340 |
| tcgccagaaa atttggccaa gacttcgatc aagctcaacg gccaggcgga gttgttttac | 2400 |
| cgtcccaagt ctcgcatgaa gcgcatggcg catcgcctcg gagagaaaat gcttaacaag | 2460 |
| aagctcaagg atcagaagac gcccatacct gatacgttgt accaggaatt gtacgactac | 2520 |
| gtgaaccacc gcctatcgca cgacctctca gacgaggccc gcgcctcct cccaaacgtg | 2580 |
| attactaagg aggtttccca tgaaataatc aaggaccgac ggttcaccag cgacaaattt | 2640 |
| tttttccacg tgcctatcac gctcaattac caggcggcca actccccatc gaagttcaac | 2700 |
| cagcgcgtga cgcctacct taaggagcac ccggagaccc caatcatcgg gatcgaccgt | 2760 |
| ggcgagcgga acctgatcta tattacggtg atcgatagca ccgggaagat cctggagcag | 2820 |
| cgctccctga acacaatcca gcagtttgac taccagaaga aactcgacaa ccgggagaag | 2880 |
| gagcgcgtcg cagcccggca agcatggagt gtggtcggca ccataaagga cctgaaacag | 2940 |
| ggttacctaa gtcaagttat ccacgagatc gttgacctga tgatacacta tcaagccgta | 3000 |
| gtcgtgctgg agaacctcaa cttcgggttt aagtccaagc gcaccggcat cgcggagaag | 3060 |
| gcggtgtacc agcagttcga gaagatgctg atcgacaagc tgaactgcct ggtgctcaag | 3120 |
| gactaccctg cggagaaggt cggcgggtc ttgaacccgt accagctaac cgaccagttc | 3180 |
| acgagcttcg ccaaaatggg cacgcagtcc ggattcttgt tttatgtccc ggctccatat | 3240 |
| acaagtaaga tcgacccgct gacagggttt gttgacccat tcgtgtggaa gaccatcaag | 3300 |
| aaccacgaga gcaggaaaca cttcttagag ggcttcgact tcctgcatta cgacgttaag | 3360 |
| acaggcgact tcatcctgca cttcaagatg aaccgcaacc tgtcgttcca gaggggcctg | 3420 |
| cccggcttca tgcccgcctg ggatatcgtc tttgagaaga tgagacgca gttcgacgcg | 3480 |
| aaggggacgc cgttcatcgc tggaaagcgg atcgtgccgg tcatcgagaa ccaccgcttc | 3540 |
| acgggtcgct accgagattt ataccccgcc aacgaactaa ttgcgctgct ggaggagaag | 3600 |
| gggatcgtgt tccgagatgg cagcaacatt ctcccgaagc tgctggagaa cgacgactcg | 3660 |
| cacgctattg acacgatggt cgccctcata cggagcgtgc ttcagatgcg gaacagtaac | 3720 |
| gctgccacgg gcgaggacta cattaactcc cccgtccgcg acctcaacgg ggtctgcttc | 3780 |
| gatagccgct tccagaaccc ggagtggcct atggatgcgg acgcgaacgg ggcctaccac | 3840 |
| atcgccctca agggccaact cctgctcaac cacttgaagg aaagcaaaga cctcaaattg | 3900 |
| cagaatggca tcagtaacca ggactggctc gcgtacatcc aggaactgag aaacgggtcc | 3960 |
| aagaagcggc gtatcaagca agattga | 3987 |

<210> SEQ ID NO 19
<211> LENGTH: 3987
<212> TYPE: DNA
<213> ORGANISM: Artificial sequence
<220> FEATURE:
<223> OTHER INFORMATION: Synthetic polynucleotide

<400> SEQUENCE: 19

| | |
|---|---|
| atggcgggaa gcaaaaagcg ccggattaag caagacacgc agttcgaggg cttcacgaac | 60 |

```
ctctaccaag tcagcaagac cctccggttc gagctgatac acagggaaa gacgctcaag      120 cacatccagg aacagggctt catcgaggag acaaggcgc gcaacgacca ctacaaggag      180
ttgaaaccga tcatcgaccg catctacaag acgtacgccg accagtgcct ccagctcgtg      240
cagctcgact gggagaacct ctccgccgcc attgactcgt accggaagga gaagactgag      300
gagacccgca acgccctgat cgaggagcaa gcaacctacc ggaacgccat ccacgactac      360
ttcatcggcc gcaccgacaa cctcaccgac gcgatcaaca gcggcacgc ggagatatac      420 aaagggctgt tcaaggcgga gctgttcaac ggcaaggtgc tcaagcagct agggacggtg      480
accacgaccg agcacgagaa cgcgctcctc cgcagcttcg acaagttcac cacctacttc      540
agcggcttct accggaaccg caagaatgtg ttcagcgcgg aggacatcag cacggccatc      600
ccgcaccgca tcgtccagga caacttcccg aagttcaagg agaactgcca catcttcacc      660
cgcctgataa ccgccgtccc ctccctgcgg gagcacttcg agaacgtcaa aaaggcaatt      720
gggatcttcg tctcgaccag cattgaggag gtgttcagct tccccttcta caaccagctc      780
ctcacccaga cgcagatcga cctgtacaat cagttgctcg gcgggataag ccgcgaggcg      840
ggaaccgaaa aaatcaaggg gctgaacgaa gtgttgaacc tcgccatcca gaagaacgac      900
gagaccgcgc acatcatcgc ctcccctgccc caccggttca tccccgctgtt caagcagatc      960 ctctctgacc ggaacaccct gtccttcatt cttgaggagt tcaagtcgga cgaggaggtc     1020
atccagagct tctgcaagta caagacgctg ctacggaacg agaacgtgct ggagacggcg     1080
gaggcactgt tcaacgagct aaacagcatc gacctcacgc acatcttcat cagtcacaag     1140
aaactggaga ccatctcctc cgcgctgtgc gaccactggg acacgctcag gaacgcgctc     1200
tacgagcgcc gaatcagtga gctgacgggc aagatcacga agtccgcgaa ggagaaggtg     1260
cagcggtccc tcaagcacga ggacatcaac ctccaggaga tcatctcagc ggctgggaaa     1320
gagctgtccg aggcgttcaa gcagaaaacg agcgaaatcc tgtcccacgc gcacgcggcc     1380
ctggatcagc ctctgccgac gaccctcaag aaacaagaag aaaaggaaat cctcaagtcg     1440
cagctcgact cgctgctggg cctgtaccat ctcctcgact ggttcgccgt ggacgagagc     1500
aacgaggtgg accccgagtt ctccgcgcgg cttacgggga tcaagctgga gatggagccc     1560
agcctgtcct tctacaacaa ggcgcgcaac tacgccacca agaagcccta cagcgtggag     1620
aagttcaagc tcaacttcca gatgcccact ctcgcacgtg ggtgggacgt caaccgcgaa     1680
aaaaataatg gggcgatcct gttcgtcaag aacggcctgt actacttggg catcatgccg     1740
aaacagaagg gccgctacaa ggccctgagc ttcgaaccga ccgagaaaac gagcgagggg     1800
ttcgacaaga tgtactacga ctacttcccc gacgccgcga agatgattcc aaagtgctcc     1860
acgcagctta aggccgtgac ggcccacttc cagacgcaca cgaccccgat cctcctcagc     1920
aacaacttca tcgagcccct ggagatcacg aaggagatat acgacctgaa caacccggag     1980
aaggagccca agaaattcca gaccgcctac gccaagaaga caggcgacca aaagggttac     2040
agggaggccc tctgcaagtg gatcgacttc actagggact tcctgtccaa gtacaccaag     2100
actacctcta tcgacctgtc cagcctccgc ccgtcgtccc agtacaaaga tttgggcgag     2160
tattacgcgg agctgaaccc actgctctac cacatcagct tccagcgcat gcggagaag      2220 gagatcatgg acgcagtgga gacgggcaag ctataccctat ttcagatata caacaaagac     2280
ttcgctaagg acaccacgg caagcctaac ctgcacaccc tctactggac ggggctcttc      2340
agcccggaga acctcgccaa gacctcgatc aagctcaacg gccaggccga gctgttctac     2400
cggcccaagt cccgcatgaa gcggatggcc caccggctcg gggagaaaat gctcaacaag     2460
```

| | |
|---|---|
| aaattgaagg accaaaaaac gccgataccc gacaccctat accaggagct gtacgactat | 2520 |
| gtgaaccacc gcctgagcca cgacctcagc gacgaggcgc gggccctcct gccgaacgtc | 2580 |
| atcacaaagg aggtcagcca cgagatcatc aaggaccggc gcttcacctc cgacaagttt | 2640 |
| ttctttcacg tgcccatcac gctcaactac caggccgcca actcgccgtc caagttcaac | 2700 |
| cagcgcgtga acgcctacct caaggagcac cccgagaccc cgatcatcgg gattgaccga | 2760 |
| ggggagcgga acctcatcta catcaccgtc atcgacagca ccgggaagat ccttgaacag | 2820 |
| cggtcgctca acaccatcca gcagttcgac taccagaaga aactcgacaa ccgggagaag | 2880 |
| gagagagtgg cggcccgcca ggcttggtcc gtcgtcggga cgattaagga cttgaaacaa | 2940 |
| ggttacctgt cgcaagtgat ccacgagatc gttgacctga tgatccacta ccaagccgtc | 3000 |
| gtggtcctgg agaacctcaa cttcggcttc aagagcaaac gaaccggcat cgcggagaag | 3060 |
| gccgtgtacc agcagttcga aaaaatgctg atcgacaagc tgaactgcct cgtgctcaag | 3120 |
| gactacccg ctgagaaggt cggcggggtg ctgaacccgt accagctcac tgaccagttc | 3180 |
| accagcttcg caaagatggg cacccagtcc ggcttcctgt tctacgtgcc tgcgccatac | 3240 |
| acctcgaaga tcgacccgct caccgggttc gtggaccct tcgtctggaa gaccatcaag | 3300 |
| aaccacgaga gccgcaagca cttcctggag ggcttcgact tcctccacta cgacgtcaag | 3360 |
| accggggact tcatcctgca cttcaagatg aaccgcaacc tcagtttcca gcgcggcctg | 3420 |
| ccggggttca tgcccgcttg ggatatagtc ttcgagaaga tgagacgca gttcgacgcg | 3480 |
| aagggcaccc cgttcatcgc cgggaagcgc atcgtgccgg tcatcgagaa ccaccggttc | 3540 |
| accgggcgct accgcgacct atacccggcg aacgagttga tcgccctcct ggaggagaag | 3600 |
| ggcatcgtgt tccgcgacgg ctccaacatc ctcccgaagc tgctcgaaaa cgacgactcc | 3660 |
| cacgccatcg acacgatggt cgcgctgatc cggtcggtgc tccagatgcg gaactccaac | 3720 |
| gccgcgacgg gcgaggacta catcaacagt ccggtccgcg atctgaacgg cgtctgcttc | 3780 |
| gactcccggt tccagaaccc cgagtggccg atggacgcgg acgcgaacgg cgcataccac | 3840 |
| atcgccctaa agggcaatt gctgctcaac cacctcaagg aatccaaaga cctaaagctc | 3900 |
| cagaacggca tctccaacca ggactggctg gcgtacatcc aggaactgcg gaacgggagc | 3960 |
| aaaaaacgtc ggatcaagca agattga | 3987 |

<210> SEQ ID NO 20
<211> LENGTH: 3987
<212> TYPE: DNA
<213> ORGANISM: Artificial sequence
<220> FEATURE:
<223> OTHER INFORMATION: Synthetic polynucleotide

<400> SEQUENCE: 20

| | |
|---|---|
| atggcgggct ccaagaaacg ccggattaag caagatacc agttcgaggg gttcacgaac | 60 |
| ctctaccaag tgagcaagac cctccgattc gaactgattc ctcaggggaa gaccctcaag | 120 |
| cacatccagg agcaagggtt catcgaggag acaaggcgc ggaacgacca ctacaaggaa | 180 |
| ctcaaaccca tcatcgaccg catctacaag acctacgccg atcagtgcct ccagctcgtg | 240 |
| cagttggact gggagaacct cagcgcggcc attgactcct accggaagga gaaaacggag | 300 |
| gagacgcgca acgcgctcat cgaggaacag gcaacctatc gcaacgccat ccacgactac | 360 |
| ttcatcggga ggactgacaa cctcactgac gcgattaaca gcgccacgc ggagatatac | 420 |
| aagggactct tcaaagcgga gctgtttaac ggcaaggttc tcaagcaact cggcactgtg | 480 |

| | |
|---|---|
| accacgaccg agcatgagaa cgccctgctc cgctccttcg acaagttcac cacctacttc | 540 |
| tccgggttct accgcaaccg caagaatgtc ttcagcgcgg aggacatcag cacggccatt | 600 |
| ccacatcgaa tcgtccaaga taacttcccg aagttcaagg agaactgcca catcttcacc | 660 |
| cgactcatta ctgctgtacc gtcgttacgc gaacacttcg agaacgtcaa gaaggcaatt | 720 |
| ggaatcttcg tctctacgtc aatagaggag gtgttcagct tcccttttcta caaccagctc | 780 |
| cttacgcaga cccagataga cctgtacaat cagctcctcg gtgggatcag ccggaggcg | 840 |
| gggactgaga agattaaagg gctcaacgag gtcttgaacc tggccatcca aaaaaacgat | 900 |
| gagacggcgc acatcatcgc ctcgctgccc accggttca tcccgctgtt caagcagatc | 960 |
| ctcagtgaca ggaacaccctt gagctttatc ctagaggagt tcaagagcga cgaggaggtg | 1020 |
| atccagagct tctgcaagta caaaaccctg ctgaggaacg agaacgtcct ggagacggcg | 1080 |
| gaggcgctgt tcaacgagct gaactctatc gacttaactc acatattcat ctcgcacaag | 1140 |
| aagctggaga ctattagctc tgcactctgc gaccactggg acaccctccg caacgcgctc | 1200 |
| tacgagcgcc gcatctcgga gctgaccggg aagatcacca atccgcgaa ggaaaaggtc | 1260 |
| cagcgttccc tcaaacacga ggatattaac ttacaggaga ttatctcagc ggctgggaag | 1320 |
| gagttgtcag aggcgttcaa gcagaaaact tccgagatcc tgagccacgc gcacgcagcg | 1380 |
| ctcgaccagc ctctgcccac caccctcaaa aagcaggaag aaaaagagat cctcaagagc | 1440 |
| cagttggact ccctgctggg gctctatcac cttctcgact ggttcgccgt cgatgagtcg | 1500 |
| aacgaggtgg accccgagtt ctccgcccgg ctgaccggca tcaagctaga gatggagccg | 1560 |
| tccctcagct tctacaataa ggcccgcaac tacgcgacca aaaaaccta cagcgtggag | 1620 |
| aagttcaagc tgaacttcca gatgccgacc ttagcacgcg gttgggacgt aaacagggag | 1680 |
| aagaacaatg gagccatcct gttcgtcaag aacgggcttt actacctcgg gataatgccc | 1740 |
| aagcagaagg gccgctacaa ggccctttcc ttcgagccga cggagaaaac ctccgagggg | 1800 |
| ttcgacaaga tgtactacga ctacttcccc gacgccgcca agatgatccc gaagtgctca | 1860 |
| acgcagctaa aagccgtgac cgcccacttc cagacccaca cgacgccgat cctgctgagc | 1920 |
| aacaacttca tcgagcccct tgagatcact aaggagatat acgacctgaa caaccccgag | 1980 |
| aaggagccca gaagtttca aaccgcctac gccaaaaaaa ctggcgacca aaagggctac | 2040 |
| agggaggcgc tgtgtaagtg gatcgacttc acacgcgact tccttccgaa gtatacgaag | 2100 |
| acaacctcta ttgacctgag cagcctgcgt cctagctccc agtacaaaga tttgggcgag | 2160 |
| tactacgcgg agcttaatcc actactctac cacatctcat tccagcgcat cgctgagaag | 2220 |
| gaaatcatgg acgcggtgga gacaggcaaa ctgtacctct tccagatata caacaaagac | 2280 |
| ttcgctaagg ggcaccacgg gaagcccaac cttcatacgc tctactggac gggcctattc | 2340 |
| agccccgaaa atctggccaa gacctccatc aagctgaacg gccaagcgga gctgttctac | 2400 |
| agacccaaga gccggatgaa gcggatggcc cacaggctcg gcgagaaaat gcttaacaaa | 2460 |
| aagttgaagg accagaaaac ccctatcccc gacaccctct accaggaact gtacgactac | 2520 |
| gtgaaccaca ggctctcgca cgacctttcc gacgaggccc gtgccctact cccgaacgtc | 2580 |
| attaccaaag aggtttcgca cgagatcatc aaggaccggc ggttcacgag cgacaagttt | 2640 |
| ttctttcacg tccccatcac ccttaactac caggcggcca actcccatc caagttcaac | 2700 |
| cagcgtgtga atgcctacct caaggagcac ccagagaccc cgatcattgg gatcgaccgg | 2760 |
| ggcgagcgga acctgatcta catcaccgtc atcgactcga cgggcaagat tcttgagcag | 2820 |
| agatcgttga ataccataca gcagttcgac taccagaaga aactcgacaa ccgcgagaag | 2880 |

```
gagcgcgtgg cggcccgcca ggcgtggtcc gtcgttggga cgattaagga cttgaaacaa    2940
ggttatctgt cccaagtcat ccacgagatc gttgatctga tgatccacta tcaggcagtg    3000
gtggtgctgg agaatctcaa cttcggcttc aagagtaagc ggacgggaat cgccgagaag    3060
gccgtgtacc agcagttcga gaagatgctg atcgacaagc tcaactgcct tgtgctgaaa    3120
gactacccgg ccgagaaggt cggcggcgtc ctcaacccgt accaacttac cgaccagttc    3180
acctccttcg ccaagatggg cactcagtcc gggttcttgt tctacgtccc cgcaccttac    3240
acctctaaga tcgaccctct gactggcttc gtagatccat tcgtgtggaa gaccattaag    3300
aaccacgaga gccgcaagca cttcctggag ggcttcgact tcctgcacta cgacgtgaag    3360
accggggact tcatccttca cttcaagatg aaccggaacc tcagcttcca gcggggcctg    3420
ccggggttca tgcccgcctg ggacatcgtg ttcgagaaga cgagaccca gttcgacgcg    3480 aagggcacgc ccttcatcgc cgggaagcgt atcgtgccgg tgatcgagaa ccatcgtttc    3540
acgggtcgct accgtgacct ctacccggcg aacgagctta tcgcactcct ggaggagaag    3600
ggcatcgtct tccgggacgg ctccaacatc ctcccgaaac tgctggaaaa cgacgactct    3660
cacgccatcg acacgatggt ggccctcatc cggtccgtgc tccaaatgcg gaacagcaac    3720
gccgccaccg gtgaggacta catcaacagc ccggtccggg atctgaacgg ggtgtgcttc    3780
gattcgcggt tccagaatcc tgagtggccg atggacgcgg atgcaaacgg ggcgtaccac    3840
atcgcgctca agggccagtt acttctgaac caccttaagg agtctaaaga tttgaaactc    3900
cagaacggga tctcgaacca ggactggctg gcctacatcc aagagttgcg gaacggcagc    3960
aagaagcggc ggattaagca agattag                                       3987

<210> SEQ ID NO 21
<211> LENGTH: 1592
<212> TYPE: DNA
<213> ORGANISM: Medicago truncatula

<400> SEQUENCE: 21
actgttaata attttttaaac gtcagcgcac taaaaaaacg aaaagacgga cacgtgaaaa      60
taaaaaacac acactagttt atgacgcaat actattttac ttatgatttg ggtacattag     120
acaaaaccgt gaaagagatg tatcagctat gaaacctgta tacttcaata cagagactta     180
ctcatatcgg atacgtacgc acgaagtatc atattaatta ttttaattt taataaatat      240 tttatcggat acttatgtga tactctacat atacacaagg atatttctaa gatactttat     300
agatacgtat cctagaaaaa catgaagagt aaaaagtga caatgttg taaaaattca       360 ttataaatgt atatgattca attttagata tgcatcagta taattgattc tcgatgaaac     420
acttaaaatt atatttcttg tggaagaacg tagcgagaga ggtgattcag ttagacaaca     480
ttaaataaaa ttaatgttaa gttcttttaa tgatgtttct ctcaatatca catcatatga     540
aaatgtaata tgatttataa gaaaattttt aaaaaattta ttttaataat cacatgtact     600
attttttaaa aattgtatct tttataataa tacaataata aagagtaatc agtgttaatt     660
tttcttcaaa tataagtttt attataaatc attgttaacg tatcataagt cattaccgta     720
tcgtatctta attttttttt aaaaaccgct aattcacgta cccgtattgt attgtacccg     780
cacctgtatc acaatcgatc ttagttagaa gaattgtctc gaggcggtgc aagacagcat     840
ataatagacg tggactctct tataccaaac ggttgtcgtat cacaaagggt taggtaacaa    900
gtcacagttt gtccacgtgt cacgttttaa ttggaagagg tgccgttggc gtaatataac     960
```

| | |
|---|---|
| agccaatcga tttttgctat aaaagcaaat caggtaaact aaacttcttc attcttttct | 1020 |
| tccccatcgc tacaaaaccg gttcctttgg aaaagagatt cattcaaacc tagcacccaa | 1080 |
| ttccgtttca aggtataatc tactttctat tcttcgatta ttttattatt attagctact | 1140 |
| atcgtttaat cgatcttttc ttttgatccg tcaaatttaa attcaattag ggttttgttc | 1200 |
| ttttctttca tctgattgaa atccttctga attgaaccgt ttacttgatt ttactgttta | 1260 |
| ttgtatgatt taatcctttg tttttcaaag acagtcttta gattgtgatt aggggttcat | 1320 |
| ataaatttt agatttggat ttttgtattg tatgattcaa aaaatacgtc ctttaattag | 1380 |
| attagtacat ggatattttt tacccgattt attgattgtc agggagaatt tgatgagcaa | 1440 |
| gttttttga tgtctgttgt aaattgaatt gattataatt gctgatctgc tgcttccagt | 1500 |
| tttcataacc catattcttt taaccttgtt gtacacacaa tgaaaaattg gtgattgatt | 1560 |
| catttgtttt tctttgtttt ggattataca gg | 1592 |

<210> SEQ ID NO 22
<211> LENGTH: 2000
<212> TYPE: DNA
<213> ORGANISM: Zea mays

<400> SEQUENCE: 22

| | |
|---|---|
| gtcgtgcccc tctctagaga taaagagcat tgcatgtcta aagtataaaa aattaccaca | 60 |
| tattttttg tcacacttat ttgaagtgta gtttatctat ctctatacat atatttaaac | 120 |
| ttcactctac aaataatata gtctataata ctaaataat attagtgttt tagaggatca | 180 |
| tataaataaa ctgctagaca tggtctaaag gataattgaa tattttgaca atctacagtt | 240 |
| ttatcttttt agtgtgcatg tgatctctct gttttttttg caaatagctt gacctatata | 300 |
| atacttcatc cattttatta gtacatccat ttaggattta gggttgatgg tttctataga | 360 |
| ctaattttta gtacatccat tttattcttt ttagtctcta aatttttaa aactaaaact | 420 |
| ctattttagt ttttttattta ataatttaga tataaaatga aataaaataa attgactaca | 480 |
| aataaaacaa ataccctta agaaataaaa aaactaagca aacatttttc ttgtttcgag | 540 |
| tagataatga caggctgttc aacgccgtcg acgagtctaa cggacaccaa ccagcgaacc | 600 |
| agcagcgtcg cgtcgggcca agcgaagcag acggcacggc atctctgtag ctgcctctgg | 660 |
| acccctctcg agagttccgc tccaccgttg gacttgctcc gctgtcggca tccagaaatt | 720 |
| gcgtggcgga gcggcagacg tgaggcggca cggcaggcgg cctcttcctc ctctcacggc | 780 |
| accggcagct acgggggatt cctttcccac cgctccttcg cttccccttc ctcgcccgcc | 840 |
| gtaataaata gacaccccct ccacaccctc tttccccaac ctcgtgttcg ttcggagcgc | 900 |
| acacacacgc aaccagatct cccccaaatc cagccgtcgg cacctccgct tcaaggtacg | 960 |
| ccgctcatcc tccccccccc cctctctcta ccttctctag atcggcgatc cggtccatgg | 1020 |
| ttagggcccg gtagttctac ttctgttcat gtttgtgtta agcaaacat gttcatgttc | 1080 |
| atgtttgtga tgatgtggtc tggttgggcg gtcgttctag atcggagtag gatactgttt | 1140 |
| caagctacct ggtggattta ttaattttgt atctgtatgt gtgtgccata catcttcata | 1200 |
| gttacgagtt taagatgatg gatggaaata tcgatctagg ataggtatac atgttgatgc | 1260 |
| gggttttact gatgcatata cagagatgct ttttttctcg cttggttgtg atgatatggt | 1320 |
| ctggttgggc ggtcgttcta gatcggagta gaatactgtt tcaaactacc tggtggattt | 1380 |
| attaaaggat aaagggtcgt tctagatcgg agtagaatac tgtttcaaac tacctggtgg | 1440 |
| atttattaaa ggatctgtat gtatgtgcct acatcttcat agttacgagt taagatgat | 1500 |

```
ggatggaaat atcgatctag ataggtata catgttgatg cgggttttac tgatgcatat    1560
acagagatgc ttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt aagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttt     1920 agccctgcct tcatacgcta tttatttgct tggtactgtt tcttttgtcc gatgctcacc    1980
ctgttgtttg gtgatacttc                                                2000
```

<210> SEQ ID NO 23
<211> LENGTH: 228
<212> TYPE: PRT
<213> ORGANISM: Rattus norvegicus

<400> SEQUENCE: 23

Ser Ser Glu Thr Gly Pro Val Ala Val Asp Pro Thr Leu Arg Arg
1               5                   10                  15

Ile Glu Pro His Glu Phe Glu Val Phe Phe Asp Pro Arg Glu Leu Arg
                20                  25                  30

Lys Glu Thr Cys Leu Leu Tyr Glu Ile Asn Trp Gly Arg His Ser
            35                  40                  45

Ile Trp Arg His Thr Ser Gln Asn Thr Asn Lys His Val Glu Val Asn
50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
            100                 105                 110

Ile Tyr Ile Ala Arg Leu Tyr His His Ala Asp Pro Arg Asn Arg Gln
        115                 120                 125

Gly Leu Arg Asp Leu Ile Ser Ser Gly Val Thr Ile Gln Ile Met Thr
130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Pro Gln Leu Thr Phe Phe Thr Ile Ala
        195                 200                 205

Leu Gln Ser Cys His Tyr Gln Arg Leu Pro Pro His Ile Leu Trp Ala
    210                 215                 220

Thr Gly Leu Lys
225

<210> SEQ ID NO 24
<211> LENGTH: 199
<212> TYPE: PRT
<213> ORGANISM: Homo sapiens

<400> SEQUENCE: 24

```
Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
            115                 120                 125

Ile Tyr Asp Tyr Asp Pro Leu Tyr Lys Glu Ala Leu Gln Met Leu Arg
        130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195
```

<210> SEQ ID NO 25
<211> LENGTH: 621
<212> TYPE: DNA
<213> ORGANISM: Petromyzon marinus

<400> SEQUENCE: 25

```
acagatgcag agtatgtgag aattcacgaa aagctggaca tctatacctt caagaagcag      60
ttctttaaca ataagaagtc tgtgagccat aggtgctacg tgctgttcga gctgaagaga     120
aggggtgaaa gaagggcatg tttttggggg tatgctgtga acaagcccca gtctggaact     180
gagagaggca ttcacgccga aatttttcagc atcagaaagg tggaggaata cctgagggat     240
aaccctggac agtttacaat taattggtat tctagctggt ctccatgcgc tgactgtgcc     300
gagaagatcc tggaatggta caaccaggag ctgagaggaa atggccatac cctgaagatt     360
tgggcctgca gctgtacta tgaaaagaac gcaagaaatc agatcggact gtggaacctg     420
agggataatg gtgtggggct gaacgtgatg gtgtccgagc actatcagtg ctgtagaaag     480
atttttcattc agtcctcaca taatcagctg aacgagaata gatggctgga aaagactctg     540
aagagggctg agaagagaag gtccgaactg tcaattatga tccaggtgaa gatcctgcac     600
accactaagt cacctgccgt g                                               621
```

<210> SEQ ID NO 26
<211> LENGTH: 160
<212> TYPE: PRT
<213> ORGANISM: Artificial sequence
<220> FEATURE:
<223> OTHER INFORMATION: Synthetic polypeptide

<400> SEQUENCE: 26

Phe Glu Arg Asn Tyr Asp Pro Arg Glu Leu Arg Lys Glu Thr Tyr Leu
1               5                   10                  15

Leu Tyr Glu Ile Lys Trp Gly Lys Ser Gly Lys Leu Trp Arg His Trp
            20                  25                  30

Cys Gln Asn Asn Arg Thr Gln His Ala Glu Val Tyr Phe Leu Glu Asn
            35                  40                  45

Ile Phe Asn Ala Arg Arg Phe Asn Pro Ser Thr His Cys Ser Ile Thr
50                  55                  60

Trp Tyr Leu Ser Trp Ser Pro Cys Ala Glu Cys Ser Gln Lys Ile Val
65                  70                  75                  80

Asp Phe Leu Lys Glu His Pro Asn Val Leu Gly Ile Tyr Val Ala Arg
                85                  90                  95

Leu Tyr Tyr His Glu Asp Glu Arg Asn Arg Gln Gly Leu Arg Asp Leu
                100                 105                 110

Val Asn Ser Gly Val Thr Ile Arg Ile Met Asp Leu Pro Asp Tyr Asn
                115                 120                 125

Tyr Cys Trp Lys Thr Phe Val Ser Asp Gln Gly Gly Asp Glu Asp Tyr
130                 135                 140

Trp Pro Gly His Phe Ala Pro Trp Ile Lys Gln Tyr Ser Leu Lys Leu
145                 150                 155                 160

<210> SEQ ID NO 27
<211> LENGTH: 207
<212> TYPE: PRT
<213> ORGANISM: Artificial sequence
<220> FEATURE:
<223> OTHER INFORMATION: Synthetic polypeptide

<400> SEQUENCE: 27

Thr Asp Ala Glu Tyr Val Arg Ile His Glu Lys Leu Asp Ile Tyr Thr
1               5                   10                  15

Phe Lys Lys Gln Phe Ser Asn Asn Lys Lys Ser Val Ser His Arg Cys
            20                  25                  30

Tyr Val Leu Phe Glu Leu Lys Arg Arg Gly Glu Arg Arg Ala Cys Phe
            35                  40                  45

Trp Gly Tyr Ala Val Asn Lys Pro Gln Ser Gly Thr Glu Arg Gly Ile
50                  55                  60

His Ala Glu Ile Phe Ser Ile Arg Lys Val Glu Glu Tyr Leu Arg Asp
65                  70                  75                  80

Asn Pro Gly Gln Phe Thr Ile Asn Trp Tyr Ser Ser Trp Ser Pro Cys
                85                  90                  95

Ala Asp Cys Ala Glu Lys Ile Leu Glu Trp Tyr Asn Gln Glu Leu Arg
                100                 105                 110

Gly Asn Gly His Thr Leu Lys Ile Trp Val Cys Lys Leu Tyr Tyr Glu
                115                 120                 125

Lys Asn Ala Arg Asn Gln Ile Gly Leu Trp Asn Leu Arg Asp Asn Gly
130                 135                 140

Val Gly Leu Asn Val Met Val Ser Glu His Tyr Gln Cys Cys Arg Lys
145                 150                 155                 160

Ile Phe Ile Gln Ser Ser His Asn Gln Leu Asn Glu Asn Arg Trp Leu
                165                 170                 175

Glu Lys Thr Leu Lys Arg Ala Glu Lys Arg Arg Ser Glu Leu Ser Ile
                180                 185                 190

Met Phe Gln Val Lys Ile Leu His Thr Thr Lys Ser Pro Ala Val
                195                 200                 205

<210> SEQ ID NO 28
<211> LENGTH: 228
<212> TYPE: PRT
<213> ORGANISM: Artificial sequence
<220> FEATURE:
<223> OTHER INFORMATION: Synthetic polypeptide

<400> SEQUENCE: 28

Ser Ser Lys Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45

Ile Trp Arg His Thr Ser Gln Asn Thr Asn Lys His Val Glu Val Asn
50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro Asn Val Thr Leu Phe
            100                 105                 110

Ile Tyr Ile Ala Arg Leu Tyr His Leu Ala Asn Pro Arg Asn Arg Gln
        115                 120                 125

Gly Leu Arg Asp Leu Ile Ser Ser Gly Val Thr Ile Gln Ile Met Thr
130                 135                 140

Glu Gln Glu Ser Gly Tyr Cys Trp His Asn Phe Val Asn Tyr Ser Pro
145                 150                 155                 160

Ser Asn Glu Ser His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Ser Gln Leu Thr Ser Phe Thr Ile Ala
        195                 200                 205

Leu Gln Ser Cys His Tyr Gln Arg Leu Pro Pro His Ile Leu Trp Ala
210                 215                 220

Thr Gly Leu Lys
225

<210> SEQ ID NO 29
<211> LENGTH: 162
<212> TYPE: PRT
<213> ORGANISM: Artificial sequence
<220> FEATURE:
<223> OTHER INFORMATION: Synthetic polypeptide

<400> SEQUENCE: 29

Ser Phe Glu Arg Asn Tyr Asp Pro Arg Glu Leu Arg Lys Glu Thr Tyr
1               5                   10                  15

Leu Leu Tyr Glu Ile Lys Trp Gly Lys Ser Gly Lys Leu Trp Arg His
            20                  25                  30

Trp Cys Gln Asn Asn Arg Thr Gln His Ala Glu Val Tyr Phe Leu Glu
        35                  40                  45

Asn Ile Phe Asn Ala Arg Arg Phe Asn Pro Ser Thr His Cys Ser Ile
    50                  55                  60

Thr Trp Tyr Leu Ser Trp Ser Pro Cys Ala Glu Cys Ser Gln Lys Ile

```
                65                  70                  75                  80
Val Asp Phe Leu Lys Glu His Pro Asn Val Asn Leu Glu Ile Tyr Val
                    85                  90                  95

Ala Arg Leu Tyr Tyr Pro Glu Asn Glu Arg Asn Arg Gln Gly Leu Arg
                    100                 105                 110

Asp Leu Val Asn Ser Gly Val Thr Ile Arg Ile Met Asp Leu Pro Asp
                    115                 120                 125

Tyr Asn Tyr Cys Trp Lys Thr Phe Val Ser Gln Gly Gly Asp Glu
                    130                 135                 140

Asp Tyr Trp Pro Gly His Phe Ala Pro Trp Ile Lys Gln Tyr Ser Leu
145                 150                 155                 160

Lys Leu

<210> SEQ ID NO 30
<211> LENGTH: 166
<212> TYPE: PRT
<213> ORGANISM: Escherichia coli

<400> SEQUENCE: 30

Ser Glu Val Glu Phe Ser His Glu Tyr Trp Met Arg His Ala Leu Thr
1                   5                   10                  15

Leu Ala Lys Arg Ala Trp Asp Glu Arg Glu Val Pro Val Gly Ala Val
                    20                  25                  30

Leu Val His Asn Asn Arg Val Ile Gly Glu Gly Trp Asn Arg Pro Ile
                    35                  40                  45

Gly Arg His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                    85                  90                  95

Arg Ile Gly Arg Val Val Phe Gly Ala Arg Asp Ala Lys Thr Gly Ala
                    100                 105                 110

Ala Gly Ser Leu Met Asp Val Leu His His Pro Gly Met Asn His Arg
                    115                 120                 125

Val Glu Ile Thr Glu Gly Ile Leu Ala Asp Glu Cys Ala Ala Leu Leu
                    130                 135                 140

Ser Asp Phe Phe Arg Met Arg Arg Gln Glu Ile Lys Ala Gln Lys Lys
145                 150                 155                 160

Ala Gln Ser Ser Thr Asp
                    165

<210> SEQ ID NO 31
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 31

Ser Glu Val Glu Phe Ser His Glu Tyr Trp Met Arg His Ala Leu Thr
1                   5                   10                  15

Leu Ala Lys Arg Ala Arg Asp Glu Arg Glu Val Pro Val Gly Ala Val
                    20                  25                  30

Leu Val Leu Asn Asn Arg Val Ile Gly Glu Gly Trp Asn Arg Ala Ile
                    35                  40                  45
```

Gly Leu His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
                100                 105                 110

Ala Gly Ser Leu Met Asp Val Leu His Tyr Pro Gly Met Asn His Arg
            115                 120                 125

Val Glu Ile Thr Glu Gly Ile Leu Ala Asp Glu Cys Ala Ala Leu Leu
            130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 32
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 32

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
                20                  25                  30

Leu Val Leu Asn Asn Arg Val Ile Gly Glu Gly Trp Asn Arg Ser Ile
                35                  40                  45

Gly Leu His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
                100                 105                 110

Ala Gly Ser Leu Met Asp Val Leu His Tyr Pro Gly Met Asn His Arg
            115                 120                 125

Val Glu Ile Thr Glu Gly Ile Leu Ala Asp Glu Cys Ala Ala Leu Leu
            130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 33
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 33

Ser Glu Val Glu Phe Ser His Glu Tyr Trp Met Arg His Ala Leu Thr
1               5                   10                  15

-continued

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 34
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 34

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 35
<211> LENGTH: 1763
<212> TYPE: PRT
<213> ORGANISM: Artificial sequence

```
<220> FEATURE:
<223> OTHER INFORMATION: Synthetic polypeptide

<400> SEQUENCE: 35

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Gly Gly Ser Ser Gly
            165                 170                 175

Ser Glu Thr Pro Gly Thr Ser Glu Ser Ala Thr Pro Glu Ser Ser Gly
        180                 185                 190

Gly Ser Ser Gly Gly Ser Ser Glu Val Glu Phe Ser His Glu Tyr Trp
            195                 200                 205

Met Arg His Ala Leu Thr Leu Ala Lys Arg Ala Arg Asp Glu Arg Glu
        210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
            260                 265                 270

Ile Asp Ala Thr Leu Tyr Val Thr Phe Glu Pro Cys Val Met Cys Ala
        275                 280                 285

Gly Ala Met Ile His Ser Arg Ile Gly Arg Val Val Phe Gly Val Arg
290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Pro Arg Gln Val
            340                 345                 350

Phe Asn Ala Gln Lys Lys Ala Gln Ser Ser Thr Asp Ser Gly Gly Ser
        355                 360                 365

Ser Gly Gly Ser Ser Gly Ser Glu Thr Pro Gly Thr Ser Glu Ser Ala
    370                 375                 380

Thr Pro Glu Ser Ser Gly Gly Ser Gly Gly Ser Asp Lys Lys Tyr
385                 390                 395                 400
```

```
Ser Ile Gly Leu Ala Ile Gly Thr Asn Ser Val Gly Trp Ala Val Ile
                405                 410                 415

Thr Asp Glu Tyr Lys Val Pro Ser Lys Lys Phe Lys Val Leu Gly Asn
                420                 425                 430

Thr Asp Arg His Ser Ile Lys Lys Asn Leu Ile Gly Ala Leu Leu Phe
                435                 440                 445

Asp Ser Gly Glu Thr Ala Glu Ala Thr Arg Leu Lys Arg Thr Ala Arg
                450                 455                 460

Arg Arg Tyr Thr Arg Arg Lys Asn Arg Ile Cys Tyr Leu Gln Glu Ile
465                 470                 475                 480

Phe Ser Asn Glu Met Ala Lys Val Asp Asp Ser Phe Phe His Arg Leu
                485                 490                 495

Glu Glu Ser Phe Leu Val Glu Glu Asp Lys Lys His Glu Arg His Pro
                500                 505                 510

Ile Phe Gly Asn Ile Val Asp Glu Val Ala Tyr His Glu Lys Tyr Pro
                515                 520                 525

Thr Ile Tyr His Leu Arg Lys Lys Leu Val Asp Ser Thr Asp Lys Ala
                530                 535                 540

Asp Leu Arg Leu Ile Tyr Leu Ala Leu Ala His Met Ile Lys Phe Arg
545                 550                 555                 560

Gly His Phe Leu Ile Glu Gly Asp Leu Asn Pro Asp Asn Ser Asp Val
                565                 570                 575

Asp Lys Leu Phe Ile Gln Leu Val Gln Thr Tyr Asn Gln Leu Phe Glu
                580                 585                 590

Glu Asn Pro Ile Asn Ala Ser Gly Val Asp Ala Lys Ala Ile Leu Ser
                595                 600                 605

Ala Arg Leu Ser Lys Ser Arg Arg Leu Glu Asn Leu Ile Ala Gln Leu
                610                 615                 620

Pro Gly Glu Lys Lys Asn Gly Leu Phe Gly Asn Leu Ile Ala Leu Ser
625                 630                 635                 640

Leu Gly Leu Thr Pro Asn Phe Lys Ser Asn Phe Asp Leu Ala Glu Asp
                645                 650                 655

Ala Lys Leu Gln Leu Ser Lys Asp Thr Tyr Asp Asp Leu Asp Asn
                660                 665                 670

Leu Leu Ala Gln Ile Gly Asp Gln Tyr Ala Asp Leu Phe Leu Ala Ala
                675                 680                 685

Lys Asn Leu Ser Asp Ala Ile Leu Leu Ser Asp Ile Leu Arg Val Asn
                690                 695                 700

Thr Glu Ile Thr Lys Ala Pro Leu Ser Ala Ser Met Ile Lys Arg Tyr
705                 710                 715                 720

Asp Glu His His Gln Asp Leu Thr Leu Leu Lys Ala Leu Val Arg Gln
                725                 730                 735

Gln Leu Pro Glu Lys Tyr Lys Glu Ile Phe Phe Asp Gln Ser Lys Asn
                740                 745                 750

Gly Tyr Ala Gly Tyr Ile Asp Gly Gly Ala Ser Gln Glu Glu Phe Tyr
                755                 760                 765

Lys Phe Ile Lys Pro Ile Leu Glu Lys Met Asp Gly Thr Glu Glu Leu
                770                 775                 780

Leu Val Lys Leu Asn Arg Glu Asp Leu Leu Arg Lys Gln Arg Thr Phe
785                 790                 795                 800

Asp Asn Gly Ser Ile Pro His Gln Ile His Leu Gly Glu Leu His Ala
                805                 810                 815
```

```
Ile Leu Arg Arg Gln Glu Asp Phe Tyr Pro Phe Leu Lys Asp Asn Arg
            820                 825                 830

Glu Lys Ile Glu Lys Ile Leu Thr Phe Arg Ile Pro Tyr Tyr Val Gly
            835                 840                 845

Pro Leu Ala Arg Gly Asn Ser Arg Phe Ala Trp Met Thr Arg Lys Ser
        850                 855                 860

Glu Glu Thr Ile Thr Pro Trp Asn Phe Glu Glu Val Val Asp Lys Gly
865                 870                 875                 880

Ala Ser Ala Gln Ser Phe Ile Glu Arg Met Thr Asn Phe Asp Lys Asn
                885                 890                 895

Leu Pro Asn Glu Lys Val Leu Pro Lys His Ser Leu Leu Tyr Glu Tyr
            900                 905                 910

Phe Thr Val Tyr Asn Glu Leu Thr Lys Val Lys Tyr Val Thr Glu Gly
            915                 920                 925

Met Arg Lys Pro Ala Phe Leu Ser Gly Glu Gln Lys Lys Ala Ile Val
            930                 935                 940

Asp Leu Leu Phe Lys Thr Asn Arg Lys Val Thr Val Lys Gln Leu Lys
945                 950                 955                 960

Glu Asp Tyr Phe Lys Lys Ile Glu Cys Phe Asp Ser Val Glu Ile Ser
                965                 970                 975

Gly Val Glu Asp Arg Phe Asn Ala Ser Leu Gly Thr Tyr His Asp Leu
            980                 985                 990

Leu Lys Ile Ile Lys Asp Lys Asp  Phe Leu Asp Asn Glu  Glu Asn Glu
            995                 1000                1005

Asp Ile Leu Glu Asp Ile Val  Leu Thr Leu Thr Leu  Phe Glu Asp
        1010                1015                1020

Arg Glu Met Ile Glu Glu Arg  Leu Lys Thr Tyr Ala  His Leu Phe
        1025                1030                1035

Asp Asp Lys Val Met Lys Gln  Leu Lys Arg Arg Arg  Tyr Thr Gly
        1040                1045                1050

Trp Gly Arg Leu Ser Arg Lys  Leu Ile Asn Gly Ile  Arg Asp Lys
        1055                1060                1065

Gln Ser Gly Lys Thr Ile Leu  Asp Phe Leu Lys Ser  Asp Gly Phe
        1070                1075                1080

Ala Asn Arg Asn Phe Met Gln  Leu Ile His Asp  Ser Leu Thr
        1085                1090                1095

Phe Lys Glu Asp Ile Gln Lys  Ala Gln Val Ser Gly  Gln Gly Asp
        1100                1105                1110

Ser Leu His Glu His Ile Ala  Asn Leu Ala Gly Ser  Pro Ala Ile
        1115                1120                1125

Lys Lys Gly Ile Leu Gln Thr  Val Lys Val Val Asp  Glu Leu Val
        1130                1135                1140

Lys Val Met Gly Arg His Lys  Pro Glu Asn Ile Val  Ile Glu Met
        1145                1150                1155

Ala Arg Glu Asn Gln Thr Thr  Gln Lys Gly Gln Lys  Asn Ser Arg
        1160                1165                1170

Glu Arg Met Lys Arg Ile Glu  Glu Gly Ile Lys Glu  Leu Gly Ser
        1175                1180                1185

Gln Ile Leu Lys Glu His Pro  Val Glu Asn Thr Gln  Leu Gln Asn
        1190                1195                1200

Glu Lys Leu Tyr Leu Tyr Tyr  Leu Gln Asn Gly Arg  Asp Met Tyr
        1205                1210                1215

Val Asp Gln Glu Leu Asp Ile  Asn Arg Leu Ser Asp  Tyr Asp Val
```

```
                     1220                     1225                     1230
Asp His Ile Val Pro Gln Ser Phe Leu Lys Asp Asp Ser Ile Asp
    1235                     1240                     1245
Asn Lys Val Leu Thr Arg Ser Asp Lys Asn Arg Gly Lys Ser Asp
    1250                     1255                     1260
Asn Val Pro Ser Glu Glu Val Val Lys Lys Met Lys Asn Tyr Trp
    1265                     1270                     1275
Arg Gln Leu Leu Asn Ala Lys Leu Ile Thr Gln Arg Lys Phe Asp
    1280                     1285                     1290
Asn Leu Thr Lys Ala Glu Arg Gly Gly Leu Ser Glu Leu Asp Lys
    1295                     1300                     1305
Ala Gly Phe Ile Lys Arg Gln Leu Val Glu Thr Arg Gln Ile Thr
    1310                     1315                     1320
Lys His Val Ala Gln Ile Leu Asp Ser Arg Met Asn Thr Lys Tyr
    1325                     1330                     1335
Asp Glu Asn Asp Lys Leu Ile Arg Glu Val Lys Val Ile Thr Leu
    1340                     1345                     1350
Lys Ser Lys Leu Val Ser Asp Phe Arg Lys Asp Phe Gln Phe Tyr
    1355                     1360                     1365
Lys Val Arg Glu Ile Asn Asn Tyr His His Ala His Asp Ala Tyr
    1370                     1375                     1380
Leu Asn Ala Val Val Gly Thr Ala Leu Ile Lys Lys Tyr Pro Lys
    1385                     1390                     1395
Leu Glu Ser Glu Phe Val Tyr Gly Asp Tyr Lys Val Tyr Asp Val
    1400                     1405                     1410
Arg Lys Met Ile Ala Lys Ser Glu Gln Glu Ile Gly Lys Ala Thr
    1415                     1420                     1425
Ala Lys Tyr Phe Phe Tyr Ser Asn Ile Met Asn Phe Phe Lys Thr
    1430                     1435                     1440
Glu Ile Thr Leu Ala Asn Gly Glu Ile Arg Lys Arg Pro Leu Ile
    1445                     1450                     1455
Glu Thr Asn Gly Glu Thr Gly Glu Ile Val Trp Asp Lys Gly Arg
    1460                     1465                     1470
Asp Phe Ala Thr Val Arg Lys Val Leu Ser Met Pro Gln Val Asn
    1475                     1480                     1485
Ile Val Lys Lys Thr Glu Val Gln Thr Gly Gly Phe Ser Lys Glu
    1490                     1495                     1500
Ser Ile Leu Pro Lys Arg Asn Ser Asp Lys Leu Ile Ala Arg Lys
    1505                     1510                     1515
Lys Asp Trp Asp Pro Lys Lys Tyr Gly Gly Phe Asp Ser Pro Thr
    1520                     1525                     1530
Val Ala Tyr Ser Val Leu Val Val Ala Lys Val Glu Lys Gly Lys
    1535                     1540                     1545
Ser Lys Lys Leu Lys Ser Val Lys Glu Leu Leu Gly Ile Thr Ile
    1550                     1555                     1560
Met Glu Arg Ser Ser Phe Glu Lys Asn Pro Ile Asp Phe Leu Glu
    1565                     1570                     1575
Ala Lys Gly Tyr Lys Glu Val Lys Lys Asp Leu Ile Ile Lys Leu
    1580                     1585                     1590
Pro Lys Tyr Ser Leu Phe Glu Leu Glu Asn Gly Arg Lys Arg Met
    1595                     1600                     1605
Leu Ala Ser Ala Gly Glu Leu Gln Lys Gly Asn Glu Leu Ala Leu
    1610                     1615                     1620
```

-continued

Pro Ser Lys Tyr Val Asn Phe Leu Tyr Leu Ala Ser His Tyr Glu
    1625                1630                1635

Lys Leu Lys Gly Ser Pro Glu Asp Asn Glu Gln Lys Gln Leu Phe
    1640                1645                1650

Val Glu Gln His Lys His Tyr Leu Asp Glu Ile Ile Glu Gln Ile
    1655                1660                1665

Ser Glu Phe Ser Lys Arg Val Ile Leu Ala Asp Ala Asn Leu Asp
    1670                1675                1680

Lys Val Leu Ser Ala Tyr Asn Lys His Arg Asp Lys Pro Ile Arg
    1685                1690                1695

Glu Gln Ala Glu Asn Ile Ile His Leu Phe Thr Leu Thr Asn Leu
    1700                1705                1710

Gly Ala Pro Ala Ala Phe Lys Tyr Phe Asp Thr Thr Ile Asp Arg
    1715                1720                1725

Lys Arg Tyr Thr Ser Thr Lys Glu Val Leu Asp Ala Thr Leu Ile
    1730                1735                1740

His Gln Ser Ile Thr Gly Leu Tyr Glu Thr Arg Ile Asp Leu Ser
    1745                1750                1755

Gln Leu Gly Gly Asp
    1760

<210> SEQ ID NO 36
<211> LENGTH: 1565
<212> TYPE: PRT
<213> ORGANISM: Artificial sequence
<220> FEATURE:
<223> OTHER INFORMATION: Synthetic polypeptide

<400> SEQUENCE: 36

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
                20                  25                  30

Leu Val Leu Asn Asn Arg Val Ile Gly Glu Gly Trp Asn Arg Ala Ile
            35                  40                  45

Gly Leu His Asp Pro Thr Ala His Ala Glu Ile Met Ala Leu Arg Gln
        50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ser Lys Arg Gly Ala
            100                 105                 110

Ala Gly Ser Leu Met Asn Val Leu Asn Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Asp Phe Tyr Arg Met Pro Arg Gln Val Phe Asn Ala Gln Lys Lys
145                 150                 155                 160

Ala Gln Ser Ser Ile Asn Ser Gly Gly Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Asp Lys Lys Tyr Ser Ile Gly Leu Ala Ile
        195                 200                 205

```
Gly Thr Asn Ser Val Gly Trp Ala Val Ile Thr Asp Glu Tyr Lys Val
210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                    245                 250                 255

Glu Ala Thr Arg Leu Lys Arg Thr Ala Arg Arg Arg Tyr Thr Arg Arg
            260                 265                 270

Lys Asn Arg Ile Cys Tyr Leu Gln Glu Ile Phe Ser Asn Glu Met Ala
        275                 280                 285

Lys Val Asp Asp Ser Phe Phe His Arg Leu Glu Glu Ser Phe Leu Val
290                 295                 300

Glu Glu Asp Lys Lys His Glu Arg His Pro Ile Phe Gly Asn Ile Val
305                 310                 315                 320

Asp Glu Val Ala Tyr His Glu Lys Tyr Pro Thr Ile Tyr His Leu Arg
                325                 330                 335

Lys Lys Leu Val Asp Ser Thr Asp Lys Ala Asp Leu Arg Leu Ile Tyr
            340                 345                 350

Leu Ala Leu Ala His Met Ile Lys Phe Arg Gly His Phe Leu Ile Glu
        355                 360                 365

Gly Asp Leu Asn Pro Asp Asn Ser Asp Val Asp Lys Leu Phe Ile Gln
370                 375                 380

Leu Val Gln Thr Tyr Asn Gln Leu Phe Glu Glu Asn Pro Ile Asn Ala
385                 390                 395                 400

Ser Gly Val Asp Ala Lys Ala Ile Leu Ser Ala Arg Leu Ser Lys Ser
                405                 410                 415

Arg Arg Leu Glu Asn Leu Ile Ala Gln Leu Pro Gly Glu Lys Lys Asn
            420                 425                 430

Gly Leu Phe Gly Asn Leu Ile Ala Leu Ser Leu Gly Leu Thr Pro Asn
        435                 440                 445

Phe Lys Ser Asn Phe Asp Leu Ala Glu Asp Ala Lys Leu Gln Leu Ser
450                 455                 460

Lys Asp Thr Tyr Asp Asp Asp Leu Asp Asn Leu Leu Ala Gln Ile Gly
465                 470                 475                 480

Asp Gln Tyr Ala Asp Leu Phe Leu Ala Ala Lys Asn Leu Ser Asp Ala
                485                 490                 495

Ile Leu Leu Ser Asp Ile Leu Arg Val Asn Thr Glu Ile Thr Lys Ala
            500                 505                 510

Pro Leu Ser Ala Ser Met Ile Lys Arg Tyr Asp Glu His His Gln Asp
        515                 520                 525

Leu Thr Leu Leu Lys Ala Leu Val Arg Gln Gln Leu Pro Glu Lys Tyr
530                 535                 540

Lys Glu Ile Phe Phe Asp Gln Ser Lys Asn Gly Tyr Ala Gly Tyr Ile
545                 550                 555                 560

Asp Gly Gly Ala Ser Gln Glu Glu Phe Tyr Lys Phe Ile Lys Pro Ile
                565                 570                 575

Leu Glu Lys Met Asp Gly Thr Glu Glu Leu Leu Val Lys Leu Asn Arg
            580                 585                 590

Glu Asp Leu Leu Arg Lys Gln Arg Thr Phe Asp Asn Gly Ser Ile Pro
        595                 600                 605

His Gln Ile His Leu Gly Glu Leu His Ala Ile Leu Arg Arg Gln Glu
610                 615                 620
```

```
Asp Phe Tyr Pro Phe Leu Lys Asp Asn Arg Glu Lys Ile Glu Lys Ile
625                 630                 635                 640

Leu Thr Phe Arg Ile Pro Tyr Tyr Val Gly Pro Leu Ala Arg Gly Asn
            645                 650                 655

Ser Arg Phe Ala Trp Met Thr Arg Lys Ser Glu Glu Thr Ile Thr Pro
        660                 665                 670

Trp Asn Phe Glu Glu Val Val Asp Lys Gly Ala Ser Ala Gln Ser Phe
    675                 680                 685

Ile Glu Arg Met Thr Asn Phe Asp Lys Asn Leu Pro Asn Glu Lys Val
690                 695                 700

Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
                725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
        755                 760                 765

Ile Glu Cys Phe Asp Ser Val Glu Ile Ser Gly Val Glu Asp Arg Phe
    770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
            820                 825                 830

Leu Lys Thr Tyr Ala His Leu Phe Asp Asp Lys Val Met Lys Gln Leu
        835                 840                 845

Lys Arg Arg Arg Tyr Thr Gly Trp Gly Arg Leu Ser Arg Lys Leu Ile
    850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895

Asp Ser Leu Thr Phe Lys Glu Asp Ile Gln Lys Ala Gln Val Ser Gly
            900                 905                 910

Gln Gly Asp Ser Leu His Glu His Ile Ala Asn Leu Ala Gly Ser Pro
        915                 920                 925

Ala Ile Lys Lys Gly Ile Leu Gln Thr Val Lys Val Val Asp Glu Leu
    930                 935                 940

Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Ser Arg Glu
                965                 970                 975

Arg Met Lys Arg Ile Glu Glu Gly Ile Lys Glu Leu Gly Ser Gln Ile
            980                 985                 990

Leu Lys Glu His Pro Val Glu Asn Thr Gln Leu Gln Asn Glu Lys Leu
        995                 1000                1005

Tyr Leu Tyr Tyr Leu Gln Asn Gly Arg Asp Met Tyr Val Asp Gln
        1010                1015                1020

Glu Leu Asp Ile Asn Arg Leu Ser Asp Tyr Asp Val Asp His Ile
        1025                1030                1035

Val Pro Gln Ser Phe Leu Lys Asp Asp Ser Ile Asp Asn Lys Val
```

1040                1045                1050
Leu Thr Arg Ser Asp Lys Asn Arg Gly Lys Ser Asp Asn Val Pro
       1055                1060                1065

Ser Glu Glu Val Val Lys Lys Met Lys Asn Tyr Trp Arg Gln Leu
       1070                1075                1080

Leu Asn Ala Lys Leu Ile Thr Gln Arg Lys Phe Asp Asn Leu Thr
       1085                1090                1095

Lys Ala Glu Arg Gly Gly Leu Ser Glu Leu Asp Lys Ala Gly Phe
       1100                1105                1110

Ile Lys Arg Gln Leu Val Glu Thr Arg Gln Ile Thr Lys His Val
       1115                1120                1125

Ala Gln Ile Leu Asp Ser Arg Met Asn Thr Lys Tyr Asp Glu Asn
       1130                1135                1140

Asp Lys Leu Ile Arg Glu Val Lys Val Ile Thr Leu Lys Ser Lys
       1145                1150                1155

Leu Val Ser Asp Phe Arg Lys Asp Phe Gln Phe Tyr Lys Val Arg
       1160                1165                1170

Glu Ile Asn Asn Tyr His His Ala His Asp Ala Tyr Leu Asn Ala
       1175                1180                1185

Val Val Gly Thr Ala Leu Ile Lys Lys Tyr Pro Lys Leu Glu Ser
       1190                1195                1200

Glu Phe Val Tyr Gly Asp Tyr Lys Val Tyr Asp Val Arg Lys Met
       1205                1210                1215

Ile Ala Lys Ser Glu Gln Glu Ile Gly Lys Ala Thr Ala Lys Tyr
       1220                1225                1230

Phe Phe Tyr Ser Asn Ile Met Asn Phe Phe Lys Thr Glu Ile Thr
       1235                1240                1245

Leu Ala Asn Gly Glu Ile Arg Lys Arg Pro Leu Ile Glu Thr Asn
       1250                1255                1260

Gly Glu Thr Gly Glu Ile Val Trp Asp Lys Gly Arg Asp Phe Ala
       1265                1270                1275

Thr Val Arg Lys Val Leu Ser Met Pro Gln Val Asn Ile Val Lys
       1280                1285                1290

Lys Thr Glu Val Gln Thr Gly Gly Phe Ser Lys Glu Ser Ile Leu
       1295                1300                1305

Pro Lys Arg Asn Ser Asp Lys Leu Ile Ala Arg Lys Lys Asp Trp
       1310                1315                1320

Asp Pro Lys Lys Tyr Gly Gly Phe Asp Ser Pro Thr Val Ala Tyr
       1325                1330                1335

Ser Val Leu Val Val Ala Lys Val Glu Lys Gly Lys Ser Lys Lys
       1340                1345                1350

Leu Lys Ser Val Lys Glu Leu Leu Gly Ile Thr Ile Met Glu Arg
       1355                1360                1365

Ser Ser Phe Glu Lys Asn Pro Ile Asp Phe Leu Glu Ala Lys Gly
       1370                1375                1380

Tyr Lys Glu Val Lys Lys Asp Leu Ile Ile Lys Leu Pro Lys Tyr
       1385                1390                1395

Ser Leu Phe Glu Leu Glu Asn Gly Arg Lys Arg Met Leu Ala Ser
       1400                1405                1410

Ala Gly Glu Leu Gln Lys Gly Asn Glu Leu Ala Leu Pro Ser Lys
       1415                1420                1425

Tyr Val Asn Phe Leu Tyr Leu Ala Ser His Tyr Glu Lys Leu Lys
       1430                1435                1440

```
Gly Ser Pro Glu Asp Asn Glu Gln Lys Gln Leu Phe Val Glu Gln
    1445                1450                1455

His Lys His Tyr Leu Asp Glu Ile Ile Glu Gln Ile Ser Glu Phe
    1460                1465                1470

Ser Lys Arg Val Ile Leu Ala Asp Ala Asn Leu Asp Lys Val Leu
    1475                1480                1485

Ser Ala Tyr Asn Lys His Arg Asp Lys Pro Ile Arg Glu Gln Ala
    1490                1495                1500

Glu Asn Ile Ile His Leu Phe Thr Leu Thr Asn Leu Gly Ala Pro
    1505                1510                1515

Ala Ala Phe Lys Tyr Phe Asp Thr Thr Ile Asp Arg Lys Arg Tyr
    1520                1525                1530

Thr Ser Thr Lys Glu Val Leu Asp Ala Thr Leu Ile His Gln Ser
    1535                1540                1545

Ile Thr Gly Leu Tyr Glu Thr Arg Ile Asp Leu Ser Gln Leu Gly
    1550                1555                1560

Gly Asp
    1565

<210> SEQ ID NO 37
<211> LENGTH: 1565
<212> TYPE: PRT
<213> ORGANISM: Artificial sequence
<220> FEATURE:
<223> OTHER INFORMATION: Synthetic polypeptide

<400> SEQUENCE: 37

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
                20                  25                  30

Leu Val Leu Asn Asn Arg Val Ile Gly Glu Gly Trp Asn Arg Ala Ile
            35                  40                  45

Gly Leu His Asp Pro Thr Ala His Ala Glu Ile Met Ala Leu Arg Gln
        50                  55                  60

Gly Gly Leu Val Met Gln Asn Tyr Arg Leu Tyr Asp Ala Thr Leu Tyr
65                  70                  75                  80

Ser Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
                100                 105                 110

Ala Gly Ser Leu Met Asp Val Leu His His Pro Gly Met Asn His Arg
            115                 120                 125

Val Glu Ile Thr Glu Gly Ile Leu Ala Asp Glu Cys Ala Ala Leu Leu
        130                 135                 140

Cys Arg Phe Phe Arg Met Pro Arg Arg Val Phe Asn Ala Gln Lys Lys
145                 150                 155                 160

Ala Gln Ser Ser Thr Asp Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Asp Lys Lys Tyr Ser Ile Gly Leu Ala Ile
        195                 200                 205

Gly Thr Asn Ser Val Gly Trp Ala Val Ile Thr Asp Glu Tyr Lys Val
    210                 215                 220
```

```
Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
            245                 250                 255

Glu Ala Thr Arg Leu Lys Arg Thr Ala Arg Arg Tyr Thr Arg Arg
        260                 265                 270

Lys Asn Arg Ile Cys Tyr Leu Gln Glu Ile Phe Ser Asn Glu Met Ala
        275                 280                 285

Lys Val Asp Asp Ser Phe Phe His Arg Leu Glu Glu Ser Phe Leu Val
        290                 295                 300

Glu Glu Asp Lys Lys His Glu Arg His Pro Ile Phe Gly Asn Ile Val
305                 310                 315                 320

Asp Glu Val Ala Tyr His Glu Lys Tyr Pro Thr Ile Tyr His Leu Arg
                325                 330                 335

Lys Lys Leu Val Asp Ser Thr Asp Lys Ala Asp Leu Arg Leu Ile Tyr
            340                 345                 350

Leu Ala Leu Ala His Met Ile Lys Phe Arg Gly His Phe Leu Ile Glu
        355                 360                 365

Gly Asp Leu Asn Pro Asp Asn Ser Asp Val Asp Lys Leu Phe Ile Gln
370                 375                 380

Leu Val Gln Thr Tyr Asn Gln Leu Phe Glu Glu Asn Pro Ile Asn Ala
385                 390                 395                 400

Ser Gly Val Asp Ala Lys Ala Ile Leu Ser Ala Arg Leu Ser Lys Ser
                405                 410                 415

Arg Arg Leu Glu Asn Leu Ile Ala Gln Leu Pro Gly Glu Lys Lys Asn
            420                 425                 430

Gly Leu Phe Gly Asn Leu Ile Ala Leu Ser Leu Gly Leu Thr Pro Asn
        435                 440                 445

Phe Lys Ser Asn Phe Asp Leu Ala Glu Asp Ala Lys Leu Gln Leu Ser
        450                 455                 460

Lys Asp Thr Tyr Asp Asp Asp Leu Asp Asn Leu Leu Ala Gln Ile Gly
465                 470                 475                 480

Asp Gln Tyr Ala Asp Leu Phe Leu Ala Ala Lys Asn Leu Ser Asp Ala
                485                 490                 495

Ile Leu Leu Ser Asp Ile Leu Arg Val Asn Thr Glu Ile Thr Lys Ala
            500                 505                 510

Pro Leu Ser Ala Ser Met Ile Lys Arg Tyr Asp Glu His His Gln Asp
        515                 520                 525

Leu Thr Leu Leu Lys Ala Leu Val Arg Gln Gln Leu Pro Glu Lys Tyr
        530                 535                 540

Lys Glu Ile Phe Phe Asp Gln Ser Lys Asn Gly Tyr Ala Gly Tyr Ile
545                 550                 555                 560

Asp Gly Gly Ala Ser Gln Glu Glu Phe Tyr Lys Phe Ile Lys Pro Ile
                565                 570                 575

Leu Glu Lys Met Asp Gly Thr Glu Glu Leu Leu Val Lys Leu Asn Arg
            580                 585                 590

Glu Asp Leu Leu Arg Lys Gln Arg Thr Phe Asp Asn Gly Ser Ile Pro
        595                 600                 605

His Gln Ile His Leu Gly Glu Leu His Ala Ile Leu Arg Arg Gln Glu
        610                 615                 620

Asp Phe Tyr Pro Phe Leu Lys Asp Asn Arg Glu Lys Ile Glu Lys Ile
625                 630                 635                 640
```

```
Leu Thr Phe Arg Ile Pro Tyr Tyr Val Gly Pro Leu Ala Arg Gly Asn
                645             650             655

Ser Arg Phe Ala Trp Met Thr Arg Lys Ser Glu Glu Thr Ile Thr Pro
            660             665             670

Trp Asn Phe Glu Glu Val Val Asp Lys Gly Ala Ser Ala Gln Ser Phe
        675             680             685

Ile Glu Arg Met Thr Asn Phe Asp Lys Asn Leu Pro Asn Glu Lys Val
690             695             700

Leu Pro Lys His Ser Leu Leu Tyr Glu Tyr Phe Thr Val Tyr Asn Glu
705             710             715             720

Leu Thr Lys Val Lys Tyr Val Thr Glu Gly Met Arg Lys Pro Ala Phe
            725             730             735

Leu Ser Gly Glu Gln Lys Lys Ala Ile Val Asp Leu Leu Phe Lys Thr
        740             745             750

Asn Arg Lys Val Thr Val Lys Gln Leu Lys Glu Asp Tyr Phe Lys Lys
    755             760             765

Ile Glu Cys Phe Asp Ser Val Glu Ile Ser Gly Val Glu Asp Arg Phe
770             775             780

Asn Ala Ser Leu Gly Thr Tyr His Asp Leu Leu Lys Ile Ile Lys Asp
785             790             795             800

Lys Asp Phe Leu Asp Asn Glu Glu Asn Glu Asp Ile Leu Glu Asp Ile
            805             810             815

Val Leu Thr Leu Thr Leu Phe Glu Asp Arg Glu Met Ile Glu Glu Arg
        820             825             830

Leu Lys Thr Tyr Ala His Leu Phe Asp Asp Lys Val Met Lys Gln Leu
    835             840             845

Lys Arg Arg Arg Tyr Thr Gly Trp Gly Arg Leu Ser Arg Lys Leu Ile
850             855             860

Asn Gly Ile Arg Asp Lys Gln Ser Gly Lys Thr Ile Leu Asp Phe Leu
865             870             875             880

Lys Ser Asp Gly Phe Ala Asn Arg Asn Phe Met Gln Leu Ile His Asp
            885             890             895

Asp Ser Leu Thr Phe Lys Glu Asp Ile Gln Lys Ala Gln Val Ser Gly
        900             905             910

Gln Gly Asp Ser Leu His Glu His Ile Ala Asn Leu Ala Gly Ser Pro
    915             920             925

Ala Ile Lys Lys Gly Ile Leu Gln Thr Val Lys Val Val Asp Glu Leu
930             935             940

Val Lys Val Met Gly Arg His Lys Pro Glu Asn Ile Val Ile Glu Met
945             950             955             960

Ala Arg Glu Asn Gln Thr Thr Gln Lys Gly Gln Lys Asn Ser Arg Glu
            965             970             975

Arg Met Lys Arg Ile Glu Glu Gly Ile Lys Glu Leu Gly Ser Gln Ile
        980             985             990

Leu Lys Glu His Pro Val Glu Asn Thr Gln Leu Gln Asn Glu Lys Leu
    995             1000            1005

Tyr Leu Tyr Tyr Leu Gln Asn Gly Arg Asp Met Tyr Val Asp Gln
    1010            1015            1020

Glu Leu Asp Ile Asn Arg Leu Ser Asp Tyr Asp Val Asp His Ile
    1025            1030            1035

Val Pro Gln Ser Phe Leu Lys Asp Asp Ser Ile Asp Asn Lys Val
    1040            1045            1050

Leu Thr Arg Ser Asp Lys Asn Arg Gly Lys Ser Asp Asn Val Pro
```

1055                1060                1065
Ser Glu Glu Val Val Lys Lys Met Lys Asn Tyr Trp Arg Gln Leu
       1070                1075                1080

Leu Asn Ala Lys Leu Ile Thr Gln Arg Lys Phe Asp Asn Leu Thr
       1085                1090                1095

Lys Ala Glu Arg Gly Gly Leu Ser Glu Leu Asp Lys Ala Gly Phe
       1100                1105                1110

Ile Lys Arg Gln Leu Val Glu Thr Arg Gln Ile Thr Lys His Val
       1115                1120                1125

Ala Gln Ile Leu Asp Ser Arg Met Asn Thr Lys Tyr Asp Glu Asn
       1130                1135                1140

Asp Lys Leu Ile Arg Glu Val Lys Val Ile Thr Leu Lys Ser Lys
       1145                1150                1155

Leu Val Ser Asp Phe Arg Lys Asp Phe Gln Phe Tyr Lys Val Arg
       1160                1165                1170

Glu Ile Asn Asn Tyr His His Ala His Asp Ala Tyr Leu Asn Ala
       1175                1180                1185

Val Val Gly Thr Ala Leu Ile Lys Lys Tyr Pro Lys Leu Glu Ser
       1190                1195                1200

Glu Phe Val Tyr Gly Asp Tyr Lys Val Tyr Asp Val Arg Lys Met
       1205                1210                1215

Ile Ala Lys Ser Glu Gln Glu Ile Gly Lys Ala Thr Ala Lys Tyr
       1220                1225                1230

Phe Phe Tyr Ser Asn Ile Met Asn Phe Phe Lys Thr Glu Ile Thr
       1235                1240                1245

Leu Ala Asn Gly Glu Ile Arg Lys Arg Pro Leu Ile Glu Thr Asn
       1250                1255                1260

Gly Glu Thr Gly Glu Ile Val Trp Asp Lys Gly Arg Asp Phe Ala
       1265                1270                1275

Thr Val Arg Lys Val Leu Ser Met Pro Gln Val Asn Ile Val Lys
       1280                1285                1290

Lys Thr Glu Val Gln Thr Gly Gly Phe Ser Lys Glu Ser Ile Leu
       1295                1300                1305

Pro Lys Arg Asn Ser Asp Lys Leu Ile Ala Arg Lys Lys Asp Trp
       1310                1315                1320

Asp Pro Lys Lys Tyr Gly Gly Phe Asp Ser Pro Thr Val Ala Tyr
       1325                1330                1335

Ser Val Leu Val Val Ala Lys Val Glu Lys Gly Lys Ser Lys Lys
       1340                1345                1350

Leu Lys Ser Val Lys Glu Leu Leu Gly Ile Thr Ile Met Glu Arg
       1355                1360                1365

Ser Ser Phe Glu Lys Asn Pro Ile Asp Phe Leu Glu Ala Lys Gly
       1370                1375                1380

Tyr Lys Glu Val Lys Lys Asp Leu Ile Ile Lys Leu Pro Lys Tyr
       1385                1390                1395

Ser Leu Phe Glu Leu Glu Asn Gly Arg Lys Arg Met Leu Ala Ser
       1400                1405                1410

Ala Gly Glu Leu Gln Lys Gly Asn Glu Leu Ala Leu Pro Ser Lys
       1415                1420                1425

Tyr Val Asn Phe Leu Tyr Leu Ala Ser His Tyr Glu Lys Leu Lys
       1430                1435                1440

Gly Ser Pro Glu Asp Asn Glu Gln Lys Gln Leu Phe Val Glu Gln
       1445                1450                1455

```
His Lys His Tyr Leu Asp Glu Ile Ile Glu Gln Ile Ser Glu Phe
    1460                1465                1470

Ser Lys Arg Val Ile Leu Ala Asp Ala Asn Leu Asp Lys Val Leu
    1475                1480                1485

Ser Ala Tyr Asn Lys His Arg Asp Lys Pro Ile Arg Glu Gln Ala
    1490                1495                1500

Glu Asn Ile Ile His Leu Phe Thr Leu Thr Asn Leu Gly Ala Pro
    1505                1510                1515

Ala Ala Phe Lys Tyr Phe Asp Thr Thr Ile Asp Arg Lys Arg Tyr
    1520                1525                1530

Thr Ser Thr Lys Glu Val Leu Asp Ala Thr Leu Ile His Gln Ser
    1535                1540                1545

Ile Thr Gly Leu Tyr Glu Thr Arg Ile Asp Leu Ser Gln Leu Gly
    1550                1555                1560

Gly Asp
    1565

<210> SEQ ID NO 38
<211> LENGTH: 364
<212> TYPE: PRT
<213> ORGANISM: Artificial sequence
<220> FEATURE:
<223> OTHER INFORMATION: Synthetic polypeptide

<400> SEQUENCE: 38

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
                20                  25                  30

Leu Val His Asn Asn Arg Val Ile Gly Glu Gly Trp Asn Arg Pro Ile
            35                  40                  45

Gly Arg His Asp Pro Thr Ala His Ala Glu Ile Met Ala Leu Arg Gln
        50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Ser Glu Val Glu Phe Ser His Glu Tyr Trp
        195                 200                 205

Met Arg His Ala Leu Thr Leu Ala Lys Arg Ala Arg Asp Glu Arg Glu
    210                 215                 220

Val Pro Val Gly Ala Val Leu Val Leu Asn Asn Arg Val Ile Gly Glu
225                 230                 235                 240
```

```
Gly Trp Asn Arg Ala Ile Gly Leu His Asp Pro Thr Ala His Ala Glu
                245                 250                 255

Ile Met Ala Leu Arg Gln Gly Leu Val Met Gln Asn Tyr Arg Leu
            260                 265                 270

Ile Asp Ala Thr Leu Tyr Val Thr Phe Glu Pro Cys Val Met Cys Ala
            275                 280                 285

Gly Ala Met Ile His Ser Arg Ile Gly Arg Val Val Phe Gly Val Arg
            290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Pro Arg Gln Val
            340                 345                 350

Phe Asn Ala Gln Lys Lys Ala Gln Ser Ser Thr Asp
            355                 360
```

<210> SEQ ID NO 39
<211> LENGTH: 167
<212> TYPE: PRT
<213> ORGANISM: Artificial sequence
<220> FEATURE:
<223> OTHER INFORMATION: Synthetic polypeptide

<400> SEQUENCE: 39

```
Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
            20                  25                  30

Val Leu Val Leu Asn Asn Arg Val Ile Gly Glu Gly Trp Asn Arg Ala
            35                  40                  45

Ile Gly Leu His Asp Pro Thr Ala His Ala Glu Ile Met Ala Leu Arg
        50                  55                  60

Gln Gly Gly Leu Val Met Gln Asn Tyr Arg Leu Tyr Asp Ala Thr Leu
65                  70                  75                  80

Tyr Ser Thr Phe Glu Pro Cys Val Met Cys Ala Gly Ala Met Ile His
                85                  90                  95

Ser Arg Ile Gly Arg Val Val Phe Gly Val Arg Asn Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
        130                 135                 140

Leu Cys Arg Phe Phe Arg Met Pro Arg Arg Val Phe Asn Ala Gln Lys
145                 150                 155                 160

Lys Ala Gln Ser Ser Thr Asp
                165
```

<210> SEQ ID NO 40
<211> LENGTH: 167
<212> TYPE: PRT
<213> ORGANISM: Artificial sequence
<220> FEATURE:
<223> OTHER INFORMATION: Synthetic polypeptide

<400> SEQUENCE: 40

Met Ser Glu Val Glu Phe Ser His Glu Tyr Trp Met Arg His Ala Leu

```
            1               5                   10                  15
            Thr Leu Ala Lys Arg Ala Arg Asp Glu Arg Glu Val Pro Val Gly Ala
                            20                  25                  30
            Val Leu Val Leu Asn Asn Arg Val Ile Gly Glu Gly Trp Asn Arg Ala
                            35                  40                  45
            Ile Gly Leu His Asp Pro Thr Ala His Ala Glu Ile Met Ala Leu Arg
                        50                  55                  60
            Gln Gly Gly Leu Val Met Gln Asn Tyr Arg Leu Ile Asp Ala Thr Leu
                    65                  70                  75                  80
            Tyr Val Thr Phe Glu Pro Cys Val Met Cys Ala Gly Ala Met Ile His
                                85                  90                  95
            Ser Arg Ile Gly Arg Val Val Phe Gly Val Arg Asn Ser Lys Arg Gly
                            100                 105                 110
            Ala Ala Gly Ser Leu Met Asn Val Leu Asn Tyr Pro Gly Met Asn His
                        115                 120                 125
            Arg Val Glu Ile Thr Glu Gly Ile Leu Ala Asp Glu Cys Ala Ala Leu
                    130                 135                 140
            Leu Cys Asp Phe Tyr Arg Met Pro Arg Gln Val Phe Asn Ala Gln Lys
            145                 150                 155                 160
            Lys Ala Gln Ser Ser Ile Asn
                            165
```

<210> SEQ ID NO 41
<211> LENGTH: 83
<212> TYPE: PRT
<213> ORGANISM: Bacillus phage AR9

<400> SEQUENCE: 41

```
            Thr Asn Leu Ser Asp Ile Ile Glu Lys Glu Thr Gly Lys Gln Leu Val
            1               5                   10                  15
            Ile Gln Glu Ser Ile Leu Met Leu Pro Glu Glu Val Glu Val Ile
                            20                  25                  30
            Gly Asn Lys Pro Glu Ser Asp Ile Leu Val His Thr Ala Tyr Asp Glu
                        35                  40                  45
            Ser Thr Asp Glu Asn Val Met Leu Leu Thr Ser Asp Ala Pro Glu Tyr
                    50                  55                  60
            Lys Pro Trp Ala Leu Val Ile Gln Asp Ser Asn Gly Glu Asn Lys Ile
            65                  70                  75                  80
            Lys Met Leu
```

<210> SEQ ID NO 42
<211> LENGTH: 19
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: n is a, c, g, or u

<400> SEQUENCE: 42 nnnnnnnnn nnnnnnnnn                                                         19

<210> SEQ ID NO 43
<211> LENGTH: 22
<212> TYPE: DNA
<213> ORGANISM: Artificial sequence
<220> FEATURE:

```
<223> OTHER INFORMATION: Synthetic oligonucleotide
<220> FEATURE:
<221> NAME/KEY: misc_feature
<222> LOCATION: (4)..(22)
<223> OTHER INFORMATION: n is a, c, g, or t

<400> SEQUENCE: 43
aaannnnnnn nnnnnnnnnn nn                                              22

<210> SEQ ID NO 44
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (4)..(22)
<223> OTHER INFORMATION: n is a, c, g, or t

<400> SEQUENCE: 44
nnnnnnnnnn nnnnnnnnnt tt                                              22

<210> SEQ ID NO 45
<211> LENGTH: 24
<212> TYPE: PRT
<213> ORGANISM: Artificial sequence
<220> FEATURE:
<223> OTHER INFORMATION: Synthetic peptide

<400> SEQUENCE: 45

Glu Glu Leu Leu Ser Lys Asn Tyr His Leu Glu Asn Glu Val Ala Arg
1               5                   10                  15

Leu Lys Lys Gly Ser Gly Ser Gly
            20

<210> SEQ ID NO 46
<211> LENGTH: 241
<212> TYPE: PRT
<213> ORGANISM: Artificial sequence
<220> FEATURE:
<223> OTHER INFORMATION: Synthetic polypeptide

<400> SEQUENCE: 46

Glu Glu Glu Leu Leu Ser Lys Asn Tyr His Leu Glu Asn Glu Val Ala
1               5                   10                  15

Arg Leu Lys Lys Gly Ser Gly Ser Gly Glu Glu Leu Leu Ser Lys Asn
            20                  25                  30

Tyr His Leu Glu Asn Glu Val Ala Arg Leu Lys Lys Gly Ser Gly Ser
        35                  40                  45

Gly Glu Glu Leu Leu Ser Lys Asn Tyr His Leu Glu Asn Glu Val Ala
    50                  55                  60

Arg Leu Lys Lys Gly Ser Gly Ser Gly Glu Glu Leu Leu Ser Lys Asn
65                  70                  75                  80

Tyr His Leu Glu Asn Glu Val Ala Arg Leu Lys Lys Gly Ser Gly Ser
                85                  90                  95

Gly Glu Glu Leu Leu Ser Lys Asn Tyr His Leu Glu Asn Glu Val Ala
            100                 105                 110

Arg Leu Lys Lys Gly Ser Gly Ser Gly Glu Glu Leu Leu Ser Lys Asn
        115                 120                 125
```

Tyr His Leu Glu Asn Glu Val Ala Arg Leu Lys Lys Gly Ser Gly Ser
130                 135                 140

Gly Glu Glu Leu Leu Ser Lys Asn Tyr His Leu Glu Asn Glu Val Ala
145                 150                 155                 160

Arg Leu Lys Lys Gly Ser Gly Ser Gly Glu Glu Leu Leu Ser Lys Asn
            165                 170                 175

Tyr His Leu Glu Asn Glu Val Ala Arg Leu Lys Lys Gly Ser Gly Ser
            180                 185                 190

Gly Glu Glu Leu Leu Ser Lys Asn Tyr His Leu Glu Asn Glu Val Ala
            195                 200                 205

Arg Leu Lys Lys Gly Ser Gly Ser Gly Glu Glu Leu Leu Ser Lys Asn
            210                 215                 220

Tyr His Leu Glu Asn Glu Val Ala Arg Leu Lys Lys Gly Ser Gly Ser
225                 230                 235                 240

Gly

<210> SEQ ID NO 47
<211> LENGTH: 277
<212> TYPE: PRT
<213> ORGANISM: Artificial sequence
<220> FEATURE:
<223> OTHER INFORMATION: Synthetic polypeptide

<400> SEQUENCE: 47

Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
            20                  25                  30

Val Thr Thr Ser Asn Tyr Ala Ser Trp Val Gln Glu Lys Pro Gly Lys
            35                  40                  45

Leu Phe Lys Gly Leu Ile Gly Gly Thr Asn Asn Arg Ala Pro Gly Val
    50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Gly Ser Gly Gly Gly Gly
            115                 120                 125

Ser Ser Gly Gly Gly Ser Glu Val Lys Leu Leu Glu Ser Gly Gly Gly
            130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
            165                 170                 175

Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asn Gly
            195                 200                 205

Lys Asn Thr Val Tyr Leu Gln Met Ser Lys Val Arg Ser Asp Asp Thr
            210                 215                 220

Ala Leu Tyr Tyr Cys Val Thr Gly Leu Phe Asp Tyr Trp Gly Gln Gly
225                 230                 235                 240

```
Thr Leu Val Thr Val Ser Ser Tyr Pro Tyr Asp Val Pro Asp Tyr Ala
                245                 250                 255

Gly Gly Gly Gly Gly Ser Gly Gly Gly Ser Gly Gly Gly Gly Ser
            260                 265                 270

Gly Gly Gly Gly Ser
        275

<210> SEQ ID NO 48
<211> LENGTH: 66
<212> TYPE: DNA
<213> ORGANISM: Saccharomyces bayanus

<400> SEQUENCE: 48
ttcttgtcgt acttatagat cgctacgtta tttcaattttt gaaaatctga gtcctgggag    60
tgcgga                                                                66

<210> SEQ ID NO 49
<211> LENGTH: 605
<212> TYPE: PRT
<213> ORGANISM: Homo sapiens

<400> SEQUENCE: 49

Met Ser Gly Trp Glu Ser Tyr Tyr Lys Thr Glu Gly Asp Glu Glu Ala
1                   5                   10                  15

Glu Glu Glu Gln Glu Glu Asn Leu Glu Ala Ser Gly Asp Tyr Lys Tyr
                20                  25                  30

Ser Gly Arg Asp Ser Leu Ile Phe Leu Val Asp Ala Ser Lys Ala Met
            35                  40                  45

Phe Glu Ser Gln Ser Glu Asp Glu Leu Thr Pro Phe Asp Met Ser Ile
    50                  55                  60

Gln Cys Ile Gln Ser Val Tyr Ile Ser Lys Ile Ile Ser Asp Arg
65                  70                  75                  80

Asp Leu Leu Ala Trp Phe Tyr Gly Thr Glu Lys Asp Lys Asn Ser Val
                85                  90                  95

Asn Phe Lys Ile Tyr Val Leu Gln Glu Leu Asp Asn Pro Gly Ala Lys
            100                 105                 110

Arg Ile Leu Glu Leu Asp Gln Phe Lys Gly Gln Gln Gly Gln Lys Arg
        115                 120                 125

Phe Gln Asp Met Met Gly His Gly Ser Asp Tyr Ser Leu Ser Glu Val
    130                 135                 140

Leu Trp Val Cys Ala Asn Leu Phe Ser Asp Val Gln Phe Lys Met Ser
145                 150                 155                 160

His Lys Arg Ile Met Leu Phe Thr Asn Glu Asp Asn Pro His Gly Asn
                165                 170                 175

Asp Ser Ala Lys Ala Ser Arg Ala Arg Thr Lys Ala Gly Asp Leu Arg
            180                 185                 190

Asp Thr Gly Ile Phe Leu Asp Leu His Leu Lys Lys Pro Gly Gly Phe
        195                 200                 205

Asp Ile Ser Leu Phe Tyr Arg Asp Ile Ile Ser Ile Ala Glu Asp Glu
    210                 215                 220

Asp Leu Arg Val His Phe Glu Glu Ser Ser Lys Leu Glu Asp Leu Leu
225                 230                 235                 240

Arg Lys Val Arg Ala Lys Glu Thr Arg Lys Arg Ala Leu Ser Arg Leu
                245                 250                 255

Lys Leu Lys Leu Asn Lys Asp Ile Val Ile Ser Val Gly Ile Tyr Asn
            260                 265                 270
```

Leu Val Gln Lys Ala Leu Lys Pro Pro Ile Lys Leu Tyr Arg Glu
            275                 280                 285

Thr Asn Glu Pro Val Lys Thr Lys Thr Arg Thr Phe Asn Thr Ser Thr
        290                 295                 300

Gly Gly Leu Leu Leu Pro Ser Asp Thr Lys Arg Ser Gln Ile Tyr Gly
305                 310                 315                 320

Ser Arg Gln Ile Ile Leu Glu Lys Glu Thr Glu Glu Leu Lys Arg
            325                 330                 335

Phe Asp Asp Pro Gly Leu Met Leu Met Gly Phe Lys Pro Leu Val Leu
            340                 345                 350

Leu Lys Lys His His Tyr Leu Arg Pro Ser Leu Phe Val Tyr Pro Glu
            355                 360                 365

Glu Ser Leu Val Ile Gly Ser Ser Thr Leu Phe Ser Ala Leu Leu Ile
            370                 375                 380

Lys Cys Leu Glu Lys Glu Val Ala Ala Leu Cys Arg Tyr Thr Pro Arg
385                 390                 395                 400

Arg Asn Ile Pro Pro Tyr Phe Val Ala Leu Val Pro Gln Glu Glu Glu
            405                 410                 415

Leu Asp Asp Gln Lys Ile Gln Val Thr Pro Pro Gly Phe Gln Leu Val
            420                 425                 430

Phe Leu Pro Phe Ala Asp Asp Lys Arg Lys Met Pro Phe Thr Glu Lys
            435                 440                 445

Ile Met Ala Thr Pro Glu Gln Val Gly Lys Met Lys Ala Ile Val Glu
            450                 455                 460

Lys Leu Arg Phe Thr Tyr Arg Ser Asp Ser Phe Glu Asn Pro Val Leu
465                 470                 475                 480

Gln Gln His Phe Arg Asn Leu Glu Ala Leu Ala Leu Asp Leu Met Glu
            485                 490                 495

Pro Glu Gln Ala Val Asp Leu Thr Leu Pro Lys Val Glu Ala Met Asn
            500                 505                 510

Lys Arg Leu Gly Ser Leu Val Asp Glu Phe Lys Glu Leu Val Tyr Pro
            515                 520                 525

Pro Asp Tyr Asn Pro Glu Gly Lys Val Thr Lys Arg Lys His Asp Asn
            530                 535                 540

Glu Gly Ser Gly Ser Lys Arg Pro Lys Val Glu Tyr Ser Glu Glu Glu
545                 550                 555                 560

Leu Lys Thr His Ile Ser Lys Gly Thr Leu Gly Lys Phe Thr Val Pro
            565                 570                 575

Leu Lys Glu Ala Cys Arg Ala Tyr Gly Leu Lys Ser Gly Leu Lys Lys
            580                 585                 590

Gln Glu Leu Leu Glu Ala Leu Thr Lys His Phe Gln Asp
            595                 600                 605

<210> SEQ ID NO 50
<211> LENGTH: 482
<212> TYPE: PRT
<213> ORGANISM: Artificial sequence
<220> FEATURE:
<223> OTHER INFORMATION: Synthetic polypeptide

<400> SEQUENCE: 50

Met Val Arg Ser Gly Asn Lys Ala Ala Trp Leu Cys Met Asp Val Gly
1               5                   10                  15

Phe Thr Met Ser Asn Ser Ile Pro Gly Ile Glu Ser Pro Phe Glu Gln
            20                  25                  30

```
Ala Lys Lys Val Ile Thr Met Phe Val Gln Arg Gln Val Phe Ala Glu
         35                  40                  45

Asn Lys Asp Glu Ile Ala Leu Val Leu Phe Gly Thr Asp Gly Thr Asp
         50                  55                  60

Asn Pro Leu Ser Gly Gly Asp Gln Tyr Gln Asn Ile Thr Val His Arg
65                  70                  75                  80

His Leu Met Leu Pro Asp Phe Asp Leu Leu Glu Asp Ile Glu Ser Lys
                 85                  90                  95

Ile Gln Pro Gly Ser Gln Gln Ala Asp Phe Leu Asp Ala Leu Ile Val
                100                 105                 110

Ser Met Asp Val Ile Gln His Glu Thr Ile Gly Lys Lys Phe Glu Lys
            115                 120                 125

Arg His Ile Glu Ile Phe Thr Asp Leu Ser Ser Arg Phe Ser Lys Ser
130                 135                 140

Gln Leu Asp Ile Ile Ile His Ser Leu Lys Lys Cys Asp Ile Ser Glu
145                 150                 155                 160

Arg His Ser Ile His Trp Pro Cys Arg Leu Thr Ile Gly Ser Asn Leu
                165                 170                 175

Ser Ile Arg Ile Ala Ala Tyr Lys Ser Ile Leu Gln Glu Arg Val Lys
            180                 185                 190

Lys Thr Thr Trp Asp Ala Lys Thr Leu Lys Lys Glu Asp Ile Gln Lys
        195                 200                 205

Glu Thr Val Tyr Cys Leu Asn Asp Asp Glu Thr Glu Val Leu Lys
    210                 215                 220

Glu Asp Ile Ile Gln Gly Phe Arg Tyr Gly Ser Asp Ile Val Pro Phe
225                 230                 235                 240

Ser Lys Val Asp Glu Glu Gln Met Lys Tyr Lys Ser Glu Gly Lys Cys
                245                 250                 255

Phe Ser Val Leu Gly Phe Cys Lys Ser Ser Gln Val Gln Arg Arg Phe
            260                 265                 270

Phe Met Gly Asn Gln Val Leu Lys Val Phe Ala Ala Arg Asp Asp Glu
        275                 280                 285

Ala Ala Ala Val Ala Leu Ser Ser Leu Ile His Ala Leu Asp Asp Leu
    290                 295                 300

Asp Ile Trp Ala Ile Val Arg Tyr Ala Tyr Asp Lys Arg Ala Asn Pro
305                 310                 315                 320

Gln Val Gly Val Ala Phe Pro His Ile Lys His Asn Tyr Glu Cys Leu
                325                 330                 335

Val Tyr Val Gln Leu Pro Phe Met Glu Asp Leu Arg Gln Tyr Met Phe
            340                 345                 350

Ser Ser Leu Lys Asn Ser Lys Lys Tyr Ala Pro Thr Glu Ala Gln Leu
        355                 360                 365

Asn Ala Val Asp Ala Leu Ile Asp Ser Met Ser Leu Ala Lys Lys Asp
    370                 375                 380

Glu Lys Thr Asp Thr Leu Glu Asp Leu Phe Pro Thr Thr Lys Ile Pro
385                 390                 395                 400

Asn Pro Arg Phe Gln Arg Leu Phe Gln Cys Leu Leu His Arg Ala Leu
                405                 410                 415

His Pro Arg Glu Pro Leu Pro Pro Ile Gln Gln His Ile Trp Asn Met
            420                 425                 430

Leu Asn Pro Pro Ala Glu Val Thr Thr Lys Ser Gln Ile Pro Leu Ser
        435                 440                 445
```

```
Lys Ile Lys Thr Leu Phe Pro Leu Ile Glu Ala Lys Lys Asp Gln
    450                 455                 460

Val Thr Ala Gln Glu Ile Phe Gln Asp Asn His Glu Asp Gly Pro Thr
465                 470                 475                 480

Ala Lys

<210> SEQ ID NO 51
<211> LENGTH: 10
<212> TYPE: DNA
<213> ORGANISM: Methanobacterium thermoautotrophicum

<400> SEQUENCE: 51
aatttttgga                                                          10

<210> SEQ ID NO 52
<211> LENGTH: 83
<212> TYPE: PRT
<213> ORGANISM: Methanobacterium thermoautotrophicum

<400> SEQUENCE: 52

Gly Ser Val Ile Asp Val Ser Ser Gln Arg Val Asn Val Gln Arg Pro
1               5                   10                  15

Leu Asp Ala Leu Gly Asn Ser Leu Asn Ser Pro Val Ile Ile Lys Leu
            20                  25                  30

Lys Gly Asp Arg Glu Phe Arg Gly Val Leu Lys Ser Phe Asp Leu His
        35                  40                  45

Met Asn Leu Val Leu Asn Asp Ala Glu Glu Leu Glu Asp Gly Glu Val
    50                  55                  60

Thr Arg Arg Leu Gly Thr Val Leu Ile Arg Gly Asp Asn Ile Val Tyr
65                  70                  75                  80

Ile Ser Pro

<210> SEQ ID NO 53
<211> LENGTH: 25
<212> TYPE: DNA
<213> ORGANISM: Bacteriophage MS2

<400> SEQUENCE: 53
gcgcacatga ggatcaccca tgtgc                                         25

<210> SEQ ID NO 54
<211> LENGTH: 116
<212> TYPE: PRT
<213> ORGANISM: Bacteriophage MS2

<400> SEQUENCE: 54

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Gly Ala Trp Arg Ser Tyr Leu Asn Met Glu Leu Thr Ile Pro
65                  70                  75                  80

Ile Phe Ala Thr Asn Ser Asp Cys Glu Leu Ile Val Lys Ala Met Gln
            85                  90                  95
```

```
Gly Leu Leu Lys Asp Gly Asn Pro Ile Pro Ser Ala Ile Ala Ala Asn
                100                 105                 110

Ser Gly Ile Tyr
        115

<210> SEQ ID NO 55
<211> LENGTH: 26
<212> TYPE: DNA
<213> ORGANISM: Bacteriophage PP7

<400> SEQUENCE: 55
ataaggagtt tatatggaaa ccctta                                        26

<210> SEQ ID NO 56
<211> LENGTH: 127
<212> TYPE: PRT
<213> ORGANISM: Bacteriophage PP7

<400> SEQUENCE: 56

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Trp Asp Cys Ser Thr Ser Val Cys Gly Glu Leu Pro Lys Val Arg Tyr
65                  70                  75                  80

Thr Gln Val Trp Ser His Asp Val Thr Ile Val Ala Asn Ser Thr Glu
                85                  90                  95

Ala Ser Arg Lys Ser Leu Tyr Asp Leu Thr Lys Ser Leu Val Ala Thr
                100                 105                 110

Ser Gln Val Glu Asp Leu Val Val Asn Leu Val Pro Leu Gly Arg
            115                 120                 125

<210> SEQ ID NO 57
<211> LENGTH: 19
<212> TYPE: DNA
<213> ORGANISM: Shigella phage

<400> SEQUENCE: 57
ctgaatgcct gcgagcatc                                                19

<210> SEQ ID NO 58
<211> LENGTH: 62
<212> TYPE: PRT
<213> ORGANISM: Shigella phage

<400> SEQUENCE: 58

Met Lys Ser Ile Arg Cys Lys Asn Cys Asn Lys Leu Leu Phe Lys Ala
1               5                   10                  15

Asp Ser Phe Asp His Ile Glu Ile Arg Cys Pro Arg Cys Lys Arg His
            20                  25                  30

Ile Ile Met Leu Asn Ala Cys Glu His Pro Thr Glu Lys His Cys Gly
        35                  40                  45

Lys Arg Glu Lys Ile Thr His Ser Asp Glu Thr Val Arg Tyr
    50                  55                  60
```

-continued

<210> SEQ ID NO 59
<211> LENGTH: 1367
<212> TYPE: PRT
<213> ORGANISM: Artificial sequence
<220> FEATURE:
<223> OTHER INFORMATION: Synthetic polypeptide

<400> SEQUENCE: 59

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
```

-continued

```
            370                 375                 380
Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
435                 440                 445

Tyr Tyr Val Gly Pro Leu Ala Arg Gly Asn Ser Arg Phe Ala Trp Met
            450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
            530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
                580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
            610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800
```

-continued

```
Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Leu Lys Asp
                835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
                915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
        1010                1015                1020

Ser Glu Gln Glu Ile Gly Lys Ala Thr Ala Lys Tyr Phe Phe Tyr
        1025                1030                1035

Ser Asn Ile Met Asn Phe Phe Lys Thr Glu Ile Thr Leu Ala Asn
        1040                1045                1050

Gly Glu Ile Arg Lys Arg Pro Leu Ile Glu Thr Asn Gly Glu Thr
        1055                1060                1065

Gly Glu Ile Val Trp Asp Lys Gly Arg Asp Phe Ala Thr Val Arg
        1070                1075                1080

Lys Val Leu Ser Met Pro Gln Val Asn Ile Val Lys Lys Thr Glu
        1085                1090                1095

Val Gln Thr Gly Gly Phe Ser Lys Glu Ser Ile Leu Pro Lys Arg
        1100                1105                1110

Asn Ser Asp Lys Leu Ile Ala Arg Lys Lys Asp Trp Asp Pro Lys
        1115                1120                1125

Lys Tyr Gly Gly Phe Asp Ser Pro Thr Val Ala Tyr Ser Val Leu
        1130                1135                1140

Val Val Ala Lys Val Glu Lys Gly Lys Ser Lys Lys Leu Lys Ser
        1145                1150                1155

Val Lys Glu Leu Leu Gly Ile Thr Ile Met Glu Arg Ser Ser Phe
        1160                1165                1170

Glu Lys Asn Pro Ile Asp Phe Leu Glu Ala Lys Gly Tyr Lys Glu
        1175                1180                1185

Val Lys Lys Asp Leu Ile Ile Lys Leu Pro Lys Tyr Ser Leu Phe
        1190                1195                1200
```

```
Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 60
<211> LENGTH: 1367
<212> TYPE: PRT
<213> ORGANISM: Artificial sequence
<220> FEATURE:
<223> OTHER INFORMATION: Synthetic polypeptide

<400> SEQUENCE: 60

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
                20                  25                  30

Val Leu Gly Asn Thr Asp Arg His Ser Ile Lys Lys Asn Leu Ile Gly
            35                  40                  45

Ala Leu Leu Phe Asp Ser Gly Glu Thr Ala Glu Ala Thr Arg Leu Lys
        50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190
```

```
Gln Leu Phe Glu Glu Asn Pro Ile Asn Ala Ser Gly Val Asp Ala Lys
            195                 200                 205
Ala Ile Leu Ser Ala Arg Leu Ser Lys Ser Arg Arg Leu Glu Asn Leu
210                 215                 220
Ile Ala Gln Leu Pro Gly Glu Lys Lys Asn Gly Leu Phe Gly Asn Leu
225                 230                 235                 240
Ile Ala Leu Ser Leu Gly Leu Thr Pro Asn Phe Lys Ser Asn Phe Asp
            245                 250                 255
Leu Ala Glu Asp Ala Lys Leu Gln Leu Ser Lys Asp Thr Tyr Asp Asp
            260                 265                 270
Asp Leu Asp Asn Leu Leu Ala Gln Ile Gly Asp Gln Tyr Ala Asp Leu
            275                 280                 285
Phe Leu Ala Ala Lys Asn Leu Ser Asp Ala Ile Leu Leu Ser Asp Ile
290                 295                 300
Leu Arg Val Asn Thr Glu Ile Thr Lys Ala Pro Leu Ser Ala Ser Met
305                 310                 315                 320
Ile Lys Arg Tyr Asp Glu His His Gln Asp Leu Thr Leu Leu Lys Ala
            325                 330                 335
Leu Val Arg Gln Gln Leu Pro Glu Lys Tyr Lys Glu Ile Phe Phe Asp
            340                 345                 350
Gln Ser Lys Asn Gly Tyr Ala Gly Tyr Ile Asp Gly Gly Ala Ser Gln
            355                 360                 365
Glu Glu Phe Tyr Lys Phe Ile Lys Pro Ile Leu Glu Lys Met Asp Gly
            370                 375                 380
Thr Glu Glu Leu Leu Val Lys Leu Asn Arg Glu Asp Leu Leu Arg Lys
385                 390                 395                 400
Gln Arg Thr Phe Asp Asn Gly Ser Ile Pro His Gln Ile His Leu Gly
            405                 410                 415
Glu Leu His Ala Ile Leu Arg Arg Gln Glu Asp Phe Tyr Pro Phe Leu
            420                 425                 430
Lys Asp Asn Arg Glu Lys Ile Glu Lys Ile Leu Thr Phe Arg Ile Pro
            435                 440                 445
Tyr Tyr Val Gly Pro Leu Ala Arg Gly Asn Ser Arg Phe Ala Trp Met
450                 455                 460
Thr Arg Lys Ser Glu Glu Thr Ile Thr Pro Trp Asn Phe Glu Glu Val
465                 470                 475                 480
Val Asp Lys Gly Ala Ser Ala Gln Ser Phe Ile Glu Arg Met Thr Asn
            485                 490                 495
Phe Asp Lys Asn Leu Pro Asn Glu Lys Val Leu Pro Lys His Ser Leu
            500                 505                 510
Leu Tyr Glu Tyr Phe Thr Val Tyr Asn Glu Leu Thr Lys Val Lys Tyr
            515                 520                 525
Val Thr Glu Gly Met Arg Lys Pro Ala Phe Leu Ser Gly Glu Gln Lys
            530                 535                 540
Lys Ala Ile Val Asp Leu Leu Phe Lys Thr Asn Arg Lys Val Thr Val
545                 550                 555                 560
Lys Gln Leu Lys Glu Asp Tyr Phe Lys Lys Ile Glu Cys Phe Asp Ser
            565                 570                 575
Val Glu Ile Ser Gly Val Glu Asp Arg Phe Asn Ala Ser Leu Gly Thr
            580                 585                 590
Tyr His Asp Leu Leu Lys Ile Ile Lys Asp Lys Asp Phe Leu Asp Asn
            595                 600                 605
Glu Glu Asn Glu Asp Ile Leu Glu Asp Ile Val Leu Thr Leu Thr Leu
```

-continued

```
            610                 615                 620
Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Tyr Thr
                645                 650                 655

Gly Trp Gly Arg Leu Ser Arg Lys Leu Ile Asn Gly Ile Arg Asp Lys
                660                 665                 670

Gln Ser Gly Lys Thr Ile Leu Asp Phe Leu Lys Ser Asp Gly Phe Ala
                675                 680                 685

Asn Arg Asn Phe Met Gln Leu Ile His Asp Asp Ser Leu Thr Phe Lys
690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
                740                 745                 750

His Lys Pro Glu Asn Ile Val Ile Glu Met Ala Arg Glu Asn Gln Thr
                755                 760                 765

Thr Gln Lys Gly Gln Lys Asn Ser Arg Glu Arg Met Lys Arg Ile Glu
770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Leu Ala Asp
                835                 840                 845

Asp Ser Ile Asp Asn Lys Val Leu Thr Arg Ser Asp Lys Asn Arg Gly
                850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
                915                 920                 925

His Val Ala Gln Ile Leu Asp Ser Arg Met Asn Thr Lys Tyr Asp Glu
930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr Pro Ala Leu Glu Ser Glu Phe Val
                995                 1000                1005

Tyr Gly Asp Tyr Lys Val Tyr Asp Val Arg Lys Met Ile Ala Lys
                1010                1015                1020

Ser Glu Gln Glu Ile Gly Lys Ala Thr Ala Lys Tyr Phe Phe Tyr
                1025                1030                1035
```

Ser Asn Ile Met Asn Phe Phe Lys Thr Glu Ile Thr Leu Ala Asn
1040                1045                1050

Gly Glu Ile Arg Lys Ala Pro Leu Ile Glu Thr Asn Gly Glu Thr
1055                1060                1065

Gly Glu Ile Val Trp Asp Lys Gly Arg Asp Phe Ala Thr Val Arg
1070                1075                1080

Lys Val Leu Ser Met Pro Gln Val Asn Ile Val Lys Lys Thr Glu
1085                1090                1095

Val Gln Thr Gly Gly Phe Ser Lys Glu Ser Ile Leu Pro Lys Arg
1100                1105                1110

Asn Ser Asp Lys Leu Ile Ala Arg Lys Lys Asp Trp Asp Pro Lys
1115                1120                1125

Lys Tyr Gly Gly Phe Asp Ser Pro Thr Val Ala Tyr Ser Val Leu
1130                1135                1140

Val Val Ala Lys Val Glu Lys Gly Lys Ser Lys Lys Leu Lys Ser
1145                1150                1155

Val Lys Glu Leu Leu Gly Ile Thr Ile Met Glu Arg Ser Ser Phe
1160                1165                1170

Glu Lys Asn Pro Ile Asp Phe Leu Glu Ala Lys Gly Tyr Lys Glu
1175                1180                1185

Val Lys Lys Asp Leu Ile Ile Lys Leu Pro Lys Tyr Ser Leu Phe
1190                1195                1200

Glu Leu Glu Asn Gly Arg Lys Arg Met Leu Ala Ser Ala Gly Glu
1205                1210                1215

Leu Gln Lys Gly Asn Glu Leu Ala Leu Pro Ser Lys Tyr Val Asn
1220                1225                1230

Phe Leu Tyr Leu Ala Ser His Tyr Glu Lys Leu Lys Gly Ser Pro
1235                1240                1245

Glu Asp Asn Glu Gln Lys Gln Leu Phe Val Glu Gln His Lys His
1250                1255                1260

Tyr Leu Asp Glu Ile Ile Glu Gln Ile Ser Glu Phe Ser Lys Arg
1265                1270                1275

Val Ile Leu Ala Asp Ala Asn Leu Asp Lys Val Leu Ser Ala Tyr
1280                1285                1290

Asn Lys His Arg Asp Lys Pro Ile Arg Glu Gln Ala Glu Asn Ile
1295                1300                1305

Ile His Leu Phe Thr Leu Thr Asn Leu Gly Ala Pro Ala Ala Phe
1310                1315                1320

Lys Tyr Phe Asp Thr Thr Ile Asp Arg Lys Arg Tyr Thr Ser Thr
1325                1330                1335

Lys Glu Val Leu Asp Ala Thr Leu Ile His Gln Ser Ile Thr Gly
1340                1345                1350

Leu Tyr Glu Thr Arg Ile Asp Leu Ser Gln Leu Gly Gly Asp
1355                1360                1365

<210> SEQ ID NO 61
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 61
gacaagaagt acagcatcgg gctggcgatc gggaccaact ccgtcggctg ggctgtgatt        60

```
accgacgagt acaaggtgcc atccaagaag ttcaaggtcc tcggcaacac tgaccggcac      120
agcattaaga agaacctgat tggggcgctg ctgttcgatt cggggagac  tgcggaggcg      180 accaggctga agcggactgc gcgccggagg tacaccagga ggaagaatcg gatctgctac      240
ctccaggaga ttttctcgaa tgagatggcc aaggtggacg attccttctt ccatcgcctg      300
gaggagtcgt tcctcgttga ggaggacaag aagcatgaga ggcatcccat tttcgggaat      360
atcgttgacg aggtggctta ccatgagaag tacccgacca tctaccatct gcggaagaag      420
ctcgtcgatt cgaccgataa ggccgacctg cggctgatct acctggccct cgcgcacatg      480
attaagttcc ggggccattt cctcatcgag ggcgacctca acccgacaa  ctcggacgtg      540 gataagctct tcattcagct cgtgcagaca tacaaccagc tcttcgagga gaatcccatt      600
aacgcctcgg gggtcgacgc taaggctatt ctctcggctc ggctgtcgaa gtcgcgccgg      660
ctggagaatc tcattgccca gctcccaggc gagaagaaga acggcctctt cggcaacctg      720
attgccctgt cgctggggct cacaccgaat ttcaagtcga acttcgacct cgccgaggac      780
gctaagctcc agctcagcaa ggatacttac gatgatgacc tcgataacct gctcgcccag      840
attggggatc agtacgcgga tctgttcctc gcggccaaga atctcagcga tgctattctc      900
ctgtcggaca ttctccgcgt caacacagag attactaagg ccccactgtc ggcgagcatg      960
attaagaggt acgatgagca tcatcaggac ctgacactgc tcaaggcgct ggtccggcag     1020
cagctccccg agaagtacaa ggagattttc ttcgatcagt caaagaatgg gtacgcgggc     1080
tacattgatg gcggcgcgtc ccaggaggag ttctacaagt tcattaagcc catcctggag     1140
aagatggacg ggaccgagga gctgctggtg aagctcaatc gggaggacct gctccggaag     1200
cagcgcacat cgacaatgg  ctcgattcct caccagattc acctgggcga gctgcacgcc     1260
attctccgca ggcaggagga cttctacccg ttcctcaagg acaaccgcga gaagatcgag     1320
aagatcctga ccttccggat tccatactac gtggggccgc tcgcgcgggg gaactcccgg     1380
ttcgcgtgga tgactcgcaa gtccgaagaa acgattacac cgtggaattt cgaggaggtc     1440
gtcgacaagg gcgctagtgc gcagtcattc attgagagga tgaccaattt cgataagaac     1500
ctgcctaacg agaaggtgct gccgaagcat tcgctgctct acgagtactt caccgtttac     1560
aatgagctga ccaaggtgaa gtatgtgact gagggcatga ggaagccagc gttcctgagc     1620
ggcgagcaga agaaggctat cgtggacctg ctcttcaaga ctaaccggaa ggtgactgtg     1680
aagcagctca aggaggacta cttcaagaag attgagtgct tcgattccgt tgagattagc     1740
ggggtggagg ggggtggagg atcggttcaa tgcttcgctc gggacatacc acgatctcct gaagatcatt     1800
aaggataagg acttcctcga caacgaggag aacgaggaca ttctcgaaga tattgtcctg     1860
accctcaccc tcttcgagga tcgggagatg atcgaggaga ggctcaagac atacgctcat     1920
ctgttcgatg ataaggtcat gaagcagctg aagcgcaggc ggtacacagg gtggggggcgg     1980 ctgagccgga agctgatcaa cgggattcgg gataagcagt ccgggaagac aattctcgac     2040
ttcctcaagt ccgacgggtt cgctaaccgg aacttcatgc agctcattca tgatgactcg     2100
ctgacattca aggaggatat tcagaaggcg caggtttcgg ggcagggcga ctcgctccac     2160
gagcatattg cgaatctggc gggctccccc gcgattaaga agggcattct gcaaaccgtc     2220
aaggtggttg atgagctggt caaggtcatg gggcggcata agccagagaa tattgtcatc     2280
gagatggcgc gggagaatca gaccacacag aaggggcaga gaactcacg  ggagcggatg     2340 aagcgcatcg aggagggcat caaggagctg gggtcgcaga tcctgaagga gcatcccgtg     2400
gagaacactc agctgcaaaa tgagaagctg tacctctact acctccagaa cgggagggac     2460
```

| | |
|---|---|
| atgtatgtgg atcaggagct ggatattaat aggctgagcg attacgatgt cgaccacatt | 2520 |
| gtcccacagt cgttcctgaa ggacgacagc attgacaaca aggtgctgac ccgctcggat | 2580 |
| aagaacaggg gcaagagcga taatgttcca agcgaggagg ttgtgaagaa gatgaagaac | 2640 |
| tactggcggc agctcctgaa cgcgaagctc atcacacagc ggaagttcga caacctcacc | 2700 |
| aaggctgagc gcggggggcct gagcgagctg gacaaggcgg ggttcattaa gaggcagctg | 2760 |
| gtcgagacac ggcagattac aaagcatgtt gcgcagattc tcgattcccg gatgaacacc | 2820 |
| aagtacgatg agaacgataa gctgattcgg gaggtcaagg taattaccct gaagtccaag | 2880 |
| ctggtgtccg acttcaggaa ggacttccag ttctacaagg ttcgggagat caacaactac | 2940 |
| caccacgcgc atgatgccta cctcaacgcg gtcgtgggga ccgctctcat caagaagtac | 3000 |
| ccaaagctgg agtcagagtt cgtctacggg gattacaagg tttacgacgt gcggaagatg | 3060 |
| atcgctaaga gcgagcagga gattggcaag gctaccgcta agtacttctt ctactccaac | 3120 |
| atcatgaact tcttcaagac agagattacc ctcgcgaatg gcgagatccg gaagaggccc | 3180 |
| ctcatcgaga caaatgggga gacaggggag attgtctggg ataaggggcg ggatttcgcg | 3240 |
| accgtccgga aggtcctgtc gatgcccag gttaatattg tcaagaagac tgaggtccag | 3300 |
| actggcggct tctcaaagga gtcgattctc ccaaagagga actccgataa gctcattgct | 3360 |
| cggaagaagg attgggaccc caagaagtac gggggattcg actcccccac tgttgcttac | 3420 |
| tctgttctgg ttgttgctaa ggtggagaag ggggaagtcga agaagctgaa gagcgtgaag | 3480 |
| gagctgctcg ggattacaat tatggagagg tcatccttcg agaagaatcc catcgacttc | 3540 |
| ctggaggcca agggctacaa ggaggtgaag aaggacctga ttattaagct gcccaagtac | 3600 |
| tcgctcttcg agctggagaa tgggcggaag cggatgctgg cgtccgcggg ggagctgcaa | 3660 |
| aaggggaacg agctggcgct ccccctccaag tatgtgaact tcctctacct ggcgtcgcac | 3720 |
| tacgagaagc tgaaggggtc cccagaggat aatgagcaga agcagctctt cgtcgagcag | 3780 |
| cataagcact acctggacga gattatcgag cagattagcg agttctcgaa gcgggtcatc | 3840 |
| ctcgcggatg cgaacctgga taaggtgctc agcgcctaca ataagcaccg ggacaagccg | 3900 |
| attcgggagc aggcggagaa tattattcac ctcttcacac tcaccaacct cggggcacca | 3960 |
| gctgcgttca gtacttcga cactactatc gaccggaagc ggtacaccctc gacgaaggag | 4020 |
| gtgctcgacg ccacccttcat tcaccagtcg atcacaggcc tgtacgagac acggattgac | 4080 |
| ctgtcccagc tcggggcgac | 4101 |

<210> SEQ ID NO 62
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 62

| | |
|---|---|
| gacaagaagt actccattgg cctggcgatt gggacaaact cggtgggggtg ggccgtgatt | 60 |
| acggatgagt acaaggttcc aagcaagaag ttcaaggtcc tcgggaacac agatcggcat | 120 |
| tcgattaaga gaatctcat tggggcgctc ctcttcgact cgggggagac agcggaggct | 180 |
| accaggctca gcggacagc caggcggcgg tacacaaggc ggaagaatcg catctgctac | 240 |
| ctccaggaga tttttctcgaa tgagatggcg aaggtggacg acagcttctt ccatcggctg | 300 |
| gaggagtcct tcctggtgga ggaggataag aagcacgaga ggcatccaat tttcgggaac | 360 |

```
atcgtggacg aggttgcgta ccatgagaag taccctacaa tctaccatct gcggaagaag    420
ctggttgact ccacagacaa ggcggacctg aggctgatct acctcgctct ggcccacatg    480
attaagttcc gcgggcattt cctgatcgag ggggacctga atcccgacaa ttcggatgtg    540
gacaagctct tcatccagct ggtgcagacc tacaaccagc tgttcgagga gaatcccatc    600
aatgcgtcgg gcgttgacgc taaggccatt ctgtccgcta ggctgtcgaa gagcaggagg    660
ctggagaacc tgatcgccca gctgccaggc gagaagaaga tgggctctt cgggaatctg     720
attgcgctct ccctggggct gacaccgaac ttcaagagca atttcgatct ggctgaggac    780
gcgaagctcc agctctcgaa ggacacttac gacgatgacc tcgataacct cctcgcgcag    840
atcggggacc agtacgctga tctcttcctc gccgctaaga acctctcgga tgctatcctg    900
ctctccgaca ttctccgggt taataccgag attacaaagg ccccactgtc ggcgtccatg    960
atcaagcggt acgatgagca tcatcaggat ctcaccctgc tcaaggccct cgtgcggcag   1020
cagctgcccg agaagtacaa ggagattttc ttcgaccaga gcaagaatgg gtacgctggc   1080
tacattgacg gcggggcctc acaggaggag ttctacaagt tcatcaagcc aatcctggag   1140
aagatggatg ggacagagga gctgctggtg aagctcaacc gggaggatct gctcaggaag   1200
cagcggacgt tcgacaacgg gtcgattccc catcagatcc acctggggga gctgcacgcg   1260
atcctgcgcc ggcaggagga tttctaccct ttcctgaagg ataatcggga gaagatcgag   1320
aagattctca ccttccggat tccctactac gtcgggccac tcgcgcgggg caatagcagg   1380
ttcgcctgga tgacacggaa gagcgaggag acaatcaccc cctggaactt cgaggaggtt   1440
gtcgacaagg gggcgtccgc ccagtcattc attgagcgga tgaccaattt cgacaagaat   1500
ctgccaaatg agaaggttct cccaaagcat agcctcctct acgagtactt cactgtttac   1560
aacgagctga ccaaggtgaa gtatgtgacc gagggcatgc ggaagcccgc gttcctgtcc   1620
ggcgagcaga agaaggccat tgtggacctc ctgttcaaga ccaatcgcaa ggtcacagtc   1680
aagcagctca aggaggatta cttcaagaag atcgagtgct tcgactcggt tgagattagc   1740
ggggtggagg atcggttcaa cgcgagcctc ggcacttacc acgacctcct gaagatcatc   1800
aaggataagg acttcctcga caacgaggag aacgaggata ttctggagga catcgtgctc   1860
accctgacgc tgttcgagga tcgggagatg atcgaggagc gcctgaagac ctacgctcat   1920
ctcttcgatg ataaggtcat gaagcagctg aagaggaggc ggtacaccgg gtggggccgc   1980
ctgagcagga agctcattaa cgggatcagg gacaagcaga gcggcaagac catcctggac   2040
ttcctcaaga gcgatggctt cgccaaccgg aatttcatgc agctcatcca cgacgactcc   2100
ctcaccttca aggaggacat tcagaaggct caggtcagcg gccagggcga ctcgctgcat   2160
gagcacatcg ctaacctggc gggcagccca gccatcaaga agggcatcct ccagacagtg   2220
aaggtcgtgg atgagctggt gaaggtcatg ggccggcata agcccgagaa tattgtgatt   2280
gagatggcgc gggagaatca gaccactcag aagggccaga gaactcgcg ggagcgcatg    2340
aagaggatcg aggagggat taaggagctg ggcagccaga ttctcaagga gcaccccgtg    2400
gagaataccc agctccagaa cgagaagctg tacctctact acctccagaa tgggcgggac   2460
atgtatgttg atcaggagct ggacatcaat cgcctctcgg attacgacgt ggaccacatc   2520
gtgccccaga gcttcctgaa ggatgatagc atcgacaata aggtcctgac ccgctccgac   2580
aagaatcgcg gcaagagcga caacgtgccg agcgaggagg tcgtgaagaa gatgaagaac   2640
tactggcggc agctgctgaa cgcgaagctc attacacagc ggaagttcga taacctgacg   2700
aaggcggaga ggggcggcct ctccgagctg gacaaggcgg gcttcattaa gaggcagctc   2760
```

```
gtggagactc gccagatcac caagcacgtg gctcagatcc tcgatagccg gatgaatacg    2820
aagtacgatg agaatgacaa gctcatccgg gaggtgaagg taatcaccct gaagtcaaag    2880
ctcgttagcg atttccggaa ggacttccag ttctacaagg tgcgggagat taacaactac    2940
catcatgcgc acgatgcgta cctcaatgcg gtggtgggca cagccctgat taagaagtac    3000
cccaagctgg agagcgagtt cgtctacggg gactacaagg tgtacgatgt tcggaagatg    3060
atcgccaaga gcgagcagga gattgggaag gccaccgcta agtacttctt ctactcgaat    3120
attatgaatt tcttcaagac cgagatcaca ctcgctaatg gggagattcg gaagcggccc    3180
ctcatcgaga ctaacgggga gactggcgag attgtgtggg acaaggggcg cgacttcgct    3240
accgtgcgca aggtcctctc gatgccccag gttaatattg ttaagaagac agaggtgcag    3300
acgggcgggt tctccaagga gtctatcctg ccgaagcgga actcggacaa gctgatcgcc    3360
cgcaagaagg attgggaccc caagaagtac gggggattcg atagcccaac cgtggcttac    3420
agcgtcctgg tggtcgccaa ggttgagaag ggaagtcga agaagctcaa gagcgttaag    3480
gagctgctgg gcatcaccat catggagcgg tccagcttcg agaagaatcc tatcgacttc    3540
ctggaggcta aggggtacaa ggaggtcaag aaggacctga tcattaagct gcccaagtac    3600
tctctgttcg agctggagaa cgggaggaag cggatgctgg cgtctgctgg cgagctacag    3660
aagggcaatg agctggcgct cccctcgaag tatgtcaact tcctctacct ggcttcccat    3720
tacgagaagc tgaagggctc gcccgaggat aatgagcaga agcagctctt cgtggagcag    3780
cacaagcact acctcgacga gatcattgag cagatttcgg agttctcgaa gcgggtcatt    3840
ctcgcggacg cgaacctcga caaggtcctc tcggcgtaca caagcaccg ggacaagccc    3900 atccgggagc aggccgagaa cattatccac ctcttcacac tgaccaacct cggcgctccc    3960
gccgcgttca gtacttcga caccaccatt gaccgcaaga gatacacatc caccaaggag    4020
gtgctggacg cgaccctcat ccaccagagc atcacaggcc tctacgagac acggatcgac    4080
ctctcgcagc tcggggcga t                                              4101
```

<210> SEQ ID NO 63
<211> LENGTH: 4092
<212> TYPE: DNA
<213> ORGANISM: Artificial sequence
<220> FEATURE:
<223> OTHER INFORMATION: Synthetic polynucleotide

<400> SEQUENCE: 63

```
gacaagaagt actcgatcgg cctggcgatt ggcacaaaca gcgtggggtg ggctgtgatc     60
actgatgagt acaaggtgcc atcgaagaag ttcaaggtgc tggggaatac agaccggcat    120
tcgatcaaga agaatctcat tggcgctctc ctcttcgatt ccggcgagac tgctgaggcg    180
acccgcctga gcgcaccgc ccggcggcgc tacactcggc ggaagaatag gatttgctac    240
ctccaggaga ttttctcgaa tgagatggcc aaggtggatg acagcttctt ccaccgcctg    300
gaggagtcgt tcctggtcga ggaggacaag aagcatgagc ggcaccctat cttcgggaat    360
atcgttgatg aggtcgccta ccacgagaag tacccccacta tctaccatct ccgcaagaag    420
ctcgtggaca gcacagataa ggccgacctc cgcctgatct acctcgccct cgcgcacatg    480
attaagttcc gggggcactt cctcattgag ggggatctga atcccgataa ctccgacgtg    540
gacaagctgt tcatccagct ggtgcagaca tacaaccagc tgttcgagga gaatcccatc    600
aacgcgagcg gcgtggacgc taaggccatt ctgtcggcta ggctctcgaa gtcgaggcgg    660
```

```
ctggagaacc tgattgcgca gctccccggc gagaagaaga acgggctgtt cgggaatctc    720
atcgccctct ccctcggcct cacaccaaac ttcaagagca atttcgacct ggctgaggac    780
gctaagctgc aactctcaaa ggatacatac gatgacgacc tggacaatct cctggctcag    840
atcggcgacc agtacgctga cctgttcctc gcggccaaga atctgtcgga cgcgattctc    900
ctcagcgaca tcctgcgcgt caataccgag attacgaagg ctccactgtc tgcgtcaatg    960
attaagcggt acgatgagca tcaccaggat ctgaccctcc tgaaggcgct cgtgcggcag   1020
cagctgcccg agaagtacaa ggagattttc ttcgatcaga gcaagaatgg ctacgccggc   1080
tacatcgacg gggcgcgag ccaggaggag ttctacaagt tcatcaagcc catcctggag   1140
aagatggacg gcaccgagga gctactcgtg aagctcaatc gggaggatct cctccggaag   1200
cagcggacat tcgataacgg gtctatccca caccagatcc acctcggcga gctgcatgcg   1260
attctgcggc ggcaggagga tttctaccct ttcctgaagg acaaccggga agatcgag    1320
aagatcctca cattccggat tccatactac gtcggcccc tggcgagggg caatagccgg   1380
ttcgcgtgga tgacaaggaa gtccgaggag actattaccc cgtggaattt cgaggaggtg   1440
gttgacaagg gcgcttccgc gcagagcttc attgagcgga tgacaaactt cgacaagaat   1500
ctccccaacg agaaggtcct gccgaagcat agcctcctgt acgagtactt caccgtctac   1560
aatgagctaa ctaaggtcaa gtatgtgaca gagggcatga ggaagccagc cttcctctca   1620
ggcgagcaga agaaggccat tgtggacctc ctgttcaaga caaaccgcaa ggtgacagtg   1680
aagcagctga aggaggatta cttcaagaag attgagtgct tcgactcagt ggagatttca   1740
ggcgtggagg atcggttcaa cgcgagcctg ggacttacc acgacctgct gaagattatt   1800
aaggacaagg acttcctgga taacgaggag aatgaggaca tcctggagga tattgtgctc   1860
accctcaccc tgttcgagga cagggagatg attgaggaga ggctcaagac ctacgcgcac   1920
ctgttcgatg acaaggtcat gaagcagctg aagaggcggc gctacactgg gtggggccgc   1980
ctgtcgcgga agctgatcaa cggcattcgg gataagcagt ccgggaagac cattctggat   2040
ttcctgaagt cggacggctt cgccaacagg aatttcatgc agctgatcca cgacgactcc   2100
ctcaccttca aggaggacat tcagaaggcc caggttagcg gccaggggga ctcactccac   2160
gagcatattg ccaatctggc cggctctcca gctatcaaga agggcatcct gcaaacagtt   2220
aaggttgttg acgagctggt taaggtcatg gggcggcata agcccgagaa cattgtcatc   2280
gagatggctc gggagaacca gacaactcag aagggccaga agaactccag ggagcgcatg   2340
aagcggattg aggagggcat taaggagctg gggtcccaga tcctcaagga gcaccctgtc   2400
gagaacactc agctgcaaaa cgagaagctc tacctgtact acctccagaa cgggcgggat   2460
atgtatgtgg atcaggagct ggacatcaac aggctctccg actacgacgt ggatcacatt   2520
gtcccacagt ctttcctcaa ggatgattcc atcgacaaca aggtgctgac gcgcagcgac   2580
aagaataggg ggaagtcgga caacgttccg agcgaggagg tcgtgaagaa gatgaagaat   2640
tactggaggc agctcctgaa tgcgaagctg atcactcaga ggaagttcga caatctgaca   2700
aaggcggaga ggggcgggct ctcggagctg gataaggcgg gcttcatcaa gcggcagctc   2760
gttgaaaccc ggcagatcac caagcatgtc gcccagatcc tcgatagccg catgaacacc   2820
aagtacgatg agaacgacaa gctcattcgg gaggttaagg tcattacgct gaagtccaag   2880
ctcgtcagcg acttcaggaa ggatttccag ttctacaagg ttcgggagat taacaactac   2940
caccacgcgc atgatgcgta cctgaacgct gttgtcggca ctgctctcat caagaagtac   3000
ccaaagctgg agtccgagtt cgtctacggg gactacaagg tctacgatgt ccggaagatg   3060
```

```
atcgccaagt cggagcagga gatcgggaag gctactgcga agtacttctt ctacagcaac    3120
attatgaatt tcttcaagac ggagattacg ctggcgaacg gggagattag gaagaggccc    3180
ctcattgaga ctaatgggga gacaggcgag attgtttggg acaagggccg cgacttcgcg    3240
actgtgcgga aggtcctgtc catgccacag gtgaatattg ttaagaagac agaggtgcag    3300
actgggggct tctcgaagga gagcattctc ccaaagcgga acagcgataa gctcatcgcg    3360
cgcaagaagg attgggaccc taagaagtac ggcggcttcg attctcccac tgtggcctac    3420
tccgttctcg tggttgccaa ggttgagaag gggaagtcga agaagctgaa gtcggtcaag    3480
gagctgctcg ggattacaat catggagcgg agcagcttcg agaagaaccc tattgatttc    3540
ctggaggcca agggctacaa ggaggttaag aaggatctca ttatcaagct ccctaagtac    3600
tctctgttcg agctggagaa tggccggaag aggatgctgg cctcggctgg cgagctacag    3660
aaggggaatg agctggccct cccgtcgaag tatgtgaatt tcctgtacct cgcgtcgcac    3720
tacgagaagc tcaagggcag cccggaggat aatgagcaga agcagctctt cgtggagcag    3780
cataagcact acctggacga gatcattgag cagatcagcg agttctcgaa gcgggttatt    3840
ctggctgatg ctaacctgga caaggttctg agcgcctaca ataagcatcg cgacaagccg    3900
attcgcgagc aggcggagaa tattatccac ctgttcaccc tcactaacct cggggctccc    3960
gcggccttca gtacttcga taccacaata gataggaagc ggtacacctc gacgaaggag    4020
gtcctcgacg ccacactcat ccatcagtcg attacaggcc tgtacgagac acggattgac    4080
ctctcgcagc tg                                                        4092

<210> SEQ ID NO 64
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 64
gacaagaagt attccatagg cctggctatc ggcaccaaca gcgtgggctg ggccgtcatc      60
accgacgagt acaaagtgcc gagtaaaaag ttcaaagtgc tcggcaacac cgaccgccac     120
tccataaaga aaaacctgat cggggcgctc ctgttcgaca cggcgagac ggcggaggcc     180
acccgcttga acgcacggc ccgacggcgc tacacgcggc gcaagaaccg gatctgttac     240
ctacaggaga ttttctctaa cgagatggcg aaggtggacg actcgttctt tcaccgcctc     300
gaagagtcct tcctcgtgga ggaggacaag aaacacgagc gccacccgat cttcggcaac     360
atcgtggacg aggtggccta ccacgagaag taccccgacca tctaccacct ccggaagaaa     420
ctcgtggaca gcacggacaa ggccgacctg aggctcatct acctcgccct ggcgcacatg     480
attaagttcc ggggccactt cctgatcgag ggcgacctga acccggacaa cagcgacgtg     540
gacaagctgt tcatccagct agtccagacc tacaaccagc ttttcgagga aaacccatc     600
aacgccagcg gggtggacgc gaaggcgatc ctgtccgccc ggctgagcaa gtcccggcgg     660
ctggagaacc tcatcgcgca gttgcccggc gagaagaaga cgggctgtt cgggaacctg     720
atcgccctct ccctggggct cacccgaac ttcaagtcca acttcgacct cgccgaggac     780
gccaaactac agctgagcaa ggacacctac gacgacgacc tcgacaacct gctggcccag     840
atcggggacc agtacgcaga cctgttcctc gccgccaaga acctctccga cgccatcctg     900
ctgtcggaca tcctgcgggt gaacacggag atcacgaagg cccccgctctc ggcctcgatg     960
```

```
attaaacgct acgacgagca ccaccaggac ttgaccctcc tcaaggcgct ggtccgccag    1020
cagcttcccg agaagtacaa ggaaatcttt ttcgatcaga gcaagaacgg gtacgccggg    1080
tacatcgacg gcggggcgtc ccaggaggag ttctacaagt tcatcaagcc catcctggag    1140
aaaatggacg ggaccgagga gctgctcgtg aagctcaacc gcgaagattt gctccgcaag    1200
cagcgcacgt tcgacaacgg gtcgatcccg caccagatcc acctgggcga gctgcacgcg    1260
atcctcaggc gtcaggaaga cttctacccc ttcctcaagg acaaccgcga gaagatagag    1320
aagattctga ccttcagaat tccttattac gtgggcccgc tggctcgggg caactcgcgc    1380
ttcgcctgga tgacgcgcaa gtccgaggag accatcaccc cgtggaactt cgaggaggtg    1440
gtggataagg gtgcctcggc ccagtccttc atcgagcgga tgaccaactt cgacaagaac    1500
ctgccgaacg agaaggtgct ccccaagcac agcctgctct acgaatattt cacggtgtac    1560
aacgagctga cgaaggtcaa gtacgtgacc gagggaatga ggaaacctgc attcctctcc    1620
ggggagcaga agaaagccat agtcgacctc ctgttcaaga ccaaccggaa ggtcaccgtc    1680
aagcagctca aggaggacta cttcaagaag atcgagtgct tcgattcagt ggagatcagc    1740
ggcgtcgagg accggttcaa cgccagcctg gcacctacc cgacctgct caagatcatc     1800
aaggacaagg acttcctcga caacgaggag aacgaggaca tcctggagga catcgtgctg    1860
accctgacgc tcttcgagga ccgcgagatg atcgaggagc gcctcaagac ctacgcccac    1920
ctgttcgacg caaggtgat gaagcagctc aagcggcgga gatatactgg gtggggccgc     1980
ctctcccgga agctcattaa cggtatcagg gataagcagt ccgggaagac gatcctcgac    2040
ttcctcaagt cggacgggtt cgccaaccgc aacttcatgc agctcatcca cgacgactcc    2100
ctgacgttca aggaggacat ccagaaggcc caagtgtctg gtcaaggtga ctcgctccac    2160
gagcacatcg ccaacctcgc gggcagcccg gccatcaaga agggaatact ccagaccgtc    2220
aaggtggtgg acgagctggt gaaggtcatg ggccgccaca agccggagaa catcgtcatc    2280
gagatggcgc gggagaacca gaccacgcag aaggggcaga aaaatagccg tgagcgcatg    2340
aagcgcatcg aggaggggat taaggagttg ggcagccaga tcctcaagga gcaccctgtg    2400
gagaacacgc agttgcaaaa cgagaagctc tacctgtact acctccagaa cgggagggat    2460
atgtacgtgg accaagaact ggacatcaac cgcctgtccg actacgacgt ggaccacatc    2520
gtgccgcaga gcttcctcaa ggacgacagc atcgacaaca aggtgctcac ccggtccgac    2580
aagaatcggg gcaagtccga caacgtgccc agcgaggagg tcgtcaaaaa gatgaaaaac    2640
tactggcgac aactactgaa cgccaagctc atcacccagc gcaagttcga caacctcaca    2700
aaagccgagc gcggcgggtt gagcgagctg gacaaggccg ggttcatcaa gcgccagctc    2760
gtcgagacgc gccagatcac gaagcacgtc gcgcagatac tcgacagccg gatgaacacc    2820
aagtacgacg agaacgacaa gctcatccgg gaggtgaagg tcatcacccT caagtcgaag    2880
ctcgtgagcg acttccgcaa ggacttccag ttctacaagg tccggagat caacaactac     2940
caccacgccc acgatgctta tcttaacgcc gtggtgggga cggccctcat taagaaatac    3000
ccgaagctgg agtcggagtt cgtgtacggc gactacaagg tgtacgacgt caggaagatg    3060
atcgccaagt ccgaacagga gatcgggaag gccacgcgca aatacttctt ctacagcaac    3120
atcatgaact tcttcaagac cgagatcacc ctcgccaacg gcgagatccg caagcgcccg    3180
ctcatcgaga cgaacgggga gaccggcgag atcgtctggg acaaggggcg cgacttcgcc    3240
actgtgcgga aggtgctgtc gatgcccag gtcaacatcg tcaagaagac ggaggtccag    3300
acgggcgggt tcagcaagga gagcatcctg ccgaagcgca acagcgacaa gctgatcgcc    3360
```

```
cgcaaaaagg actgggatcc aaaaaagtac ggcggcttcg acagccccac cgtcgcctac    3420
agcgtcctcg tcgtcgctaa agtcgagaag ggcaagtcca aaaagctcaa gagcgtcaag    3480
gagctgctcg ggatcaccat catggagcgg tccagcttcg agaagaaccc aattgatttc    3540
ctggaggcga agggctacaa ggaggtcaag aaagacctca tcataaagct gccgaagtac    3600
tcactcttcg agctggagaa cgggcgcaag cggatgctgg cgtcggccgg agagctccaa    3660
aagggcaacg agctggcgct gccgagcaag tacgtgaact tcctctacct ggcgtcccac    3720
tacgagaagc tcaagggcag tccagaggat aacgagcaga agcagctatt cgtggagcag    3780
cacaagcact acctggacga gatcatcgag cagatcagcg agttctccaa gcgcgtcatc    3840
ctggcggacg ccaacctgga caaggtgctg tccgcgtaca acaagcaccg cgacaagccg    3900
atccgcgagc aagccgagaa catcatccac ctgttcaccc tcacgaacct cggggcaccc    3960
gccgccttca atatttcga cacgaccatc gaccgcaagc gctacaccag cacgaaggag    4020
gtgctcgacg ccaccctgat ccaccagagc atcaccgggc tgtacgagac ccgcatcgac    4080
ctctcgcagc tcggcgggga c                                              4101
```

<210> SEQ ID NO 65
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 65

```
gacaagaagt acagtattgg attggccatc gggacgaaca gcgtgggctg ggccgtcatc      60
accgacgagt acaaggtgcc atccaagaag tttaaggttc tggggaatac cgaccgccac     120
tcgatcaaga aaaatctcat cggggcgctg cttttcgaca cggcgagac ggcggaagcg     180 acgcggctca gcggacggc tcgtcgccgt tacacccggc gtaagaaccg catctgttac     240
ctccaggaga tattcagcaa cgagatggcg aaggtggacg actccttttt ccaccgtctt     300
gaggagtcct tcctggtcga ggaggacaag aagcacgagc gccacccgat cttcgggaac     360
atcgtggacg aggtggccta ccacgagaag taccccacga tctaccacct ccgcaaaaaa     420
ctcgtggact caactgacaa ggccgatttg aggcttatct acctcgccct cgcccacatg     480
attaagttcc gtgggcactt cctaatcgag ggtgacctca accccgacaa ctctgacgtg     540
gacaagctgt tcatccagct tgtgcagacc tacaatcagc tctttgagga gaatccgatc     600
aacgcatctg gtgtggacgc aaaggccatc ctcagcgcgc ggctgagcaa gtctaggcgg     660
ttggagaacc tgatcgccca actgcccggc gagaagaaaa atggcctctt cggcaacctg     720
atcgccctgt cgctgggct cacgccgaac ttcaagagta actttgacct ggcggaggac     780
gctaagctcc agctatctaa ggacacatac gacgacgacc tggacaacct gctggcccag     840
atcggcgacc agtacgccga cctcttccta gccgccaaga acctgtccga cgccatcctc     900
ctcagcgaca tcctgcgcgt gaacacggag atcacgaagg ctccgctcag cgcctccatg     960
attaagcggt acgacgagca ccaccaagac ctaactttac tcaaagccct cgtgcggcag    1020
cagcttcccg agaagtacaa agagatattt tttgatcagt ccaagaacgg ttatgcgggc    1080
tacatcgacg gcggcgcgag ccaggaggag ttctacaagt tcatcaagcc catcctggag    1140
aagatggacg gcacggagga gctgctcgtg aagctcaacc gtgaagacct cctgcgaaag    1200
cagcgaacct tcgacaacgg ttcgatcccg caccagatcc acctcgggga gctgcacgcc    1260
```

```
atcctgaggc gacaggagga cttctaccct ttcctaaagg acaaccgcga gaagattgaa    1320
aaaatcctga cgtttcgcat accctactac gtcggcccgc tggcgcgcgg caactcccgg    1380
ttcgcctgga tgacccgtaa gagcgaggag acgatcaccc cgtggaactt cgaggaggtc    1440
gtggacaagg cgcgcagcgc gcagagcttc atcgagcgca tgaccaactt cgacaagaac    1500
ctcccgaacg agaaggtgct cccaaagcac tccctcctgt acgagtattt caccgtgtac    1560
aacgagttga caaggtgaa gtacgtgacg gagggaatgc ggaagcctgc gttcctctcg    1620
ggcgagcaga agaaggcaat cgtggacctg ctcttcaaga ccaaccggaa ggtgacggtg    1680
aagcagctca aggaggacta cttcaaaaaa atcgagtgct tcgactccgt ggagataagc    1740
ggcgtggagg accgattcaa cgcctccctc ggcacctacc acgacctcct taagatcatc    1800
aaggacaagg acttcctgga caacgaggag aacgaggaca tcctggagga catcgtgctc    1860
accctgaccc tcttcgagga ccgggagatg atcgaggagc gcctcaagac gtacgcccac    1920
ttgttcgacg acaaggtgat gaagcagctc aagcggcggc gatacaccgg gtggggccgc    1980
ctatcccgca aacttatcaa cggcatccgc gacaagcagt ccggcaagac gatcctggat    2040
ttcctcaagt cggacgggtt cgccaaccgg aacttcatgc agctcatcca cgacgacagc    2100
ctcacgttca aggaggacat ccagaaggcc caagtgagcg gtcaagggga cagcctccac    2160
gagcacattg cgaaccttgc tgggagcccct gcgatcaaga aggggatatt gcaaaccgtg    2220
aaggtcgtgg acgagttggt gaaggtcatg gggcgacaca agcccgagaa catcgtgatc    2280
gagatggcca gggaaaatca gaccacgcag aagggccaaa aaaacagccg cgagcggatg    2340
aagcggatcg aggagggcat caaggagctg gggtcgcaga tcctcaagga gcacccggtg    2400
gagaacacgc agctccagaa cgagaagctg tacctctatt acctacagaa cgggcgggat    2460
atgtacgtgg accaggagct agacatcaac cgcctgtccg actacgacgt ggaccatatc    2520
gtcccgcagt cgttcttgaa ggacgacagc atcgacaaca aggtgctcac aagatcggat    2580
aagaatcgag gcaagtccga caacgtgccc tcggaggagg tggtcaagaa aatgaaaaac    2640
tactggcggc agttgctgaa cgccaagctc attacgcagc ggaagttcga caacctgacg    2700
aaggctgaac gtggtgggct cagcgagcta gacaaggcgg ggttcatcaa gcggcagctc    2760
gtcgagaccc ggcagatcac caagcacgtg gcgcagatcc tggactcgcg catgaacacc    2820
aagtacgacg agaacgacaa gctcatccgt gaggtgaagg tcatcacccct taagtctaag    2880
ctggtcagtg acttccgcaa ggacttccag ttctacaagg tccgggagat caacaactac    2940
caccacgcgc acgacgccta cctcaacgcg gtggtgggga cggcgcttat taagaaatat    3000
cccaagctgg aaagcgagtt cgtttacggc gactacaagg tgtacgacgt ccgcaagatg    3060
atcgcaaagt cggaacagga aatcggaaag gcgacggcca atatttctt ttactccaac    3120
atcatgaatt ttttaagac ggagatcacc ctggcgaacg gggagatccg caagcggccc    3180
ctcatcgaga ccaacgggga gacgggcgag atcgtctggg acaagggccg ggacttcgcc    3240
accgtgcgga aggtgctttc tatgcctcaa gtcaatatcg tcaaaaagac agaggtgcag    3300
accggcgggt tcagcaagga gtctatcctg ccgaagcgca actcggacaa gctcatcgcg    3360
cgcaagaaag actgggaccc caaaaaatat ggcgggttcg actcgccgac cgtcgcctac    3420
agcgtcctcg tggtggctaa ggtcgagaag ggcaagagca aaaagctaaa gtcggtgaag    3480
gagctgctgg gcatcaccat catggagcgc tcgtctttcg agaagaatcc aatcgacttc    3540
ctagaggcga aggggtacaa ggaggtcaaa aaggatctta tcatcaaact gccgaagtac    3600
agtctgttcg agctggagaa cgggcggaag cggatgctgg ctagtgcggg cgagttgcag    3660
```

```
aagggcaacg agttggcact gccctccaag tacgtgaact tcctgtacct ggcctcccac    3720
tacgagaagc tcaaggggag ccccgaggac aacgagcaga agcagctatt cgtcgagcag    3780
cacaagcact acctggacga gatcatcgag cagatcagtg agttctccaa gcgggtcatc    3840
ctcgcggacg ccaacctgga caaggtgctg agcgcgtaca acaagcacag ggacaagcca    3900
atcagggaac aggccgagaa catcatccac ctgttcaccc tgaccaacct gggtgcaccg    3960
gctgccttca agtactttga cacgaccatc gaccggaagc gctacacctc cacgaaggag    4020
gtgctggacg ccacgctgat ccaccagagc atcaccgggc tctacgagac acggatcgac    4080
ctgagccagc ttggcgggga c                                              4101
```

<210> SEQ ID NO 66
<211> LENGTH: 4092
<212> TYPE: DNA
<213> ORGANISM: Artificial sequence
<220> FEATURE:
<223> OTHER INFORMATION: Synthetic polynucleotide

<400> SEQUENCE: 66

```
gacaaaaagt attccattgg actcgctatc ggcacgaaca cgtcgggtg ggcggtcatc      60 actgacgagt acaaggtgcc gagcaagaag tttaaggtgc tgggaaacac cgacaggcac    120
tcgatcaaga aaatcttat cggggcccta ctcttcgact ccggagaaac cgccgaggcc    180
acccggttga agcgcacggc ccgccgtcgc tacaccaggc gcaagaaccg gatctgctac    240
ctccaggaga tattcagcaa tgagatggcg aaggtggacg actcgttttt tcacaggcta    300
gaggagtctt cctcgtgga ggaggacaag aaaacacgagc gccacccccat cttcggcaac    360 atcgtggatg aggtggcata tcacgagaag tacccaacca tctaccacct ccgcaaaaag    420
ctcgtggact ctaccgacaa ggccgacctc cgtctgatct acctcgcgct ggcccacatg    480
attaagttcc gaggacactt tctgatcgag ggcgacctga acccagacaa cagcgacgtg    540
gacaagctgt tcatccaact tgtccagacc tacaatcagc tcttcgagga aaccctatc    600 aacgcctcgg gcgtgacgc gaaggccatc ctgtccgccc gcctgagcaa gtcgcggcgg    660
ctggagaacc tgatcgccca gctccccggc gaaaaaaaga acggcctctt cggcaacctc    720
atcgcgttgt cgctggggct caccccgaac ttcaagtcca acttcgacct ggccgaggac    780
gctaaactcc agctctcgaa ggatacctac gacgacgacc tcgacaacct gctggcccag    840
atcggcgacc agtacgcgga ccttttcctg gcggccaaga acctgagcga cgcgatcctc    900
cttagcgaca tactccgtgt gaacaccgag atcacgaagg cccgctctc cgcgtccatg    960 attaagcgct acgacgagca ccaccaagac cttaccctgc ttaaggcgct ggtcaggcag   1020
cagttaccgg agaagtacaa ggagatcttt tttgatcaat ctaagaacgg ttacgccggg   1080
tacatcgacg gcggcgcgtc ccaggaggag ttctacaagt tcatcaagcc gatcttggag   1140
aaaatggacg gaccgaggag gctgctcgtg aagctcaacc gcgaagacct cctccgcaag   1200
cagcgcacct tcgacaacgg gagcatcccg caccagatcc acctgggaga gctgcacgcg   1260
atcctgcgga acaagagga cttctacccc ttcctcaagg acaaccggga gaagattgaa   1320
aaaatactta ctttcgtat cccgtactac gtcgggcccc ttgcgagggg caactccaga   1380
ttcgcgtgga tgaccgcaa gtccgaggag accatcaccc cgtggaactt cgaggaggtg   1440
gtggacaagg gcgcgtcggc ccagtcgttc atcgagcgca tgaccaactt cgacaagaac   1500
cttccgaacg agaaggtgct cccgaagcac agcctgctct acgaatattt tactgtgtac   1560
```

```
aacgagctga cgaaggtcaa gtacgttacg gaggggatga ggaagcccgc cttcctctcc      1620
ggcgagcaga agaaagccat tgtggatctc ctgttcaaga ccaaccgcaa ggtgacggtg      1680
aaacagctca agaggactac cttcaagaag atcgagtgct tcgactccgt agagatcagc      1740
ggggtcgagg accgcttcaa cgcctcgctg ggcacgtacc acgacctgct aaagattatc      1800
aaggacaaag acttcctaga caatgaggag aacgaggaca ttctggagga catcgtgctg      1860
actctgacgc tgttcgaaga ccgcgagatg atcgaggagc ggcttaagac gtacgcccac      1920
ctgttcgacg acaaggtgat gaagcagttg aaacggcggc gctacaccgg gtggggccgc      1980
ctctcccgca agctcatcaa cggcatccgc gacaagcagt cggggaagac gatcctggac      2040
ttcctcaaga gcgacggctt cgccaaccga aacttcatgc agctaatcca cgacgacagc      2100
ctgacgttca aggaggacat ccagaaggcc aagtgagcg gccagggaga ctcgctacac       2160
gagcatatcg ccaacctggc tggcagcccg gcgattaaga aggaatcct ccaaaccgtc       2220
aaagtggtgg acgagctggt gaaggtgatg ggccgccaca agcccgagaa cattgtgatc      2280
gagatggcgc gggagaacca cgacgcag aagggccaaa aaaatagcag ggaaaggatg        2340
aagcgaatag aggaggggat caaggagctg gggagccaga ttctcaaaga gcacccggtc      2400
gagaacacac agctccagaa cgagaagctg tacctctact acctcaaaaa cggccgcgat      2460
atgtacgtgg accaggaact agacatcaac cggctgagcg actatgacgt ggaccacatc      2520
gtgccgcagt ccttcctcaa ggacgactcg attgacaaca agtgctcac tagatccgac       2580
aagaacagag gcaagagcga taacgtcccg tcggaggagg tcgtcaagaa aatgaaaaac      2640
tactggcggc agctcctaaa cgccaagctc atcacgcagc gtaagttcga caacctgacg      2700
aaggcggagc ggggcgggct gagcgagctg gacaaagcgg ggttcatcaa gcggcagctc      2760
gttgagacgc ggcagatcac aaagcacgtc gcgcaaatcc tcgactcccg catgaacacc      2820
aagtacgacg agaacgacaa gctcatccgg gaggtgaagg tcattaccct taaatcgaag      2880
ctcgtcagcg actttcgtaa ggacttccag ttctacaagg tcagagagat caacaactac      2940
caccacgccc acgacgccta tctgaacgcc gtggtgggca ccgcgcttat taagaagtac      3000
cccaagctgg agtccgagtt cgtgtacggc gactacaagg tttatgacgt caggaagatg      3060
atcgccaagt cggaacagga gatcggaaaa gctaccgcca aatatttctt ctatagcaac      3120
atcatgaact tcttcaaaac cgagatcacc ctcgccaacg gcgagatccg gaagcgcccg      3180
ctcatcgaga ccaacgggga gaccggggag atcgtctggg acaaggggcg ggacttcgct      3240
actgtccgaa aggtgctctc catgccacaa gtgaatatcg tcaagaaaac agaggtgcag      3300
accggagggt tcagtaagga gtccatcctg cccaagcgga actccgacaa gctaattgct      3360
cgcaaaaagg attgggatcc taaaaaatat ggcggcttcg actcgcccac ggtcgcctac      3420
tctgtgctgg tcgtggcgaa ggtggagaag ggcaagtcca agaagctcaa gagcgtcaag      3480
gagctgctgg ggatcacgat catggagcgt agttcgtttg agaagaatcc catcgacttc      3540
ctggaggcta agggctacaa ggaggtcaaa aaggacctca tcattaagct gccgaagtac      3600
agcctcttcg agctggagaa cgggcggaag cgtatgctcg cctccgctgg ggagttacaa      3660
aaggggaacg agctggcgct gccgtctaag tacgtcaact tcctgtacct ggcctcccac      3720
tacgagaagc tcaagggggtc gccggaggac aacgagcaga agcagctctt cgtagagcag      3780
cacaagcact acctgacga gatcatcgag cagatttcag agttctcaaa gcgggtcatc      3840
ctcgccgacg ccaacctgga caaggtgctc tcggcctaca acaagcaccg ggacaagccg      3900
atccgcgaac aggccgaaaa catcatccac ctgttcacgc tcaccaacct cggtgccccg      3960
```

```
gcggccttca agtactttga cacgaccatc gaccggaagc gctatacctc gacgaaggag    4020
gtgctggacg ccaccctgat ccaccagtcc atcaccgggc tttacgagac ccggatcgac    4080
ctctcgcagc ta                                                         4092

<210> SEQ ID NO 67
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 67
gacaagaagt atagtattgg actcgccatc ggaaccaact ctgtggggtg ggctgttatt      60
acagatgaat ataaggtgcc atccaaaaag tttaaagttc tgggcaatac tgatagacac     120
tcaatcaaga agaatctgat aggtgcactt ctgtttgata gtggagagac tgccgaggca     180
accagactta aaggactgc aagaagaaga tataccagaa gaaagaatag gatttgctat      240
ttgcaggaaa tcttcagcaa cgaaatggcc aaggttgatg actcattttt ccataggttg     300
gaggagagtt tccttgtgga ggaagataag aagcacgaaa gacacccaat tttcgggaat     360
atagtggacg aggtggctta tcatgagaag tatcccacta tctaccacct gagaaagaaa     420
cttgtggact caaccgataa ggctgatctt aggcttatat acttggccct tgcacatatg     480
atcaaattca ggggccattt tcttatcgaa ggcgatctta atcccgataa ctcagatgtg     540
gacaagctgt ttatacaact tgtgcaaacc tacaatcaac tcttcgagga gaatcccatt     600
aacgcctccg gcgtggatgc aaaagccata ctgtcagcca gactgagcaa aagtaggaga     660
ctggagaatc ttatagccca actgcccggt gaaaagaaga atgggctctt cggaaatctg     720
atcgctcttt cattggggtt gacacccaac tttaagagta actttgactt ggcagaagat     780
gcaaagttgc agctcagtaa agacacatat gacgatgacc ttgacaatct cttggcacaa     840
ataggggatc aatacgctga ccttttcctc gctgccaaga acctcagcga cgctatactg     900
ttgtccgaca ttcttagggt taataccgaa attacaaagg cccctcttag tgcaagtatg     960
atcaaaaggt atgatgagca tcaccaagac cttacactgc tgaaggctct ggttagacag    1020
caactccctg aaaagtataa ggaaatattc ttcgaccaaa gtaagaacgg gtacgccggt    1080
tatattgatg ggggcgcaag tcaagaagaa ttttacaaat tcatcaagcc aattcttgaa    1140
aagatggacg ggactgagga attgctggtg aaactgaata gagaggacct tcttagaaaa    1200
cagaggacat ttgacaatgg gtccatccca caccagattc atctggggga actccacgca    1260
atattgagga gacaagaaga cttttaccca ttccttaagg ataatagaga gaaaatcgaa    1320
aaaatcctga ctttcaggat tccttactat gttgggccac tggccagggg gaactcaaga    1380
ttcgcttgga tgacaaggaa gtcagaagaa accataaccc cttggaattt tgaagaggtg    1440
gttgataagg gggcatcagc ccagtctttc atagagagga tgaccaactt tgataaaaat    1500
cttccaaatg agaaggtttt gccaaaacat agtcttttgt acgagtactt tactgtttat    1560
aacgaattga ccaaggtgaa gtatgtgacc gagggaatga ggaagccagc attttttgtcc   1620 ggggagcaaa agaaagcaat cgttgatctt ctccttcaaga ccaacagaaa agtgaccgtg   1680
aaacaactga aggaagacta cttcaaaaag atagaatgtt tcgattcagt ggaaattagc    1740
ggtgttgaag acaggttcaa tgcttcattg ggtacttacc acgacctgtt gaagataatc    1800
aaagacaagg actttctcga taatgaggag aacgaagaca tcttggaaga cattgtgctt    1860
```

```
acactcactt tgtttgagga cagggaaatg attgaggaaa gactcaaaac ttacgctcat    1920
ttgtttgatg ataaggttat gaaacaacta aaaagaagaa ggtacaccgg ctggggaaga    1980
ttgagtagga aactgatcaa cggtattaga gataaacaat ccggaaagac tatcctcgat    2040
ttccttaaga gtgatggctt tgcaaatagg aattttatgc agctgattca tgacgactca    2100
cttaccttca aagaagacat ccaaaaagct caggtgtctg gcaaggcga cagtctgcat    2160
gaacatatag ctaacttggc tgggagtccc gccatcaaga aggggatact tcaaacagtt    2220
aaagttgtgg acgaattggt gaaggtaatg ggaaggcaca agcctgaaaa tatagtgata    2280
gaaatggcaa gggaaaatca aacaacccag aagggacaga agaacagtag ggaaaggatg    2340
aaaaggatag aagagggat caaagagctt ggtagccaga tcctcaagga acatccagtg    2400
gagaataccc aacttcaaaa cgagaaactc tatttgtact acttgcagaa cggaagagat    2460
atgtatgtgg accaagagct tgatattaac aggctgagcg attatgacgt tgaccacata    2520
gtgcccaat cattcctcaa ggatgactct attgataata aggtgctgac aaggagtgac    2580
aagaatagag ggaaatccga caacgttcca tccgaggaag ttgtgaagaa gatgaagaac    2640
tactggaggc agttgctgaa cgctaagctc attacccaga ggaaattcga taacctgacc    2700
aaaagcagaga gaggcgggct gagcgaactc gataaagcag gtttcatcaa gagacaactc    2760
gtggagacta ggcaaattac taagcacgtg gctcaaatac tcgacagcag gatgaacaca    2820
aagtacgacg agaacgacaa gctcattaga gaggttaagg ttattactct gaaaagtaaa    2880
ttggttagcg atttcagaaa ggatttccaa ttctataagg ttagagagat caacaattat    2940
catcatgcac atgatgccta tctgaatgct gtggttggta cagcccttat caagaagtac    3000
cctaagctag agagcgagtt tgtgtacgga gattataagg tgtatgatgt gaggaaaatg    3060
atcgctaaaa gtgagcaaga gattggaaag gctaccgcca aatacttctt ttattccaat    3120
attatgaatt tcttcaagac agaaatcacc ctggctaacg gcgagataag gaagaggccg    3180
cttatcgaaa ctaatgggga gacaggcgaa atagtgtggg acaaagggag ggatttcgca    3240
actgtgagga aggttttgag catgcctcag gtgaatatcg ttaagaaaac cgaagttcaa    3300
actggagggt tctctaagga aagcattctc cccaagagga actccgacaa gctgattgct    3360
agaaagaaag actgggaccc caagaagtat ggcggattcg actcacccac tgtggcatat    3420
agcgttctcg tggtggcaaa ggttgaaaag ggtaaatcca aaaaactcaa atccgtgaag    3480
gaactccttg gcataactat tatggaaagg agtagctttg aaaagaatcc catcgacttt    3540
ctcgaagcta agggctataa ggaagttaag aaggaccta taatcaaact tccaaaatac    3600
tccctttttg agttggaaaa cggcagaaag agaatgttgg ccagtgccgg ggagcttcaa    3660
aagggcaacg aactggctct gcctagcaaa tatgtgaact tttgtatct ggcatcacac    3720
tacgagaaac ttaaaggctc tcctgaggac aacgagcaaa aacagctctt tgttgaacag    3780
cataagcact acctcgacga gattattgag cagatcagcg agttctcaaa gagagttatt    3840
ctggctgacg ctaatcttga caaggttttg tccgcttaca caaacacag gataagcca    3900
atcagggagc aggcagaaaa cataatccat ctctttaccc tgacaaacct cggtgccccc    3960
gctgctttca gtattttga tactaccatt gacaggaaga gatatacttc cactaaggaa    4020
gtgctcgacg caaccctcat acaccaaagt atcacaggcc tctatgaaac taggatagat    4080
ttgtctcaac ttgggggcga t                                              4101
```

<210> SEQ ID NO 68
<211> LENGTH: 4101

<212> TYPE: DNA
<213> ORGANISM: Artificial sequence
<220> FEATURE:
<223> OTHER INFORMATION: Synthetic polynucleotide

<400> SEQUENCE: 68

| | | | | | |
|---|---|---|---|---|---|
| gacaaaaagt | attccatcgg | gcttgctatc | ggaaccaact | ctgtggggtg | ggcagttatt | 60 |
| accgacgaat | acaaggtgcc | cagcaagaag | tttaaggttc | tggggaacac | agatagacat | 120 |
| agcataaaga | aaaacctgat | aggcgcactg | ttgttcgact | ccggggaaac | agccgaagct | 180 |
| accaggctga | agagaactgc | aagaagaagg | tacaccagaa | gaaaaaacag | aatatgttat | 240 |
| ctccaagaga | ttttctctaa | cgagatggcc | aaggtggacg | actcattctt | tcacagactg | 300 |
| gaagaatctt | tccttgtgga | agaagataag | aaacacgaga | ggcaccctat | ttttggcaat | 360 |
| atcgtggatg | aggtggctta | ccacgaaaaa | taccctacaa | tataccacct | caggaaaaaa | 420 |
| ttggttgata | gtacagacaa | ggccgacctc | aggctcatct | atttggccct | ggcccatatg | 480 |
| attaaattca | gggggcactt | tctcatcgag | ggagatttga | accccgacaa | cagtgatgtt | 540 |
| gataagctct | ttattcagct | cgtgcagact | acaatcagt | tgtttgagga | aaaccccatt | 600 |
| aatgcttccg | gggtggacgc | caaggcaatc | ctttctgcaa | gactctcaaa | gtcaaggaga | 660 |
| ctcgaaaatc | tgatagcaca | gcttccagga | gagaagaaga | acgggctctt | tggaaacctg | 720 |
| atcgctctgt | cactcggact | cacacccaat | ttcaaaagca | attttgattt | ggcagaggac | 780 |
| gctaagctgc | aactcagtaa | ggatacctac | gacgatgact | tggataatct | gctcgcacaa | 840 |
| attggggacc | agtatgcaga | cctgtttctc | gcagctaaga | acttgagtga | cgccatattg | 900 |
| ctcagtgaca | tcctcagggt | taataccgag | attacaaaag | ctccactctc | tgcaagcatg | 960 |
| atcaagaggt | atgacgagca | ccatcaagac | ctgacactcc | ttaaggcgtt | ggttaggcag | 1020 |
| caacttcctg | aaaagtataa | ggaaatcttc | ttcgatcaaa | gcaaaaacgg | ctacgccggc | 1080 |
| tatatagacg | ggggagcatc | ccaagaagaa | ttttataagt | tcataaaacc | tatattggag | 1140 |
| aagatggacg | ggacagagga | attgctcgtg | aaactgaaca | gggaggatct | cctcaggaag | 1200 |
| caaaggacct | tcgacaatgg | ctccatccca | catcagattc | acctcggcga | actgcacgca | 1260 |
| atactgagaa | gacaagagga | cttttatcct | ttcctgaagg | acaacaggga | gaaaatcgag | 1320 |
| aaaatcttga | cattcagaat | cccatactac | gttgggcctc | tggccagagg | taacagtagg | 1380 |
| ttcgcctgga | tgactaggaa | atcagaggag | actattacac | cctggaactt | gaagaagtt | 1440 |
| gttgataagg | gagcttcagc | acaatcattc | atcgaaagaa | tgacaaactt | gacaaaaat | 1500 |
| ctgcctaatg | agaaagtgct | cccaaaacat | tccctgctgt | atgagtattt | taccgttat | 1560 |
| aacgagctta | ccaaggtgaa | atacgttact | gaaggtatga | gaaagccagc | ttttctttca | 1620 |
| ggggagcaaa | agaaggctat | cgtggatctt | ctctttaaga | ccaacagaaa | ggttaccgtg | 1680 |
| aagcagctta | ggaagactac | ctttaaaaag | atcgagtgtt | ttgactcagt | ggaaataagc | 1740 |
| ggtgttgaag | atagattcaa | cgcatccttg | ggaacttatc | atgatcttct | taagataatc | 1800 |
| aaggataaag | actttctcga | caacgaggaa | aacgaagata | tactggagga | catagttctg | 1860 |
| acacttactt | tgttcgagga | tagggagatg | atcgaggaaa | gactgaaaac | atatgctcac | 1920 |
| cttttcgacg | acaaagttat | gaaacaactc | aagagaagga | gatatacagg | gtggggagaa | 1980 |
| ttgagcagga | aactgattaa | tggtatcaga | gacaaacagt | caggaaaaac | aatactcgac | 2040 |
| tttttgaaat | cagacgggtt | cgcaaatagg | aatttcatgc | agcttataca | cgacgattca | 2100 |
| cttactttta | aagaggacat | tcaaaaggct | caagttagtg | gacaaggtga | ctccctccac | 2160 |

```
gaacacatcg caaatctcgc tggcagccct gcaattaaga agggtatact ccagacagtt     2220
aaggttgttg acgagctggt taaagtgatg ggaagacaca aacccgagaa catagtgata     2280
gagatggcca gggaaaacca aaccactcaa aaagggcaga aaaattccag agagaggatg     2340
aaaaggattg aagaaggtat caaggagctg ggtagccaaa ttctgaaaga acatcctgtg     2400
gaaaacactc aactccagaa tgagaaactc tatctgtact atctgcaaaa tgggagagat     2460
atgtatgtgg accaggaact ggacataaac aggctctcag attacgatgt ggatcatatc     2520
gtgccacagt cctttcttaa ggatgatagc atcgacaata aggtgcttac caggtccgac     2580
aagaacaggg gaaagtcaga taacgtgcct tctgaagaag ttgttaaaaa gatgaagaac     2640
tactggagac agctgcttaa cgctaagctc ataacacaga ggaagtttga aacttgacc      2700 aaggccgaga gaggcggact ctcagaattg gataaggcag ggttcataaa aaggcagctg     2760
gtggaaacaa ggcagataac taaacatgtg gctcagatcc tcgatagtag gatgaataca     2820
aaatacgatg agaacgacaa gctcataagg gaggttaaag tgataactct gaaatccaaa     2880
ctggttagcg attttaggaa ggatttccag ttttacaaag ttagggagat caacaattat     2940
catcacgccc acgatgccta cttgaacgca gttgtgggta ctgcacttat caaaaagtac     3000
cctaagctgg aatccgagtt tgtttatgga gactataagg tgtacgacgt tagaaaaatg     3060
attgcaaagt cagagcagga gatagggaaa gccactgcaa atatttcttt tatagcaat     3120 atcatgaatt tctttaagac agaaatcaca ctggccaatg gggaataag gaagaggccc      3180 ctgatcgaaa ctaatggcga gacaggggag attgtgtggg ataaaggtag ggactttgca     3240
acagtgagga aagtgctgag catgccccaa gttaatatcg ttaaaaagac cgaggttcaa     3300 acaggggggct ttagtaagga aagcattttg cccaagagga atagtgacaa attgattgct    3360
aggaaaaaag attgggaccc caaaaagtat ggcggatttg atagccccac tgttgcttac     3420
tccgtgctcg tggttgcaaa ggtggagaag ggaaagagca agaaactgaa gtcagttaag     3480
gaactccttg gtatcactat catggaaaga agctcctttg agaagaaccc tattgacttc     3540
ctggaggcta aagggtacaa agaggttaag aaagacctta tcattaaatt gcccaaatat     3600
agtcttttcg agcttgaaaa cggaagaaag aggatgcttg catccgctgg cgaattgcaa     3660
aagggcaatg agcttgctct cccttccaag tatgtgaact tcctttatct tgcctcacac     3720
tatgaaaaac tcaaaggttc acccgaagac aacgaacaaa agcaactatt tgtggaacaa     3780
cacaagcact acctggacga aatcattgag caaatttctg agttttcaaa aagggtaatc     3840
ttggctgacg caaatctcga caaagttttg tcagcttaca caaacatag agataagcca      3900 attagagagc aagctgagaa tatcatccat ctgtttaccc tgactaacct tggagcgcct     3960
gctgctttta aatatttcga caccacaatc gacaggaaga ggtacactag cactaaggaa     4020
gttctcgacg ccaccctcat ccaccagagt attacaggcc tgtacgagac aagaattgat     4080 cttttctcaac ttggtggtga c                                             4101
```

<210> SEQ ID NO 69
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 69

```
gataagaagt actcaatcgg tctggcaatc ggaaccaact ctgtgggttg ggcagtgatt       60
acagatgagt ataaggtgcc aagcaaaaaa ttcaaggtgc tgggtaatac cgacagacac      120
```

```
agcattaaga agaatttgat tggagcactc ctctttgact caggggaaac agcagaggca      180
acaaggctga agaggacagc aaggcggagg tacacaaggc ggaaaaacag gatatgctac      240
ctccaggaaa tctttagcaa cgagatggct aaagtggatg atagcttttt ccatagactc      300
gaagaatcct ttcttgttga agaggacaaa agcatgaaa  ggcatcccat cttcggcaat      360
atagttgatg aggttgcata ccatgagaag taccccacaa tctaccacct cagaaagaaa      420
cttgtggact ccacagataa agcagacctg aggctcatat acctcgcact cgcacacatg      480
atcaagttca gagggcactt tctcatcgaa ggtgacctga atccagataa ttcagatgtg      540
gataaactgt ttatacagct ggtgcaaaca taaccaac   ttttcgagga aaacccaatc      600
aatgcctccg gtgttgatgc aaaggccatc ctgtcagcaa gactcagcaa aagcaggcgg      660
ctcgaaaacc tcatcgccca gcttccggt  gaaaagaaga acgggctctt tggtaatctc      720
atcgcattga gccttggtct tactccaaac ttcaagagca attttgatct ggcagaggat      780
gctaaactgc aactctcaaa ggacacatat gacgatgacc ttgacaatct gttggcccag      840
atcggggacc aatatgcaga cctcttcctg ccgcaaaaga atcgtcaga  tgcaatcctc      900 ttgtccgaca tactgagagt taacactgag atcacaaagg cacctctgtc cgcctccatg      960
attaagagat acgatgagca tcaccaggat ctgactttgc tcaaagccct cgttagacag     1020
cagttgccag aaaagtacaa agaaatattc tttgatcaat caaaaaacgg atatgcaggg     1080
tacatcgacg gtggggcaag ccaggaagag ttctacaaat tcatcaaacc tatcctggaa     1140
aagatggatg ggacagaaga gctgctggtt aagctgaata gggaagacct cctcagaaag     1200
cagaggacat ttgataacgg gagcatccct catcaaatcc acctcggtga actccatgct     1260
atcctgagaa ggcaggaaga cttttatcca ttttttgaagg acaataggga gaaaatcgaa     1320
aaaatcctga cattcagaat cccatactac gttggtcctc tggcaagagg taacagtagg     1380
ttcgcatgga tgacaaggaa aagcgaggag acaatcacac cctggaattt tgaggaagtt     1440
gttgacaagg gtgccagcgc acaatccttt atcgaaagaa tgacaaattt cgacaagaat     1500
ctgcctaacg aaaaggttct cccaaagcat tcactcctgt acgaatattt tacagtttat     1560
aacgaactga ctaaagttaa atacgttacc gagggtatga ggaagccagc attcctttcc     1620
ggggaacaga agaaagctat tgtggacctc ctgttcaaga caaatagaaa agtgacagtt     1680
aagcaactca aagaggatta cttcaaaaag atcgaatgtt ttgactctgt ggagatcagc     1740
ggggtggagg atagattcaa cgccagcctg ggtacatatc atgatctcct gaaaatcatt     1800
aaagacaagg acttccttga caacgaggag aacgaggaca ttctggaaga cattgttctg     1860
accctcacac tctttgagga tagggagatg attgaggaaa gactgaagac ctacgcccac     1920
ctctttgacg ataaagtgat gaaacagctc aagagaagaa ggtatacagg ttgggggaga     1980
ctgagcagga agttgatcaa tgggattagg gacaaacagt ccgggaaaac aatcctcgat     2040
tttctgaagt cagacggttt cgcaaacaga aattttatgc agctcattca cgatgacagc     2100
ttgacattca aggaagacat ccaaaaggct caagtgagcg gccaagggga tagcctccac     2160
gagcatattg caaatctggc aggttcacca gccatcaaaa agggcatact tcagacagtt     2220
aaggttgtgg acgaattggt taagttatg  ggcaggcata agccagagaa tatcgttatc     2280
gaaatggcaa gggagaacca aacaactcaa aaagggcaga aaatagcag  agagaggatg     2340 aaaagaatcg aggaagggat caaggaactt ggtcccaaaa tcctcaagga gcacccagtt     2400
gaaaatactc aactgcaaaa cgagaagctc tatctctact atctccaaaa cgggagggat     2460
```

| | | | |
|---|---|---|---|
| atgtatgttg | accaggagct ggatattaac agactgtcag attatgatgt tgatcatatc | 2520 |
| gtgccccagt | cattcctgaa ggacgattcc atcgacaaca aagttctcac aaggtccgat | 2580 |
| aaaaacaggg | gcaagtccga taacgttcca agcgaagaag tggtgaaaaa gatgaaaaac | 2640 |
| tattggagac | aacttctgaa tgcaaagttg attactcaga gaaagtttga caacctcaca | 2700 |
| aaagcagaaa | gaggcgggct tagcgaactc gataaggcag ggtttatcaa aagacagctg | 2760 |
| gttgagacaa | ggcagatcac aaaacatgtg cacagatcc ttgactcaag gatgaatacc | 2820 |
| aagtatgatg | agaatgataa gttgatcagg gaggttaaag ttatcacact caaatccaaa | 2880 |
| ctggtgtcag | acttcaggaa agactttcaa ttttataagg tgagggagat caataactac | 2940 |
| caccatgcac | atgacgccta cctgaacgca gtggtgggta cagcattgat taaaaaatac | 3000 |
| cctaagctgg | agtctgagtt tgtgtacggg gactacaagg tgtacgcgt gaggaaaatg | 3060 |
| atagccaagt | ccgagcagga gatcgggaaa gcaacagcta agtatttctt ttacagtaat | 3120 |
| atcatgaatt | tctttaaaac tgagattact ctggcaaacg gggagatcag gaaaagaccc | 3180 |
| ctcatcgaga | ctaatggtga aacaggtgag atcgtttggg acaaggggag ggattttgct | 3240 |
| actgttagaa | aagttctgag tatgccacaa gtgaatattg tgaaaaagac agaagttcag | 3300 |
| acaggtgggt | tctccaaaga atccatcctg cccaagagaa attcagacaa gctcatcgca | 3360 |
| agaaagaagg | actgggaccc taagaagtac ggaggatttg acagccccac cgtggcctat | 3420 |
| tccgtgcttg | ttgtggcaaa ggtggagaaa gggaagagca aaaaactgaa atccgtgaaa | 3480 |
| gaactgctgg | gaattaccat catggaaaga agctcctttg agaagaaccc aatcgacttc | 3540 |
| ctggaagcaa | aaggatataa ggaagtgaaa aaggacctca ttatcaagct cccaaaatac | 3600 |
| tcactttcg | agttggagaa cggtagaaag aggatgctgg caagcgcagg ggaacttcag | 3660 |
| aaaggcaatg | agctggcatt gccatcaaag tatgtgaact tcctctactt ggccagccat | 3720 |
| tacgagaaac | ttaaggtag cccagaagat aacgagcaaa acagctctt tgtggaacag | 3780 |
| cataagcatt | atctggatga gatcatagaa caaatctcag agttttccaa gagagttatc | 3840 |
| ctcgcagatg | caaacctgga taaggttctc tcagcctata taagcatag agacaagcca | 3900 |
| attagagagc | aagcagagaa cattatccac ttgttcactc ttacaaacct gggggcacca | 3960 |
| gccgccttca | aatatttcga tacaacaata gacagaaaga ggtataccag caccaaagaa | 4020 |
| gttctcgacg | ccacactgat ccatcaatca atcacaggcc tttacgaaac taggatcgac | 4080 |
| ttgtcacaac | tgggtgggga t | 4101 |

<210> SEQ ID NO 70
<211> LENGTH: 3307
<212> TYPE: DNA
<213> ORGANISM: Artificial sequence
<220> FEATURE:
<223> OTHER INFORMATION: Synthetic polynucleotide

<400> SEQUENCE: 70

| | | |
|---|---|---|
| gagcaaggac acctacgacg acgacttgga caacctattg gcccagatag gtgaccagta | 60 |
| tgcagacctc ttccttgcgg ccaagaactt gagtgacgct atactgctca gtgacatcct | 120 |
| gagggtgaac actgagatca ctaaggcccc tctctctgcc tcaatgatta agcgttacga | 180 |
| cgagcatcac caggatctca ccctgcttaa ggcccttgtt cggcagcagc tccctgagaa | 240 |
| gtacaaggag atattttttg accagtctaa gaacggctac gccggttaca ttgacggtgg | 300 |
| ggcaagccag gaggagttct acaagttcat caagccgatc cttgagaaga tggacggcac | 360 |
| cgaggagcta cttgtcaagt tgaaccggga agacctgctc cggaaacagc gtacattcga | 420 |

-continued

```
caacggcagc atccctcacc agatccacct gggcgaacta cacgccatcc tccgacgtca    480
ggaggacttc tatccattct tgaaagataa cagggaaaaa atcgaaaaaa tacttacgtt    540
tcgaatacct tactacgtgg ggcccttgc tcggggaaac tccagattcg catggatgac     600
caggaagtca gaggagacca tcacccctg aactttgag gaggtggttg acaaaggtgc      660
ttctgcccag tccttcattg agcggatgac taacttcgac aagaacctgc ccaacgagaa    720
ggtgctgcca aagcacagcc tgctctacga atactttact gtgtacaatg agctgacgaa    780
ggtgaagtac gtgacagagg ggatgcggaa gcccgctttc ctgagcggcg agcaaaaaaa    840
agcaatcgtg gacctactgt tcaagaccaa ccgaaaggtg acagtgaagc agctcaagga    900
ggactacttc aaaaaaatcg agtgcttcga ctctgttgag ataagcggcg tggaggaccg    960
attcaacgcc tcattgggaa cctatcacga cctgctcaag atcattaagg acaaggactt   1020
cctggataat gaggagaatg aggacatcct ggaggatatt gtgctgaccc ttactctatt   1080
cgaggacagg gagatgatcg aggagcgact caagacctac gctcacctgt tcgacgacaa   1140
ggttatgaag caattgaagc gtaggcgata cacggggtgg ggaagactct cccgaaaact   1200
gataaacggc atcagggaca agcagtcagg gaagacgatc ttggacttcc tgaaatccga   1260
cgggttcgcc aaccgcaact tcatgcagct cattcacgac gactcactaa cgttcaaaga   1320
ggacattcag aaggctcaag tcagtggaca aggcgactcc ctgcacgagc acattgcaaa   1380
ccttgcgggc tccccggcga ttaaaaaggg cattctccaa acggttaagg tggtggacga   1440
gctggtgaag gtgatgggcc gacacaagcc tgagaacatc gtgatcgaga tggccaggga   1500
gaaccagact acccagaagg gtcagaagaa ctctcgggaa cgtatgaagc gtattgagga   1560
ggggattaag gagttgggct ctcaaatcct caaggagcac cctgtggaga cactcagct    1620 ccaaaacgag aagctgtacc tgtactacct gcaaaacggg cgcgatatgt acgtggatca   1680
ggagttggac atcaacaggc ttagcgatta cgacgtggac cacatcgtgc cacagtcatt   1740
cttaaaggac gacagcatcg acaacaaggt tctgacgagg agcgacaaga atcgagggaa   1800
aagtgacaat gttccatccg aggaggtggt caagaaaatg aagaactatt ggcgtcagct   1860
tctgaacgcc aagctcatca cccagcggaa attcgacaac ctgactaagg ctgagcgagg   1920
cggactctcc gagcttgaca aggctggctt catcaagcgg cagttggtcg aaacccgaca   1980
gataacgaag cacgttgccc agatacttga ctcccgtatg aacaccaagt acgacgaaa    2040 cgacaagctc atcagggagg tgaaggtcat taccccttaag tccaaactcg tcagcgactt   2100
tcgtaaggac ttccagttct acaaggtgcg cgagatcaat aactaccacc acgcacacga   2160
cgcctacctg aacgcagtgg ttggaaccgc gttgattaaa aagtaccca agttggagtc    2220 ggagttcgtt tacgggact acaaggtgta cgacgttcgg aagatgatcg ccaagtctga    2280
acaggagatc gggaaagcaa ccgccaagta tttcttctat agcaacatca tgaacttctt   2340
taaaaccgag atcacacttg ccaatggcga gatccgtaag aggccgctga tcgagacaaa   2400
tggggagact ggcgagatcg tgtgggacaa gggccgcgac ttcgcaaccg ttcggaaagt   2460
cttgtccatg cctcaagtca acatcgtcaa gaagactgag gtgcaaacag gcgggttctc   2520
gaaggagtcc atactgccca agaggaactc agacaagctc atagcacgca aaaaagactg   2580
ggatccaaag aaatacggcg ggttcgactc gccgacagtc gcatactccg tgttagtggt   2640
ggctaaagtg gaaaagggga agtccaagaa gctcaagtcc gtcaaggagt tgctcgggat   2700
caccattatg gaacggtcct cattcgagaa gaatcccatt gacttcctag aggcgaaggg   2760
```

```
ctacaaagag gtcaaaaagg acctaattat taagctcccc aagtattcac tcttcgaact    2820
tgaaaatggt cgtaagcgga tgttggcaag cgctggagag cttcagaagg ggaacgagct    2880
tgcactgcct tccaagtacg tgaacttcct gtacctcgcc tctcattacg agaagttgaa    2940
gggctcaccg gaggacaacg agcagaagca gttgttcgtg gagcagcaca agcactacct    3000
cgacgagatc attgagcaga taagtgagtt cagcaaacgg gtgatccttg ccgacgctaa    3060
cctggacaag gtgctgagcg cctacaacaa gcacagagac aagccgatcc gagagcaagc    3120
ggagaacatc atacacctgt tcaccctcac gaacctcggg gctcccgcag ccttcaaata    3180
ttttgacacg accatcgacc gtaaacgcta cactagcacg aaggaggtgc tggacgctac    3240
ccttatccac cagtccatca ccggcctgta cgagacgaga atcgacttgt cgcagctcgg    3300
tggtgac                                                              3307
```

<210> SEQ ID NO 71
<211> LENGTH: 4101
<212> TYPE: DNA
<213> ORGANISM: Artificial sequence
<220> FEATURE:
<223> OTHER INFORMATION: Synthetic polynucleotide

<400> SEQUENCE: 71

```
gacaaaaaat actcaattgg tctggcaatt gggaccaaca gtgtcggatg ggccgtgatt      60
accgacgagt acaaggtgcc gtccaaaaaa ttcaaggtgc ttgggaacac cgaccgccac     120
tcgatcaaga aaaacctaat cggtgcgttg cttttcgaca gtggggagac cgccgaggca     180
acacgcttaa aacgcacagc taggaggaga tatacacggc gcaagaaccg aatatgctac     240
ttacaggaga tattctccaa tgagatggcg aaggtggacg actctttctt ccatcggctt     300
gaggaatcct tcctggtcga ggaggacaag aagcacgagc gacacccgat attcgggaac     360
atcgttgatg aggtggcgta ccacgagaag tacccaacga tataccactt acgcaagaag     420
ctcgtggact ctacgacaa ggccgacttg cgccttatct acttggcact ggcccacatg     480
attaagttcc gaggccactt ccttatcgag ggtgacctga accccgataa ctccgacgtg     540
gacaagctct tcatccaact cgtccagaca tacaaccagc tattcgagga gaatcctatc     600
aacgcctctg gggtggacgc taaagctatc ctctcagccc gcctgtcaaa gtcgaggagg     660
ttggagaacc taatcgccca gcttccaggc gagaagaaaa atgggctgtt cggaaacctt     720
atcgcactct cactgggcct aaccccgaac ttcaagtcca acttcgacct ggcagaggac     780
gcgaaattgc agttgtcgaa agacacctat gacgatgacc tggacaacct gttggcccag     840
ataggggacc agtacgccga cctgttccta gcggccaaga acctgtccga cgccatcttg     900
ctgtcggata tactgcgggt gaacaccgag atcactaaag cacctctctc cgccagcatg     960
attaagcgtt acgacgagca ccaccaagat ttgaccctgc taaaggcact tgtacggcag    1020
cagcttcccg agaagtacaa ggagatcttt ttcgaccaaa gcaagaacgg ctacgccggg    1080
tacatcgacg gaggtgccag ccaggaggag ttctacaagt tcattaagcc catcctggag    1140
aagatggacg ggactgagga actacttgtg aagctgaacc gggaagactt actacggaag    1200
cagcgtacct tcgacaacgg ttctatccca catcagatcc atcttgggga ttgcacgcg     1260 atcctgcgac gccaggagga ctttttacccc ttcctgaaag acaaccgcga gaaaatcgag    1320
aagatactga ccttcagaat accttactac gtcggacccc ttgcgcgagg caactcaaga    1380
ttcgcgtgga tgaccaggaa atcagaggag accatcacac cctggaattt cgaggaggtg    1440
gttgacaagg gtgcctccgc ccagtccttt atcgaacgaa tgaccaactt cgacaagaac    1500
```

```
ttgcccaacg agaaggtgct ccccaaacac agcctcctct acgaatattt cacagtgtac    1560
aacgagctta ctaaagttaa gtatgttact gagggcatga ggaaacccgc cttcctgtca    1620
ggcgagcaga agaaagctat tgtggacctc cttttcaaga ccaaccggaa ggtgacagtg    1680
aagcagctca aggaggacta cttcaagaag atagagtgct tcgacagcgt ggagatcagc    1740
ggggtggagg acagattcaa tgcctctctc ggaacatacc acgacttgct taagatcatc    1800
aaggacaagg acttcctcga caacgaggaa aacgaggata ttctggagga tattgttctg    1860
actcttaccc tgttcgagga ccgggagatg atcgaggagc gtctcaagac ctacgcccac    1920
ctgttcgacg acaaagttat gaagcagctc aagcgtcgga gatataccgg atggggccgt    1980
ctgtctcgga agctcatcaa cgggatcagg gacaagcagt cagggaagac gatcttagac    2040
ttccttaagt ctgacggctt cgccaacagg aacttcatgc agttgatcca cgacgacagc    2100
cttaccttca aggaggacat ccagaaggcc caagtgagtg gccagggtga cagcctccac    2160
gagcatattg ctaatcttgc gggttcccca gcgattaaaa agggcatact tcaaaccgtt    2220
aaggtggtgg acgagcttgt caaggtgatg gggcgacaca gcccgagaa catcgtgatc    2280 gagatggcca gggagaacca gaccacccag aaggggcaga agaatagccg agaacgcatg    2340
aagcgcatcg aggaggggat taaggagcta gggagccaga tcctcaagga catcccgtc    2400 gagaacaccc agctccagaa cgagaagcta tacctctact acttgcaaaa cgggagggat    2460
atgtacgtgg atcaggagtt ggacattaac cgcctaagcg actacgacgt agatcacatc    2520
gtgcctcagt cattcctcaa agacgacagc attgacaaca aagtcttgac ccgatccgac    2580
aagaaccgag gaaaatccga caatgtgccc tcagaggagg tcgtcaagaa aatgaagaac    2640
tattggaggc agctacttaa cgccaaactc ataacccagc ggaagttcga caacctgaca    2700
aaggctgagc ggggtgggct cagcgagctt gacaaggctg gcttcatcaa gcggcagttg    2760
gtggagacaa gacagataac gaagcacgtg gctcagatcc tggactctcg catgaacacg    2820
aagtacgacg agaacgacaa attgatccgc gaggtcaagg ttattacgct caagagcaaa    2880
cttgtcagcg atttccgcaa ggacttccag ttctacaagg tgagggagat taacaactac    2940
caccatgcac atgatgccta cttgaacgca gtggtgggga ccgcgcttat taaaaagtac    3000
cctaagttgg agtcagagtt cgtttatggg gactacaagg tgtacgacgt ccggaagatg    3060
attgcaaagt ctgaacagga aatcgggaag gccaccgcca atatttctt ctacagtaac    3120 attatgaatt tttttaagac tgaaattact ctcgcaaacg gcgagatcag gaagcgtccc    3180
ctcatcgaga caaacgggga gaccggggag atagtctggg acaaggggcg ggacttcgct    3240
acggtgagga aggtgctctc gatgccacaa gtgaacatcg tcaaaaagac agaggtgcag    3300
accggtggct tctcaaagga gtcaatcctg ccaaaacgta acagcgacaa gctcatcgcc    3360
cgcaagaaag actgggaccc taagaagtat ggtgggttcg actcaccgac ggtcgcatac    3420
tccgttctgg tcgtggcaaa ggtggaaaag ggcaagtcca aaaaactgaa atccgtgaag    3480
gagttgcttg gcattaccat catggaacgc agcagcttcg agaagaaccc cattgacttc    3540
ctggaggcta agggtacaa ggaggtcaag aaagatttaa ttattaagct acctaagtac    3600
agcttgttcg agctggagaa cggccgaaaa cgaatgctcg catccgccgg gaacttcaa    3660 aagggcaacg agcttgcgct gccctccaag tacgtgaact tcctgtactt ggcatcccac    3720
tacgagaaac tcaagggtag cccagaggac aacgagcaga agcagctatt cgtggagcag    3780
cacaagcact acctcgacga gataatcgag cagatcagtg agttcagtaa gcgggtgata    3840
```

| | |
|---|---|
| ctcgcggacg ccaacttgga caaggtgctt agtgcctaca acaagcaccg tgacaagccc | 3900 |
| atccgagaac aggctgagaa catcatccac cttttcactc tgacaaacct cggtgctccc | 3960 |
| gccgccttca aatacttcga cactaccatc gacaggaagc gctacacatc tacgaaggaa | 4020 |
| gttcttgacg ctacgcttat tcatcagtct atcacagggc tgtacgagac aaggatcgac | 4080 |
| cttagccaac tcggcgggga t | 4101 |

<210> SEQ ID NO 72
<211> LENGTH: 3490
<212> TYPE: DNA
<213> ORGANISM: Zea mays

<400> SEQUENCE: 72

| | |
|---|---|
| cgatgatatg agctacccaa ggcattgaat ggtcgcttcc taaaatgata tcaccctagt | 60 |
| gtatgtcgag atgcttaaag aaccaatgga ttcatataga gttgtataca acttctatca | 120 |
| agcgcttttg gtttgcttaa gcttacccca aaaagcggag gcataggtt gagcaccata | 180 |
| tttggtacct gggcacggtc agatggtctg gccatgtggc ccagacggtc tgcggggtat | 240 |
| agctcgaatg gtccacgatt agatttactt gggcgagggt ccttacccc cgtgtactta | 300 |
| tccaagctaa tcacgcggga atatattgag atacgcctag gaacgggtcc agatctcccc | 360 |
| atatatatat gaagggggtac aacctattga catgacacaa tcaatctatt tactagttcg | 420 |
| cttacatttc ttgccctagg agcatttgta gttagtcttc ctcatcctca attttcacca | 480 |
| ccctccact ctacgtcgtt tagatgcgcc ttgggtggcc taccgacccc aacacaacca | 540 |
| tatgatcttt ccttcctgat ggggtacctc tcgggagcga gatccaggtt ctgcaagaga | 600 |
| tccatgaagc cctctacgtg cctcgtggac ggtctgccac tgatacacgg acggtctgca | 660 |
| tgcccacaga gaaaaccaga gcccctctat gcattcgcgg atggtccggc cgctcatcac | 720 |
| ggacggtcct cgctcaagta gagaagaccc caaggttcag tgcgtcgtgc gccggcccta | 780 |
| gggttccttt attgattggc cccaaatgcg agccaacaat aggttggtaa acagtttgta | 840 |
| gtattgctag atgctacctc tagaacattt gtttaattat ttagactgtg tcaaacactt | 900 |
| tatccatata gttatccaaa atattgtttt gcactgatct gtactgtaga ctatattgtt | 960 |
| cgtaaagtga agtttgaata taaaaatagg gatggataag ctactgaagg cagtcttaca | 1020 |
| aaagaggagg ctatgaattt aggcttttcg ttcgatcatt catcaatgta ttagatcatg | 1080 |
| taatatgttg taaattttgt atctatattt aattgtgtat aaccttcctt tatataatta | 1140 |
| gtaattgtaa taatcgtgtt aaacacacca catattgtag ttgacatcaa tcattgtttt | 1200 |
| ttttaccatt gattatagat gagaacatgg acaactaatt atcgctcata attaaggaca | 1260 |
| aactatttga atcccgatgc accatactta tgccgtatga taatgtattc acaccattgg | 1320 |
| gcatggccgc atgagtcaat tccttaggtc gttgtcaata gataaaatag ttttgttctt | 1380 |
| attaaatagc atgtcacata aataagtagg acgacataac atgcaattta ataaagaaag | 1440 |
| atatggtaga gttttatgaa agacgaggaa ttttgaaaga cgaggaattt tatggatatg | 1500 |
| gactatagac acactatttt ttagactgac agccttaaaa acaatacgat aaaattatgc | 1560 |
| attgagaatg acattatttt ccatcgaaaa gaattgaatg ctctgtttgc attggtgtgt | 1620 |
| caacaacaac tgataataaa aaagaagaaa ttaagatgct aaagttatag taaaaacatt | 1680 |
| tgctataaaa atagctccgt gctactttaa ctaggtctcc tgtgatcact accctagctc | 1740 |
| ttctgtgatc acaatcgaat acacactttg gttcccaatt tttatcccaa ataagcccca | 1800 |
| cgacaatata tggtagttgg cagcatgtgc tttcttaaac tccaagcaaa tctgcctatc | 1860 |

```
ccatttggca ctagaattta gtggaagtac acgcgctgct acaagtagca gcatccccgc   1920
tactaattgc caattttata ctagatcaat tactaatctc cagctattta agcctaatcc   1980
tcctctaggc aggggaccaa acagcctcac tctcacagtc tcactcactc actgagagct   2040
ctcactccat tggcctgttg agaagatact caaaagggcc ggcttctctc tctctctctg   2100
ggaccaacca gagaacccct gaatctaagt cctatatatc gccatagccc agtggctccc   2160 cgccccacg gcattctttg ctcaaagtcg ttggaggtga atctaaagct cacagattct    2220
tggaaccaga caacaatggg ggtaagtaaa cttcactggc attattatag ggagtttaga   2280
caagaactgg cgcatgaccg atccttggtt gttggctgca gatcatcaac tggatgcaga   2340
gcagattcca tgggaagacg gagaccagca gaatctttga cggcgcaacc gccaccagtt   2400
catatagagg taactgccag ctctctcatt tgcagtgcac ctgcacttgc attgcaggtt   2460
cagcgctgga gtgctaaaac gtgcgtgcgt acattgagcc aggtggtgct ggagcccaag   2520
ggacgacgca agggacgatc gttcacgaat cagagaagcg tctcgacgcc gagccatggc   2580
ctcaggcggg catcctctcc atcggcacgc tcggcagcga ggagcctccc gcgcaggagc   2640
aggacctgcc ggagttcacc gtggaggagg tgaagaagct ccaggacgcg ctggccatgc   2700
tcctgcggcg ggccaagtcc aagtccagcg cccgcggctc cggggccggg gccggcgagg   2760
acaggccgcc gctggacagg ttcctcaact gcccgtcctg cctggaggtg gagaggaggg   2820
tcgtccagac gacggcgacg aatcacggcg gccaggaaga aggagacctc tcgccggaca   2880
ccaagatcat cctgaacagg gccagggacc tgctcgatag cggcggcggc ggcggcggca   2940
tcaagcagag gtcgttcaag ttcctgctca agaagatgtt cgcctgcaat ggcggcttct   3000
cggccgcgcc gccccggagc ttgaaggacc cagtggagtc aagaatggag aaggtaggcg   3060
cacgcgtgcg aacggtcggc agacacacac aacacaacac aatgaagcta gctgcttcgt   3120
tcgaccatgt ctagtctagt agctaaacaa ataccctctg gtggtggact gtcttttcag   3180
ttcttccgaa cgatgatcgg gaagaagatg aacgccaggt cggggaacgg gtcggcgtcg   3240
tccaggaaat acttcttgga ggacggaacc aaaggcagga ggcgaggcgg tcgtcgttgc   3300
ggttgccaag aagaagagga gagggaagca gagagttgca ggtgggacag aacagattct   3360
gaatgtaagt tcactatcgc tcgctactac tcattgtcca tcacaggcaa ttttgatgtc   3420
acaattctgt gtctgaacct tttctaaac cttttttttt ctctcgtgca gtcattgttt    3480
tggagatatg                                                           3490

<210> SEQ ID NO 73
<211> LENGTH: 848
<212> TYPE: DNA
<213> ORGANISM: Zea mays

<400> SEQUENCE: 73
atggggatca tcaactggat gcagagcaga ttccatggga agacggagac cagcagaatc     60
tttgacggcg caaccgccac cagttcatat agaggtggtg ctggagccca agggacgacg    120
caagggacga tcgttcacga atcagagaag cgtctcgacg ccgagccatg gcctcaggcg    180
ggcatcctct ccatcggcac gctcggcagc gaggagcctc ccgcgcagga gcaggacctg    240
ccggagttca ccgtggagga ggtgaagaag ctccaggacg cgctggccat gctcctgcgg    300
cgggccaagt ccaagtccag cgcccgcggc tccggggccg ggccggcga ggacaggccg     360 ccgctggaca ggttcctcaa ctgcccgtcc tgcctggagg tggagaggag gtcgtccag     420
```

```
acgacggcga cgaatcacgg cggccaggaa gaaggagacc tctcgccgga caccaagatc    480
atcctgaaca gggccaggga cctgctcgat agcggcggcg gcggcggcgg catcaagcag    540
aggtcgttca agttcctgct caagaagatg ttcgcctgca atggcggctt ctcggccgcg    600
ccgccccgga gcttgaagga cccagtggag tcaagaatgg agaagttctt ccgaacgatg    660
atcgggaaga agatgaacgc caggtcgggg aacgggtcgg cgtcgtccag gaaatacttc    720
ttggaggacg gaaccaaagg caggaggcga ggcggtcgtc gttgcggttg ccaagaagaa    780
gaggagaggg aagcagagag ttgcaggtgg gacagaacag attctgaatt cattgttttg    840
gagatatg                                                             848
```

<210> SEQ ID NO 74
<211> LENGTH: 282
<212> TYPE: PRT
<213> ORGANISM: Zea mays

<400> SEQUENCE: 74

```
Met Gly Ile Ile Asn Trp Met Gln Ser Arg Phe His Gly Lys Thr Glu
1               5                   10                  15

Thr Ser Arg Ile Phe Asp Gly Ala Thr Ala Thr Ser Ser Tyr Arg Gly
            20                  25                  30

Gly Ala Gly Ala Gln Gly Thr Thr Gln Gly Thr Ile Val His Glu Ser
        35                  40                  45

Glu Lys Arg Leu Asp Ala Glu Pro Trp Pro Gln Ala Gly Ile Leu Ser
    50                  55                  60

Ile Gly Thr Leu Gly Ser Glu Glu Pro Pro Ala Gln Glu Gln Asp Leu
65                  70                  75                  80

Pro Glu Phe Thr Val Glu Glu Val Lys Lys Leu Gln Asp Ala Leu Ala
                85                  90                  95

Met Leu Leu Arg Arg Ala Lys Ser Lys Ser Ser Ala Arg Gly Ser Gly
            100                 105                 110

Ala Gly Ala Gly Glu Asp Arg Pro Pro Leu Asp Arg Phe Leu Asn Cys
        115                 120                 125

Pro Ser Cys Leu Glu Val Glu Arg Arg Val Val Gln Thr Thr Ala Thr
    130                 135                 140

Asn His Gly Gly Gln Glu Glu Gly Asp Leu Ser Pro Asp Thr Lys Ile
145                 150                 155                 160

Ile Leu Asn Arg Ala Arg Asp Leu Leu Asp Ser Gly Gly Gly Gly Gly
                165                 170                 175

Gly Ile Lys Gln Arg Ser Phe Lys Phe Leu Leu Lys Lys Met Phe Ala
            180                 185                 190

Cys Asn Gly Gly Phe Ser Ala Ala Pro Pro Arg Ser Leu Lys Asp Pro
        195                 200                 205

Val Glu Ser Arg Met Glu Lys Phe Phe Arg Thr Met Ile Gly Lys Lys
    210                 215                 220

Met Asn Ala Arg Ser Gly Asn Gly Ser Ala Ser Ser Arg Lys Tyr Phe
225                 230                 235                 240

Leu Glu Asp Gly Thr Lys Gly Arg Arg Gly Gly Arg Arg Cys Gly
                245                 250                 255

Cys Gln Glu Glu Glu Arg Glu Ala Glu Ser Cys Arg Trp Asp Arg
            260                 265                 270

Thr Asp Ser Glu Phe Ile Val Leu Glu Ile
        275                 280
```

<210> SEQ ID NO 75
<211> LENGTH: 5322
<212> TYPE: DNA
<213> ORGANISM: Zea mays

<400> SEQUENCE: 75

| | | | | | | |
|---|---|---|---|---|---|---|
| aagtttcctt | atcatttaga | tatttattat | cgtttatata | tttcaaatat | tgccacttttt | 60 |
| cattagtatt | taaattttttt | atttttttttc | aattttatgc | tcatataaga | cttgattttg | 120 |
| tttgatatat | catgtgtatg | ctataaaatt | gttgccatgt | aatatattat | ggtattatat | 180 |
| ataccaaata | gttagagttt | atgcggtaat | atatatacta | ttttttaccct | cttagcaatt | 240 |
| tcaaatactc | atccttaaaa | tcctaggccc | gccactagtt | tctaattggt | ccttacatgt | 300 |
| gccatgtcag | caagctattt | tgtaactatt | tatagtccaa | aaataaaaat | aaaaatccta | 360 |
| gaatcgagtc | tataaattag | attctatttta | tgaattttttt | atttttttata | tttaagttat | 420 |
| gtaactttat | ttataaatta | tgtctttata | tttatatttg | agttatgtat | tttttaaatt | 480 |
| gtttttatga | attatatatt | ttgttgactt | gattaattaa | ttatatgtat | ttgttttttca | 540 |
| ataaaacacc | atgtgttata | tcacctaaca | atctactcca | tccgttcaaa | tttataatta | 600 |
| taattcgttt | gatttttttaa | ccctaagttt | gactgactcg | tcttattaaa | aaaattatta | 660 |
| ttattattaa | tttttttgata | ttatttagta | tataatatac | ttcaaatgtg | gttttgaatt | 720 |
| tttcattttt | cccagaaaga | tgaatagcac | gagccggtca | aatgttacac | aaaaaagtca | 780 |
| aacagattat | aatttggaac | ataaggagta | taaaataaaa | gttaatgttg | tgatgagatg | 840 |
| gttatatgcc | gatgataaag | gttatgcact | gaagcctcgt | caaggtagac | tggtagaggt | 900 |
| ttgcaacagc | ggacgtgaca | atatatatag | ggtcgtacct | gagggggtgc | ggagggtgcg | 960 |
| gccgcaccgg | gccccaaaaa | cagagggccc | cctagccact | ggacgctagc | acttttttcct | 1020 |
| gttaaatcta | tctattctag | acataaatac | acaaagagcg | atgcgctatt | gaccagtctc | 1080 |
| gtttagattg | ttaaagtaat | gtctcgatta | cttatcgaat | aatccatccg | tttcaaaata | 1140 |
| gtatttgttt | tagctcttga | tttttatgtt | tatattcaac | tagatgatga | taaatccact | 1200 |
| aaagaagcaa | aacaaattct | attttttatat | atagagagta | ttatttacta | tacacatgat | 1260 |
| ggttgtatct | gcatagagaa | gcttttttaga | attgaaatat | ttttgtgaac | tatttatggt | 1320 |
| caacaataac | tcaagagagg | ttatatgtct | tgtcgattct | atatatcgaa | aaagttgttg | 1380 |
| aatggtattg | atctcaattg | tataagtaat | gactttgtat | cacaaaatgt | tagaggatat | 1440 |
| ttttaatgat | atcagataac | aagtacgtgt | ttttagctat | attttacatt | tgttatctta | 1500 |
| taaacatcaa | aacagtgcat | aataatttttt | acacgtcaaa | tattcgatac | tatagtctat | 1560 |
| atataattat | atatatttat | gtgtggacgg | agccttcata | tcggatttcg | caccgggccc | 1620 |
| ctgaaaagtc | aggaacggcc | ctaggtatat | attatccgaa | agggttggat | atagccttat | 1680 |
| gcttcatgta | atcaaagaaa | taaaaataaa | gcttttctac | tatgcttgtt | tttggtttgt | 1740 |
| ctactttaaa | aaatgtgctc | taattgatgt | ccatgactcg | cctcggcagg | tgtaaaaaaa | 1800 |
| ctcccacata | cattggtccc | agaaccagaa | aagaggtgct | acgagctttg | ttattattga | 1860 |
| ttgggaaaat | attaaaaaaa | cgcagtaata | caataccgac | atagtatttt | atacttcact | 1920 |
| caagtagtaa | aatttctcat | gtaattaaca | gctcatgcac | atgtaagaac | gtaactctgg | 1980 |
| gcgcgattgt | gcaatttggc | cactaccatc | aatctagcta | gccctgggtt | tattaggccc | 2040 |
| tccctagtcc | ctaaccctat | ttaattgggg | gaaggggggac | cctggttgca | tccaaactcc | 2100 |
| aaagccactc | cgatccacca | cccctctctt | ctttcactgc | atgcttagct | tcttctcctt | 2160 |

```
ttcaacatcc tggagctgcc caatcacagg acaccttcaa aacactggaa ccggccggtc    2220
gagcttctgt tgcctcccct gccgccgctc ttgcagactg tcaccacaga ctgctctgct    2280
cggccggata ttcacgggtc cttctccggg agcagtacgt accatacaag gacatggggg    2340
taaattcctc ccactgaaat taagctagct agcttttggt tttcatccac tgacagctat    2400
gttcttcctt ccatatatgt gttcttttcc agtgttccgc ggttaatttt gcattattgt    2460
ctgcagatca ttaactggat gcaggatcgc ttcaacggta aacacgataa gaggcgaccc    2520
gccgccatta actcgggatc agctcgcggt tagtgattct ctgaatcctt tcgtgctact    2580
ggtacggtaa ttgtcaattt gttaccacgc ccggccggcg cacttacgtg gcgttcttct    2640
tagctttcgt gctgacgaac gaactggccg gccgctgctc tttttgctgc atgcatgcat    2700
gacgcctcgt ttgtacgtca gaaataagct gccgccaaga cgaccgcgcg cgcgagggca    2760
agagccgcaa cgacggcggc gactggccgg cgccacagca gggcctcctg tcgatcggga    2820
cgctgggaga cgacgtcgac ccgccgccgc gcgcgtcgtc gcaggccgac gacgtgctgg    2880
acttcaccat cgaggaggtg aaaaagctcc aggacgcgct gaacaagctg ctccggcgcg    2940
ccaagtccaa gtccagctcc agctcctccc gcgggtcggg cgccagcgcc accgacgagg    3000
accgccgcgc cagccacagc cagctgccgc tcgacaggtt cctcaactgc ccctccagcc    3060
tcgaggtcga ccggagggtc tcgctgatca ggcacgacgg tggtgccgag agcggcgagt    3120
tctcgccgga cacgcagatc atactcagca aggccaggga tctcctcgtc cacagcaacg    3180
gcaccgccat caggaagaag tcgttcaagt tcctcctgaa gaagatgttc gtctgccatg    3240
gcggcttcgc ccccgcgccg agcttgaagg atccagttga atcgagaatg gagaaggtat    3300
atgttatgtg taagcagcgg acatggatat atgtctgaat tcatgcattg tcagtcgtaa    3360
gattaaatgc tagtaatgta tacgtacatg gttctctcct tttgttgttt ttgagtgcac    3420
gcacatacag ttgttcagaa cgatgcttca gaagaagatg aatgctcgcc cgagcaacgc    3480
tgcagtgtca tccaggaagt actacctcga cgacaagccg agtgggagga tgatgacacg    3540
ggatggtcgt cgtcgtcacg atggagagga cgatgacgag aagggctctg acagaatcaa    3600
gtgggataaa actgatactg actgtaagaa catatttata cgctgctagc cgcacatatg    3660
tacggttaaa caacgatgca tatatatata tatatatata tatatatata tatatatata    3720
tatatatata tatatatata tatatatata tatatatata tatatatata tatatatata    3780
tatatatata tatatatata tatatatata tatatatata tatatatata tatatatata    3840
tatagaagct tcatgcgatg agctctgcta gtaataataa gcaataaggg atcactgaat    3900
gaaatctcgc ttgcgctttc cagtcatcgt tctggagatc tagatcaaga ggctcgagtt    3960
caaaggtcct tgtgatatcc agtatgtggt aagctacatt gaaacgcctg tcgaagtttt    4020
atgatacgat gacggtgttt ttttgctggt gctaaaattt tgtggtggtt tgatctttat    4080
ttcgcagctt acgagtggtg atggtgacct tgagtcagag gagaaataca ctacaataat    4140
ccgtattaaa ggagtgttca gttgaactgc gaatagatca gacaagatat atatgcatgc    4200
ctgatgccac cagggtgtaa tactggatga agatcagaat tcacacgcaa tggaggtgtt    4260
aataggaaga aagagttctc agctttgcac tctcgatcct ttcccatctc atcttcagat    4320
cgtcctacac acacacacac gctatcctac tacgttttgt agttcttttg catcatatct    4380
tgtggacaaa ttaagaggga tgatttcagt tagtgaacgt aaccctgatg atatatataa    4440
aattaatgtt aaattgtggc cccatcatca tctcaggaac atggcattgc tcgtgaagca    4500
tatgactgcg tgaaattttt atacatacat agcaggagtc ccgagtgtac agaaatagca    4560
```

```
ttgcaactgg ggcgcttgga acatgctcat tgccgaaacc ggaaagctgg ctaggctgga    4620
cctggaagtg cgtccgagat ctccattggc cgtcaggatc cggaggcagc tccccggcac    4680
atttgtgtgt gttcgtgccc agttgtaggc ggggagaaga aaaaaaaggg ggcgccaagg    4740
agtgagtgcc aagcaacatt gcacaccttt ggcagatgcc gatgtgccat tgaatatctg    4800
ctcgctgctc gctatagtcg tatctattct atatatctat agatatattt ccaggcttgc    4860
agatatatat aataataata cttaattagc aatacatcta acttggtaga gatggtttct    4920
gaggatctcc acccaccttc tagtgacacc tggtctttgt tagttatggg aaggatccta    4980
gggatccaca agataaaaag gttgccatcg ggagctagac gacgacctat tgtttagttg    5040
atctagaacc gagctcatgc gtctcttttc tccctggctg gacaagaat gtttgggcag    5100 ggtggagaca cctatcactt catctttttgg tgcatggatg gatcgatgca caagactatc    5160
gggaaaaaat cggcgaatcg tggccaaaat ctgccgcgat gtgatcctga attgggtgtc    5220
acattcttct ttttcttttt ctgaatggcg tgctccagat ttcggagagg atctagatcc    5280
gtccgagcga gttccttcgt gttgcataaa ggattttttt tc    5322
```

```
<210> SEQ ID NO 76
<211> LENGTH: 864
<212> TYPE: DNA
<213> ORGANISM: Zea mays

<400> SEQUENCE: 76
```

```
atgcaggatc gcttcaacgg taaacacgat aagaggcgac ccgccgccat taactcggga     60
tcagctcgcg aaataagctg ccgccaagac gaccgcgcgc gcgagggcaa gagccgcaac    120
gacggcggcg actggccggc gccacagcag ggcctcctgt cgatcgggac gctgggagac    180
gacgtcgacc cgccgccgcg cgcgtcgtcg caggccgacg acgtgctgga cttcaccatc    240
gaggaggtga aaaagctcca ggacgcgctg aacaagctgc tccggcgcgc caagtccaag    300
tccagctcca gctcctcccg cgggtcgggc gccagcgcca ccgacgagga ccgccgcgcc    360
agccacagcc agctgccgct cgacaggttc ctcaactgcc cctccagcct cgaggtcgac    420
cggagggtct cgctgatcag gcacgacggt ggtgccgaga gcggcgagtt ctcgccggac    480
acgcagatca tactcagcaa ggccagggat ctcctcgtcc acagcaacgg caccgccatc    540
aggaagaagt cgttcaagtt cctcctgaag aagatgttcg tctgccatgg cggcttcgcc    600
cccgcgccga gcttgaagga tccagttgaa tcgagaatgg agaagttgtt cagaacgatg    660
cttcagaaga agatgaatgc tcgcccgagc aacgctgcag tgtcatccag gaagtactac    720
ctcgacgaca gccgagtgg gaggatgatg acacgggatg gtcgtcgtcg tcacgatgga    780
gaggacgatg acgagaaggg ctctgacaga atcaagtggg ataaaactga tactgactgt    840
aagaacatat ttatacgctg ctag    864
```

```
<210> SEQ ID NO 77
<211> LENGTH: 287
<212> TYPE: PRT
<213> ORGANISM: Zea mays

<400> SEQUENCE: 77
```

```
Met Gln Asp Arg Phe Asn Gly Lys His Asp Lys Arg Arg Pro Ala Ala
1               5                   10                  15

Ile Asn Ser Gly Ser Ala Arg Glu Ile Ser Cys Arg Gln Asp Asp Arg
            20                  25                  30
```

```
Ala Arg Glu Gly Lys Ser Arg Asn Asp Gly Gly Asp Trp Pro Ala Pro
         35                  40                  45

Gln Gln Gly Leu Leu Ser Ile Gly Thr Leu Gly Asp Asp Val Asp Pro
 50                  55                  60

Pro Pro Arg Ala Ser Ser Gln Ala Asp Asp Val Leu Asp Phe Thr Ile
 65                  70                  75                  80

Glu Glu Val Lys Lys Leu Gln Asp Ala Leu Asn Lys Leu Leu Arg Arg
                 85                  90                  95

Ala Lys Ser Lys Ser Ser Ser Ser Arg Gly Ser Gly Ala Ser
                100                 105                 110

Ala Thr Asp Glu Asp Arg Arg Ala Ser His Ser Gln Leu Pro Leu Asp
                115                 120                 125

Arg Phe Leu Asn Cys Pro Ser Ser Leu Glu Val Asp Arg Arg Val Ser
        130                 135                 140

Leu Ile Arg His Asp Gly Gly Ala Glu Ser Gly Glu Phe Ser Pro Asp
145                 150                 155                 160

Thr Gln Ile Ile Leu Ser Lys Ala Arg Asp Leu Leu Val His Ser Asn
                165                 170                 175

Gly Thr Ala Ile Arg Lys Lys Ser Phe Lys Phe Leu Leu Lys Lys Met
                180                 185                 190

Phe Val Cys His Gly Gly Phe Ala Pro Ala Pro Ser Leu Lys Asp Pro
        195                 200                 205

Val Glu Ser Arg Met Glu Lys Leu Phe Arg Thr Met Leu Gln Lys Lys
        210                 215                 220

Met Asn Ala Arg Pro Ser Asn Ala Ala Val Ser Ser Arg Lys Tyr Tyr
225                 230                 235                 240

Leu Asp Asp Lys Pro Ser Gly Arg Met Met Thr Arg Asp Gly Arg Arg
                245                 250                 255

Arg His Asp Gly Glu Asp Asp Glu Lys Gly Ser Asp Arg Ile Lys
                260                 265                 270

Trp Asp Lys Thr Asp Thr Asp Cys Lys Asn Ile Phe Ile Arg Cys
        275                 280                 285

<210> SEQ ID NO 78
<211> LENGTH: 362
<212> TYPE: DNA
<213> ORGANISM: Zea mays

<400> SEQUENCE: 78
tgaaagacga ggaattttat ggatatggac tatagacaca ctattttta gactgacagc     60 cttaaaaaca atacgataaa attatgcatt gagaatgaca ttattttcca tcgaaaagaa    120
ttgaatgctc tgtttgcatt ggtgtgtcaa caacaactga taataaaaaa gaagaaatta    180
agatgctaaa gttatagtaa aaacatttgc tataaaaata gctccgtgct actttaacta    240
ggtctcctgt gatcactacc ctagctcttc tgtgatcaca atcgaataca cactttggtt    300 cccaatttt atcccaaaat aagcccacga caatatatgg tagttggcag catgtgcttt    360
ct                                                                   362

<210> SEQ ID NO 79
<211> LENGTH: 318
<212> TYPE: DNA
<213> ORGANISM: Zea mays

<400> SEQUENCE: 79
aactccaaag ccactccgat ccaccacccc tctcttcttt cactgcatgc ttagcttctt     60
```

```
ctccttttca acatcctgga gctgcccaat cacaggacac cttcaaaaca ctggaaccgg    120
ccggtcgagc ttctgttgcc tcccctgccg ccgctcttgc agactgtcac cacagactgc    180
tctgctcggc cggatattca cgggtccttc tccgggagca gtacgtacca tacaaggaca    240
tgggggtaaa ttcctcccac tgaaattaag ctagctagct tttggttttc atccactgac    300
agctatgttc ttccttcc                                                  318
```

<210> SEQ ID NO 80
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 80

```
aactccaaag ccactccgat cca                                             23
```

<210> SEQ ID NO 81
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 81

```
ctgacagcta tgttcttcct tcc                                             23
```

<210> SEQ ID NO 82
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 82

```
agaaagcaca tgctgccaac tac                                             23
```

<210> SEQ ID NO 83
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 83

```
tgaaagacga ggaattttat gga                                             23
```

<210> SEQ ID NO 84
<211> LENGTH: 3421
<212> TYPE: DNA
<213> ORGANISM: Artificial Sequence
<220> FEATURE:
<223> OTHER INFORMATION: Synthetic polynucleotide

<400> SEQUENCE: 84

```
cgatgatatg agctacccaa ggcattgaat ggtcgcttcc taaaatgata tcaccctagt     60
gtatgtcgag atgcttaaag aaccaatgga ttcatataga gttgtataca acttctatca    120
agcgcttttg gtttgcttaa agcttaccca aaaagcggag gcataggtt gagcaccata     180 tttggtacct gggcacggtc agatggtctg gccatgtggc ccagacggtc tgcggggtat    240
agctcgaatg gtccacgatt agatttactt gggcgagggt ccttacccg cgtgtactta     300
```

```
tccaagctaa tcacgcggga atatattgag atacgcctag gaacgggtcc agatctcccc    360
atatatatat gaagggtac aacctattga catgacacaa tcaatctatt tactagttcg    420
cttacatttc ttgccctagg agcatttgta gttagtcttc ctcatcctca attttcacca    480
cccctccact ctacgtcgtt tagatgcgcc ttgggtggcc taccgacccc aacacaacca    540
tatgatcttt ccttcctgat ggggtacctc tcgggagcga gatccaggtt ctgcaagaga    600
tccatgaagc cctctacgtg cctcgtggac ggtctgccac tgatacacgg acggtctgca    660
tgcccacaga gaaaaccaga gcccctctat gcattcgcgg atggtccggc cgctcatcac    720
ggacggtcct cgctcaagta gagaagaccc caaggttcag tgcgtcgtgc gccggcccta    780
gggttccttt attgattggc cccaaatgcg agccaacaat aggttggtaa acagtttgta    840
gtattgctag atgctacctc tagaacattt gtttaattat ttagactgtg tcaaacactt    900
tatccatata gttatccaaa atattgtttt gcactgatct gtactgtaga ctatattgtt    960
cgtaaagtga agtttgaata taaaaatagg gatggataag ctactgaagg cagtcttaca   1020
aaagaggagg ctatgaattt aggcttttcg ttcgatcatt catcaatgta ttagatcatg   1080
taatatgttg taaattttgt atctatattt aattgtgtat aaccttcctt tatataatta   1140
gtaattgtaa taatcgtgtt aaacacacca catattgtag ttgacatcaa tcattgtttt   1200
ttttaccatt gattatagat gagaacatgg acaactaatt atcgctcata attaaggaca   1260
aactatttga atcccgatgc accatactta tgccgtatga taatgtattc acaccattgg   1320
gcatggccgc atgagtcaat ttcttaggtc gttgtcaata gataaaatag ttttgttctt   1380
attaaatagc atgtcacata aataagtagg acgacataac atgcaattta ataaagaaag   1440
atatggtaga gttttatgaa agacgaggaa ttttttagac tgacagcctt aaaaacaata   1500
cgataaaatt atgcattgag aatgacatta ttttccatcg aaaagaattg aatgctctgt   1560
ttgcattggt gtgtcaacaa caactgataa taaaaaagaa gaaattaaga tgctaaagtt   1620
atagtaaaaa catttgctat aaaaatagct ccgtgctact ttaactaggt ctcctgtgat   1680
cactacccta gctcttctgt gatcacaatc gaatacacac tttggttccc aattttttatc   1740
ccaaaataag cccacgacaa tatatgtaaa ctccaagcaa atctgcctat cccatttggc   1800
actagaattt agtggaagta cacgcgctgc tacaagtagc agcatccccg ctactaattg   1860
ccaatttat actagatcaa ttactaatct ccagctattt aagcctaatc ctcctctagg   1920
caggggacca aacagcctca ctctcacagt ctcactcact cactgagagc tctcactcca   1980
ttggcctgtt gagaagatac tcaaaagggc cggcttctct ctctctctct gggaccaacc   2040
agagaacccc tgaatctaag tcctatatat cgccatagcc cagtggctcc ccgcccccac   2100
ggcattcttt gctcaaagtc gttggaggtg aatctaaagc tcacagattc ttggaaccag   2160
acaacaatgg gggtaagtaa acttcactgg cattattata gggagtttag acaagaactg   2220
gcgcatgacc gatccttggt tgttggctgc agatcatcaa ctggatgcag agcagattcc   2280
atgggaagac ggagaccagc agaatctttg acggcgcaac cgccaccagt tcatatagag   2340
gtaactgcca gctctctcat ttgcagtgca cctgcacttg cattgcaggt tcagcgctgg   2400
agtgctaaaa cgtgcgtgcg tacattgagc caggtggtgc tggagcccaa gggacgacgc   2460
aagggacgat cgttcacgaa tcagagaagc gtctcgacgc cgagccatgg cctcaggcgg   2520
gcatcctctc catcggcacg ctcggcagcg aggagcctcc cgcgcaggag caggacctgc   2580
cggagttcac cgtggaggag gtgaagaagc tccaggacgc gctggccatg ctcctgcggg   2640
gggccaagtc caagtccagc gcccgcggct ccggggccgg ggccggcgag gacaggccgc   2700
```

-continued

| | |
|---|---|
| cgctggacag gttcctcaac tgcccgtcct gcctggaggt ggagaggagg gtcgtccaga | 2760 |
| cgacggcgac gaatcacggc ggccaggaag aaggagacct ctcgccggac accaagatca | 2820 |
| tcctgaacag ggccagggac ctgctcgata gcggcggcgg cggcggcggc atcaagcaga | 2880 |
| ggtcgttcaa gttcctgctc aagaagatgt tcgcctgcaa tggcggcttc tcggccgcgc | 2940 |
| cgccccggag cttgaaggac ccagtggagt caagaatgga gaaggtaggc gcacgcgtgc | 3000 |
| gaacggtcgg cagacacaca caacacaaca caatgaagct agctgcttcg ttcgaccatg | 3060 |
| tctagtctag tagctaaaca aatacccttct ggtggtggac tgtcttttca gttcttccga | 3120 |
| acgatgatcg ggaagaagat gaacgccagg tcggggaacg gtcggcgtc gtccaggaaa | 3180 |
| tacttcttgg aggacggaac caaggcagg aggcgaggcg tcgtcgttg cggttgccaa | 3240 |
| gaagaagagg agagggaagc agagagttgc aggtgggaca gaacagattc tgaatgtaag | 3300 |
| ttcactatcg ctcgctacta ctcattgtcc atcacaggca attttgatgt cacaattctg | 3360 |
| tgtctgaacc tttttctaaa cctttttttt tctctcgtgc agtcattgtt ttggagatat | 3420 |
| g | 3421 |

<210> SEQ ID NO 85
<211> LENGTH: 3444
<212> TYPE: DNA
<213> ORGANISM: Artificial Sequence
<220> FEATURE:
<223> OTHER INFORMATION: Synthetic polynucleotide

<400> SEQUENCE: 85

| | |
|---|---|
| cgatgatatg agctacccaa ggcattgaat ggtcgcttcc taaaatgata tcaccctagt | 60 |
| gtatgtcgag atgcttaaag aaccaatgga ttcatataga gttgtataca acttctatca | 120 |
| agcgcttttg gtttgcttaa agcttacccaa aaaagcggag ggcataggtt gagcaccata | 180 |
| tttggtacct gggcacggtc agatggtctg gccatgtggc ccagacgtc tgcggggtat | 240 |
| agctcgaatg gtccacgatt agatttactt gggcgagggt ccttaccccg cgtgtactta | 300 |
| tccaagctaa tcacgcggga atatattgag atacgcctag gaacgggtcc agatctcccc | 360 |
| atatatatat gaagggtac aacctattga catgacacaa tcaatctatt tactagttcg | 420 |
| cttacatttc ttgccctagg agcatttgta gttagtcttc ctcatcctca attttcacca | 480 |
| cccctccact ctacgtcgtt tagatgcgcc ttgggtggcc taccgacccc aacacaacca | 540 |
| tatgatcttt ccttcctgat ggggtacctc tcgggagcga gatccaggtt ctgcaagaga | 600 |
| tccatgaagc cctctacgtg cctcgtggac ggtctgccac tgatacacgg acggtctgca | 660 |
| tgcccacaga gaaaccagag cccctctat gcattgcgg atggtccggc cgctcatcac | 720 |
| ggacggtcct cgctcaagta gagaagaccc caaggttcag tgcgtcgtgc gccggccta | 780 |
| gggttccttt attgattggc cccaaatgcg agccaacaat aggttggtaa acagtttgta | 840 |
| gtattgctag atgctaccctc tagaacattt gtttaattat ttagactgtg tcaaacactt | 900 |
| tatccatata gttatccaaa atattgttt gcactgatct gtactgtaga ctatattgtt | 960 |
| cgtaaagtga agtttgaata taaaatagg gatggataag ctactgaagg cagtcttaca | 1020 |
| aaagaggagg ctatgaattt aggcttttcg ttcgatcatt catcaatgta ttagatcatg | 1080 |
| taatatgttg taaattttgt atctatatt aattgtgtat aaccttcctt tatataatta | 1140 |
| gtaattgtaa taatcgtgtt aaacacacca catattgtag ttgacatcaa tcattgtttt | 1200 |
| ttttaccatt gattatagat gagaacatgg acaactaatt atcgctcata attaaggaca | 1260 |

-continued

| | |
|---|---|
| aactatttga atcccgatgc accatactta tgccgtatga taatgtattc acaccattgg | 1320 |
| gcatggccgc atgagtcaat ttcttaggtc gttgtcaata gataaaatag ttttgttctt | 1380 |
| attaaatagc atgtcacata aataagtagg acgacataac atgcaattta ataaagaaag | 1440 |
| atatggtaga gttttatgaa agacgaggaa ttttatggac tatagacaca ctattttta | 1500 |
| gactgacagc cttaaaaaca atacgataaa attatgcatt gagaatgaca ttattttcca | 1560 |
| tcgaaaagaa ttgaatgctc tgtttgcatt ggtgtgtcaa caacaactga taataaaaaa | 1620 |
| gaagaaatta agatgctaaa gttatagtaa aaacatttgc tataaaaata gctccgtgct | 1680 |
| actttaacta ggtctcctgt gatcactacc ctagctcttc tgtgatcaca atcgaataca | 1740 |
| cactttggtt cccaattttt atcccaaaat aagcccacga caatatatgt aaactccaag | 1800 |
| caaatctgcc tatcccattt ggcactagaa tttagtggaa gtacgcgc tgctacaagt | 1860 |
| agcagcatcc ccgctactaa ttgccaattt tatactagat caattactaa tctccagcta | 1920 |
| tttaagccta atcctcctct aggcagggga ccaaacagcc tcactctcac agtctcactc | 1980 |
| actcactgag agctctcact ccattggcct gttgagaaga tactcaaaag ggccggcttc | 2040 |
| tctctctctc tctgggacca accagagaac ccctgaatct aagtcctata tatcgccata | 2100 |
| gcccagtggc tccccgcccc cacggcattc tttgctcaaa gtcgttggag gtgaatctaa | 2160 |
| agctcacaga ttcttggaac cagacaacaa tggggtaag taaacttcac tggcattatt | 2220 |
| atagggagtt tagacaagaa ctggcgcatg accgatcctt ggttgttggc tgcagatcat | 2280 |
| caactggatg cagagcagat tccatgggaa gacggagacc agcagaatct ttgacggcgc | 2340 |
| aaccgccacc agttcatata gaggtaactg ccagctctct catttgcagt gcacctgcac | 2400 |
| ttgcattgca ggttcagcgc tggagtgcta aaacgtgcgt gcgtacattg agccaggtgg | 2460 |
| tgctggagcc caagggacga cgcaagggac gatcgttcac gaatcagaga agcgtctcga | 2520 |
| cgccgagcca tggcctcagg cgggcatcct ctccatcggc acgctcggca gcgaggagcc | 2580 |
| tcccgcgcag gagcaggacc tgccggagtt caccgtggag gaggtgaaga agctccagga | 2640 |
| cgcgctggcc atgctcctgc ggcgggccaa gtccaagtcc agcgcccgcg ctccggggc | 2700 |
| cggggccggc gaggacaggc cgccgctgga caggttcctc aactgcccgt cctgcctgga | 2760 |
| ggtggagagg agggtcgtcc agacgacggc gacgaatcac ggcggccagg aagaaggaga | 2820 |
| cctctcgccg acaccaaga tcatcctgaa cagggccagg gacctgctcg atagcggcgg | 2880 |
| cggcggcggc ggcatcaagc agaggtcgtt caagttcctg ctcaagaaga tgttcgcctg | 2940 |
| caatggcggc ttctcggccg cgccgccccg gagcttgaag gacccagtgg agtcaagaat | 3000 |
| ggagaaggta ggcgcacgcg tgcgaacggt cggcagacac acacaacaca acacaatgaa | 3060 |
| gctagctgct tcgttcgacc atgtctagtc tagtagctaa acaaataccc tctggtggtg | 3120 |
| gactgtcttt tcagttcttc cgaacgatga tcgggaagaa gatgaacgcc aggtcgggga | 3180 |
| acgggtcggc gtcgtccagg aaatacttct tggaggacgg aaccaaaggc aggaggcgag | 3240 |
| gcggtcgtcg ttgcggttgc caagaagaag aggagaggga agcagagagt tgcaggtggg | 3300 |
| acagaacaga ttctgaatgt aagttcacta tcgctcgcta ctactcattg tccatcacag | 3360 |
| gcaattttga tgtcacaatt ctgtgtctga acctttttct aaacctttt ttttctctcg | 3420 |
| tgcagtcatt gttttggaga tatg | 3444 |

<210> SEQ ID NO 86
<211> LENGTH: 23
<212> TYPE: DNA
<213> ORGANISM: Zea mays

<400> SEQUENCE: 86
attttatgga ctatagacac act                                          23

<210> SEQ ID NO 87
<211> LENGTH: 23
<212> TYPE: DNA
<213> ORGANISM: Zea mays

<400> SEQUENCE: 87
gtagttggca gcatgtgctt tct                                          23

<210> SEQ ID NO 88
<211> LENGTH: 5304
<212> TYPE: DNA
<213> ORGANISM: Artificial Sequence
<220> FEATURE:
<223> OTHER INFORMATION: Synthetic polynucleotide

<400> SEQUENCE: 88
gtccaaaaat aaaataaaa atcctagaat cgagtctata aattagattc tatttatgaa      60
ttttttattt tttatattta agttatgtaa ctttatttat aaattatgtc tttatattta    120
tatttgagtt atgtattttt taaattgttt ttatgaatta tatattttgt tgacttgatt    180
aattaattat atgtatttgt ttttcaataa aacaccatgt gttatatcac ctaacaatct    240
actccatccg ttcaaattta taattataat tcgtttgatt ttttaaccct aagtttgact    300
gactcgtctt attaaaaaaa ttattattat tattaatttt ttgatattat ttagtatata    360
atatacttca aatgtggttt tgaattttc attttttccca gaaagatgaa tagcacgagc    420
cggtcaaatg ttacacaaaa aagtcaaaca gattataatt tggaacataa ggagtataaa    480
ataaaagtta atgttgtgat gagatggtta tatgccgatg ataaaggtta tgcactgaag    540
cctcgtcaag gtagactggt agaggtttgc aacagcggac gtgacaatat atatagggtc    600
gtacctgagg gggtgcggag ggtgcggccg caccgggccc ccaaaaacag agggccccct    660
agccactgga cgctagcact ttttcctgtt aaatctatct attctagaca taaatacaca    720
aagagcgatg cgctattgac cagtctcgtt tagattgtta agtaatgtc tcgattactt    780 atcgaataat ccatccgttt caaaatagta tttgttttag ctcttgatt ttatgtttat    840 attcaactag atgatgataa atccactaaa gaagcaaaac aaattctatt tttatatata    900
gagagtatta tttactatac acatgatggt tgtatctgca tagagaagct ttttagaatt    960
gaaatatttt tgtgaactat ttatggtcaa caataactca agagaggtta tatgtcttgt   1020
cgattctata tatcgaaaaa gttgttgaat ggtattgatc tcaattgtat aagtaatgac   1080
tttgtatcac aaaatgttag aggatatttt taatgatatc agataacaag tacgtgtttt   1140
tagctatatt ttacatttgt tatcttataa acatcaaaac agtgcataat aatttttaca   1200 cgtcaaaatat tcgatactat agtctatata taattatata tatttatgtg tggacggagc   1260
cttcatatcg gatttcgcac cgggccctg aaaagtcagg aacggcccta ggtatatatt   1320
atccgaaagg gttggatata gccttatgct tcatgtaatc aaagaaataa aaataaagct   1380
tttctactat gcttgttttt ggtttgtcta ctttaaaaaa tgtgctctaa ttgatgtcca   1440
tgactcgcct cggcaggtgt aaaaaaactc ccacatacat tggtcccaga accagaaaag   1500
aggtgctacg agctttgtta ttattgattg ggaaaatatt aaaaaaacgc agtaatacaa   1560
taccgacata gtattttata cttcactcaa gtagtaaaat ttctcatgta attaacagct   1620

```
catgcacatg taagaacgta actctgggcg cgattgtgca atttggccac taccatcaat    1680
ctagctagcc ctgggtttat taggccctcc ctagtcccta accctattta attgggggaa    1740
gggggaccct ggttgcatcc aaactccaaa gccacaccac ccctctcttc tttcactgca    1800
tgcttagctt cttctccttt tcaacatcct ggagctgccc aatcacagga caccttcaaa    1860
acactggaac cggccggtcg agcttctgtt gcctcccctg ccgccgctct tgcagactgt    1920
caccacagac tgctctgctc ggccggatat tcacgggtcc ttctccggga gcagtacgta    1980
ccatacaagg acatgggggt aaattcctcc cactgaaatt aagctagcta gcttttggtt    2040
ttcatccact gacagctatg ttcttccata tatgtgttct tttccagtgt tccgcggtta    2100
attttgcatt attgtctgca gatcattaac tggatgcagg atcgcttcaa cggtaaacac    2160
gataagaggc gacccgccgc cattaactcg ggatcagctc gcggttagtg atttctctgaa   2220
tcctttcgtg ctactggtac ggtaattgtc aatttgttac cacgcccggc cggcgcactt    2280
acgtggcgtt cttcttagct ttcgtgctga cgaacgaact ggccggccgc tgctcttttt    2340
gctgcatgca tgcatgacgc ctcgtttgta cgtcagaaat aagctgccgc caagacgacc    2400
gcgcgcgcga gggcaagagc cgcaacgacg gcggcgactg gccggcgcca cagcagggcc    2460
tcctgtcgat cgggacgctg ggagacgacg tcgacccgcc gccgcgcgcg tcgtcgcagg    2520
ccgacgacgt gctggacttc accatcgagg aggtgaaaaa gctccaggac gcgctgaaca    2580
agctgctccg gcgcgccaag tccaagtcca gctccagctc ctcccgcggg tcgggcgcca    2640
gcgccaccga cgaggaccgc cgcgccagcc acagccagct gccgctcgac aggttcctca    2700
actgcccctc cagcctcgag gtcgaccgga gggtctcgct gatcaggcac gacggtggtg    2760
ccgagagcgg cgagttctcg ccggacacgc agatcatact cagcaaggcc agggatctcc    2820
tcgtccacag caacggcacc gccatcagga gaagtcgtt caagttcctc ctgaagaaga     2880
tgttcgtctg ccatggcggc ttcgcccccg cgccgagctt gaaggatcca gttgaatcga    2940
gaatggagaa ggtatatgtt atgtgtaagc agcggacatg gatatatgtc tgaattcatg    3000
cattgtcagt cgtaagatta aatgctagta atgtatacgt acatggttct ctccttttgt    3060
tgtttttgag tgcacgcaca tacagttgtt cagaacgatg cttcagaaga agatgaatgc    3120
tcgcccgagc aacgctgcag tgtcatccag gaagtactac ctcgacgaca agccgagtgg    3180
gaggatgatg acacgggatg gtcgtcgtcg tcacgatgga gaggacgatg acgagaaggg    3240
ctctgacaga atcaagtggg ataaaactga tactgactgt aagaacatat ttatacgctg    3300
ctagccgcac atatgtacgg ttaaacaacg atgcatatat atatatatat atatatatat    3360
atatatatat atatatatat atatatatat atatatatat atatatatat atatatatat    3420
atatatatat atatatatat atatatatat atatatatat atatatatat atatatatat    3480
atatatatat atatatagaa gcttcatgcg atgagctctg ctagtaataa taagcaataa    3540
gggatcactg aatgaaatct cgcttgcgct ttccagtcat cgttctggag atctagatca    3600
agaggctcga gttcaaaggt ccttgtgata tccagtatgt ggtaagctac attgaaacgc    3660
ctgtcgaagt tttatgatac gatgacggtg ttttttgct ggtgctaaaa ttttgtggtg     3720
gtttgatctt tatttcgcag cttacgagtg gtgatggtga ccttgagtca gaggagaaat    3780
acactacaat aatccgtatt aaaggagtgt tcagttgaac tgcgaataga tcagacaaga    3840
tatatatgca tgcctgatgc caccagggtg taatactgga tgaagatcag aattcacacg    3900
caatggaggt gttaatagga agaaagagtt ctcagctttg cactctcgat cctttcccat    3960
ctcatcttca gatcgtccta cacacacaca cacgctatcc tactacgttt tgtagttctt    4020
```

```
ttgcatcata tcttgtggac aaattaagag ggatgatttc agttagtgaa cgtaaccctg    4080
atgatatata taaaattaat gttaaattgt ggccccatca tcatctcagg aacatggcat    4140
tgctcgtgaa gcatatgact gcgtgaaatt tttatacata catagcagga gtcccgagtg    4200
tacagaaata gcattgcaac tggggcgctt ggaacatgct cattgccgaa accggaaagc    4260
tggctaggct ggacctggaa gtgcgtccga gatctccatt ggccgtcagg atccggaggc    4320
agctccccgg cacatttgtg tgtgttcgtg cccagttgta ggcggggaga agaaaaaaaa    4380
gggggcgcca aggagtgagt gccaagcaac attgcacacc tttggcagat gccgatgtgc    4440
cattgaatat ctgctcgctg ctcgctatag tcgtatctat tctatatatc tatagatata    4500
tttccaggct tgcagatata tataataata atacttaatt agcaatacat ctaacttggt    4560
agagatggtt tctgaggatc tccacccacc ttctagtgac acctggtctt tgttagttat    4620
gggaaggatc ctagggatcc acaagataaa aaggttgcca tcgggagcta gacgacgacc    4680
tattgtttag ttgatctaga accgagctca tgcgtctctt ttctccctgg ctgggacaag    4740
aatgtttggg cagggtggag acacctatca cttcatcttt tggtgcatgg atggatcgat    4800
gcacaagact atcgggaaaa aatcggcgaa tcgtggccaa aatctgccgc gatgtgatcc    4860
tgaattgggt gtcacattct tcttttttctt tttctgaatg gcgtgctcca gatttcggag    4920
aggatctaga tccgtccgag cgagttcctt cgtgttgcat aaaggatttt ttttctcgtg    4980
aatttgagtc agttttttaaa cgtaggattc tggttccacc caaggatatg tataacaaca    5040
tatttgatgc atgtgtgtgt agccttactc gacacacact tcgcatagcc tgaaagtcga    5100
aggacaaata tctgcagcaa tatcactatg ggaactagca caaggctggg gttcagacgc    5160
tgacgcacag taggactcag agcaagacga ccggaagtcc ggaacgagtt gtttcttatg    5220
tagctcaagc tgagggagt gtagtagttg actagtagac attcagggct cgcgtttgtt    5280
cagatcccaa caggcagacg actg                                          5304
```

<210> SEQ ID NO 89
<211> LENGTH: 5305
<212> TYPE: DNA
<213> ORGANISM: Artificial Sequence
<220> FEATURE:
<223> OTHER INFORMATION: Synthetic polynucleotide

<400> SEQUENCE: 89

```
gtccaaaaat aaaataaaa atcctagaat cgagtctata aattagattc tatttatgaa      60
ttttttattt tttatattta agttatgtaa ctttatttat aaattatgtc tttatattta     120
tatttgagtt atgtattttt taaattgttt ttatgaatta tatattttgt tgacttgatt     180
aattaattat atgtatttgt ttttcaataa aacaccatgt gttatatcac ctaacaatct     240
actccatccg ttcaaattta taattataat tcgtttgatt ttttaaccct aagtttgact     300
gactcgtctt attaaaaaaa ttattattat tattaatttt ttgatattat ttagtatata     360
atatacttca aatgtggttt tgaattttttc atttttccca gaaagatgaa tagcacgagc     420
cggtcaaatg ttacacaaaa aagtcaaaca gattataatt tggaacataa ggagtataaa     480
ataaaagtta atgttgtgat gagatggtta tatgccgatg ataaaggtta tgcactgaag     540
cctcgtcaag gtagactggt agaggtttgc aacagcggac gtgacaatat atatagggtc     600
gtacctgagg gggtgcggag ggtgcggccg caccgggccc ccaaaaacag agggccccct     660
agccactgga cgctagcact ttttcctgtt aaatctatct attctagaca taaatacaca     720
```

-continued

```
aagagcgatg cgctattgac cagtctcgtt tagattgtta aagtaatgtc tcgattactt    780
atcgaataat ccatccgttt caaaatagta tttgttttag ctcttgattt ttatgtttat    840
attcaactag atgatgataa atccactaaa gaagcaaaac aaattctatt tttatatata    900
gagagtatta tttactatac acatgatggt tgtatctgca tagagaagct ttttagaatt    960
gaaatatttt tgtgaactat ttatggtcaa caataactca agagaggtta tatgtcttgt   1020
cgattctata tatcgaaaaa gttgttgaat ggtattgatc tcaattgtat aagtaatgac   1080
tttgtatcac aaaatgttag aggatatttt taatgatatc agataacaag tacgtgtttt   1140
tagctatatt ttacatttgt tatcttataa acatcaaaac agtgcataat aatttttaca   1200
cgtcaaatat tcgatactat agtctatata taattatata tatttatgtg tggacggagc   1260
cttcatatcg gatttcgcac cgggcccctg aaaagtcagg aacggcccta ggtatatatt   1320
atccgaaagg gttggatata gccttatgct tcatgtaatc aaagaaataa aaataaagct   1380
tttctactat gcttgttttt ggtttgtcta ctttaaaaaa tgtgctctaa ttgatgtcca   1440
tgactcgcct cggcaggtgt aaaaaaactc ccacatacat tggtcccaga accagaaaag   1500
aggtgctacg agctttgtta ttattgattg ggaaaatatt aaaaaaacgc agtaatacaa   1560
taccgacata gtattttata cttcactcaa gtagtaaaat ttctcatgta attaacagct   1620
catgcacatg taagaacgta actctgggcg cgattgtgca atttggccac taccatcaat   1680
ctagctagcc ctgggtttat taggccctcc ctagtcccta accctattta attggggaa    1740
gggggaccct ggttgcatcc aaactccaaa gccactcccc tctcttcttt cactgcatgc   1800
ttagcttctt ctccttttca acatcctgga gctgcccaat cacaggacac cttcaaaaca   1860
ctggaaccgg ccggtcgagc ttctgttgcc tcccctgccg ccgctcttgc agactgtcac   1920
cacagactgc tctgctcggc cggatattca cgggtccttc tccgggagca gtacgtacca   1980
tacaaggaca tgggggtaaa ttcctcccac tgaaattaag ctagctagct tttggttttc   2040
atccactgac agctatgttc ttccttccat atatgtgttc ttttccagtg ttccgcggtt   2100
aattttgcat tattgtctgc agatcattaa ctggatgcag gatcgcttca acggtaaaca   2160
cgataagagg cgacccgccg ccattaactc gggatcagct cgcggttagt gattctctga   2220
atcctttcgt gctactggta cggtaattgt caatttgtta ccacgcccgg ccggcgcact   2280
tacgtggcgt tcttcttagc tttcgtgctg acgaacgaac tggccggccg ctgctctttt   2340
tgctgcatgc atgcatgacg cctcgtttgt acgtcagaaa taagctgccg ccaagacgac   2400
cgcgcgcgcg agggcaagag ccgcaacgac ggcggcgact ggccggcgcc acagcagggc   2460
ctcctgtcga tcgggacgct gggagacgac gtcgacccgc cgccgcgcgc gtcgtcgcag   2520
gccgacgacg tgctggactt caccatcgag gaggtgaaaa agctccagga cgcgctgaac   2580
aagctgctcc ggcgcgccaa gtccaagtcc agctccagct cctcccgcgg gtcgggcgcc   2640
agcgccaccg acgaggaccg ccgcgccagc cacagccagc tgccgctcga caggttcctc   2700
aactgcccct ccagcctcga ggtcgaccgg agggtctcgc tgatcaggca cgacggtggt   2760
gccgagagcg gcgagttctc gccggacacg cagatcatac tcagcaaggc cagggatctc   2820
ctcgtccaca gcaacggcac cgccatcagg aagaagtcgt tcaagttcct cctgaagaag   2880
atgttcgtct gccatggcgg cttcgccccc gcgccgagct tgaaggatcc agttgaatcg   2940
agaatggaga aggtatatgt tatgtgtaag cagcggacat ggatatatgt ctgaattcat   3000
gcattgtcag tcgtaagatt aaatgctagt aatgtatacg tacatggttc tctccttttg   3060
ttgttttga gtgcacgcac atacagttgt tcagaacgat gcttcagaag aagatgaatg   3120
```

```
ctcgcccgag caacgctgca gtgtcatcca ggaagtacta cctcgacgac aagccgagtg    3180
ggaggatgat gacacgggat ggtcgtcgtc gtcacgatgg agaggacgat gacgagaagg    3240
gctctgacag aatcaagtgg gataaaactg atactgactg taagaacata tttatacgct    3300
gctagccgca catatgtacg gttaaacaac gatgcatata tatatatata tatatatata    3360
tatatatata tatatatata tatatatata tatatatata tatatatata tatatatata    3420
tatatatata tatatatata tatatatata tatatatata tatatatata tatatatata    3480
tatatatata tatatataga agcttcatgc gatgagctct gctagtaata ataagcaata    3540
agggatcact gaatgaaatc tcgcttgcgc tttccagtca tcgttctgga gatctagatc    3600
aagaggctcg agttcaaagg tccttgtgat atccagtatg tggtaagcta cattgaaacg    3660
cctgtcgaag ttttatgata cgatgacggt gttttttttgc tggtgctaaa attttgtggt    3720
ggtttgatct ttatttcgca gcttacgagt ggtgatggtg accttgagtc agaggagaaa    3780
tacactacaa taatccgtat taaaggagtg ttcagttgaa ctgcgaatag atcagacaag    3840
atatatatgc atgcctgatg ccaccagggt gtaatactgg atgaagatca gaattcacac    3900
gcaatggagg tgttaatagg aagaaagagt tctcagcttt gcactctcga tcctttccca    3960
tctcatcttc agatcgtcct acacacacac acacgctatc ctactacgtt ttgtagttct    4020
tttgcatcat atcttgtgga caaattaaga gggatgattt cagttagtga acgtaaccct    4080
gatgatatat ataaaattaa tgttaaattg tggccccatc atcatctcag gaacatggca    4140
ttgctcgtga agcatatgac tgcgtgaaat ttttatacat acatagcagg agtcccgagt    4200
gtacagaaat agcattgcaa ctggggcgct tggaacatgc tcattgccga aaccggaaag    4260
ctggctaggc tggacctgga agtgcgtccg agatctccat tggccgtcag gatccggagg    4320
cagctccccg gcacatttgt gtgtgttcgt gcccagttgt aggcggggag aagaaaaaaa    4380
agggggcgcc aaggagtgag tgccaagcaa cattgcacac cttttggcaga tgccgatgtg    4440 ccattgaata tctgctcgct gctcgctata gtcgtatcta ttctatatat ctatagatat    4500
atttccaggc ttgcagatat atataataat aatacttaat tagcaataca tctaacttgg    4560
tagagatggt ttctgaggat ctccacccac cttctagtga cacctggtct ttgttagtta    4620
tgggaaggat cctagggatc cacaagataa aaaggttgcc atcgggagct agacgacgac    4680
ctattgttta gttgatctag aaccgagctc atgcgtctct tttctccctg gctgggacaa    4740
gaatgtttgg gcagggtgga gacacctatc acttcatctt ttggtgcatg gatggatcga    4800
tgcacaagac tatcgggaaa aaatcggcga atcgtggcca aaatctgccg cgatgtgatc    4860
ctgaattggg tgtcacattc ttcttttttct ttttctgaat ggcgtgctcc agatttcgga    4920
gaggatctag atccgtccga gcgagttcct tcgtgttgca taaggatttt tttttctcgt    4980
gaatttgagt cagttttttaa acgtaggatt ctggttccac ccaaggatat gtataacaac    5040
atatttgatg catgtgtgtg tagccttact cgacacacac ttcgcatagc ctgaaagtcg    5100
aaggacaaat atctgcagca atatcactat gggaactagc acaaggctgg ggttcagacg    5160
ctgacgcaca gtaggactca gagcaagacg accggaagtc cggaacgagt tgtttcttat    5220
gtagctcaag ctgaggggag tgtagtagtt gactagtaga cattcagggc tcgcgtttgt    5280
tcagatccca acaggcagac gactg                                         5305

<210> SEQ ID NO 90
<211> LENGTH: 11
<212> TYPE: DNA
```

```
<213> ORGANISM: Zea mays

<400> SEQUENCE: 90
ccgatccacc a                                                                11
```